(12) United States Patent
Pauley et al.

(10) Patent No.: US 12,131,661 B2
(45) Date of Patent: Oct. 29, 2024

(54) PERSONALIZED HEALTH COACHING SYSTEM

(71) Applicant: Willow Laboratories, Inc., Irvine, CA (US)

(72) Inventors: Kevin Hughes Pauley, Lake Forest, CA (US); Merlin Stonecypher, Irvine, CA (US); Anderson Briglia, Irvine, CA (US); Gerry Hammarth, Irvine, CA (US); Gregory A. Olsen, Lake Forest, CA (US); Jesse Chen, Foothill Ranch, CA (US)

(73) Assignee: Willow Laboratories, Inc., Irvine, CA (US)

( * ) Notice: Subject to any disclaimer, the term of this patent is extended or adjusted under 35 U.S.C. 154(b) by 0 days.

(21) Appl. No.: 17/062,418

(22) Filed: Oct. 2, 2020

(65) Prior Publication Data

US 2021/0104173 A1 Apr. 8, 2021

Related U.S. Application Data

(60) Provisional application No. 63/007,232, filed on Apr. 8, 2020, provisional application No. 62/910,205, filed on Oct. 3, 2019.

(51) Int. Cl.
*G09B 19/00* (2006.01)
*A61B 5/00* (2006.01)
*A61B 5/145* (2006.01)

(52) U.S. Cl.
CPC .......... *G09B 19/00* (2013.01); *A61B 5/14532* (2013.01); *A61B 5/7267* (2013.01); *G09B 19/0092* (2013.01)

(58) Field of Classification Search
CPC ................ G09B 19/00; G09B 19/0092; A61B 5/14532; A61B 5/7267
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |

(Continued)

OTHER PUBLICATIONS

US 2022/0192529 A1, 06/2022, Al-Ali et al. (withdrawn)
US 2024/0016391 A1, 01/2024, Lapotko et al. (withdrawn)

*Primary Examiner* — Peter R Egloff
(74) *Attorney, Agent, or Firm* — Knobbe, Martens, Olson & Bear, LLP

(57) ABSTRACT

Systems and methods for a comprehensive and personalized approach to health and lifestyle coaching are described. The system may determine health metrics of a user based on detected physiological parameters. The health metrics may be used to determine health recommendations and transmit feedback to the user based on user compliance with the recommendations.

20 Claims, 89 Drawing Sheets

(56) References Cited

U.S. PATENT DOCUMENTS

| | | |
|---|---|---|
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |

(56) References Cited

U.S. PATENT DOCUMENTS

| | | |
|---|---|---|
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |

(56) References Cited

U.S. PATENT DOCUMENTS

| | | |
|---|---|---|
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |

(56) References Cited

U.S. PATENT DOCUMENTS

| | | |
|---|---|---|
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kian |
| 2008/0154513 A1* | 6/2008 | Kovatchev .............. G16H 15/00 |
| | | 702/19 |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0123234 A1* | 5/2012 | Atlas ...................... G16H 50/50 |
| | | 600/365 |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0039383 A1* | 2/2014 | Dobbles .............. A61M 15/008 |
| | | 604/66 |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2016/0092790 A1* | 3/2016 | Ribeiro Mendes Júnior ............... |
| | | G06N 20/10 |
| | | 706/12 |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0220751 A1* | 8/2017 | Davis ..................... G06N 5/048 |
| 2017/0251974 A1 | 9/2017 | Shreim et al. |
| 2017/0277863 A1* | 9/2017 | Subra ................. G09B 19/0092 |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0290172 A1* | 9/2019 | Hadad .................... G06N 20/00 |
| 2019/0320906 A1 | 10/2019 | Olsen |
| 2019/0369108 A1* | 12/2019 | Breschi ................. G16H 20/10 |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |

(56) References Cited

U.S. PATENT DOCUMENTS

| | | |
|---|---|---|
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Klani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |

\* cited by examiner

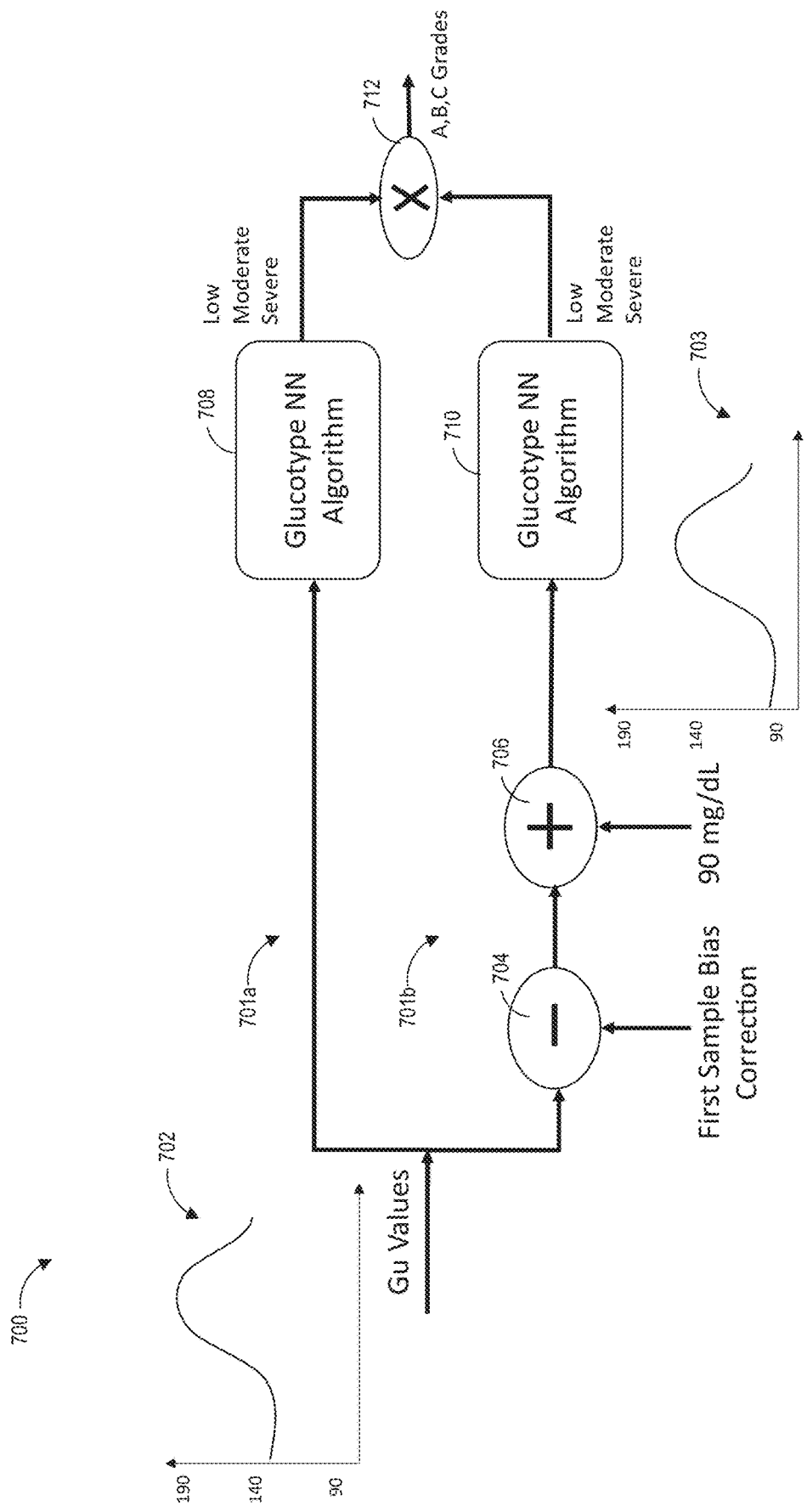

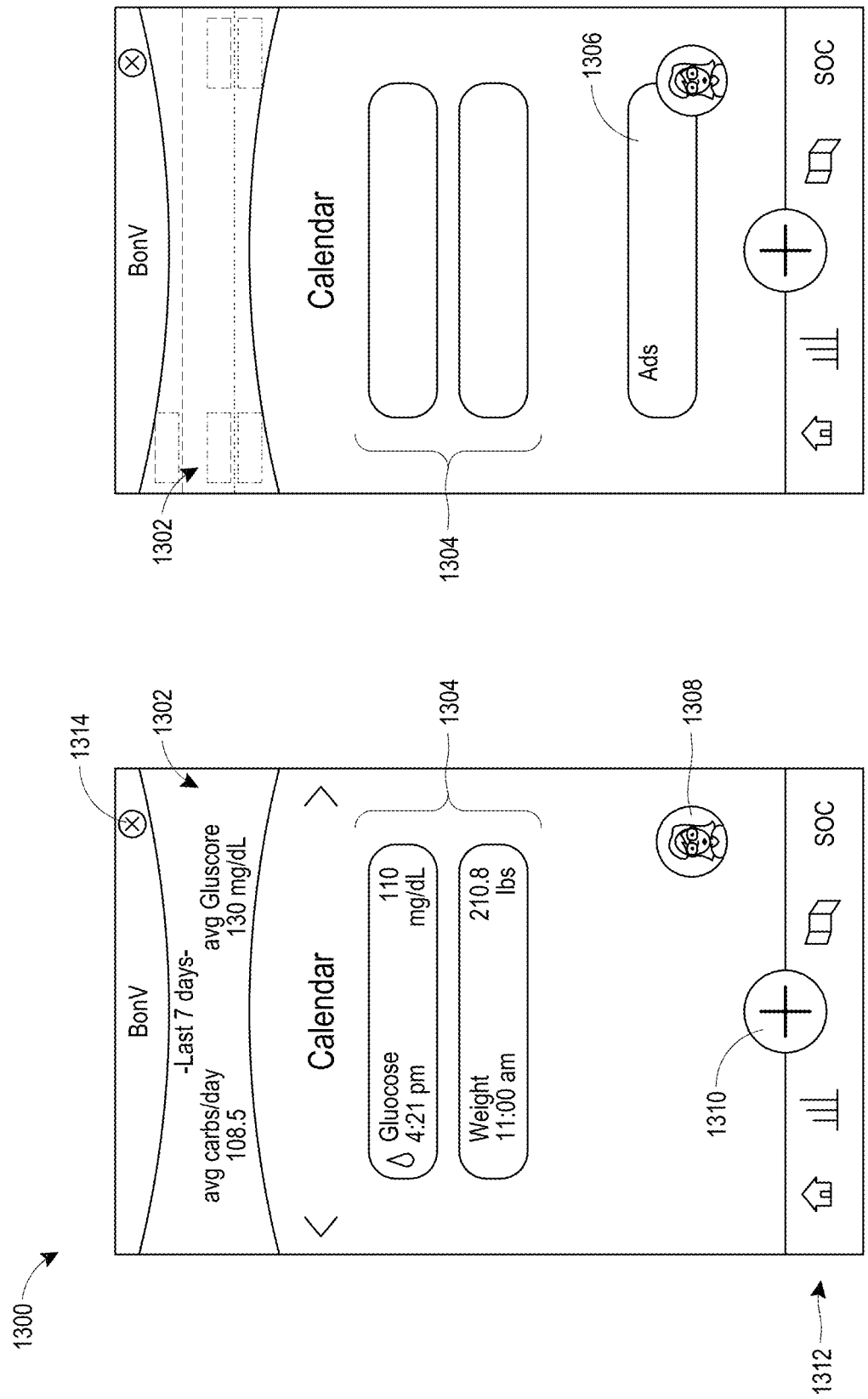

FIG. 18C-1

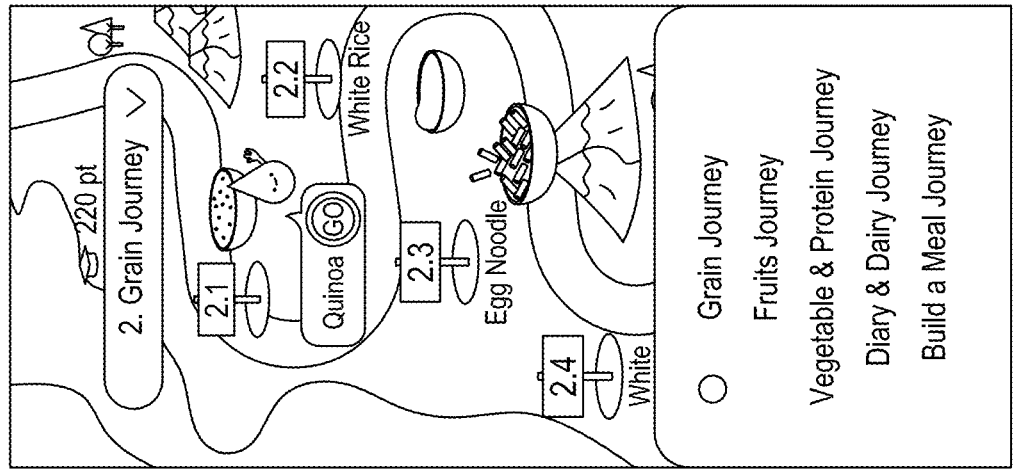
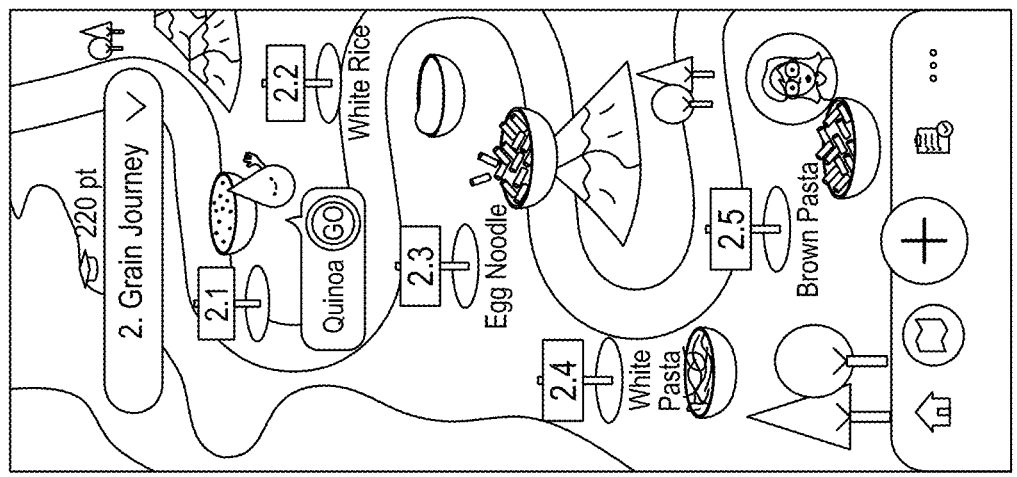
FIG. 22B

1.1 Quinoa
B-

70 mg/dL [Actions] 130 mg/dL
Before Meal          Max Post Meal

Recommend ✕

- Barley >
- Brown rice >
- Buckwheet >
- Wheat Pasta >

Avoid

- Popcorn
- Ryebread
- Flaxseed Bread
- Wild Rice
- Squaw

FIG. 23C

Brown Rice
B-

70 mg/dL [Actions] 130 mg/dL
Before Meal          Max Post Meal

Brown Rice is recommended for your Glucotypes. It's predict that you may have less blood glucose elevation and fluctuation compare to quiona, therefore it can be a great substitutions for other grains.
Brown pasta is a highly nutritious food. It is a whole grain that is high in fiber, gluten-free — Pair with... —

Eating the right food together can result in better Glucotype Score

| Brown Rice | B- | + | Chicken | A |

---

Recipe
Brown Pasta & Brussel Sprout
🕐 20min  🍴 5 ingrdients
☆ Mark as Favorite

INGREDIENTS
- ⅓ placerat et dolor quis mattis
- ½ Cras tortor tortor
- ¼ purus in interdum tempus orci
- 1 cup proin in interdum mi
- 1 tsp duis quis ullamcorper augue

COOKING INSTRUCTIONS

Step 1
Preheat the grill to medium-high heat. Brush corn with olive oil, and season with salt and pepper.

Step 2
Grill for 5 to 6 minutes, rotating on all sides, until the corn has some nice charred spots.

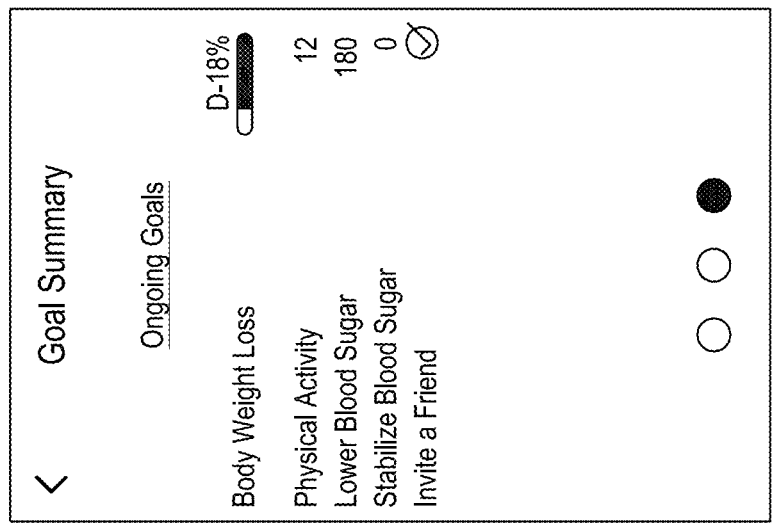
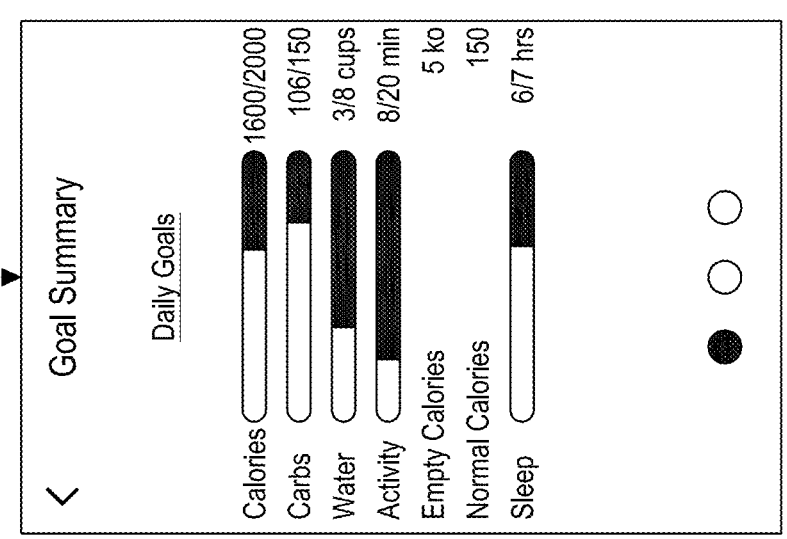
FIG. 26C

| | | | | | |
|---|---|---|---|---|---|
| ≡ Dashboard | Search | | Search | | Check |
| NEW | | | | | |
| ⊙ Dashboard | | | | | |
| Patients | Premium Filter | 32 Pipeline | 0 Scheduled Appointment | 1 Unanswered Message | |
| ⊕ Register | | | | | |
| ⚲ Search | | | | | |
| 📋 Questionaires | Patient | Trigger | Date | Priority | Progress |
| Events | Anderson test, 27 | Physical activity not logged for 3 days. | 11/11/19 04:18 pm | Moderate | Late |
| ≡ History | Anderson test, 27 | Weight not logged for 3 days. | 11/20/19 05:35 pm | Moderate | Late |
| Policy & Consent | Anderson test, 27 | Physical activity not logged for 3 days. | 12/13/19 01:56 pm | Moderate | Late |
| ⚙ Update Policy | Liliana Hernandez, 23 | Meals not logged for 3 days. | 12/17/19 05:02 pm | Moderate | Late |
| Achievements | Kevin Pauley, 20 | Weight not logged for 3 days. | 12/17/19 05:51 pm | Moderate | Late |
| 🎁 Reward Transaction | mike, 20 | Physical activity not logged for 3 days. | 12/17/19 05:51 pm | Moderate | Late |
| Coach | mike, 20 | Meals not logged for 3 days. | 12/22/19 04:38 pm | Moderate | Late |
| 💬 Chat | mike, 20 | Physical activity not logged for 3 days. | 12/25/19 11:14 am | Moderate | Late |
| 🔗 Pipeline | Liliana Hernandez, 20 | Weight not logged for 3 days. | 12/28/19 04:41 pm | Moderate | Late |
| 👤 User Profile | | | | | |
| ⚲ Search | | | | | |
| NEW | | | | | |

FIG. 27A

PERSONALIZED HEALTH COACHING SYSTEM

FIELD OF THE DISCLOSURE

The present disclosure relates to personalized health coaching using data analytics.

BACKGROUND

Individuals at risk of certain lifestyle diseases, such as diabetes, cardiovascular disease, and stroke can conventionally receive health and wellness care through a variety of behavioral, clinical, or social programs, such as calorie counting applications, fitness trackers, weight loss support groups, and clinical care. However, many people have difficulty complying with these programs and ultimately fail to improve their health.

SUMMARY

The health of a person can hinge on a variety of behavioral, genetic, social, and other factors. In particular, behavioral and social factors such as diet, exercise, sleep, and stress are significant contributors to the development of so-called lifestyle diseases, such as heart disease, stroke, and type 2 diabetes. To persons at risk for developing such diseases, the general notion of reducing their risk through a regimen of stress reduction, sleeping more, eating better and exercising regularly may be known and understood. However, compliance with such a regimen is difficult. While there are programs that may aid a person with following such a regimen, they typically only address a limited number of factors that contribute to a person's health, such as merely diet and exercise. Such a segmented approach is of limited help to a person trying to change their lifestyle because it ignores other important factors that may significantly contribute to the person's health risk. Furthermore, lifestyle programs rarely take into account the fuller picture of a person's health beyond merely weight gain or loss in monitoring progress. The present disclosure describes a comprehensive and personalized approach to health and lifestyle coaching that monitors a variety of health related factors in order to track a person's progress in reducing their health risk for so-called lifestyle diseases, such as heart disease, stroke, and type 2 diabetes.

Disclosed herein is a health coaching system that aims to help its users make better meal and lifestyle choices with the aim of lowering the chances of becoming diabetic. It achieves this goal, in part, by using grading for meals and allowing the users to identify which meals are good for them with regards to glycemic regulation. The predictive grades can also enable users to see potential effects of certain food items and portion sizes and thus make better meal choices.

Disclosed herein are systems and methods for personalized health coaching. A personalized health coaching system can include at least one sensor configured to detect blood glucose values of a user, an input configured to receive the blood glucose values from the at least one sensor, and one or more hardware processors. The one or more hardware processors can be configured to analyze a plurality of historical glucose values to determine a GluScore of the user, determine a recommendation threshold based at least in part on the GluScore, receive a glucose value from the at least one sensor, determine that the current glucose value passes the recommendation threshold, and generate a user recommendation based on the current glucose value.

The GluScore can include a variation of glucose values over a period of time. The period of time can include 2 hours.

The user recommendation can include a food intake change. The user recommendation can include a glucose measurement schedule including times of day to measure glucose. The user recommendation can include an interaction with educational materials.

The recommendation threshold can include a glucose value over a threshold percentage of an average glucose value over the period of time. The threshold percentage can include a value greater than fifty percent of the maximum glucose value of the historical glucose values.

To analyze a plurality of historical glucose values, the one or more hardware processors can be configured to classify the historical glucose values as being at least one of: low variability, moderate variability, and severe variability. The low variability can include a variability in historical glucose values of less than twenty percent over two hours. The moderate variability can include a variability in historical glucose values of between twenty and forty percent over two hours. The severe variability can include a variability in historical glucose values of greater than forty percent over two hours.

The one or more hardware processors can be configured to: communicate the user recommendation to the user, receive user data comprising at least one of a second glucose value, and determine a user compliance with the recommendation based at least in part on the second glucose value.

The one or more hardware processors can be configured to: determine a user encouragement based at least in part on the user compliance, and transmit the user encouragement.

The one or more hardware processors can be configured to: determine a user reward based at least in part on the user compliance and transmit the user reward. The one or more hardware processors can be configured to transmit the user compliance to a third party. The third party can include a support user. The third party can include an insurance provider.

In another example, a system for providing personalized health coaching recommendations to a user can include: a non-transitory memory configured to store executable instructions and one or more hardware processors in communication with the non-transitory memory configured to: receive a first set of data associated with a user, analyze the first set of data to determine a first health score of the user, generate a lifestyle recommendation based on the first health score of the user, transmit the lifestyle recommendation to the user, receive a second set of data associated with the user, the second set of data comprising data received from at least one of a tracking device, a third party, or a user input, analyze the second set of data to determine a user compliance with the lifestyle recommendation, and transmit feedback to the user based on the user compliance.

The first set of data can include data received from at least one of a tracking device, a third party, or a user input.

The feedback can include an encouragement or a reward. The encouragement can include an encouraging message. The reward can include access to a monetary discount on a retail item.

The one or more hardware processors can be configured to transmit the user compliance to a third party. The third party can include a support user. The third party can include an insurance provider.

The lifestyle recommendation can be based on a user goal. The lifestyle recommendation can be based on a clinician input.

In another example, a system for providing health education materials to a user can include a non-transitory memory configured to store executable instructions and one or more hardware processors in communication with the non-transitory memory configured to: receive a first set of data associated with a user, analyze the first set of data to determine a first health score of the user, determine educational content relevant to the user based on the first health score, and facilitate user access to at least a portion of the educational content according to a release schedule.

The first set of data can include data received from at least one of a tracking device, a third party, or a user input.

The one or more hardware processors can be configured to: receive a user interaction comprising a question associated with the health of the user, determine a response to the user interaction, transmit the response to the user interaction to the user. The response can include educational content. The educational content can include interactive educational modules associated with the first health score. The educational content can include videos or articles associated with the first health score. The release schedule can include once a week.

The one or more hardware processors can be configured to: receive a second set of data associated with the user, the second set of data comprising data received from at least one of a tracking device, a third party, or a user input, determine an amount of user interaction with the educational content, determine a feedback based on the amount of user interaction, and transmit the feedback to the user. The feedback can include an encouragement or a reward. The one or more hardware processors can be configured to transmit the amount of user interaction to a third party. The third party can include a support user. The third party can include an insurance provider.

In another example, a system for providing health education materials to a user can include: a non-transitory memory configured to store executable instructions and one or more hardware processors in communication with the non-transitory memory configured to: receive a first set of data associated with a user, the first set of data comprising data received from at least one of a tracking device, a third party, or a user input, analyze the first set of data to determine a presence of one or more risk factors for a first health condition, analyze the first set of data to determine a presence of one or more mitigating factors for the first health condition, and determine a scaled score associated with the first health condition of the user based on the presence of the one or more risk factors and the presence of the one or more mitigating factors.

The first health condition can include an athletic fitness level, an injury, or a disease.

The scaled score can include a value between 1 and 10. The scaled score can include a percentage value between 0 and 100 percent. The first health condition can be associated with a user health goal.

The one or more hardware processors can be configured to: generate a lifestyle recommendation based on the scaled score and transmit the lifestyle recommendation to the user.

The one or more hardware processors can be configured to: receive a second set of data associated with the user, the second set of data comprising data received from at least one of a tracking device, a third party, or a user input, analyze the second set of data to determine a user compliance with the lifestyle recommendation, and transmit feedback to the user based on the user compliance. The feedback can include an encouragement or a reward. The encouragement can include an encouraging message. The reward can include access to a monetary discount on a retail item.

The one or more hardware processors can be configured to transmit the user compliance to a third party. The third party can include a support user. The third party can include an insurance provider.

The lifestyle recommendation can be based on a user goal. The lifestyle recommendation can be based on a clinician input.

For purposes of summarizing the disclosure, certain aspects, advantages, and novel features have been described herein. Of course, it is to be understood that not necessarily all such aspects, advantages, or features will be embodied in any particular embodiment.

BRIEF DESCRIPTION OF THE DRAWINGS

FIG. 7E illustrates an example multi-branch process that may be utilized to generate a glucose score.

FIGS. 14-16 illustrate example aspects of a health coaching interface that may facilitate easier use and understanding of the health coaching system and its recommendations.

FIGS. 19A-19F-5 illustrate aspects of a meal logging interface that may be part of a health coaching system.

FIGS. 22A-C illustrate example aspects of a health coaching system related to meal or ingredient choice.

FIGS. 23A-E illustrate example aspect of a health coaching system related to comparing food items.

FIGS. 25A-G illustrates aspects of a meal planning tool that may be part of a health coaching system.

FIGS. 26A-C illustrates example aspects of a reward system that may be part of a health coaching system.

FIGS. 27A-C illustrates example aspects of a chat system that may be part of a health coaching system.

DETAILED DESCRIPTION

Effective health and lifestyle coaching should ideally include systems and methods for not only collecting comprehensive data regarding behavioral, physiological, and other health related data associated with a user, but also effectively analyzing the collected data and communicating coaching recommendations, insights, encouragements, or the like based on the analysis. The health coaching system 100 described herein includes various systems and methods for coaching a user 101 of the health coaching system by collecting, processing, and outputting data related to a user's health. The health coaching system 100 disclosed herein may help its users make better meal and lifestyle choices with the aim of lowering the chances of becoming diabetic. It may achieve this goal by using various interactive tools, such as grading for meals and allowing the users to identify which meals are good for them with regards to glycemic regulation. A predictive health or glucose score or grade, such as a glucose score grade, may also enable users to see potential effects of certain food items and portion sizes and thus make better meal choices.

Figure 1:
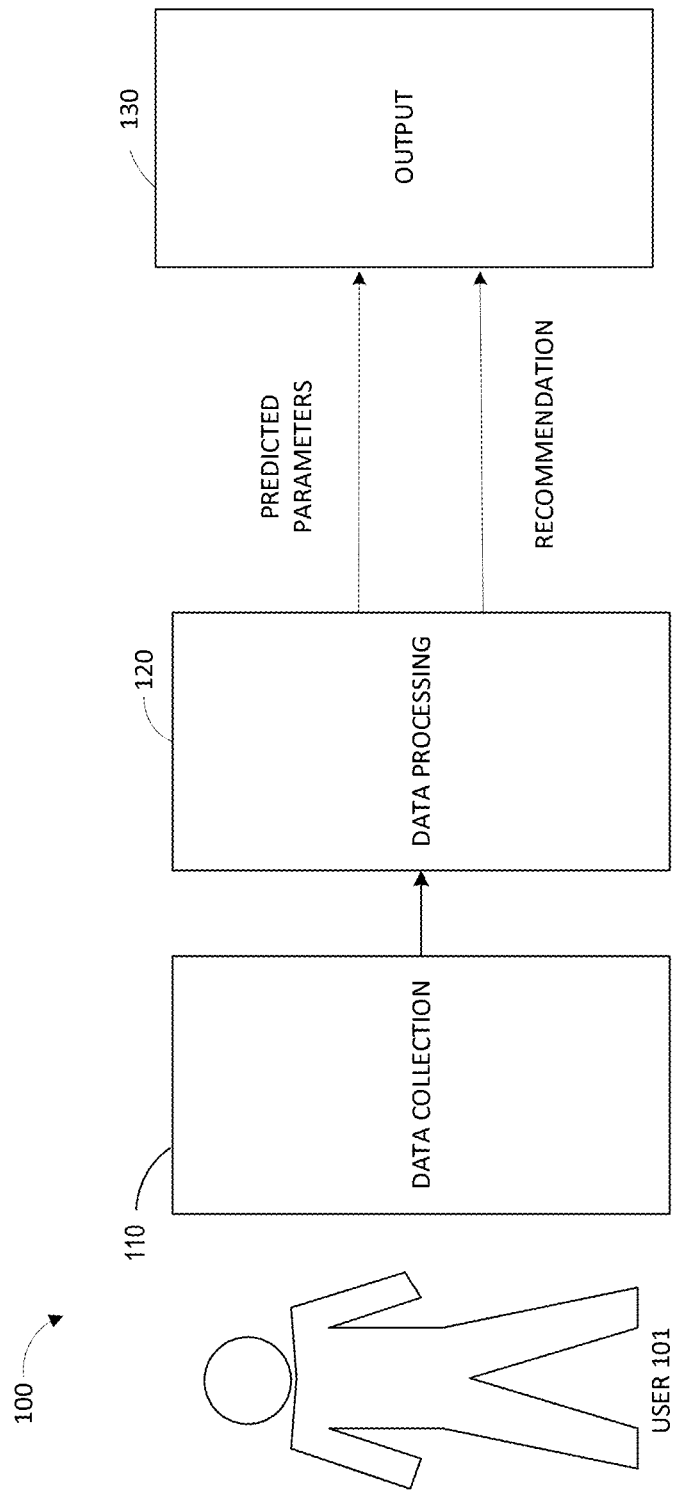
FIG. 1 shows an example personal health coaching system.

FIG. 1 shows a block diagram of an example personal health coaching system 100. The personal health coaching system 100 may include, but is not limited to, a data collection block 110 to collect or access data related to a user 101, a data processing block 120 for analyzing user data from data collection block 110 to determine information related to a user health, and an output block 130.

At a data collection block 110, the system 100 can include processes for collecting any number of different types of data from any number of sources. For example, a system 100 may receive sensor data associated with one or more physiological parameters from at least one physiological sensor, such as a glucose sensor or monitor, smart watch, mobile device, photopleth sensor, EEG sensor, ECG sensor, the like or a combination thereof. In some examples, a system 100 can include data collected from non-sensor based sources, including but not limited to user input, third party input, device tracking data, the like or a combination thereof. Advantageously, the system 100 can provide more inclusive, comprehensive, and effective coaching over systems with device specific data collection by collecting data from a number of different data sources. For example, as described below with reference to FIG. 5, the data can include device tracking data, third party data, user input data, or other user related data.

At a data processing block 120, the system 100 can process the user data from block 110 to produce health risk information, health recommendation information, or another output associated with the user, the coaching system 100, a user's health condition, a user device, the like or a combination thereof. Advantageously, the data processing block 120 may use a variety of user data to generate this output. For example, the data processing block 120 may determine a relationship between physiological factors, such as blood glucose and heart rate, and behavioral factors, such as sleep and activity information, to generate a uniquely personalized health recommendation and determine health risks specific to the user's lifestyle challenges and successes. In some examples, the data processing block 120 may determine a relationship by accessing relationship data from an external, cloud-based, or third party source. For example, a system 100 may download or access NIH, WHO, or other third party information relating to the relationship between a physiological factor, such as obesity, and a disease, such as a heart disease. In some examples, the data processing block 120 may involve processing of user data, including but not limited to, processing of signals from one or more physiological sensors, user devices, the like or a combination thereof. In some examples, data processing block 120 may involve communicating with an external hardware processor or database to transmit or retrieve predicted parameters, a health recommendation, or other output of a health coaching system 100. Other data processing may also be possible.

At output block 130, the system 100 can include a database storage, display, audible alarm, or other means of conveying, storing, or transmitting data collected by the system 100 or information generated by the system 100. Advantageously, the system 100 may utilize one or more means or devices to output information to a user in order to increase the likelihood that a user interacts with output data of the system 100. For example, an output block 130 can include an output device such as a user's mobile device, which a user may be likely to interact with on a consistent basis.

In some examples, a system 100 may convey, store, or transmit output data from the health coaching system 100 through data sharing. For example, user health risks or raw monitored data may be shared with a third party who has an interest in the health of the user. The third party may be an insurance carrier, an employer, a clinical care provider, or another user. The data may be anonymous or user specific. In some configurations, the sharing may be part of an incentive program for the user, such as a program to lower insurance premiums if the user agrees to participate in the personal health coaching system 100. In other configurations, the sharing may be done as a part of a clinician or social support aspect of the personal health coaching system 100. For example, if a user fails to log their meals for a period of time, the system may share with a designated support user or coach that the support user or coach should check in with the user to ensure they are still complying with the program.

A. HEALTH COACHING ENVIRONMENT

Figure 2:
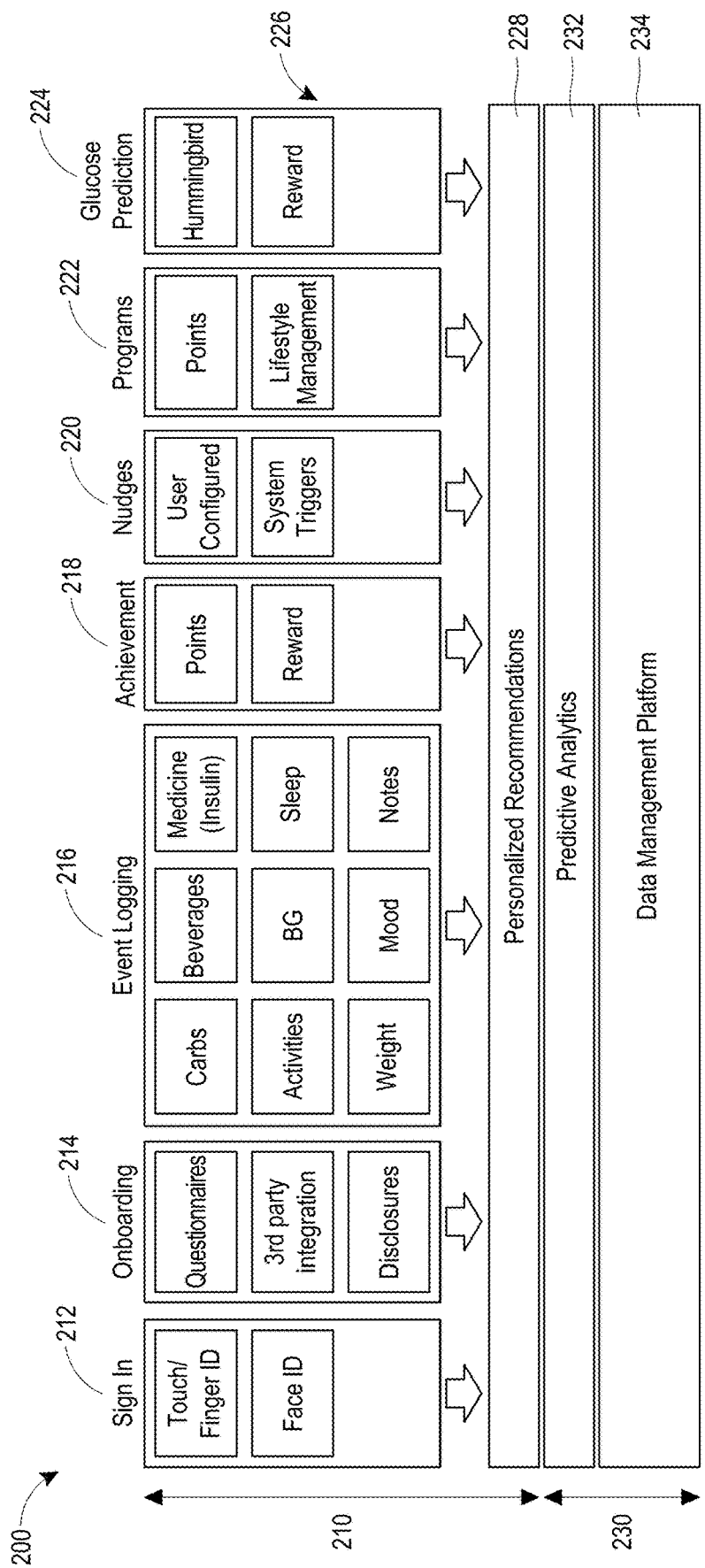
FIG. 2 is a block diagram of an example personal health coaching platform and application.

A health coaching system 100 may utilize some combination of interactive application and backend platform to provide health and lifestyle coaching to a user 101. FIG. 2 illustrates an example software environment 200 that may include an application 210 and a platform 230 for a health coaching system 100. The application 210 can include one or more interactive elements that may be integrated with a user interface. The one or more interactive elements may include, but is not limited to, one or more coaching modules 226, which provide data to one or more data modules or the platform 230. In some examples, the one or more data modules can include, but is not limited to, a recommendation module 228, an analytics module 232, and a data management platform 234. The data modules can be included in the application 210 or the platform 230.

The one or more modules 226 can include modules for acquiring, analyzing, and outputting data. For example, the one or more coaching modules 226 can include a sign in module 212, an onboarding module 214, an event logging module 216, an achievement module 218, a nudge module 220, a learning program module 222, and a glucose prediction module 224.

The sign in module 212 can include any number of user authentication or enrollment processes. For example, the sign in module 212 can include user authentication methods including knowledge-based authentication, possession-based authentication, inherence-based authentication, location-based authentication, the like, or some combination thereof. In another example, the sign in module 212 can include one or more enrollment processes for registering a user in order to allow the user to access and use one or more aspects of the application 210 and platform 230.

The onboarding module 214 can include any number of means for collecting and processing data relating to the user. The application 210 or the platform 230 can use data from the onboarding module 214 to initialize other modules that may be part of the health coaching system 100, such as one or more coaching modules 226, recommendation module 228, or analytics module 232. The onboarding module 214 can include one or more data collection processes for receiving information directly from the user or third parties. For example, the onboarding module 214 can include questionnaires, forms, or other disclosures in which a user or another party can input data. In another example, the onboarding module 214 can include processes for collecting data from user devices, such as a mobile device, digital scale, smart watch, fitness tracker, glucose monitor, or other device capable of measuring physiological parameters associated with the user. In another example, the onboarding module 214 can include processes for integration with third party applications or for collecting third party data associated with the user. The third party application integration can include integration with applications that track and collect user data, such as food logging applications, shopping applications, weight tracking applications, healthcare applications, location mapping applications, or other applications that collect user data.

The event logging module 216 can include any number of processes for collecting, storing, and processing user data. The application 210 or the platform 230 can use data from the event logging module 216 in other modules that may be part of the health coaching system 100, such as one or more coaching modules 226, recommendation module 228, or analytics module 232. The event logging module 216 can include one or more data collection processes for receiving information directly from the user or third parties. For example, the event logging module 216 can include questionnaires, forms, or other disclosures in which a user or another party can input data. For example, the event logging module 216 can include a diary, form, questionnaire, or other data log for a user, a user's device, another party, or application to input one or more parameters associated with the user. In another example, the event logging module 216 can include processes for accessing one or more parameters associated with the user that may be recorded by a device, such as a blood glucose monitor, heart rate monitor, a mobile device, digital scale, smart watch, fitness tracker, or other device capable of measuring physiological parameters associated with the user. In another example, the event logging module 216 can include processes for integration with third party applications or for collecting third party data associated with the user. The third party application integration can include integration with applications that track and collect user data, such as food logging applications, shopping applications, weight tracking applications, healthcare applications, location mapping applications, or other applications that collect user data.

The one or more parameters logged by the event logging module 216 can include data related to the physical health, mental health, food intake, activity, mood, or other parameter that can relate to the health or wellbeing of the user. For example, parameters can include carbohydrate intake, beverage intake, medicine intake (for example, insulin), activity, sleep, blood glucose values, weight, mood, notes, some combination thereof or the like.

The achievement module 218 can include any number of processes for tracking, rewarding, or monitoring achievements associated with a user's progress in one or more aspects of a health coaching system 100. For example, as described below, a health coaching system 100 can include goals, achievements, rewards, points, or other metrics to encourage a user to continue engagement with the health coaching system 100. The achievement module 218 can include one or more processes to alert a user of the health coaching system 100 to failed or successful achievement of a goal that may be part of the health coaching system 100. The achievement module 218 can include one or more processes to track achievements of one or more goals that may be part of the health coaching system 100. For example, achievement module 218 can include a point system to track achievements. The achievement module 218 can include one or more processes for rewarding one or more achievements of a goal that may be part of the health coaching system 100. For example, the processes for rewarding can include unlocking features of the application 210, providing monetary rewards or discounts to the user, or facilitating user access to other incentives or rewards.

The nudge module 220 can include any number of processes for encouraging a user to follow one or more aspects of a health coaching system 100. For example, as described below, a health coaching system 100 can have interactive elements to encourage a user to continue engagement with the health coaching system 100. The encouragement can include alerts or other interactions with the user or other party, such as a health care provider. The nudge module 220 can include triggers for the interactive elements. The triggers can be configured to initiate an interaction with the user, such as an alert, encouragement, persuasion, some combination thereof or the like. The triggers can be user configured or built into the application 210. The triggers can be based on data associated with one or more coaching modules 226, recommendation module 228, analytics module 232, or other data associated with the user. For example, a trigger may be configured to interact with a user where the nudge module 220 (or one or more coaching modules 226) determines that a user has failed to log a parameter as part of event logging module 216 within a determined period of time. For example, if a user has not logged their food in the past week, the nudge module 220 may send an alert to the user. In another example, a trigger may be configured to send an encouragement to a user to complete an education module that may be part of a learning program module 222.

The learning program module 222 can include any number of interactive elements to provide or engage a user with educational materials. The educational materials can include interactive learning modules, videos, articles, or other multimedia associated with a health coaching system 100. The educational materials can include any number of learning materials that may be successively or otherwise released to the user regarding aspects of the health coaching system 100 or the user's health. For example, the educational materials can include diabetes prevention materials, lifestyle management materials, heart disease prevention materials, or other health related educational materials.

The glucose prediction module 224 can include any number of predictive models related to a user's blood glucose. For example, as described below, the glucose prediction module 224 can include one or more predictive models of glucose based on data received or stored by one or more coaching modules 226. The one or more predictive models can include, but are not limited to predetermined models, such as a Glucose-Insulin-Meal-Model (GIMM), the hummingbird model, models learned by a machine learning algorithm, or other models determined by analyzing user data.

Data from the one or more coaching modules 226, which can include data from the sign in module 212, onboarding module 214, event logging module 216, achievement module 218, nudge module 220, learning program module 222, and glucose prediction module 224 can be utilized by some combination of the recommendation module 228, the analytics module 232, or the data management platform 234.

The recommendation module 228 can include any number of processes to recommend an action designed to improve the user's health. For example, as described below, a recommendation module 228 can include processes for analyzing user data, determining recommendations based on the user data, or other processes related to recommending user or healthcare provider actions to improve a user's health.

The analytics module 232 can include any number of processes to analyze user data and to make predictions about a future event associated with the user. For example, as described below, the analytics module 232 can include a process to predict a future health condition of the user based on the user data from the one or more coaching modules 226. The prediction can include any number of statistics, risks, models, or other predictive data associated with the health of the user. Output from the analytics module 232 can be output to the user, used to generate recommendations with the recommendation module 228, or used with the one or more coaching modules 226.

The data management platform 234 can include any number of processes for collecting or managing data. For example, the data management platform 234 can include processes for gathering, managing, storing, organizing, and analyzing data. The data management platform 234 can include algorithms to process user data from one or more sources of information using artificial intelligence or other big data algorithms.

B. EXAMPLE DATA PROCESSING

Figure 3:
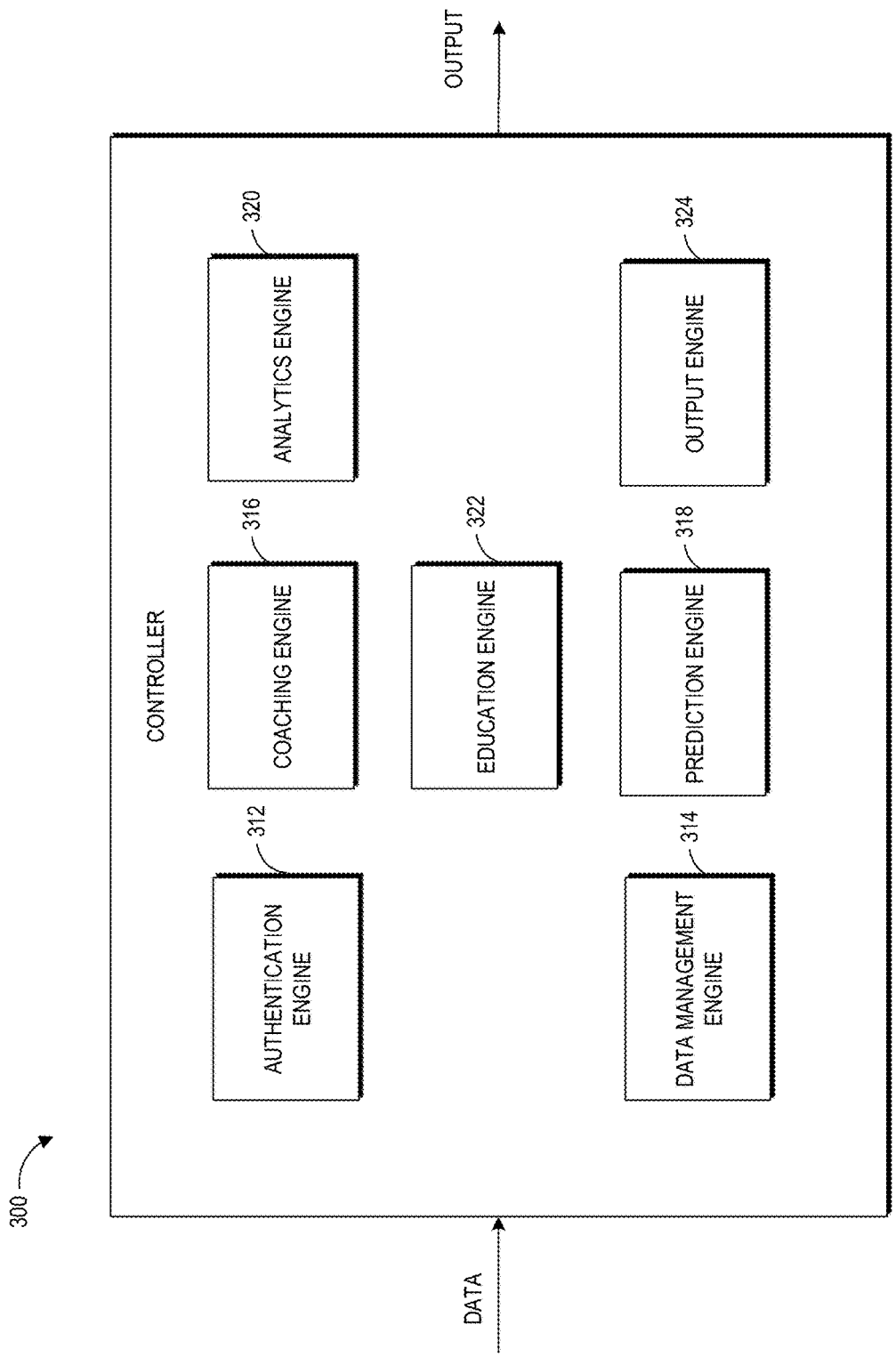
FIG. 3 shows an example controller that may implement engines associated with the health coaching system.

The health coaching system 100 can include a controller 300 for collecting, processing, and outputting data. For example, the controller 300 can operate the one or more coaching modules 226, recommendation module 228, analytics module 232, or data management platform 234 using one or more software engines. The controller 300 can operate the engines using one or more hardware processors. The one or more hardware processors can be local hardware processors (for example, on a user mobile device) or remote hardware processors (for example, on a remote server). FIG. 3 illustrates an example controller 300 to collect, process, and output user data. The controller 300 can include an authentication engine 312, a data management engine 314, a coaching engine 316, a prediction engine 318, an analytics engine 320, an education engine 322, and an output engine 324.

An authentication engine 312 can include one or more processes for authenticating a user. The authentication engine 312 may operate in conjunction with the sign in module 212 or other coaching modules 126 as discussed with reference to FIG. 2. The authentication engine 312 can register or verify a user's identify for the purposes of accessing aspects of the health coaching system 100. For example, the authentication engine 312 can verify a user's identity to secure access to a user's health data that may be accessible within the health coaching system 100. The authentication engine 312 can register or verify a third party's credentials to access or edit user data. For example, a third party may be a health care provider. The authentication engine 312 may verify the third party's credentials to allow the health care provider to access a user's data, such as a food or activity log.

A data management engine 314 can include one or more processes for processing, storing, or accessing data acquired by the health coaching system 100. For example, the data management engine 314 can process signals for analysis by the controller 300 from physiological sensors monitoring a user. In another example, the data management engine 314 can access, store, or edit user data from a variety of data sources, such as user logs, user tracking devices, third party sources, or other sources of user data. The data management engine 314 can operate in conjunction with other modules of the application 210, such as the sign in module 212, onboarding module 214, event logging module 216, or other coaching modules 126, such as discussed with reference to FIG. 2.

A coaching engine 316 can include one or more processes for interacting with a user. For example, the coaching engine 316 can include processes for recommending behavioral or other changes to a user based on user data. In some configurations, the coaching engine 316 can provide feedback to the user based on the user data or the recommendations. As described below, the feedback may take the form of encouragements (or nudges) or rewards designed to push the user to improve their lifestyle or follow the recommendations.

In some configurations, the coaching engine 316 can provide a recommendation that includes a regimen of educational materials and user specific behavioral recommendations based on user health risks or user capabilities. For example, if a health risk determined by analytics engine 320 is that the user is at a 75% risk of type 2 diabetes, the system may recommend, among other things, a set of interacting diabetes learning modules for the user to interact with as well as a new diet that cuts out refined sugars. However, if the user were to indicate that they had a recent hip replacement, the system may not recommend a regimen of intense cardio, but rather a regimen of light walking as a means of increasing exercise level.

In some configurations, the coaching engine 316 can provide feedback based on triggers. The triggers may be identified by the system 100, user, or third party. For example, the system 100 may identify specific activities that result in poor lifestyle choices and send feedback to the user designed to push the user to make change to those activities. For example, the system 100 may identify that where a user skips a meal, the user eats more foods with high sugar content during the subsequent meal time than they would if they did not skip a meal. The coaching engine 316 may provide feedback to the user in the form of an alert to eat if the system 100 identifies the skipped meal trigger.

In another example, the coaching engine 316 can provide feedback based on a user's compliance with a recommendation. The coaching engine 316 may provide encouragements or rewards to comply with a recommendation, identified goals, or when a user achieves an achievement. For example, the coaching engine 316 can provide third party rewards, provide monetary rewards or discounts to the user, or facilitate user access to other incentives or rewards.

A prediction engine 318 can include any number of processes for analyzing and predicting user physiological parameters or behaviors. For example, as discussed below, the prediction engine 318 can include processes to predict a user's blood glucose based on a user's recorded data. In another example, the prediction engine 318 can include processes to predict a user's lifestyle behaviors based on a user's recorded data. In particular, the prediction engine 318 can determine that a user may purchase unhealthy foods if a user is located at a fast food location.

An analytics engine 320 can include any number of processes for analyzing user data and determining health risks associated with the user data. The analytics engine 320 can calculate health risk by analyzing the user data in the context of identified health risk factors. For example, the analytics engine 320 may compare the user data to health risks recognized by health authorities, such as the WHO or the CDC, risks identified by the health coaching system 100, or risks identified through AI analysis of a database of users. Recognized risks within user data may be flagged for the user or used to calculate health scores. For example, where the user data indicates that the user has an obese BMI and an elevated HbA1c, the system may calculate a risk of diabetes at 70%. The analytics engine 320 may use this risk to calculate a health score on a set scale or as a means to calculate a recommendation for improvement. However, mitigating factors may also be identified in user data and used within the health score calculation. For example, a user may have an obese body mass index (BMI), but a resting heart rate of 45 beats per minute. The fact that the user has a lower resting heart rate may be utilized in the health risk calculation to mitigate the increased risk for cardiovascular disease that is recognized with an increased BMI because the user's resting heart rate indicates a healthy heart despite the BMI.

An education engine 322 can include any number of processes for providing a user access to educational materials. The education engine 322 can provide access to different types of educational materials based on user data. For example, the controller 300 can determine that a user has a high risk for diabetes. The education engine 322 can provide access to diabetes educational materials. The education engine 322 can provide access to educational materials as part of an educational course. For example, the education engine 322 can provide educational materials that are part of a ten week educational course on lifestyle management. The education engine 322 can release a series of educational materials on a periodic basis or based on a user interaction with the educational materials. For example, the education engine 322 can provide a user access to educational materials where the user receives a passing score on quizzes or tests associated with the system 100.

The educational materials can include interactive learning modules, videos, articles, or other multimedia associated with a health coaching system 100. The educational materials can include a number of learning materials that may be successively, collectively, or otherwise released to the user regarding aspects of the health coaching system 100 or the user's health. For example, the educational materials can include diabetes prevention materials, lifestyle management materials, heart disease prevention materials, or other health related educational materials.

An output engine 324 can include any number of processes for outputting data to a user, a user device, third party, third party device, or database. For example, the output engine 324 can output data collected, accessed, analyzed, or generated by the system 100, such as health risk, recommendations, physiological parameter predictions, user data logs, or other data associated with the user. The output engine 324 can output data based on any number of criteria. For example, data may be output periodically, continuously, or on demand. Access to the output data may be provided as a matter of course for authenticated users, for a fee, or as part of an incentive program for the user.

C. AUTHENTICATION ENGINE

In some examples, a coaching system 100 may facilitate access to user data or other content based on user credentials. For example, a user may be granted credentials associated with a level of access to aspects of a coaching system 100. In some examples, different types of users may have different levels of access. For example, there may be a patient user, a healthcare user, a third party user, or other users. A patient user may be a user about whom data is collected or to whom recommendations or other output data is directed. A healthcare user may be a user who may be involved in treating or managing a patient user's healthcare, such as a doctor, nurse, coach, support user, or the like. A third party user may be a user involved in managing the health coaching system 100, a user granted access to view or otherwise edit data within the health coaching system 100 by another user, such as a patient user or healthcare user, or another user. In some examples, a user may be granted a level of access to edit, view, or otherwise control or access data or features of an application 210 based on a user type, user capacity, the like or a combination thereof. For example, a child user may be granted a lower level or different level of access to application features or editing access than an adult user. In some examples, different features may be accessible to a user based on the credentials.

Figure 4:
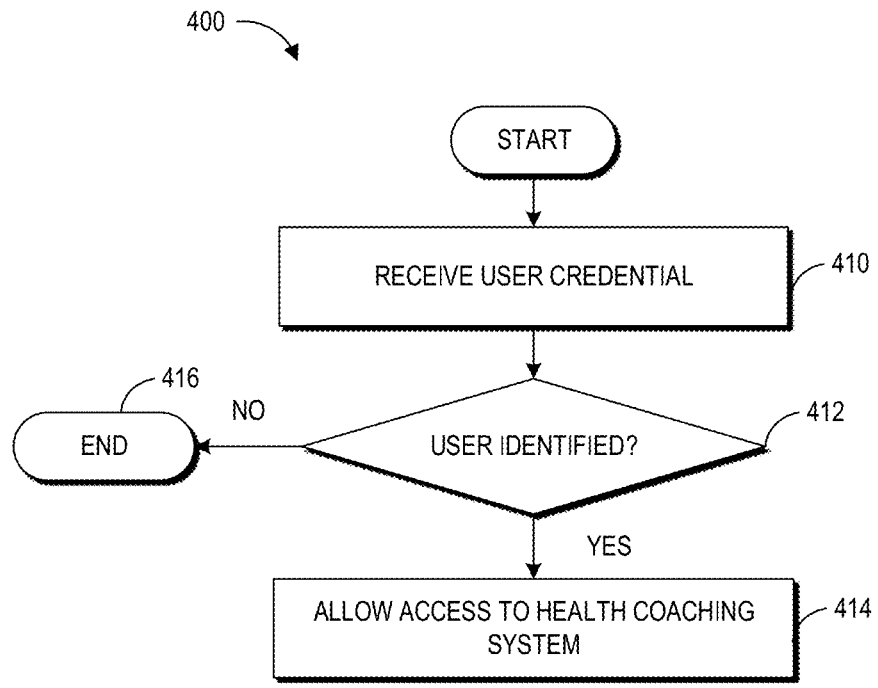
FIG. 4 is a block diagram of an example authentication process that may be part of a health coaching system.

In some examples, the controller 300 can operate an authentication engine 312 that can include one or more processes for authenticating a user. FIG. 4 illustrates an example authentication process 400 that may be part of an authentication engine 312. For example, the authentication process 400 can include a credential receiving block 410, an identification block 412, an access block 414, and an end block 416.

At credential receiving block 410, a controller 300 can receive one or more credentials associated with the user or a third party. The credentials can include one or more authentication factors, including but not limited to knowledge-based factors, possession-based factors, inherence-based factors, location-based factors, the like, or some combination thereof. Knowledge-based factors can include but are not limited to password, pin, or other security information factor. Possession-based factors can include but are not limited to password tokens, ID cards or fobs, or other item that a user may need to possess in order to log in. In some examples, possession of a user device, such as a glucose sensor, may provide an indication of a patient credential. For example, a glucose sensor may be paired to a user's mobile device. The glucose sensor may provide a unique identifier to the coaching system 100 to identify that a user wearing the glucose sensor is an authenticated user. Inherence-based factors can include but are not limited to biometric factor, such as iris codes, fingerprints, facial recognition, or voice recognition. Location-based factors can include but are not limited to the physical or digital address of a user.

At an identification block 412, the controller 300 can analyze the one or more credentials from credential receiving block 410 to determine if the credentials match an authorized set of credentials. For example, an authorized set of credentials can include an authorized passcode, biometric ID, authorized location, or other credential associated with a recognized user of the health coaching system. If the controller 300 determines that the credentials match the authorized set of credentials, the controller 300 may allow the user access at an access block 414. If the controller 300 determines that the credentials do not match the authorized set of credentials, the controller 300 may refuse access to one or more aspects of the health coaching system at an end block 416.

At access block 414, the controller 300 can allow access to one or more aspects of the health coaching system 100 based on the credentials. For example, the controller 300 can allow editing access to personalized recommendations if the controller 300 determines that the credentials match a health care provider with editing access. In another example, the controller 300 can allow writing access to user data logs if the controller 300 determines that the credentials match a user enrolled in the health coaching system 100. In another example, the controller 300 can allow viewing access to user data if the controller 300 determines that the credentials match an authenticated third party, such as an insurance provider. In another example, the controller 300 may facilitate access to user specific aspects of a health coaching system 100. For example, if the credentials match a coach access level, the controller 300 may allow the user to view aspects of the health coaching system 100 associated with a health coach as opposed to a patient user, such as a review of a patient user's progress within the health coaching system 100 or coach messaging.

D. DATA MANAGEMENT ENGINE

Figure 5:
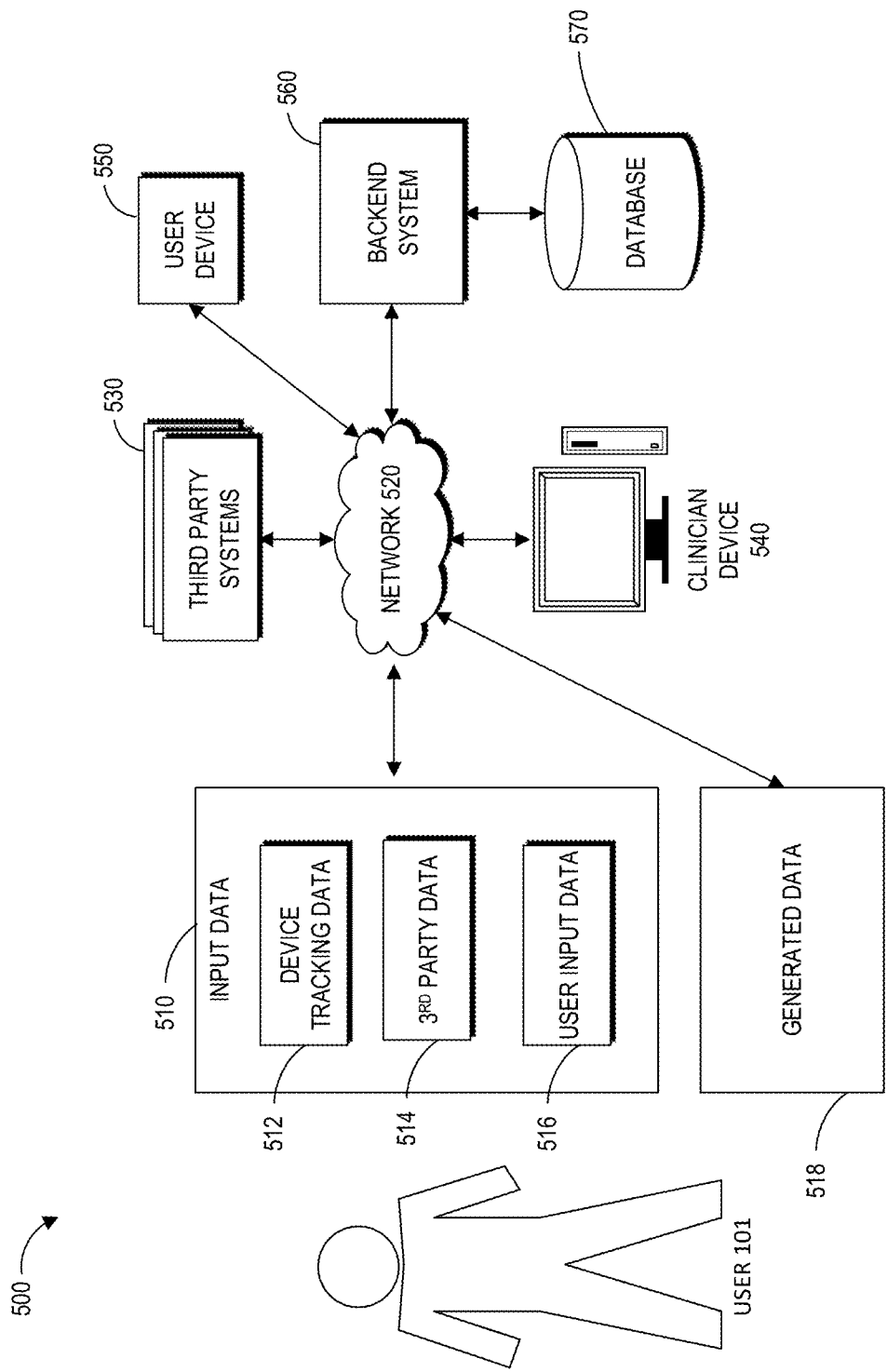
FIG. 5 is a block diagram of an example data management environment for a health coaching system.

The controller 300 can operate a data management engine 314 that can include one or more processes for processing, storing, or accessing data acquired by the health coaching system 100. FIG. 5 is a block diagram showing an example data management environment 500 that may be part of a data management engine 314. For example, the data management environment 500 can include input data 510 and generated data 518 associated with a user 501, a network 520 a clinician device 540, one or more third party systems 530, one or more user devices 550, a backend system 560, and a database 570.

The input data 510 can include data from any number of sources, including but not limited to device tracking data 512, third party data 514, and user input data 516. Device tracking data 512 can include data gathered by user or other devices. For example, the user 101 may be monitored by physiological sensors or through device applications. The physiological sensors can include any number of physiological sensors that may measure physiological parameters associated with the user, including but not limited to analyte monitors (such as blood glucose monitors, including an SMBG or CGM, or other invasive or non-invasive analyte monitor), scales, pulse oximeters, fitness trackers, smart wearable devices, some combination thereof or the like. The device applications can include mobile device applications that may monitor or track user activity. For example, the device application data can include step counters, location trackers, camera data, or other data from a mobile device.

In some configurations, the system 100 can collect data from devices designed to integrate with the system 100. For example, as described below, the system 100 may utilize a body scale equipped with a variety of sensors that enable the scale to measure user information, such as weight, heart rate, heart rate variability, height, Body Mass Index (BMI), waist circumference, the like, or some combination thereof. In another example, the system 100 may utilize a glucose monitor equipped to measure blood glucose of the user. The system 100 may communicate with a device to track health metrics at certain intervals or provide prompting to the user to engage with a device in order to measure metrics. In the case of a glucose monitor, the system may prompt a user to measure their glucose using the glucose monitor at certain times, such as after food intake or at intervals during the day.

An input device may connect to a hardware processor associated with system 100. For example, the input device may collect device tracking data 512. The input device may wirelessly or with wires transmit the device tracking data 512 to a hardware processor associated with a user's mobile device 550 or to a backend system 560. In some configurations, the input device may optionally connect to the user device 550 or backend system 560 over a network 520.

Third party data 514 can include data from any number of external sources of data related to the health of the user 101. For example, the third party data 514 can include, but is not intended to be limited to, medical data, hospital data, or user activity data from third parties. The third party data may be obtained through direct third party interaction with the system 100 (for example, through manual clinician input) or through a connection with a third party database.

Third party data 514 can include medical data collected by a third party. The medical data can include data from a user's medical history that has the potential to affect the current or future health of the user 101, such as medication history, treatment history, family history, or the like. The medical data can be accessed or retrieved from any number of sources, including but not limited to information from clinical visits, previous laboratory work, genetic testing results, or other sources of historical medical data. For example, medical data can include information obtained by clinicians regarding the health of the user 101 during a medical appointment or hospital admission, such as vital sign measurements, diagnosis information, treatment plan information, or the like.

Third party data 514 can include user activity data collected by a third party. As described below, the user activity data can include data related to an activity or health of the user 101. The user activity data can include data related to the shopping, exercise, eating, social, or other activities of the user. For example, a user may use a particular grocery chain for their food needs. The grocery chain may track the user's food purchases. The food purchases may be used as third party data by the data processing block 120. In another example, the user's shopping habits may be tracked through the use of their credit or debit cards by their bank or credit card company. Those purchases may be used as third party data by the controller 300.

In some examples, third party data 514 may be collected or stored in cloud based storage associated with the health coaching system 100. A controller 300 may be configured to authenticate the collected third party data 514 or other data using the third party data 514. For example, a controller 300 may be configured to corroborate a user input with third party data 514, such as electronic medical record data. For example, a user input may indicate that they have type 1 diabetes. The controller 300 may validate this information by accessing electronic medical record data (EMR) data to detect if type 1 diabetes has been diagnosed for the user. If the controller 300 determines that an input is incorrect or invalid, the controller 300 may notify the user, limit access to one or more aspects of the application or health coaching system 100, attempt to re-validate, or perform another action, such as described herein. If the controller 300 determines that an input is valid, the controller 300 may or may not notify the user, facilitate access to aspects of the application or health coaching system 100 (for example, appropriate educational modules), prompt a user for further inputs, or perform another action, such as described herein.

User input data 516 can include data from the user 101 that relates to the health of the user 101. For example, the user input data 516 can include but may not be limited to lifestyle information such as activity information, location history, sleep information, food intake information, shopping information, or other user lifestyle information. The user input data 516 can be obtained through manual input as prompted by the user or components of the system 100. For example, the user can be asked a series of health-related questions at the start of the program that the system 100 can periodically prompt the user to update if appropriate. This approach is particularly advantageous to use for historical user information, such as medical history and medical genetic markers. For example, a user may start the program with a broken wrist. The user may input this information and the controller 300 may facilitate upload of this information to a database that the system 100 or controller 300 is configured to access or communicate with in order analyze information or to provide recommendations. In some examples, the controller 300 may validate the input with third party data. In some examples, the system may use this information to provide recommendations based on the information. For example, the controller 300 may provide exercise recommendations based on the user input recommendations, such as exercises designed to help avoid aggravating the user's broken wrist. Additionally, the system may prompt the user to update the database about the status of their ongoing health issues. For example, the system may ask the user about the current status of their broken wrist at periodic intervals in order to update user recommendations.

Generated data 518 can include data generated by one or more engines, such as authentication engine 312, coaching engine 316, education engine 322, prediction engine 318, or analytics engine 320.

The controller 300 can optionally process the input data 510 or the generated data 518 to store, analyze, normalize, or otherwise process the input data 510 or the generated data 518 for further analysis by the controller 300. For example, the controller 300 can compress the input data 510 for storage in a database 570. The controller 300 can output the input data 510 or generated data 518 to a user device 550. The user device 550 or controller 300 may transmit data to a backend system 560 (such as a remote server or cloud server) over a network 520. The user device 550, the backend system 560, and other devices can be in communication over the network 520. In some cases, the user device 550 can download processed data from the backend system 560 after the controller 300 transmits the input data 510 or generated data 518 to the backend system 560 for further processing. These other devices can include, such as in the example shown, a clinician device(s) 540, and third party systems 1530. However, more or fewer devices may access the input data 510 or generated data 518 with other systems or devices. The controller 300 can enable a user and others (such as clinicians) to monitor various aspects related to the user's data, such as food logs, activity logs, recommendations, or health risks that may be generated by the system 100.

E. PREDICTION ENGINE

Figure 6A:
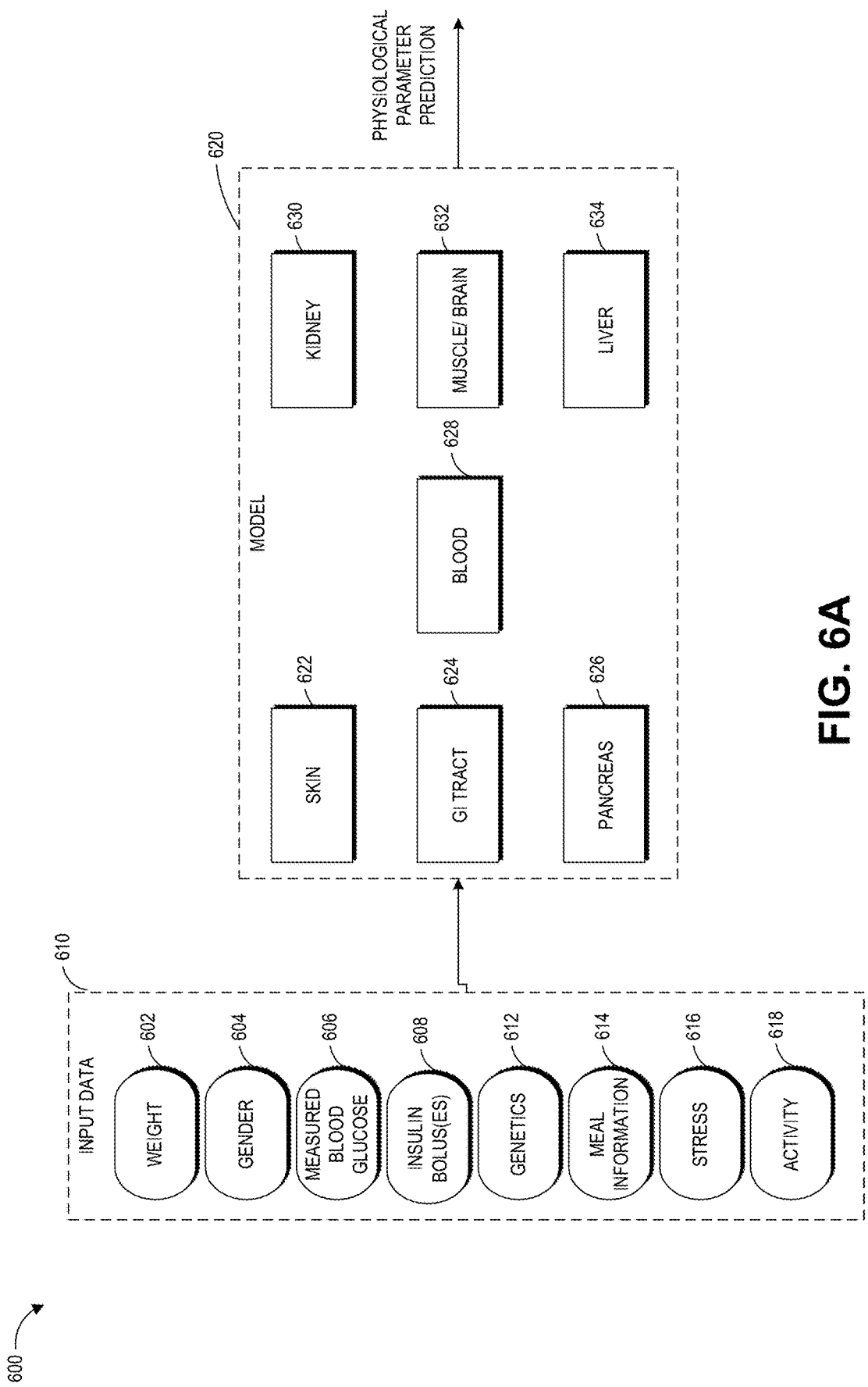
FIG. 6A is a block diagram showing an example physiological parameter prediction model.

The controller 300 can include a prediction engine 318 configured to use one or more processes for analyzing user data and predicting user physiological parameters or behaviors based on user data. FIG. 6A is a block diagram showing an example physiological parameter prediction process 600 that may be part of a prediction engine 318. For example, a prediction engine 318 can predict one or more physiological parameter values associated with a user based on analyzing input data 610 using one or more prediction models 620.

As illustrated in FIG. 6A, the input data 610 can include one or more types of user data from one or more sources of information. In some configurations, one or more of the input data 610 can be part of the input data 510 described with reference to FIG. 5 above. In the example illustrated in FIG. 6A, the input data 610 can include a user's weight 602, gender 604, measured blood glucose 606, data related to insulin bolus(es) 608, genetic history 612, meal information 614, stress 616, and activity 618.

A user's weight 602 can include a user's body weight or other weight related parameters, such as a user's body mass index, body fat percentage, muscle mass, some combination thereof or the like.

A user's measured blood glucose 606 can include a blood glucose value, an HbA1c value, some combination thereof or the like. The blood glucose value can include a value of blood glucose measured invasively, such as through a blood test, or non-invasively, such as through a spectroscopic measurement. The blood glucose value can be a fasting blood glucose or a non-fasting blood glucose or some combination thereof.

Data related to insulin boluses 608 can include the timing or quantity of insulin or other data related to insulin intake. For example, a user weighing 68 kilograms or 150 pounds may take 68 units of insulin a day. The data related to the insulin bolus(es) may include that the user took the 68 units of insulin at certain times of day.

A user's genetic history 612 can include a user's family history of heart disease or diabetes, a user's genetic markers, other genetic data, some combination thereof or the like. For example, a user may have a genetic marker for insulin resistance. The genetic history 612 may include the genetic marker for insulin resistance.

A user's meal information 614 can include data related to a quantity, type, or timing of a user's food and liquid intake.

For example, a user's meal information 614 can include a time and quantity of carbohydrate intake, protein intake, or fat intake.

A user's stress 616 can include data related to a user's mood, environmental, physical, or emotional stress. The level of a user's stress may be determined by user report of feelings of stress, determination of increased cortisol levels, increased heart rate, decreased memory function, decreased immune function, other autonomic nervous and adrenal system metrics, or other biological metrics related to stress. For example, a user may report chronic stress due to a mental health condition, such as anxiety. The stress 616 may include an indication of increased stress based on the user report.

A user's activity 618 can include data related to a user's quantity, quality, and type of physical activity. For example, the user's physical activity can include a number of steps taken per day, a type and quantity of cardiovascular exercise, a type and quantity of strength training, a number of waking or sleeping hours in a person's day, the like, or some combination thereof.

Each data type of the input data 610 may be obtained from the same or different sources or at the same or different times depending on the data type. For example, a user's gender 604 or genetic history 612 may be collected once. In another example, a user's weight 602 or stress 616 may be collected on a periodic basis, such as once a day or once a week.

A prediction model 620 can include a mathematical model that analyzes the input data based on determined relationships of the input data with various aspects of a user's biology, including but not limited to the user's endocrine or gastrointestinal (GI) system. For example, as described below with reference to the GIM model of FIG. 6B, the prediction model 620 can analyze the input data in relation to a user's skin/adipose tissue 622, GI tract 624, pancreas 626, blood 628, kidney 630, muscle/brain 632, liver 634, and other biological components. The prediction model 620 may utilize different input data 610 for different aspects of a model 620. For example, a controller 300 may utilize a user's weight 602 and gender 604 as variables that affect the entire model. In another example, a controller 300 may utilize other input data 610 as variables that affect one or more individual aspects of the user's biological system.

The controller 300 may determine or modify the prediction model 620 based on any number of suitable criteria. For example, the controller 300 may utilize one or more processes to determine a prediction model 620 for one or more physiological parameters, such as blood glucose. In another example, the controller 300 may utilize a predetermined model for one or more physiological parameters, such as blood glucose. Additionally or alternatively, the controller 300 can modify a base model to optimize one or more aspects of the model, such as accuracy, computational resources, timing, some combination thereof or the like. For example, the controller 300 may modify the prediction model 620 to increase its accuracy based on measured blood glucose values. In another example, the controller 300 may modify the prediction model 620 based on increasing the accuracy of other specific parameters, such as glucose depletion. In some configurations, the controller 300 may modify the prediction model using one or more optimization methods. For example, the controller 300 may analyze the input and output data of the prediction model using a machine learning algorithm, such as a neural network, support vector machine, Bayesian network, genetic algorithm, or other data analysis algorithm.

1. Glucose Insulin Meal Model

Figure 6B:
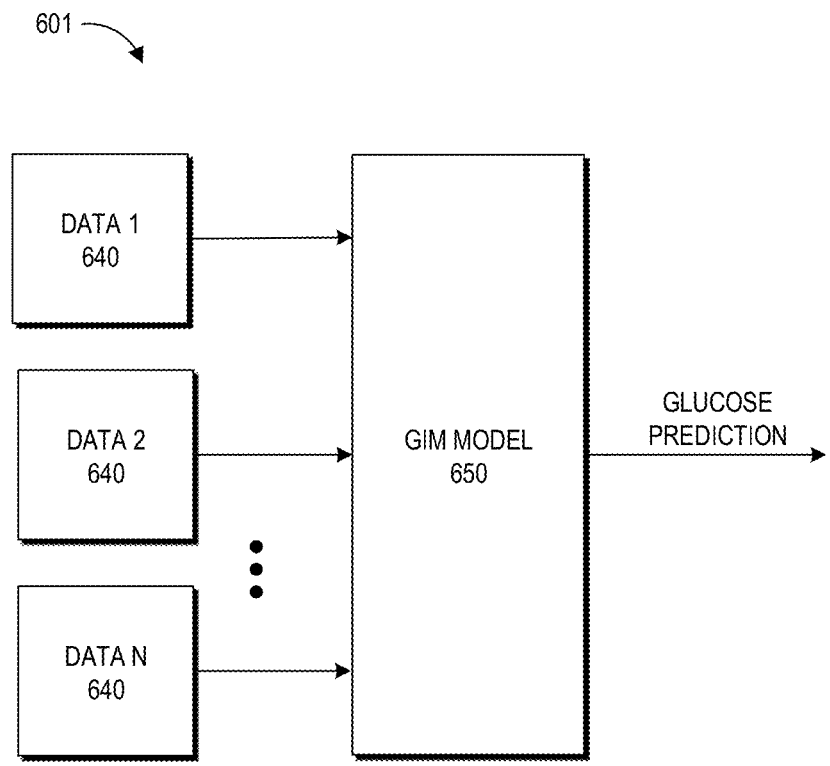
FIG. 6B is a block diagram of an example parameter prediction process that may be part of a health coaching system.

One example prediction process can include a model for determining a user's blood glucose concentration or a parameter related to blood glucose based on user data. FIG. 6B illustrates an example prediction process 601 for determining a physiological parameter related to blood glucose that may be part of a prediction engine 318. For example, a Glucose-Insulin-Meal Model (GIM model) 650 may analyze one or more sources of data 640, including but not limited to a user's weight 602, gender 604, measured blood glucose 606, data related to insulin bolus(es) 608, genetic history 612, meal information 614, stress 616, and activity 618.

A GIM model 650 can include a mathematical model that analyzes the data 640 to determine a parameter related to blood glucose based on determined relationships of the data 640 with various aspects of a user's biological system, including but not limited to the user's endocrine or gastrointestinal (GI) system. The GIM model 650 may utilize different types of data 640 for different purposes within the model 650. For example, a controller 300 may utilize a user's weight 602 and gender 604 as variables that affect the entire model. In another example, a controller 300 may utilize other input data 610 as variables that affect one or more individual aspects of the user's biological system.

In some configurations, a user may take insulin boluses 608. The insulin boluses 608 may interact with a user's skin and adipose tissue 622. For example, the skin and adipose tissue 622 may result in a transport delay of the insulin that may be modeled by the system. The controller 300 may model this transport delay when analyzing the insulin boluses data 608. The controller 300 may analyze this modeled transport delay independently or in conjunction with other variables to determine a current blood glucose value, insulin need, glucose usage, or other endocrine related parameter. Additionally or alternatively, the controller 300 may directly or indirectly analyze the input data 610 that may affect the transport delay without first modeling the transport delay to determine a current blood glucose value, insulin need, glucose usage, or other endocrine related parameter.

In some configurations, a user's genetic history 612, such as genetic markers related to insulin regulation, and meal information 614, such as a the type and quantity of a user's food and liquid intake, may affect a user's digestion in their GI tract 624. The controller 300 may model this digestive state based on the genetics 612 or meal information 614. The digestive state may have an effect on the user's blood glucose. The controller 300 may analyze the modeled digestive state independently or in conjunction with other variables to determine a current blood glucose value, insulin need, glucose usage, or other endocrine related parameter. Additionally or alternatively, the controller 300 may directly or indirectly analyze the input data 610 that may affect the user's digestive state without first modeling the digestive state to determine a current blood glucose value, insulin need, glucose usage, or other endocrine related parameter.

In some configurations, a user may determine a measured glucose value or values 606 based on one or more invasive or non-invasive measurements of the user's blood glucose. The measured glucose value 606 may or may not be current. For example, the user may have measured the glucose value 606 one to two hours prior to the current time. The measured glucose values 606 may be determined occasionally, as needed, at periodic intervals, or any suitable interval. For example, the user may measure blood glucose once a day, after each meal, once a month, or during their annual physical. The controller 300 may analyze the measured glucose value 606 independently or in conjunction with other variables to determine a current blood glucose value, insulin need, glucose usage, or other endocrine related parameter. Additionally or alternatively, the controller 300 may directly or indirectly analyze the input data 610 that may affect the user's blood glucose without first modeling the blood glucose to determine a current blood glucose value, insulin need, glucose usage, or other endocrine related parameter.

In some configurations, a user's stress level 616 may affect a user's liver function 634. The user's liver function 634 may include glucose production, glucose storage, and insulin regulation. The controller 300 may model this liver function 634 based on the stress level 616. The controller 300 may analyze the modeled liver function 634 independently or in conjunction with other variables to determine a current blood glucose value, insulin need, glucose usage, or other endocrine related parameter. Additionally or alternatively, the controller 300 may directly or indirectly analyze the input data 610 that may affect the user's liver function 634 without first modeling the liver function 634 to determine a current blood glucose value, insulin need, glucose usage, or other endocrine related parameter.

In some configurations, a user's activity 618 may affect a user's muscle or brain function 632. For example, a user's activity 618 may affect a user's glucose usage by the muscle or brain. The controller 300 may model this muscle or brain function 632 based on the activity level 618. The controller 300 may analyze the modeled muscle or brain function 632 independently or in conjunction with other variables to determine a current blood glucose value, insulin need, glucose usage, or other endocrine related parameter. Additionally or alternatively, the controller 300 may directly or indirectly analyze the input data 610 that may affect the user's muscle or brain function 632 without first modeling the muscle or brain function 632 to determine a current blood glucose value, insulin need, glucose usage, or other endocrine related parameter.

In some configurations, the controller 300 may analyze other data 610 that may affect the user's current blood glucose value, insulin need, glucose usage, or other endocrine related parameter. For example, the data 610 may include user output values, such as renal excretion. The renal excretion my indicate kidney function, which may be related to the current blood glucose value, insulin need, glucose usage, or other endocrine related parameter.

In some configurations, the controller 300 may predict an amount of glucose in a user's body using a non-linear state space model. The non-linear state space model may abstract the differential equations governing glucose and insulin reactions in the human body. For example, the non-linear state space model can include state equations having a set of inputs, such as insulin intake and/or glucose intake, a set of parameters associated with a user, and an output of predicted blood glucose level. In some examples, the set of parameters can include, but is not limited to, patient body weight, basal insulin, basal exogeneous insulin infusion rate, basal blood glucose level, and/or basal endogenous glucose production.

State equations may differ between subjects or types of subjects, such as a normal, or type I, or type II diabetic, or by GluScore. The state equations may be varied with one or more variations in model parameters used in the state equations. For example, model parameters relating to, for example, glucose kinetics, insulin kinetics, rate of appearance, endogenous production, insulin utilization, insulin secretion, or renal excretion, may be different based on subject type. In some examples, the model parameters may relate to modeling whether insulin is secreted and injected.

For example, in a normal patient, parameters may be tailored to indicate that insulin is secreted and not injected. In another example, in a type I diabetic, parameters may be tailored to indicate that insulin is not secreted but is injected. In another example, in a type II diabetic, parameters may be tailored to indicate that insulin is secreted and is injected. For example some parameters may be tied to insulin secretion and some parameters may be tied to external insulin injection. Parameters tied to insulin secretion may be disabled by setting the state variable and derivative to zero where there is no insulin secretion, such as for type I diabetes subjects. Parameters tied to external insulin injection may be related to different brands of insulin that have a different absorption and dissociation rates.

In some examples, a glucose insulin meal model may run using standard values for various parameters, such as user's weight, age, digestion rate, insulin sensitivity etc. In some examples, a model may start out with these global parameters, but as more data is available about the user, the model may be personalized for each individual. Personalization can be achieved from meta data collected at sign up such as age, height, weight, race etc., as well as any blood glucose values they enter as part of a glucose score measurement. When blood glucose values are supplied along with meal nutrition information, model results may be fit against the blood values with the model parameters being modified to get a more user personalized value. Once fit, the personalized models may be stored for future use in predictive glucose scores for that user.

2. Glucose Dysregulation

Glucose response may differ per individual. Differences in response may be categorized based on the variability of glucose over a period of time. In some examples, a prediction model 620 may categorize a user based on their variability using the input data 610, 640 or one or more glucose values determined by the model and associated with the patient. The glucose variability may be used within the context of data analysis and/or user recommendations.

Figures 7A, 7B, 7C:
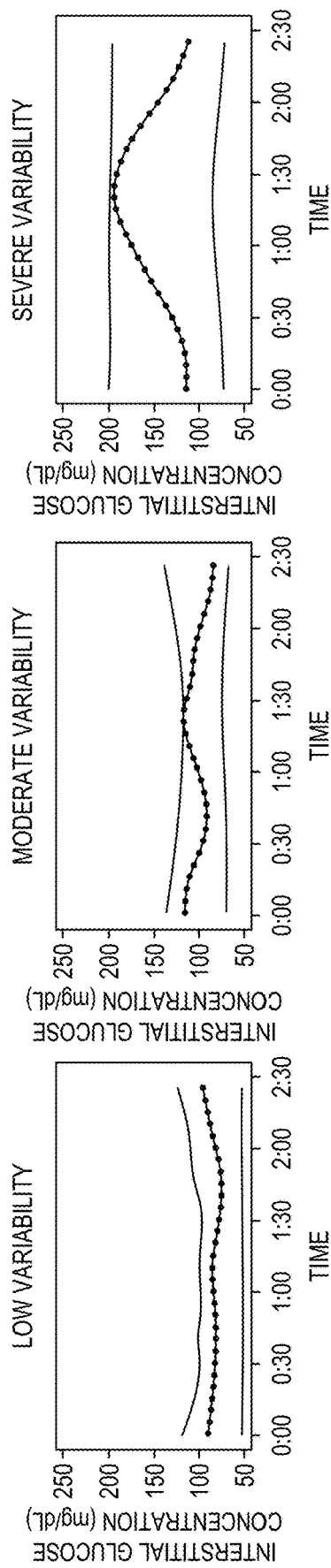
FIGS. 7A, 7B, and 7C are graphs showing example glucose variability.

FIGS. 7A-7C illustrate different types of glucose variability or GluScores. For example, FIG. 7A illustrates a low variability GluScore where there is less variation between interstitial glucose concentration values over a period of time. FIG. 7B illustrates a moderate variability GluScore where there is a moderate amount of variation between interstitial glucose concentration values over the same period of time as shown in FIG. 7A. FIG. 7C illustrates a severe variability GluScore where there is a high amount of variation between interstitial glucose concentration values over the same period as shown in FIG. 7A.

In some examples, a controller 300 may categorize a user for association with certain health risks, health recommendations, or coaching system parameters based on their variability of glucose response. For example, a controller 300 using the input data 610, 640 or one or more glucose values determined by the model and associated with the patient. In some examples, a controller 300 may use outputs of a glucose model 620 in order to aid categorization of a GluScore. In some examples, a controller 300 may use collected data from, for example, one or more physiological sensors, such as a glucose sensor or analyte monitor (for example, a CGM, blood glucose meter, or other glucose sensing device or analyte monitor). In some examples, a controller 300 may use a combination of model outputs and collected data.

A controller 300 may categorize a user into one of a number of GluScores (e.g., low, moderate, or severe) based on data 610, 640 or one or more glucose values determined by a prediction model 620, 650 and associated with the patient. For example, the controller 300 may determine that a GluScore or glucose variability based on some combination of HbA1c, fasting glucose, one hour post meal glucose, 2 hour post meal glucose, predicted glucose or the like. The controller 300 may categorize a user based on a variation in one or more of the aforementioned values or data determined based on one or more of those values. For example, the controller 300 may categorize a user as low variability GluScore where the variability in a user's glucose concentration is between zero and twenty percent over a period of time. The period of time may include a number of minutes, hours, or days, including but not limited to 30 minutes, one hour, two hours, three hours, four hours, 24 hours, or more or less time. In some examples, a low variability GluScore may be defined in a different range, including, but not limited to between zero and 10 percent, 5 and 20 percent, 15 and 30 percent, or other range at least equivalent to or below the moderate or severe variability ranges. In another example, the controller 300 may categorize a user as moderate variability GluScore where the variability in a user's glucose concentration is between twenty and forty percent over a period of time. The period of time may include a number of minutes, hours, or days, including but not limited to 30 minutes, one hour, two hours, three hours, four hours, 24 hours, or more or less time. In some examples, a moderate variability GluScore may be defined in a different range, including, but not limited to between 10 percent to 50 percent, 20 percent to 50 percent, 30 percent to 40 percent, or other range at least equivalent to or below the severe variability range or at least equivalent to or greater than the low variability range. In another example, the controller 300 may categorize a user as severe variability GluScore where the variability in a user's glucose concentration is greater than forty percent over a period of time. The period of time may include a number of minutes, hours, or days, including but not limited to 30 minutes, one hour, two hours, three hours, four hours, 24 hours, or more or less time. In some examples, a severe variability GluScore may be defined in a different range, including, but not limited to between 40 percent to 100 percent, 50 to 100 percent, 60 to 70 percent, 40 to 80 percent, or other range at least equivalent to or greater than the low or moderate variability ranges. However, while specific variability values are indicated, other variability ranges are possible, such as less than fifteen percent variability for low variability GluScore and greater than fifty percent variability for severe variability GluScore.

3. Glucose Scores

In some examples, a coaching system may determine a score or grade associated with a meal's effect on a user by utilizing some combination of short and long term data. For example, the coaching system may apply a scoring or algorithm. The controller 300 may determine a grade, score, or other value representative of the effect of a meal on a user's glucose regulation in the body, such as a GLUSCORE™. A grade, score, or glucose score may be a metric that grades the glycemic response of a user to a meal. After a meal, each user's body responds uniquely to the nutritional content in the meal and the glucose score grades of different meals will enable users to grade which meals caused postprandial glucose spikes and hence not healthy long-term choices.

In some examples, the glucose score may be an alphanumeric scale, such as an A through D scale, with A grade meals being meals that do not cause much glucose dysregulation and D graded meals are meals that may cause severe spikes in blood glucose. Advantageously, this algorithm may help reduce the barrier to entry for meal planning and glucose regulation in a number of ways. For example, such an algorithm may help relieve or even remove the need to have a CGM in order to accurately monitor glucose and instead only require as few as 3 analyte monitor measurements (such as CGM or SMBG measurements), thereby by greatly improving the accessibility of the algorithm to normal people. In another example, pairing a scoring algorithm with a glucose insulin meal model or other glucose estimation algorithm to make predictive glucose scores can allow a user to accurately monitor glucose without the need for even a single drop of blood.

To evaluate the score, a controller may use at least one pre-meal glucose value (baseline) and at least one post-meal glucose value to assess the extent of glucose spikes as well as the rate of increase and return to baseline. A set of GluScore data may be used to establish baseline that may include data associated with the user, a generic user, or a group of users. For example, a baseline may be established with a set of CGM or other analyte monitor measurements sampled periodically, such as every 5-7 minutes or other period, over a time window, such as a 2.5-hour window or other time window, to assign a GluScore grade for that time window. A controller 300 may label the glucose response within a time window as either "Severe", "Moderate" or "Low" based on a glucose response within that time window. However, in using a set time window to establish a baseline, a glucose score determined by a glucose score algorithm may be overly sensitive to the variations in the glucose values during the window and less sensitive to variations in glucose values outside of that time window. For example, someone with elevated glucose values is highly likely to get a "Severe" grade, even if there is not a major change in the glucose values during the time window of analysis. A coaching system described herein may improve the sensitivity and decrease the number of samples required to estimate glucose or a glucose parameter, such as a glucose score. Advantageously, this coaching system may allow users to utilize grades in situations in which users may not have availability to a continuous glucose monitor (CGM) but instead use less consistent glucose monitors, such as blood stick meters (SMBGs) or other analyte monitors.

Figure 7D:
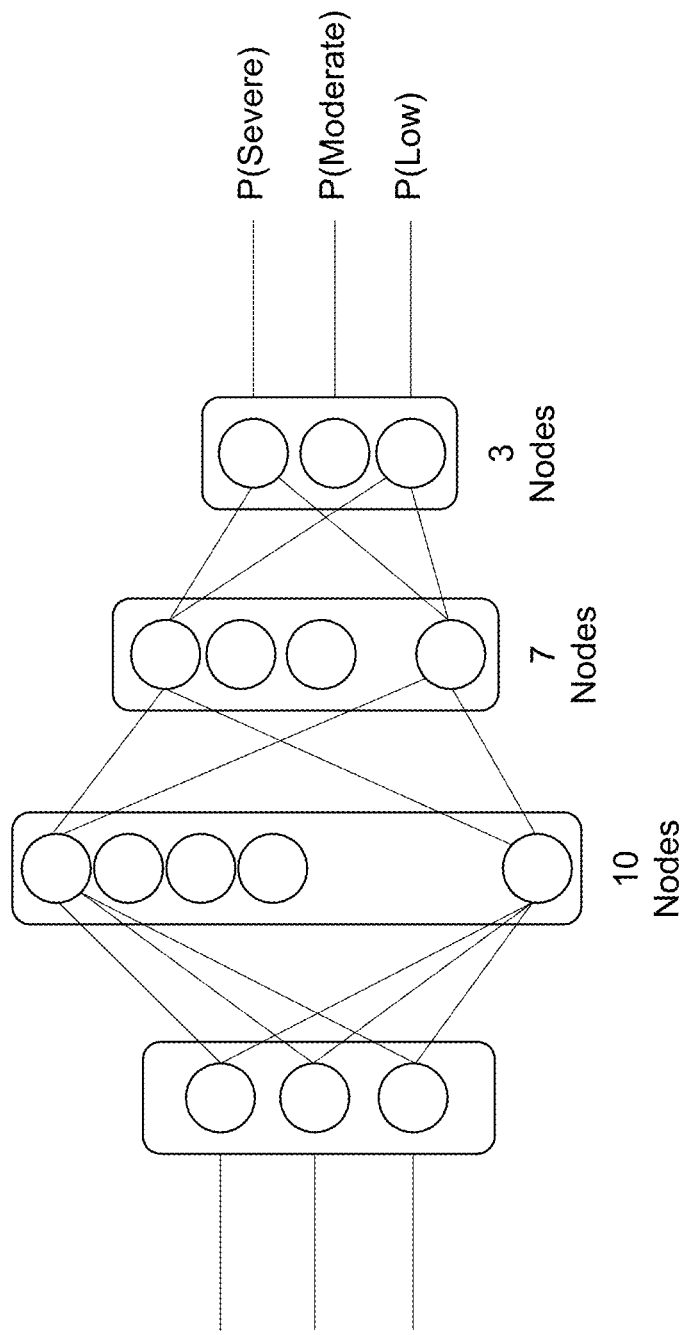
FIG. 7D illustrates an example neural network that may be trained to identify a glucose score.

In order to make GluScores applicable to SMBGs and other non-CGM analyte monitors, it can be important to decrease the number of samples required to estimate glucose. Assuming a more practical number of 3 samples over the 2.5 hour window, a glucose score algorithm may replicate the grading mechanism of the GluScore algorithm that is configured to use a relatively large number of samples, using much fewer samples. For example, up to 10 times fewer samples, 5 times fewer samples, 2 times fewer samples, or a different range. To do this, a glucose score algorithm may include a 3 layer neural network classifier (depicted in FIG. 7D) with the 3 glucose samples as input and the output being the three graded classes (Severe, Moderate, and Low). In some examples, trained networks achieve a 92.6% accuracy compared to other methods of determining GluScore grades on a test set.

In order to help users really understand the response to a meal, the glucose score algorithm was made more responsive to the glucose variations using the 2 Branch Algorithm depicted in FIG. 7E. As illustrated in FIG. 7E, a controller 300 may utilize two or more different analyses to identify a user's GluScore. For example, as illustrated in FIG. 7E, a GluScore classification process 700 that may be implemented by a controller 300 may have two or more branches of analyses 701a, 701b for analyzing glucose values 702.

Each branch 701*a*, 701*b* may generate a GluScore, such as a low, moderate, or severe type.

For example, a branch 701*a* may analyze glucose values 702 according to a machine learning algorithm 708. In another example, a branch 701*b* may analyze glucose values 702 or 703 according to a machine learning algorithm 710. One or some of the branches 701*a*, 701*b* can include other data processing steps, such as bias correction 704, 706 to produce glucose data 703. GluScores classified by the branches can be analyzed using decision logic to produce a GluScore score.

In the first branch, the glucose values are input as supplied by the user to compute a grade for the window. In the second branch, the glucose values are bias corrected to 90 mg/dL and as a result the grades calculated from this branch are more sensitive to the glucose variations and not the absolute value. The results from the 2 branches may be combined using a table heuristic as shown in Table 1. Advantageously, the glucose score algorithm in this form is able to grade user meals on an alphanumeric grading scale (for example, A-D, A-F, A+-D-, or other grading scale) using only a few blood glucose values and is a more customer focused solution than the original GluScore algorithm.

TABLE 1

| Long Term (Lifestyle) | Short Term (Meal Sensitivity) | GluScore Grade |
| --- | --- | --- |
| Low | Low | A |
| Low | Moderate | A- |
| Low | Severe | B+ |
| Moderate | Low | B |
| Moderate | Moderate | B- |
| Moderate | Severe | C+ |
| Severe | Low | C |
| Severe | Moderate | C- |
| Severe | Severe | D |

Table 1 illustrates example scores or grades associated with different types of foods or meals that may be based on long term and short term data. Long term data can include, for example, a GluScore of a user, such as described above with reference to FIGS. 7A-7C. Short term data can include, for example, a classification based on a glycemic load or other parameter associated with the food, meal, or other item being graded.

As illustrated in Table 1, different combinations of short term and long term data may be analyzed to determine a grade or score. For example, a GluScore of low paired with a short term glycemic parameter associated with a user's intake of low, moderate, or severe may generate a grade of A, A-, or B+ respectively. In another example, a long term GluScore of moderate paired with a short term glycemic parameter associated with a user's intake of low, moderate, or severe may generate a grade of B, B-, or C+ respectively. In another example, a long term GluScore of severe paired with a short term glycemic parameter associated with a user's intake of low, moderate, or severe may generate a grade of C, C-, and D respectively.

A score or grade of A (such as A+, A, or A-) may indicate that a user's blood sugar doesn't change very much after eating a particular food and that food has a more stabilizing effect. A score or grade of B (such as B+, B, or B-) may indicate that there was a moderate elevation in the user's blood sugar from food. A score or grade of C (such as C+ or C) may indicate that a user's blood sugar spike quite a bit after eating. As a result, the controller 300 may transmit recommendations relating to avoiding foods or beverages that are more likely to cause blood sugar spikes and/or limiting food portions. A score or grade of D may indicate that a user has a sever spike in glucose for a long period of time after eating. As a result, the controller 300 may transmit recommendations related to avoiding foods that are more likely to cause blood sugar spikes or other appropriate recommendations. Additionally or alternatively to providing recommendations to avoid foods, the controller 300 may transmit recommendations relating to increasing or maintaining intake of foods or beverages that are less likely to cause unwanted blood sugar spikes and/or suggest foods or beverage substitutions based on the score or grade of foods or beverages to improve a user's blood sugar control.

To help users make better choices regarding their meals, a health coaching system may also provide predictive glucose scores when logging or planning the meal. When a user searches for a food item or meal in a nutritional database, the nutritional information is used to run GIMM or another predictive algorithm, which returns the predicted glucose response for the user for that meal based on a standard set of parameters. Glucose score grades (or GluScores) may be computed on this glucose response and provided to the user as an information tool in deciding what meals to consume.

Since a glucose prediction model (such as GIMM referenced above) may be responsive to the total carbs, protein and fat in the meal, a user can visualize the effect of portion sizes, different food items and substitutions on their meal's glucose score grade. By doing so the health coaching system proactively nudges the user to make healthier choices in their meal selections.

4. Example Personalized Prediction Model

A controller 300 may utilize the predicted physiological parameter from model 620, 650 or the classified GluScore to determine an output from one or more engines operated by the controller 300. For example, the controller 300 may determine a recommendation from coaching engine 316 or education program from education engine 322 to output to a user based on a threshold glucose variability (e.g., a determination of severe variability GluScore). In another example, the controller 300 may determine a risk of diabetes from an analytics engine 320 based on a threshold glucose variability (e.g., a determination of severe variability GluScore).

Figure 8:
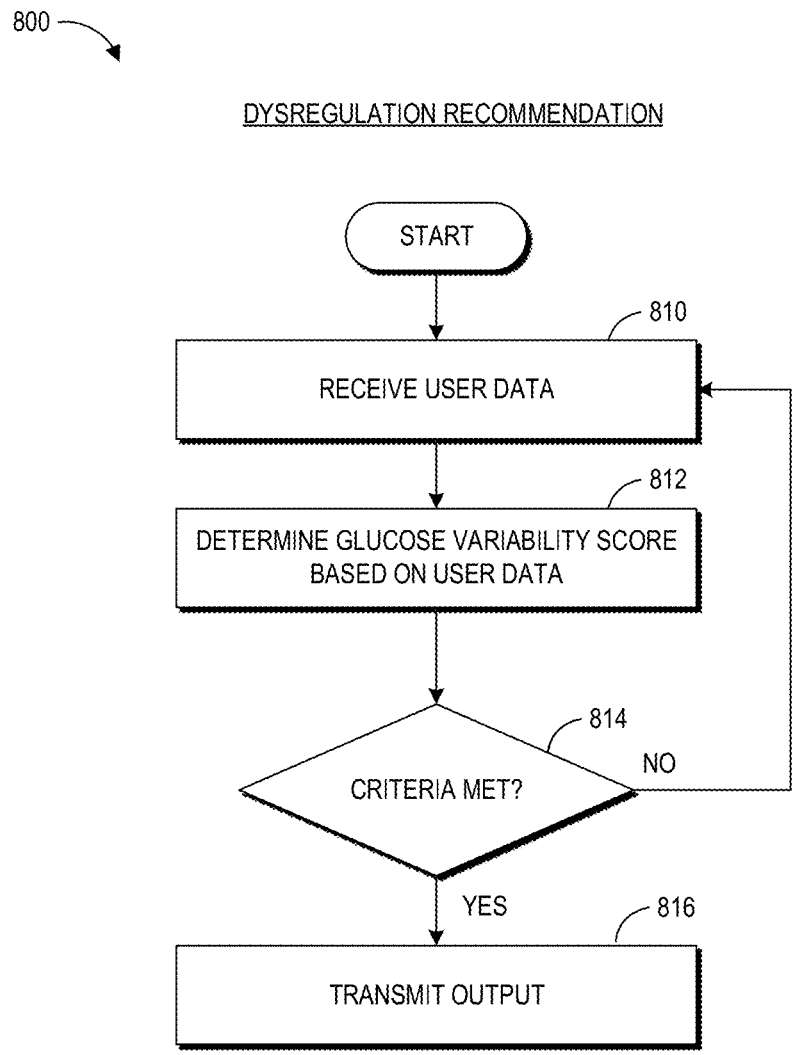
FIG. 8 shows an example recommendation process based on glucose variability.

FIG. 8 is a block diagram of an example dysregulation recommendation process 800. For example, a process 800 can include a data receiving block 810, a variability determination step 812, an evaluation step 814, and a transmission step 816.

At data receiving block 810, the controller 300 can receive one or more types of user data. For example, the user data can include but may not be limited to data 510, such as device tracking data 512, third party data 514, and user input data 516 as discussed with reference to FIG. 5.

At variability determination step 812, the controller 300 can determine a GluScore, glucose variability, glucose score or other metric related to a user's glucose or estimated glucose. As discussed above, the controller 300 may determine a GluScore, glucose variability, or glucose score based on some combination of HbA1c, fasting glucose, one hour post meal glucose, 2 hour post meal glucose, predicted glucose or the like. Additionally or alternatively, the controller 300 may categorize a user based a variation in one or more of the aforementioned values or data determined based on one or more of those values. Additionally or alternatively, the controller 300 may determine a confidence score associated with the GluScore or glucose variability. The confidence score may be a value indicative of a level of confidence in the validity of the GluScore or glucose variability.

At evaluation step 814, the controller 300 can determine if one or more values determined at block 812 meets one or more criteria. For example, the controller 300 can determine that a user's GluScore or glucose score is associated with a threshold risk of certain health conditions, such as diabetes or heart disease. The threshold risk can be any amount of risk of contracting any number of health conditions. For example, the threshold risk can be a greater than 50% risk of developing heart disease or a greater than 80% risk of developing diabetes. In another example, the controller 300 can determine that a confidence score associated with a GluScore or glucose variability meets a threshold confidence. The threshold confidence can be any number of confidence values, including but not limited to 10% confidence, 30% confidence, 85% confidence, or 99% confidence. Additionally or alternatively, the controller 300 can determine whether both a GluScore meets a threshold risk and whether a confidence score meets a threshold confidence. In some configurations, criteria can vary depending on the calculated values from step 812. For example, where the controller 300 determines a greater risk of developing a health condition, the controller 300 can lower the threshold confidence.

If the controller 300 determines that the one or more values determined at block 812 meets the one or more criteria, then the controller 300 may transmit an output at transmission block 816. The output can include information determined by the controller 300 related to the one or more values determined at block 812, such as a long term or short term lifestyle change. For example, the controller 300 can determine a risk reduction recommendation to the user based on an increased risk of developing diabetes as recognized by increased glucose variability. In another example, the controller 300 can determine a risk reduction recommendation that includes a food substitution in order to decrease a user's anticipated glycemic response. The controller 300 can transmit the risk reduction recommendation at block 816. The recommendation or other output can be transmitted to the user or third party over a network to a user device, backend system, or third party system.

Figure 9:
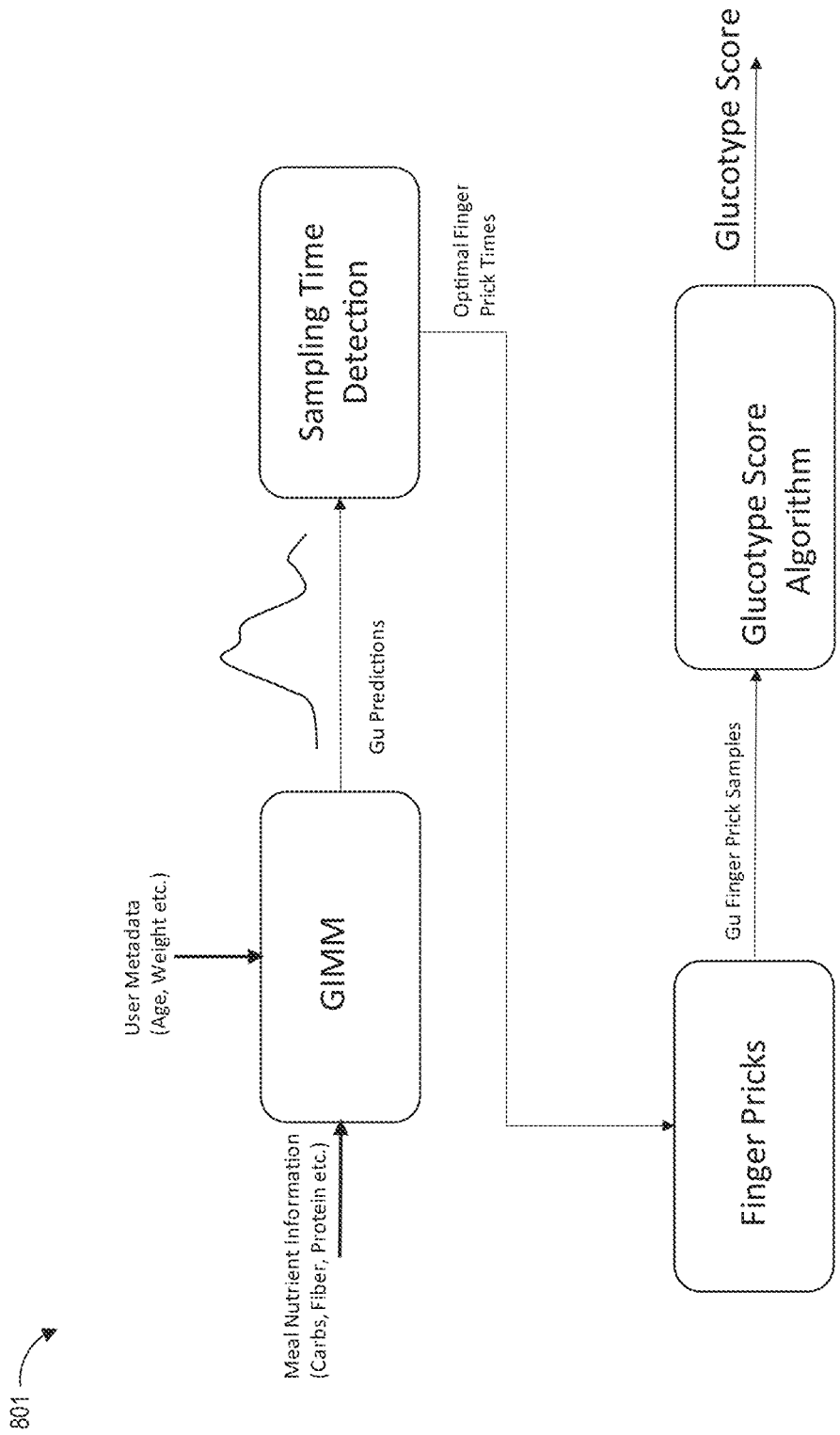
FIG. 9 is a block diagram of an example recommendation process based on glucose variability.

In some examples, a GIMM can be used to help predict optimal glucose measurement times for a user of the personalized health coaching system. FIG. 9 illustrates an example score process 801 that may utilize a GIMM in order to identify ideal sampling times for training or classification in a GluScore scoring algorithm, such as described above with reference to FIGS. 7D and 7E. For example, input to a GIMM can include, but is not limited to, meal or nutrient information, such as the quantity and type of macro or micronutrients in a user's food, and metadata associated with the user, such as age, weight, gender, or other information. The GIMM may generate a glucose prediction based on the input information. The glucose prediction may be used by the controller 300 to identify or determine a sampling time that is optimal for a glucose measurement in order to provide a better score or better recommendation based on the glucose measurement. For example, the controller 300 may identify a time or set of times by which a user should ideally measure glucose invasively or non-invasively. The controller 300 may alert the user to measure glucose through, for example, a finger prick or non-invasive measurement. The glucose measurements may be analyzed by the controller 300 to determine a score.

Figure 10:
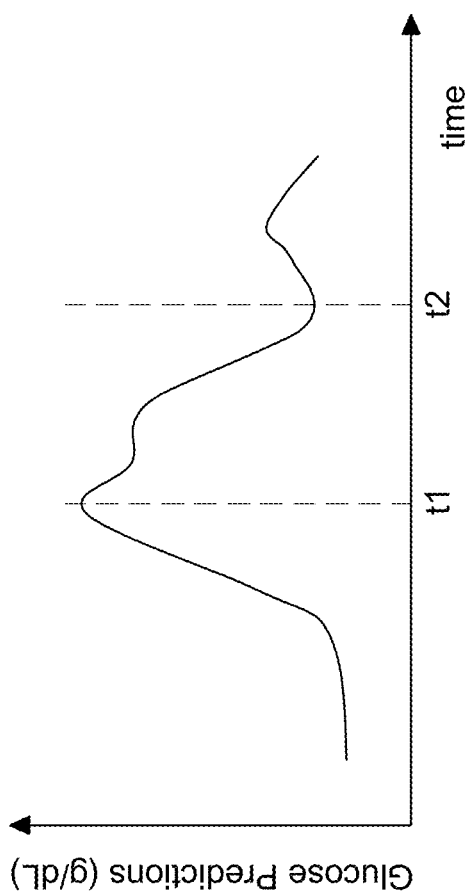
FIG. 10 illustrates example sampling times that may be identified by a process based on glucose predictions or estimations.

FIG. 10 illustrates an example of sampling times, t1, t2 that may be identified by the process 801 based on glucose predictions generated by a GIMM. For example, a GIMM may identify a spike in glucose values based on one or more inputs, such as a quantity of carbohydrates eaten by a user at mealtime. The controller 300 may predict a peak in predicted glucose values based on those inputs and identify a time t1 to measure glucose that corresponds to that peak. Additionally or alternatively, the controller 300 may identify a dip in the predicted glucose values. The controller 300 may identify a time t2 to measure glucose that corresponds to that dip.

F. ANALYTICS ENGINE

Figure 11:
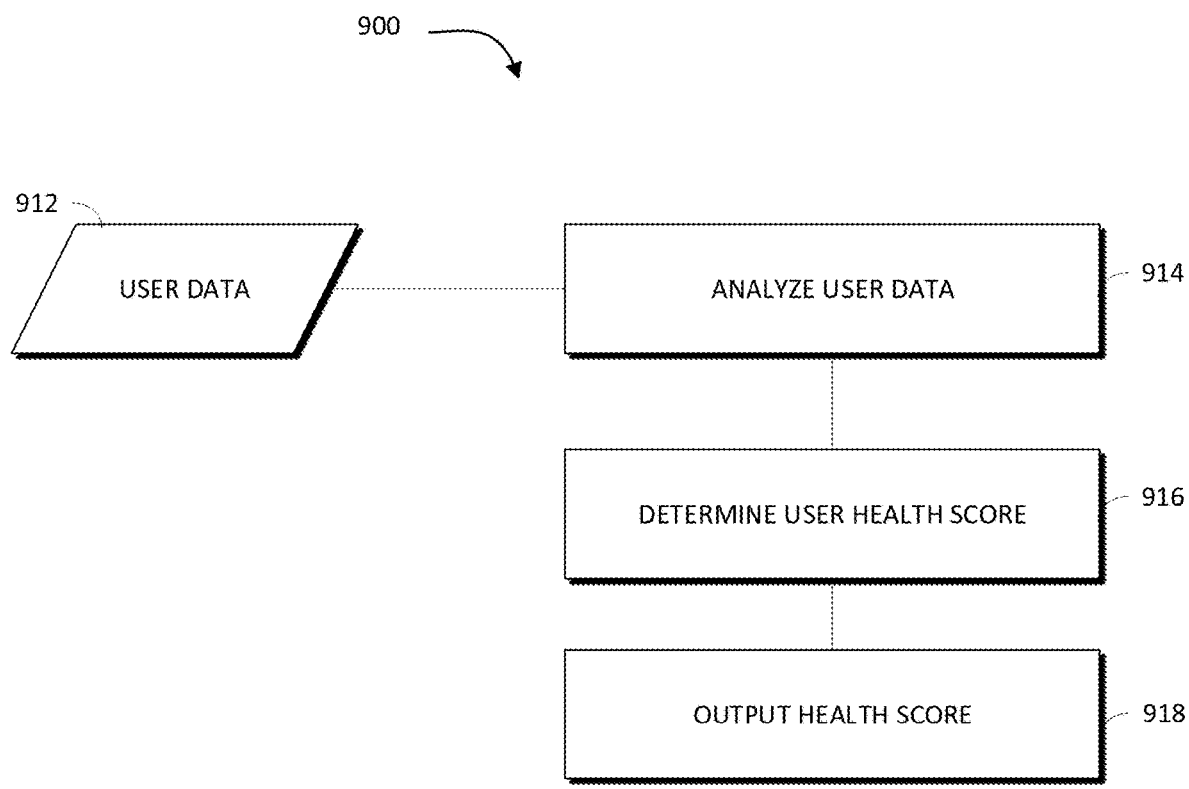
FIG. 11 is a block diagram of an example health score determination process.

The controller 300 can operate an analytics engine 320 that can include one or more processes for analyzing user data and determining health scores associated with the user data. FIG. 11 illustrates an example health score determination process 900 that may be employed by the analytics engine 320. For example, the process 900 can include an analysis block 914, a health score block 916, and a transmission block 918.

At an analysis block 914, the controller 300 can analyze the user data 912 to determine markers or other health related factors that may be present in the user data 912. For example, the controller 300 may determine whether the user data 912 includes risk factors for injury or disease, that the user data 912 contains certain markers of improved health or fitness, the like, or some combination thereof. For example, the user data 912 may include a user's GluScore, such as determined by a process such as described with reference to FIG. 8. For example, the risk factors may include that a severe variability GluScore is associated with a 50% increased risk in developing diabetes.

The user data 912 can include any amount or type of data related to a user's health, including but not limited to activity information, location history, sleep information, food intake information, medical records history, family history, shopping information, and various physiological factors such as blood glucose, weight and heart rate. For example, the user data 912 can include user data 510 collected by the system 100 as described with reference to FIG. 5.

In some configurations, the controller 300 may determine whether the user data 912 has markers related to adequate, improved, ideal, or other fitness capacity. For example where the controller 300 determines health scores related to a user's fitness capacity, the controller 300 can analyze user data (e.g., user data 510) using one or more fitness models. A fitness model can include mathematical model(s) for determining a fitness capability. For example, a fitness model can include an oxygen performance capability model that can utilize one or more of respiratory rate, pulse variability, hemoglobin concentration (or hematocrit), oxygen saturation, and oxygen content to assess how effective a person's ability to take in air, transport it, and oxygenate it. The model may include using a ratio of respiratory rate moving average versus the current value to understand if an individual is requiring more breaths per minute or fewer. Additionally or alternatively, the model may include looking at the quantity of Oxygen carrying capacity expressed as Hemoglobin, being flat or increasing as good sign. Additionally or alternatively, the model may include checking the saturation quality with high (with staying high as better compared with a flat or trending down PR and trending up PRV). In some configurations, the controller 300 may determine a health score at block 916 based on the number of breaths needed for the same amount or more oxygen quality and quantity.

In some configurations, the controller 300 may determine whether the user data 912 includes risk factors for injury or disease. For example, the controller 300 may analyze the user data 910 to determine if the user data 910 includes one or more risk factors. The one or more risk factors can include indicators or factors related to an increased likelihood of developing a health condition. The risk factors can include risks based on user specific factors, global health factors, or any other indicators or factors. For example, the controller 300 may recognize that when a user's resting heart rate is greater than user 90 beats per minute and that user is classified as having an obese BMI, the user has an increased risk of developing cardiovascular disease than if their resting heart rate were 70 beats per minute at that BMI.

In some configurations, the risk factors may include attributes or characteristics of a user's genetic, behavioral, or physiological health that may be learned by the system 100 as factors that increase the likelihood of the user developing a disease or injury. The controller 300 can analyze data associated with one or more users of the system 100 to learn and identify risk factors. For example, the system 100 can include a database of a group of users' health related data. The system may analyze the database to determine a relationship between certain behaviors and certain health risks. For example, the system may determine that users who record potato chips as part of their daily intake also have a higher risk of developing diseases like cardiovascular disease. Based on the recognized correlation, the system may determine a risk factor, such as, for example that eating potato chips on a daily basis is associated with an increased likelihood of developing cardiovascular disease. The controller 300 may make these determinations using any number of learning algorithms. For example, the controller 300 can use machine learning algorithms, such as a neural network, support vector machine, Bayesian network, genetic algorithm, or other data analysis algorithm.

In another example, the risk factors could include factors that increase likelihood of developing disease or injury as determined by a health authority, including but not limited to the World Health Organization (WHO). For example, the WHO may recognize that cigarettes smoking results in a 15 to 30 fold increase in lung cancer risk. A risk factor for lung cancer may therefore include a history of cigarette smoking.

Additionally or alternatively, the controller 300 may determine one or more mitigating factors in conjunction with other the one or more risk factors. Advantageously, taking mitigating factors into account can allow the controller 300 to determine if an identified health risk is a false negative, false positive, or misleading. The controller 300 can analyze the user data 912 to identify both risk factors and mitigating factors at block 914. The controller 300 can utilize the mitigating factors in any number of ways in analyzing the user data 912 and one or more risk factors. For example, the controller 300 can ignore mitigating factors, modify an identified health risk or health score, determine or modify a confidence score for an identified health risk or health score based on the mitigating factors, determine a mitigation score or value, or produce or modify any other information produced by the system 100.

In some configurations, the controller 300 can modify, in block 916, a user's health score or value based on identifying mitigating factors in a user's data 912. For example, the controller 300 may determine without analyzing mitigating factors that a user has an increased risk of developing cardiovascular disease because their BMI is classified as overweight or obese. The controller 300 may determine by analyzing the user data for mitigating factors, such as a user's resting heart rate or waist circumference, that the user is not at increased risk of developing cardiovascular disease because the BMI is not an accurate representation of a user's cardiovascular health. For example, a muscular athlete may have a BMI classified as overweight or obese. Overweight or obese BMI may be an identified risk factor for developing cardiovascular disease due, in part, to an accumulation of excessive fat. However, a muscular athlete may not have excessive fat and therefore may not have an increased risk of developing cardiovascular disease due to that fat. If a user's BMI were the only thing used to identify risk, then the system might return a misleadingly high identified risk for an otherwise healthy athlete. Therefore, to correct this, the controller 300 may analyze the user's BMI in relation to their resting heart rate. For example, an athlete's resting heart rate may be 40 beats per minute. The controller 300 may recognize that the user does not have an increased risk of developing cardiovascular disease because the athlete's heart rate is within a healthy range despite the user having an obese BMI. In another example, a male athlete may have a waist circumference of 34 inches and an obese BMI. The controller 300 may recognize that the user does not have increased risk of developing cardiovascular disease because the athlete's waist circumference is within a healthy range despite the athlete having an obese BMI.

At a score determination block 916, the controller 300 can determine a health score based on the analysis performed at block 914. The health score may be a scaled score (for example, on a scale of 1 to 10, with 10 being perfect health) or the health score may be a percentage representative of risk of developing a certain disease (for example, 40% risk of developing cardiovascular disease). A single or a combination of identified risks, health factors, or other indications related to a user's health based on the user data 912 may be used to determine a health score. For example, a number of health risks may be found in analysis block 914, such as a risk associated with cigarette smoking, a risk associated with excessive sedentary activity, and a risk associated with a genetic history of diabetes.

A health score can include any number of values associated with a user's health, athletic performance, or other physiological value. For example, the health score can be a value associated with a user's identified risk of developing one or more diseases or injuries. Additionally or alternatively, a health score can be a value associated with a user's athletic capability, such as a user's breathing quantity, quality or speed, a user's heart rate or heart rate variability, a user's cardiovascular fitness, or other fitness metric.

The controller 300 may determine multiple different health scores that may be associated with different health risks, fitness capacity, the like, or some combination thereof. Additionally or alternatively, the controller 300 may determine a single overall health score. For example, the analysis block 914 may determine that the user has a 70% risk of developing lung cancer based on the user's cigarette smoking habits and may determine that the user has a 40% chance of developing diabetes based on the user's genetic history and activity history. The system may also determine that the user has an overall health score of 4/10 based on the identified risks associated with the user's cigarette smoking, genetic and activity history.

Additionally or alternatively, the controller 300 may have different health scores based on the user or one or more user goals in using the health coaching system 100. For example, a user may be an athlete with a goal of improving their athletic capacity. The controller 300 may determine health scores related to a user's athletic capacity and may or may not determine health scores related to a user's risk of developing lifestyle diseases. In another example, a user may be a diabetic with a goal of fat loss. The controller 300 may determine health scores related to a user's risk of developing lifestyle diseases other than diabetes.

At transmission block 918, the controller 300 can output a health score at a transmission block 918. Additionally or alternatively, the controller 300 can output information based on the health score. For example, the controller 300 may transmit a health recommendation based on the health score. The recommendation may indicate to the user how to reduce their risks and improve their health by modifying their behavior in some way that is likely to reduce their risk. For example, where the system identifies a user has a 70% risk of developing diabetes based on trending increases in the user's HbA1c, the system may recommend a diet regimen to the user to lower their HbA1c and thus reduce their risk of developing diabetes.

G. COACHING ENGINE

A coaching engine 316 can include one or more processes for interacting with a user in order to provide information related to a user's health or fitness. For example, a coaching engine 316 can include one or more processes for providing health based recommendations to the user or one or more processes for providing feedback to the user related to the user's compliance with the user's health goals, compliance with recommendations, or other behavior associated with the user's health or fitness.

Figure 12:
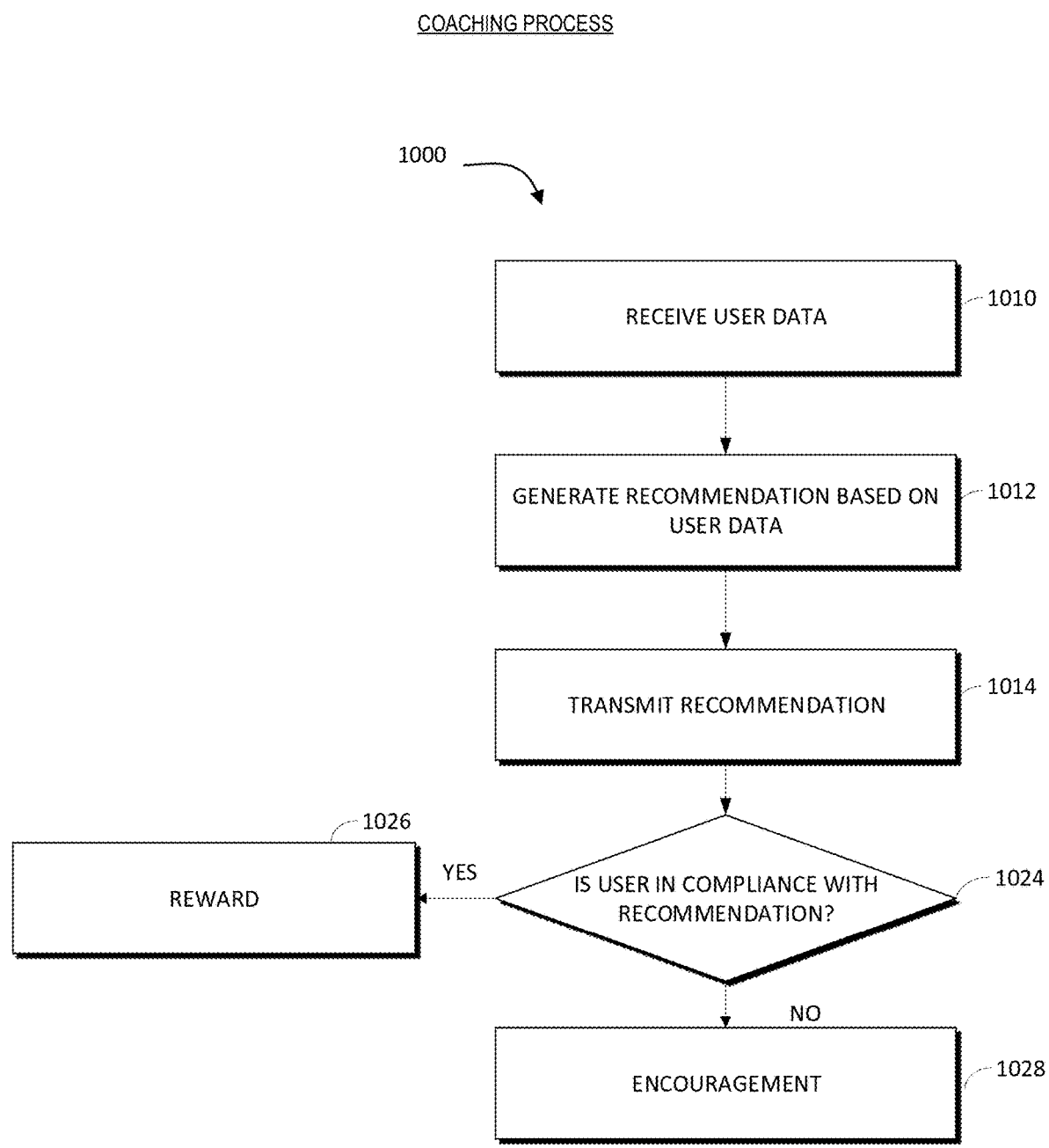
FIG. 12 is a block diagram of an example coaching process.

FIG. 12 is a block diagram showing a coaching process 1000 that can be part of a coaching engine 316. The coaching process 1000 can include a data receiving block 1010, a recommendation generation block 1012, a transmission block 1014, an analysis block 1024, a reward block 1026, and an encouragement block 1028.

At data receiving block 1010, the controller 300 can receive one or more types of user data and generated data or information associated with the user data. For example, the controller 300 can receive data 510, such as device tracking data 512, third party data 514, and user input data 516 as discussed with reference to FIG. 5. In another example, the controller 300 can receive predicted data, such as the one or more physiological parameter predictions or categorizations discussed with reference to FIGS. 6A-8. In another example, the controller 300 can receive one or more health scores associated with the user, such as the health scores discussed with reference to FIG. 11.

At a recommendation generation block 1012, the controller 300 can analyze the data from block 1010 to determine a health or fitness recommendation. The health or fitness recommendation may be based on user data or generated information associated with the same or different user data. For example, the controller 300 may determine a regimen of recommended lifestyle behaviors, such as a specific diet or an exercise routine based on, alone or in combination, the user's health scores, user specified health and wellness goals, a regimen provided by a health care provider, and user capability to comply with a regimen as determined by their current physical health.

In some configurations, the controller 300 can determine a recommendation based on a threshold output from another engine. For example, the controller 300 can determine the generated information that the user has a severe GluScore. Where a user's food intake includes foods that the controller 300 determines spikes the user's glucose above a certain threshold as defined by the user's GluScore, the controller 300 can transmit a recommendation to the user to avoid that food type in the future. In another example, the user data may include an intake history and at least one blood glucose value. The engine may determine a relationship between content of the food intake history, such as chocolate chip cookies, and a pattern in the blood glucose values, such as an insulin spike. The relationship may be represented using a grade or score based on the intake or other value, such as a GluScore or Glucose Score or Grade discussed above. In some examples, the controller 300 may generate a recommendation for the user to stop eating chocolate chip cookies in order to avoid an insulin spike.

In some configurations, the health or fitness recommendation may be based on a set of predetermined recommendations. The controller 300 can determine the health or fitness recommendation based on one or more user goals. For example, a user may have a goal of managing their blood sugar. The controller 300 may determine, based on the goal, that the user should measure their blood glucose every 3 hours. The controller 300 may transmit the recommendation to measure the user's blood glucose every 3 hours. Additionally or alternatively, a recommendation may be determined or based on a health care provider's direction. For example, a health care provider may determine that a user should engage in cardiovascular exercise for 45 minutes, five days a week. The controller 300 may transmit a recommendation once a day for five days a week to exercise for 45 minutes.

Additionally or alternatively, the controller 300 may determine more than one healthcare regimen and select a particular regimen to recommend to the user using decision logic. A default exercise regimen based on the user's data may be 30 minutes of exercise, five days a week. The system may prioritize the health care provider's regimen over the default regimen. In another example, the system may determine a regimen based on the user's health scores to include 30 minutes of walking daily. However, the user's physical health may dictate that they have limited mobility. The system may take the user's limited mobility into account and alter the regimen to include a 30 minute regimen of seated exercises daily.

At an analysis block 1024, the system may analyze the data received at block 1022 to determine if a user is in compliance with a system recommendation, goal, or other measure and determine a type of feedback to transmit to the user. The feedback may take the form of encouragements or rewards. The feedback may be adapted to be specific to the user based on user behavior, user interactions with the system, or user identified preferences. If the user is in compliance with a recommendation, goal, or other measure, the system may determine or transmit a reward at a reward block 1026. If the user is not in compliance with the recommendation, goal, or other measure, the system may determine or transmit an encouragement at an encouragement block 1028.

At reward block 1026, the controller 300 can determine or transmit a reward to the user based on the analysis at block 1024 or user data received at block 1022. For example, user data may include an activity history. The system may analyze the activity history at block 1024 to determine that the user has not engaged in the recommended 30 minutes of daily exercise. If a user is in compliance with the recommendation, the system may generate a reward at block 1026. The reward can take the form of access to third party rewards, providing monetary rewards or discounts to the user, access to other aspects of the system 100, or facilitating user access to other incentives or rewards. For example, the reward can be access to a locked or partially locked program or application on a user's mobile device. In another example, the reward can be facilitating a discount on a user's health insurance premium. In another example, the reward can be a discount on or receipt of a hardware device, such as a glucose monitor. The reward may be specific to the user, the user's goals, or the user's data. For example, a user whose goal is to reduce weight may receive rewards associated with new clothing discounts, healthy restaurant discounts, or a new scale. In another example, a user whose goal is managing their diabetes may receive rewards associated with glucose monitors.

At encouragement block 1028, the controller 300 can determine or transmit an encouragement to the user based on the analysis at block 1024 or user data received at block 1022. For example, the controller 300 may determine a series of milestones by which the user can track their progress in lowering their health risk as part of a recommendation. These milestones can represent a variety of progress metrics, such as reaching an improved health score, interacting with the system for a certain number of days in a row, or reducing waist circumference. If a user fails to reach a milestone, the system may provide an encouragement to the user to continue with the recommended regimen, such as a reminder or alert. In another example, a user may receive a recommendation to engage in 30 minutes of light activity a day. If the user has not engaged in the recommended 30 minutes of light activity on a particular day, the encouragement may include one or more activity directed messages, such as a message directing the user to walk around their neighborhood, a message relaying the user's health risk by continuing to remain sedentary, or a message relaying the reduction to the user's health risk by engaging in the recommended 30 minutes of light activity.

1. Example Triggers

Table 2 illustrates example goals, nudges, triggers, and coaching interactions that may be part of a health coaching system 100. For example, as illustrated, a user may have one or more goals. A trigger event associated with that goal may result in one or more nudges or coaching interactions.

TABLE 2

| Goal | Nudges | Triggers | Method |
| --- | --- | --- | --- |
| Weight Weight loss Weight maintenance | Weight "tickling" reminder Positive reinforcement in tracking/goal/weight loss (for example, "congrats" message) | Logging frequency threshold (for example, ≤ 1 weight logging event/week) Goal related threshold (for example, ≥ X percent weight gain in Y days or a week, a number of pounds away from goal weight) | Coach Interaction Chatbot In-app message Email Home screen Notification |
| Blood Sugar Fasting Blood Glucose ("BG") Postprandial BG Random time BG | Notifications relating to time in range (for CGM users) Positive reinforcement on achieving BG goal Corrective nudges/notifications (for example, "be more active", "try to drink fewer sugary beverages", suggestions associated with a health plate or simple carbohydrate intake) | Average fasting BG is greater than a threshold value over a determined period (for example, average BG today or this week is higher than last week) Average postprandial BG is greater than a threshold value over a determined period (for example, average BG today or this week is higher than last week) | Coach Interaction Chatbot In-app message Email Home screen notification |
| GluScore Improve score | GluScore time reminder Compare gluscore with user or group Predictive model help user to improve score (for example, brown in day-time) | ≤2 gluscore/week More low (for example, grade C/D/F) scores compared to a previous period (for example, last week) | Coach Interaction Chatbot In-app message Email Home screen notification |
| Food Improve score | Corrective notifications (for example, "high fat content," "high sodium content") Positive reinforcement (for example, "Good Job! Balanced meal!") | More calories "in" than "out" The proportion of empty calories are increased over a previous period Balanced meal Healthy plate is implemented Calories down | Coach Interaction Chatbot In-app message Email Home screen notification |

TABLE 2-continued

| Goal | Nudges | Triggers | Method |
| --- | --- | --- | --- |
| Sleep Duration (for example, >7 hrs/day) Quality (such as longer, deep sleep, fewer awakenings) | Reminders/ corrective notifications (for example, "time to go to bed" or "time to set aside devices") | Sleep hours changed from previous period Sleep quality changed a threshold percentage over a period (for example, down over 3 days) Sleep goal is reached | Coach Interaction Chatbot In-app message Email Home screen notification |
| Water more than X cups a day (for example, 8 cups a day) replacement of carbohydrate heavy beverages with water | reminders or corrective notifications (for example, "let's work on your hydration: X cups today," "have you been sipping on water today?") positive reinforcement | water intake increased or decreased over previous period goal is reached | Coach Interaction Chatbot In-app message Email Home screen notification |
| Physical Activity ≥number of active minutes/week (for example, 150 min/week) Add cardio or strength training Increase intensity | Encouragement notifications (for example, X more minutes to reach the goal) Corrective notifications (for example, "add strength training," "time for a 10-minute walk") | Physical activity increased or decreased over previous period Less than threshold amount of minutes over period (for example, less than X min/week, inactivity for X days) Goal is reached | Coach Interaction Chatbot In-app message Email Home screen notification |

In one example, a user may have a weight related goal, such as a weight loss or maintenance. In order to help achieve this goal, a system may include goal related nudges, such as weight tracking reminders or positive reinforcement related to tracking or weight goals (for example, a message of congratulations for tracking a certain number of days in a row or progress in weight loss). In some examples, a system may monitor triggers associated with a goal in order to help a user achieve their goal. A trigger associated with a weight related goal can include weight logging less than or equal to one time (or other amount) per week (or other amount of time), greater than or equal to a percentage weight gain in a set amount of time, such as a certain number of days, a week, or weeks, a certain number of pounds (or other measurement) away from a goal weight, other trigger indicating progress or lack of progress associated with a goal, the like, or some combination thereof. In the event that a system identifies the trigger, a coaching interaction may be initiated. A coaching interaction can include an in-app message from a coach (live or AI). The coaching interaction may additionally or alternatively appear on the home interface of a user interface.

In another example, a user may have a blood sugar related goal, such as a fasting blood glucose, postprandial blood glucose or other blood sugar related parameter or goal. In order to help achieve this goal, a system may include goal related nudges, such as notifications associated with a time where a user is measured or estimated to be in range of a goal blood glucose value, positive reinforcement in achieving a blood glucose goal, and/or notifications associated with an average blood sugar over a period of time. Such notifications may include lifestyle changes and/or suggestions to help a user achieve their blood sugar goal(s), such as a suggestion for food and beverage swaps, increased activity, the like, or a combination thereof. In some examples, a system may monitor triggers associated with a goal in order to help a user achieve their goal. A trigger associated with a blood sugar related goal can include an average fasting blood glucose being greater than or equal to a value, an average postprandial blood glucose being greater than or equal to a value, the like, or a combination thereof. In the event that a system identifies the trigger, a coaching interaction may be initiated. A coaching interaction can include an in-app message from a coach (live or AI). The coaching interaction may additionally or alternatively appear on the home interface of a user interface.

In another example, a user may have a glucose score related goal, such as to improve a glucose score, GluScore score or grade, or other health risk or health related score or grade. In order to help achieve this goal, a system may include goal related nudges, such as notifications associated with a comparison of a score or grade with a user score or group score, notifications or suggestions associated with a predictive model that may help a user improve their score, time reminders relating to a score or grade, the like, or some combination thereof. In some examples, a system may monitor triggers associated with a goal in order to help a user achieve their goal. A trigger associated with a glucose score goal can include less than or equal to a number of determined grades or scores in a set period of time (such as less than or equal to 2 GuScores in a week), more lower scores in a recent time frame as compared to a previous time frame, the like, or some combination thereof. In the event that a system identifies the trigger, a coaching interaction may be initiated. A coaching interaction can include an in-app message from a coach (live or AI). The coaching interaction may additionally or alternatively appear on the home interface of a user interface.

In another example, a user may have a food related goal, such as a calorie goal, nutritional goals (such as less refined carbohydrates, less refined sugar, less fat, less saturated fat, more fiber, less sodium, the like, or some combination thereof), or another food related goal or some combination thereof. In order to help achieve this goal, a system may include goal related nudges, such as notifications or suggestions associated with nutritional food content, such as a high fat or sodium value in a recorded food, positive reinforcements associated with food, such as encouragements related to positive nutritional values of a recorded food (such as a good amount of fiber or vitamin C) or encouragements or notifications related to a balance of a recorded meal, the like, or some combination thereof. In some examples, a system may monitor triggers associated with a goal in order to help a user achieve their goal. A trigger associated with a food related goal can include that recorded food In the event that a system identifies the trigger, a coaching interaction may be initiated. A coaching interaction can include an in-app message from a coach (live or AI). The coaching interaction may additionally or alternatively appear on the home interface of a user interface. Additionally or alternatively, to a coach message, a system may display a warning or positive reinforcement pop-up message while a user is in the process of logging their food.

In another example, a user may have a sleep related goal, such a duration or quality of sleep. In order to help achieve this goal, a system may include goal related nudges, such as a reminder to go to bed or a suggestion to set aside devices. In some examples, a system may monitor triggers associated with a goal in order to help a user achieve their goal. A trigger associated with a sleep goal can include a detected decrease in sleep hours, a detected decrease in sleep quality, or an identification that a goal has been reached. In the event that a system identifies the trigger, a coaching interaction may be initiated. A coaching interaction can include an in-app message from a coach (live or AI). The coaching interaction may additionally or alternatively appear on the home interface of a user interface.

In another example, a user may have a water related goal, such as an amount of water to drink in a day or a goal to replace carbohydrate heavy beverages with water. In order to help achieve this goal, a system may include goal related nudges, such as a notification to work on hydration by implementing a certain number of cups of water into the user's routine, or a suggestion to log water. In some examples, a system may monitor triggers associated with a goal in order to help a user achieve their goal. A trigger associated with a water goal can include an increase or decrease in water intake, or a identification that a water goal is reached In the event that a system identifies the trigger, a coaching interaction may be initiated. A coaching interaction can include an in-app message from a coach (live or AI or a simple notification message). The coaching interaction may additionally or alternatively appear on the home interface of a user interface.

In another example, a user may have a physical activity related goal, such as an amount of active minutes over a period of time (for example, greater than or equal to 150 active minutes per week), an addition of a type of exercise (for example, cardiovascular and/or weight lifting), an increase in intensity, the like or some combination thereof. In order to help achieve this goal, a system may include goal related nudges, such as a notification or suggestion to add an exercise (for example, strength training), a reminder to increase physical activity (such as taking a 10 minute walk), or an encouragement to reach a daily goal or milestone (for example a number of active minutes a day). In some examples, a system may monitor triggers associated with a goal in order to help a user achieve their goal. A trigger associated with a physical activity goal can include a lower than minimum number of active minutes over a period of time, such as a week, a lower recorded intensity of physical activity over a period of time, a detected period of inactivity, or a detection that a goal is reached. In the event that a system identifies the trigger, a coaching interaction may be initiated. A coaching interaction can include an in-app message from a coach (live or AI). The coaching interaction may additionally or alternatively appear on the home interface of a user interface.

2. Example Engagements

Table 3 illustrates example user engagements of a health coaching system based on one or more logging events or expected logging events. A logging value can include recorded data such as weight, meal or food, blood sugar or glucose score, sleep, physical activity, water, other lifestyle value, physiological parameter, or combination thereof. A trigger associated with that logging value may result in a nudge via one or more methods, such as a chatbot interaction, coach interaction, email interaction, home interface interaction, the like or some combination thereof.

TABLE 3

| Logging | Nudges | Trigger | Method |
|---|---|---|---|
| Weight | "let's see your progress, log your weight here." "you are close to your goal." "keep up the good work." "log your weight here" | No weight input after a threshold period (for example, No weight input ≥ 1 week or ≥ 3 days) | Coach Interaction Chatbot In-app message Email Home screen Notification |
| Meal/Food | "logging your food can keep you on track. Let's keep it up" Positive reinforcement on logging daily | Below or greater than a threshold input over a threshold period (for example, ≤ 1 meal logged per day, 0 beverage logging, ≥ 2 meal logging/day) | Coach Interaction Chatbot In-app message Email Home screen notification |
| Blood Sugar or GluScore | "We haven't reviewed your GluScore for awhile. Let's see how your individualized plan is going." | No BG input Incomplete GluScore sessions | Coach Interaction Chatbot In-app message Email Home screen notification |
| Sleep | "How's your sleep recently?" "Have you logged/synced your sleep data?" | No sleep input Haven't synced input device | Coach Interaction Chatbot In-app message Email Home screen notification |
| Physical Activity | "How's your week going? Let's log your physical activity." "great job! I see you have been working out." Positive reinforcement messages | No input Logging greater than or less than a threshold amount of times over a threshold period | Coach Interaction Chatbot In-app message Email Home screen notification |

TABLE 3-continued

| Logging | Nudges | Trigger | Method |
| --- | --- | --- | --- |
| Water | Positive reinforcement messages | Water input greater than or less than a threshold amount over a threshold period | Coach Interaction Chatbot In-app message Email Home screen notification |

In one example, a logging value may be weight. In response to an event associated with a weight value, such as logged value or lack of logging, a system may nudge the user to, for example, log their weight or transmit positive reinforcement regarding successes towards a weight goal or logging goal. A system may be triggered to provide the nudge through a lack of user input over a period of time, such as 1 week or 3 days.

In another example, a logging value may be a meal or food. In response to an event associated with meal or food logging, such as a logged food or a lack of logging, a system may nudge the user to log their food to keep up with tracking or provide positive reinforcement, such as one or more messages to continue logging daily. A system may be triggered to provide the nudge based on a lack of meal logging, an amount of logging that is less than or equal to an amount of expected logged meals over a period of time, a greater than or equal to amount of poor nutritional meals, the like or some combination thereof.

In another example, a logging value may be blood sugar or glucose score. In response to an event associated with blood sugar or glucose score, a system may nudge the user to lower their health risk associated with their expected or current blood sugar or glucose score, provide positive reinforcement, the like or some combination thereof. A system may be triggered to provide the nudge based on a lack of expected input (such as a missing blood glucose value), incomplete glucose score determination, or other event associated with a user's blood sugar.

In another example, a logging value may be sleep. In response to an event associated with sleep, a system may nudge the user to improve their sleep by, for example, reminding the user to log their sleep or identifying different lifestyle choices that may help improve sleep. A system may be triggered to provide the nudge based on a lack of expected input (such as a missing sleep value), a determined poor quantity or quality of sleep, the like, or some combination thereof.

In another example, a logging value may be physical activity. In response to an event associated with physical activity, a system may nudge the user to improve their physical activity by, for example, sending a notification to the user of how to improve their quantity or quality of physical activity, sending a reminder to a user to log their physical activity, the like, or some combination thereof. A system may be triggered to provide the nudge based on a lack of expected physical activity input, a determined poor quantity or quality of physical activity, the like or some combination thereof.

In another example, a logging value may be water. In response to an event associated with logging water, a system may nudge the user to drink an appropriate amount of water, log their water intake, replace a particular beverage with water, or provide other positive reinforcement. A system may be triggered to provide the nudge based on a lack of logged water or other event associated with a log of water.

FIGS. 13A-13F illustrate example interface interactions associated with different types of user engagements that may include logging events, associated triggers, and coaching interactions.

Figure 13A:
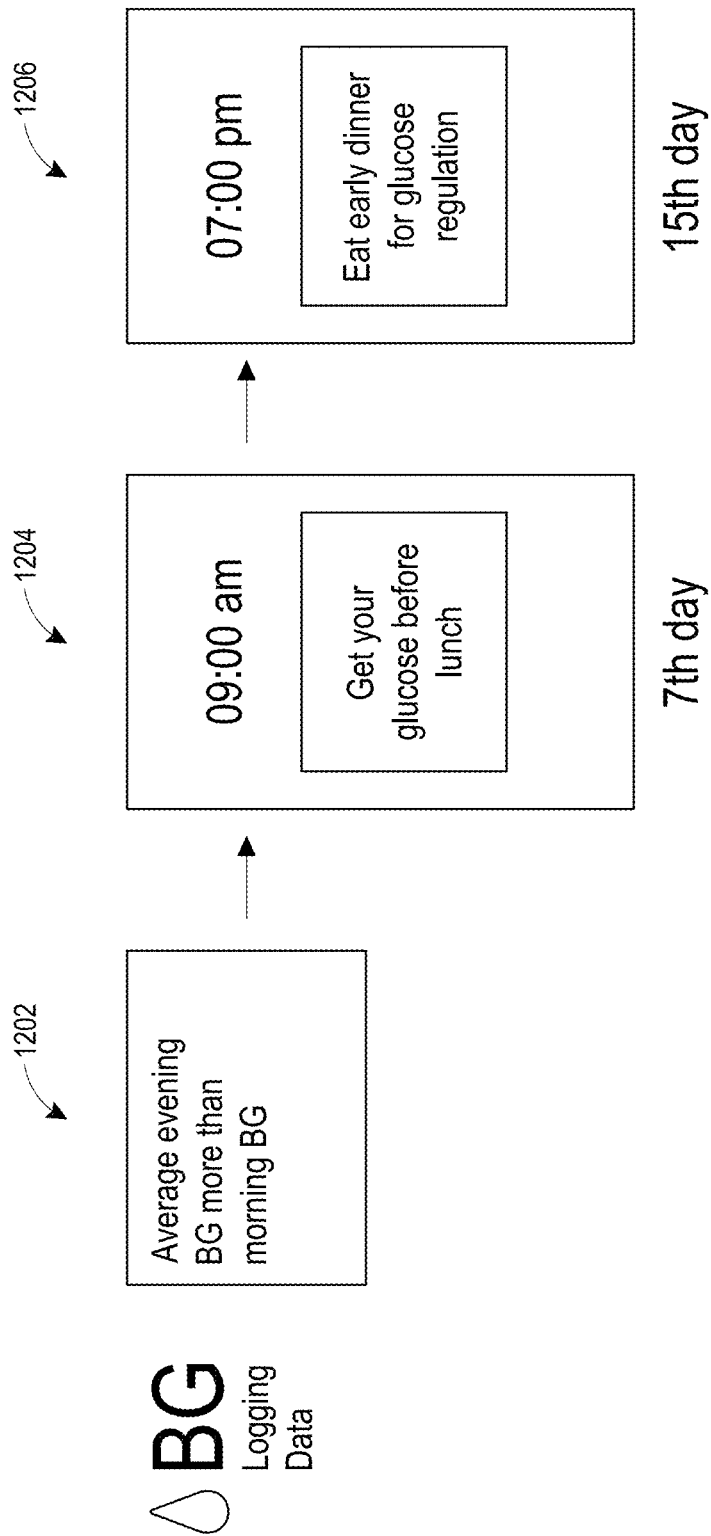
FIGS. 13A-F illustrate example interface interactions associated with different types of user engagements that may include logging events, associated triggers, and coaching interactions.

FIG. 13A illustrates an example interaction associated with a blood glucose logging event 1202. For example, a blood glucose logging event 1202 may be that an average evening blood glucose is greater than an average morning blood glucose. In response, a controller 300 may generate one or more notifications 1204, 1206 associated with blood glucose. For example, at a time before lunch (such as at 9:00 AM), the controller 300 may issue a reminder to measure or record glucose before lunch. In another example, at a time later in the day (for example, at 7:00 PM), the controller 300 may issue a recommendation to eat an early dinner for the purposes of glucose regulation. The one or more notifications 1204, 1206 may be based on an analysis of logging data associated with blood glucose or other values that may affect blood glucose.

Figure 13B:
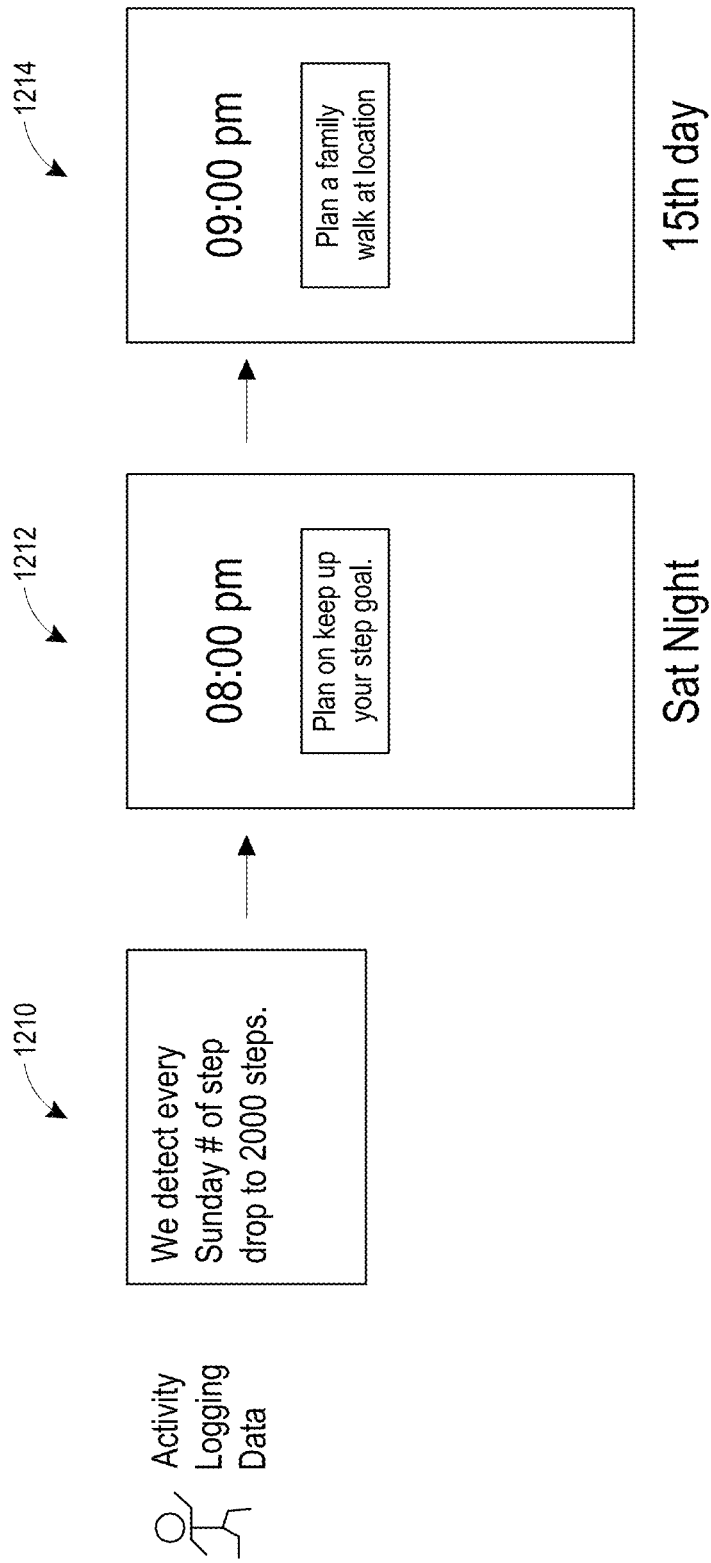

FIG. 13B illustrates an example interaction associated with an activity logging event 1210. For example, an activity logging event 1210 may be that every Sunday (or other day of the week), a number of steps drops to a lower than a stated step goal, such as 2000 steps where a step goal is 10000 steps. In response, a controller 300 may generate one or more notifications 1212, 1214 associated with user activity. For example, on a night before the predicted lower steps day, such as Saturday night, a controller 300 may issue an encouragement to keep up on a stated step goal. In another example, a controller 300 may provide a recommendation to plan an appropriate activity to raise a step count, such as plan a family walk at a recommended location. The one or more notifications 1212, 1214 may be based on an analysis of logging data associated with activity data.

Figure 13C:
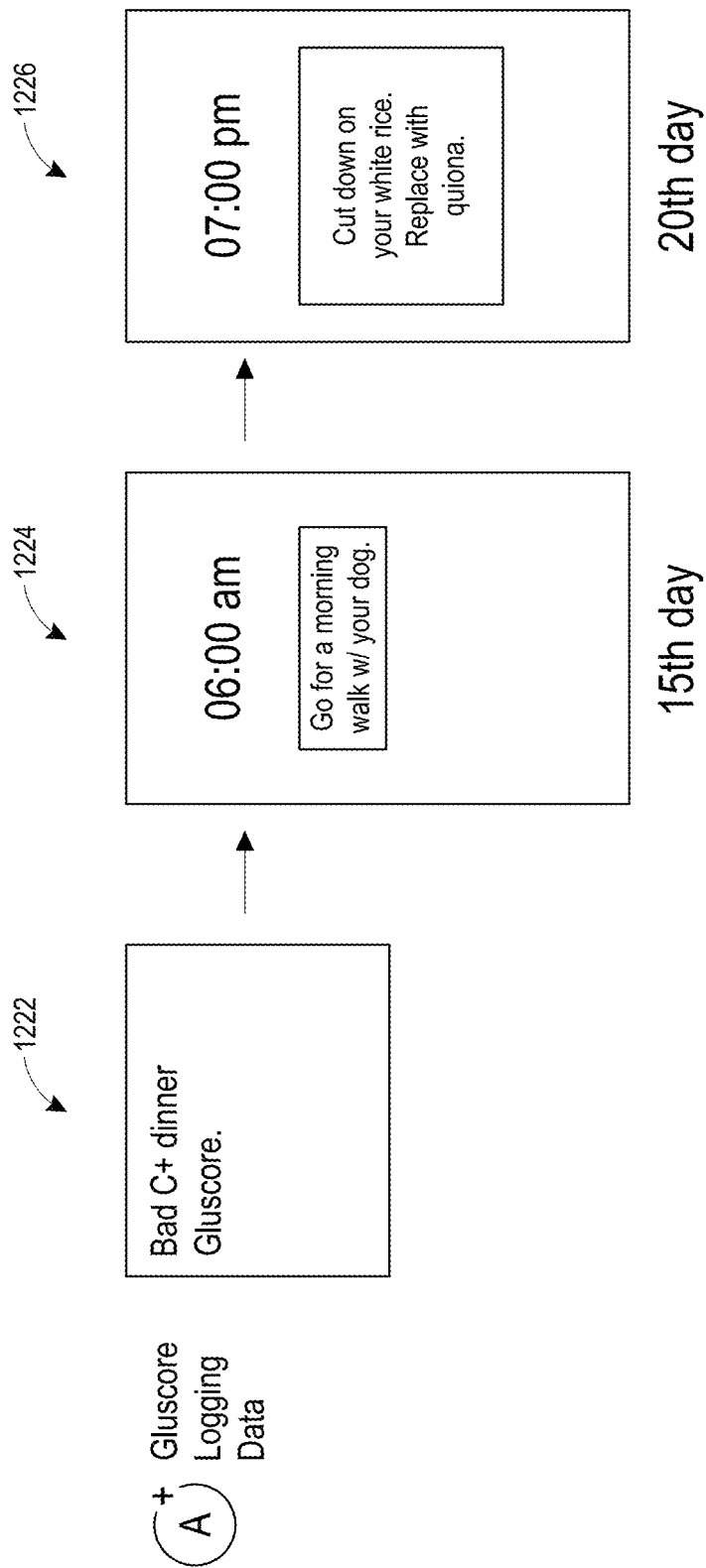

FIG. 13C illustrates an example interaction associated with a GluScore logging event 1222. For example, a GluScore logging event 1222 may include a bad recorded GluScore for a food or a meal (such as a C+ score). A bad GluScore may indicate or imply a fasting blood glucose on a following day or a bad GluScore the next day. In response, a controller 300 may generate one or more notifications 1224, 1226 associated with GluScore logging data. For example, a controller 300 may recommend an activity to improve a GluScore the next morning, such as a recommendation to go for a morning walk. In another example, a controller 300 may recommend a substitution of food ingredients or other intake to improve a GluScore around a dinner time. For example, the controller 300 may recommend cutting down on white rice and replacing white rice with another grain, such as quinoa. The one or more notifications 1224, 1226 may be based on an analysis of logging data associated with GluScore data.

Figure 13D:
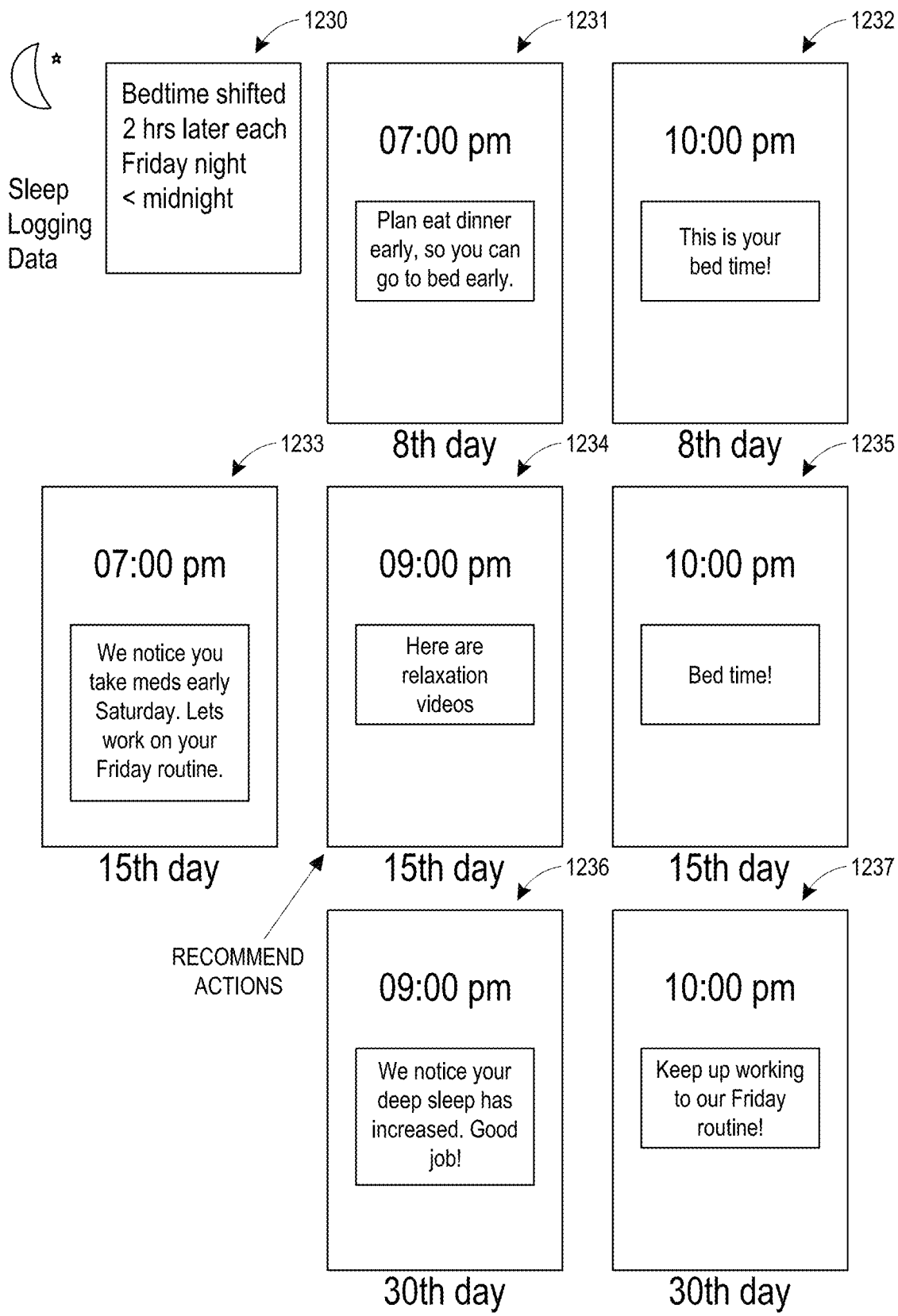

FIG. 13D illustrates an example interaction associated with a sleep logging event 1230. For example, a sleep logging event 1230 may include a shift in bed time on certain nights of the week, such as Friday night. In response, a controller 300 may generate one or more notifications 1231, 1232, 1233, 1234, 1235, 1236, 1237 associated with sleep logging data. For example, a controller 300 may recommend that the user eat dinner early to be able to go to bed on time. In another example, a controller 300 may remind a user that bed time is approaching or has been reached. In another example, a controller 300 may recommend to work on a daily routine in order to improve a bed time. In another example, a controller 300 may recommend or display relaxation videos or audio to facilitate eased sleep. In another example, a controller 300 may recommend other actions to facilitate better or earlier sleep. In another example, a controller 300 may encourage positive behavior by, for example, issuing encouraging messages such as "we noticed your deep sleep has increased. Good Job!" or "Keep up working on our Friday routine." The one or more notifications 1231, 1232, 1233, 1234, 1235, 1236, 1237 may be based on an analysis of data associated with sleep logging data.

Figure 13E:
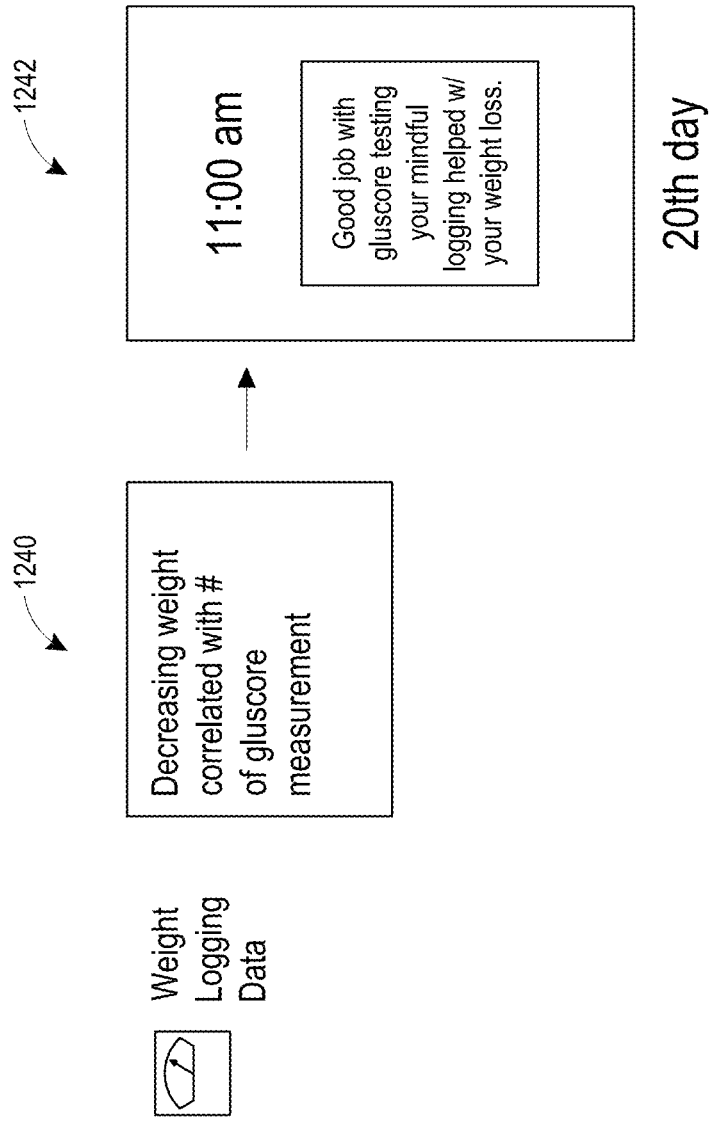

FIG. 13E illustrates an example interaction associated with a weight logging event 1240. For example, a weight logging event 1240 may include a decrease of increase in weight that may or may not be correlated with a GluScore measurement. In response, a controller 300 may include one or more notifications 1242 associated with weight logging data. For example, a controller 300 may transmit encouraging messages associated with positive weight changes, such as "Good Job with GluScore testing, your mindful logging helped with your weight loss." The one or more notifications 1242 may be based on an analysis of data associated with weight logging data.

Figure 13F:
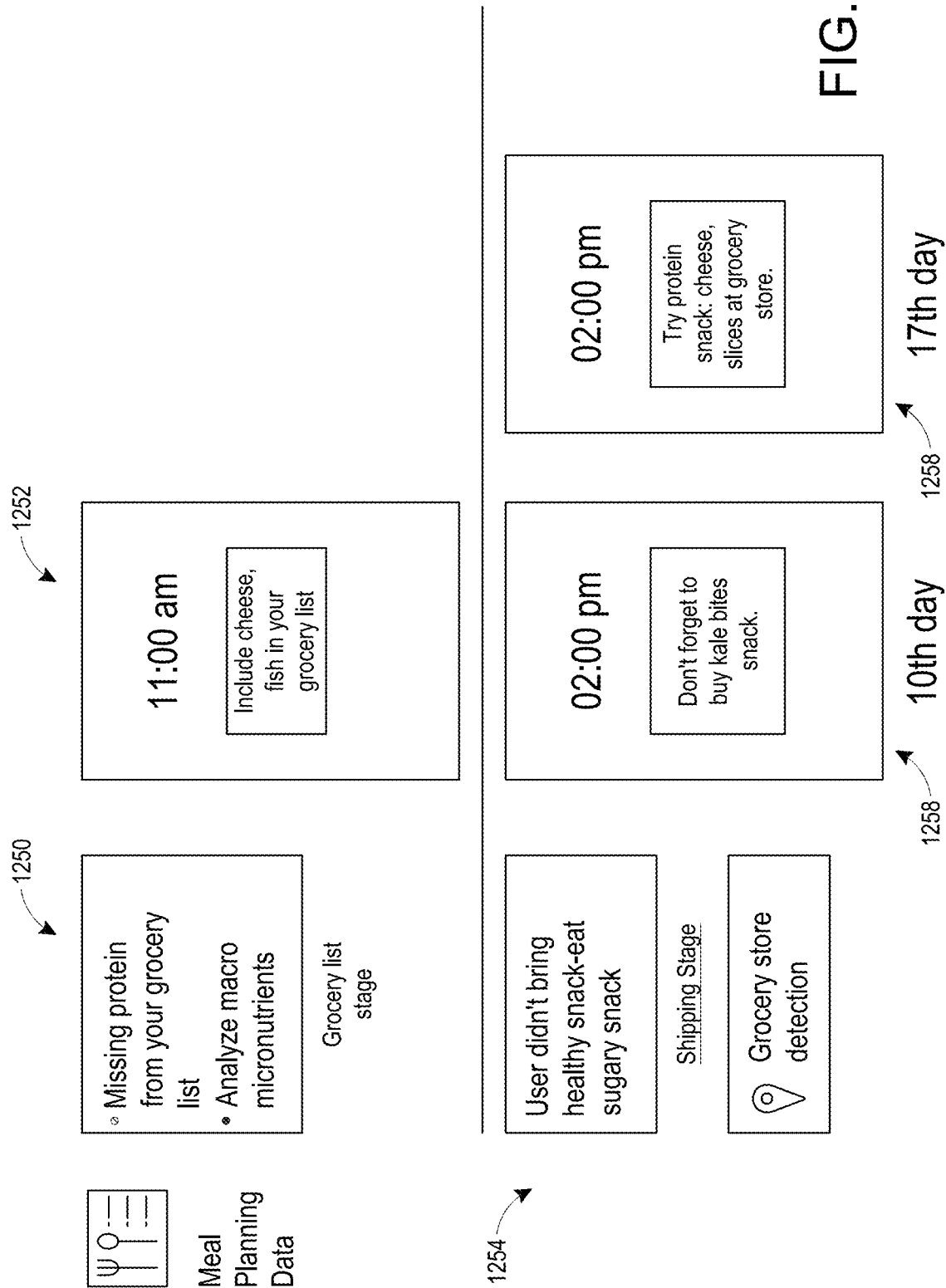

FIG. 13F illustrates an example interaction associated with one or more meal planning events 1250, 1254. For example, a meal planning event 1250, 1254 can include that a protein is missing form a grocery list, or macro or micronutrients are analyzed at a grocery list stage of meal planning or that a user didn't bring or buy a health snack, that the user ate a sugary snack, or that the user is at a grocery store based on detection location during a shopping stage of meal planning. In response, a controller 300 may issue one or more notifications 1252, 1256, 1258 associated with one or more meal planning events 1250, 1254. For example, a controller 300 may transmit recommendations to include a protein (such as a cheese or fish) or other aspect of a healthy plate that is determined as missing from a meal plan. In another example, a controller 300 may transmit a reminder to buy a healthy snack, such as kale bites or kale chips during a shopping stage. In another example, a controller 300 may recommend to buy a protein snack, such as cheese slices at a grocery store during a shopping stage. The one or more notifications 1250, 1256, 1258 may be based on an analysis of data associated with meal planning data.

Other types of interactions may also be possible.

3. Other Example Coach Interactions

Discussed herein are various configurations of how a personalized health coaching system 100 may utilize various behavioral and physiological factors to provide feedback through the calculation of health risks and analysis of user behavior.

Activity history may be used to encourage, monitor, and calculate the health risks associated with a user's day to day activity level. For example, when a person is working to reduce their health risks, the system may determine that the person needs to implement a daily walking routine. The system may determine that a person usually remains sedentary during the day and encourage the user to get up and walk for a set amount of time if the person does not record a certain number of minutes in which they walk by the end of a day.

An activity log can also be used to help determine a person's health risk for certain diseases. For example, the health guidelines for prevention of diabetes may indicate that a person should engage in light activity every thirty minutes during periods of sedentary activity. The system may compare the person's activity as tracked through a wearable device to the health guidelines and determine that the user is in compliance or contravention of the health guidelines. The system may generate a health score based on the person's activity that indicates the person's health risk by continuing to act against or with the health guidelines. The system may use the activity history to determine and transmit some feedback to the person regarding their activity, such as an encouragement or reward.

Food intake information may be used to encourage, monitor, and calculate the health risks associated with a user's food intake. For example, the system may determine that a user should eat a certain number of calories per day based on the user's health goals or risks. The system may determine that a person has eaten over their calorie limit for the day or is on track to do so based on their current intake level. In another example, the system may determine that a user may be allotted a certain number amount of salt intake for the day. The system may determine that a person has eaten over their salt limit or is on track to do so based on their intake level. Based on these types of determinations, the system may transmit some feedback to the person regarding their food intake, such as an encouragement.

The food history can also be used to help determine a person's risk for certain diseases. For example, the system may analyze the food history to determine whether the person's overall diet is in compliance or contravention of certain health guidelines. The system may generate a health score based on trends in the person's diet that indicates the person's health risk by continuing to act against or with the health guidelines. The system may also use the food history to determine and transmit some feedback to the person regarding their activity, such as an encouragement or reward.

Sleep history may be used to encourage, monitor, and calculate the health risks associated with a user's sleep patterns. For example, the system may utilize the notion that sleep plays a role in endocrine function and glucose metabolism to provide sleep recommendations to a user. For instance, a user's sleep history may indicate that they wake up at 6 am every day to get to work. The system may calculate that to meet a recommended sleep quantity of 8 hours a night, the user should go to sleep by 10 pm. The system may transmit an encouragement to the user at a time around 10 pm to encourage the user to go to sleep. The system may also reward the user for going to sleep at a recommended time.

Location history may be used to encourage and monitor user behavior based on a person's behavior as tied to a particular location. For example, where a person is working to reduce their health risks, the system may determine that the person needs to take more daily steps. Factors such as location history and activity information may be analyzed to determine a correlation or relationship between a person's location and the number of steps they take at that location. For instance, an office worker's location history may show that they are in their office from 9 am to 5 pm on Monday through Friday. At the same time, that office worker's activity information may show that they mostly sit during the same period of time. The system may determine that when the office worker is at their office location, they are more likely to sit. Thus, the system may send an encouragement to walk around or be more active whenever it determines the person is at their office location for more than a certain period of time, regardless of time of day.

A person's location history can be analyzed in conjunction with their food logs to determine a relationship between a person's location and the type of food they may eat as a result of being at that location. For instance, a person's location may show that they are visiting a location in which that person previously logged unhealthy food options. Alternatively, the person's location may show that they are visiting a location in which there are many unhealthy food options, such as a fast food chain that primarily sells burgers, french fries, or pizza. The system may send a reminder or encouragement to the person to make healthy food choices. If the location is a restaurant, the system may analyze the menu for the location and provide recommendations for healthy food choices based on the general nutritional quality of the available food or based on specific dietary recommendations for the person.

A person's location history may also be analyzed in conjunction with a person's shopping history to determine a relationship between a person's location and the type of food they buy at that location. For instance, a person's location may show that they are visiting a certain grocery chain. The system may have access to the person's purchase history at that particular grocery chain and recognize that the person has a history of purchasing a particular type of ice cream at that grocery chain. The system may send an encouragement to the person to purchase healthier alternatives to ice cream. The system may also determine what purchases who liked that ice cream also enjoyed. For example, instead of ice cream, the system may determine that other shoppers enjoyed frozen fruit and transmit that recommendation to the user.

A person's location history may also be used to help prompt a user to enter input into the system. For example, the person's location history may show that the person is in or has recently visited a restaurant. The system may recognize that the person is at the restaurant and prompt the person to enter any food that they intend to or have eaten into the system. Similarly, a person's location history may show that the person is in or has recently visited a gym. The system may recognize that the person has visited the gym and prompt the person to enter any workout that they have engaged in at that location.

Shopping history may be used to encourage, monitor, and calculate the health risks associated with a user's purchases. For example, a user's shopping history may be analyzed to determine that a person likes to purchase potato chips. The system may make a recommendation to the user to purchase a different snack food item as an alternative to the potato chips, such as kale chips. The recommendation may be based on, for example, what other people who purchased that particular brand or type of potato chip enjoyed as an alternative. The recommendation may also be based on the similarities between the two foods. For example, the system may recognize that potato chips are categorized as crunchy and recommend a healthy alternative with a similar texture.

In another example, the user's shopping history may be analyzed to determine that a person has purchased health or medical equipment, such as an activity tracker. The system may prompt the user to connect the activity tracker to the system. The system may also provide feedback to the user such as a reward, encouragement to use the purchased device, or a recommendation on best practices in utilizing the device to meet the user's health goals.

Family and medical history may be used to encourage, monitor, and calculate the health risks associated with a user's family and medical history. For example, a user's family records may show that members of the user's immediate family developed type 2 diabetes. Family history of type 2 diabetes is one factor that increases risk of an individual developing type 2 diabetes. The system may utilize this information to calculate a health score based on that family history and transmit that health score to the user.

In another example, a user's medical records may show a trending increase in HbA1c. Higher HbA1c levels serve as an indicator of diabetes and pre-diabetes. The system may utilize this information to transmit feedback to the user, such as an encouragement or recommendation. The system may also utilize this information to calculate a health score and transmit that score to the user.

Weight can be analyzed and used to encourage, monitor, and calculate the health risks associated with a user's body mass. In some configurations, a user's weight can be analyzed in conjunction with other factors, like height, to determine a user's body mass index (BMI). BMI can act as an indicator of health risk for certain lifestyle diseases. The system may use this information to calculate a health score and transmit that score to the user.

Waist circumference can be analyzed and used to encourage, monitor, and calculate the health risks associated with excessive abdominal fat. A high waist circumference is associated with increased risk for certain lifestyle diseases, such as type 2 diabetes and cardiovascular disease. Changes in waist circumference can serve as an approximate indicator of health risk for those diseases. In some configurations, waist circumference can be analyzed in conjunction with other factors, such as weight and height to determine a health score.

Heart rate can be analyzed and used to encourage, monitor, and calculate the health risks associated with a user's cardiovascular health. In some configurations, the heart rate can be analyzed in conjunction with a user's weight to determine a health score for the user. While a user's weight may be an approximate metric for user health, it alone does not show a full picture of a user's health. By utilizing both the heart rate and the weight of a user, a more accurate picture of health can be determined. For instance, where a user's heart rate is regularly recorded, an average heart rate can be determined. If the average heart rate starts to decrease while the user's weight is also decreasing, that is an indicator of improving health that is not merely tied to weight loss. Thus, the system can analyze the user's heart rate in conjunction with weight to determine a health score. That health score can be transmitted to the user as feedback to the user regarding their progress. The health score can also be used to determine recommendations to send to the user.

In other configurations, heart rate history can be used to calculate separate indicators of cardiovascular health. For example, heart rate variability (HRV) can be used to calculate a user's cardiovascular health and can be used as another indicator of overall health of the user. The HRV can also be used in conjunction with weight to determine a user's health score.

Blood glucose values, such as HbA1c, can be used to encourage, monitor, and calculate the health risks associated with a user's cardiovascular health. For example, an HbA1c value between 5.7% and 6.4% may classify someone as having pre-diabetes. In some configurations, the system may examine trends in the HbA1c values of a user to calculate a health score. That health score can be used to provide feedback or recommendations to the user.

In another example, blood glucose may be monitored on a regular basis as part of the treatment of diabetes. In some configurations, the system may analyze the blood glucose values in conjunction with the user's food history to determine a relationship between the user's blood glucose and items in the user's food intake history. The system may make a recommendation to modify the user's food intake in order to regulate the user's blood glucose values.

H. EDUCATION ENGINE

An education engine 322 can include one or more processes for interacting with a user in order to provide educational information. For example, an education engine 322 can include one or more processes to facilitate a user interacting with training modules, reading, viewing, or listening to educational content, or otherwise teaching a user about health and fitness.

The education engine 322 can provide access to different types of educational materials based on user data. For example, the controller 300 can determine that a user has a high risk for diabetes. The education engine 322 can provide access to diabetes educational materials. The education engine 322 can provide access to educational materials as part of an educational course. For example, the education engine 322 can provide educational materials (e.g., training modules) that are part of a ten week educational course on lifestyle management.

Training modules may include videos or interactive sessions through which the user can learn about their health and ways to improve it. The modules may be released to the user on a periodic basis, as the user reaches or fails to reach milestones, or in batches. For example, a user may be directed to view or interact with an introductory training module in the first week of their using the system. Subsequently, the user may be directed to view or interact with follow up training modules every week for ten weeks. Advantageously, releasing the training modules sequentially (for example, week by week) may keep the material fresh and result in more effective learning. The modules may be personalized to the user based on the user's particular health risks or health scores. For example, a user may have a health score that indicates a high risk of developing diabetes. The system may direct the user to a module or series of modules associated with addressing the risk of developing diabetes.

Additionally or alternatively, the education engine 322 can include one or more interactive learning components, such as a chatbot or artificial intelligence (AI) entity. The chatbot can include an automated coach that may conduct textual, audible, or graphical conversation with the user regarding information associated with the system 100 or information associated with health and fitness. For example, the user may be able to transmit a question to the chatbot regarding an aspect of the health coaching system 100, a meaning of a health score, a glucose reading, educational materials, food or liquid nutritional content, the like or some combination thereof. The chatbot may respond to the user with an answer to the user's questions, other feedback, recommendations, or requests for further information.

1. Example Education Modules

Different education modules may be used to apply to different users, different diseases, or different situations. For example, a module or set of modules may be designed to teach a user about a particular topic relevant to them. Table 4 illustrates example education modules that may be part of an education engine 322 that are relevant to a diabetic user of a health coaching system. However, other modules or combinations of modules, submodules, or the like may be used for other situations or users.

TABLE 4

| Example Modules | Example Content |
|---|---|
| Module 1: Introduction | |
| 1.1 Diabetes and you | National statistics |
| 1.2 What is Diabetes? | Prevention importance |
| 1.3 Blood sugar and your health | Psychology of diabetes |
| 1.4 What is GluScore? | Blood sugar impact |
| 1.5 How the coaching program works | GluScoring of meals |
| | Commitment, signature |
| Module 2: How to eat well | |
| 2.1 Know your food | Healthy plate food groups |
| 2.2 All about nutrients | Nutrients: micro and macro |
| 2.3 Building balanced meals | Food to choose: How GluScore helps to |
| Tips for eating well | make this choice |
| Foods to choose and limit | What do you know about sugar? |
| 2.4 Sugar | |
| 2.5 Ways to cope | |
| Module 3: How to get active | |
| 3.1 Why should you exercise? | The benefits and getting started |
| 3.2 Blood Sugar and Exercise | GluScore result and activity |
| 3.3 How to get active | Relationship between blood sugar and |
| 3.4 Be active, be safe | activity |
| 3.5 Ways to cope | How to get active |
| | How much or what different intensities |
| | look like |
| | Talk test |
| | Safety tipes |
| Module 4: Tracking your food | |
| 4.1 Why we track food | Log your meal |
| 4.2 Blood sugar and exercise | Take a picture of your meal |
| 4.3 How to get active | The purpose of tracking |
| 4.4 Be active, be safe | Calories goals |
| 4.5 Ways to cope | How to measure portions |

TABLE 4-continued

| Example Modules | Example Content |
|---|---|
| Module 5: Tracking your ability | |
| 5.1 Scheduling your workout | How to get more active |
| 5.2 Increasing your activity | Relationship between food and calories |
| 5.3 Boosting your energy | X food in = Y calories out |
| 5.4 Stretching and strength training | |
| 5.5 Ways to Cope | |
| Module 6: More about healthy eating | |
| 6.1 More about carbs | Fun food tips |
| 6.2 Your water intake | Complex carbs |
| 6.3 Off-tracking rating | Simple carbs |
| 6.4 Does blood sugar affect weight | Hidden carbs |
| 6.5 Ways to cope | HFCS |
| | H20 |
| Module 7: Burning more than you eat | |
| 7.1 Calories and weight gain | Calories in vs calories out |
| 7.2 Eaten calories | BMR |
| 7.3 Burned calories | What leads to weight gain? |
| 7.4 Calories and weight loss | |
| 7.5 Ways to cope | |
| Module 8: How to improve your GluScore? | |
| 8.1 Internal factors | H20, menstrual cycle, alcohol, time of |
| 8.2 External factors | day, cooking method, medication |
| 8.3 Improving your score | What affects your score? |
| 8.4 Fine-tuning your meals | Sleep, hormone, weather, medicine, |
| 8.5 Ways to cope | food, time of day, water - dehydration, carb quantity and quality, portion size, cooking method, meal planning - healthy plate |
| Module 9: How to shop healthy | |
| 9.1 How to shop healthy? | Ingredient list |
| 9.2 Shopping list | Organic vs non-organic |
| 9.3 How to pick the best one of all? | HFCS |
| 9.4 Healthy shopping on budget | |
| 9.5 Ways to cope | |
| Module 10: Cook healthy to eat better | |
| 10.1 Healthy cooking tips | Tips on preparation, tools, foods, |
| 10.2 Secrets to healthy cooking | creative ideas, spice/herbs, |
| 10.3 Sharpen your cooking skill | ingredients/substitutions, cooking |
| 10.4 Coach Cora's recipe | methods, prepping meals, how to make |
| 10.5 Ways to cope | vegetarian dishes, veganism, how to sneak vegetables to dishes, preserve nutritions |
| Module 11: Manage Success | |
| 11.1 Causes of success | Do's and Don'ts |
| 11.2 The link between stress and chronic disease | Ways to reduce stress |
| 11.3 Success and blood sugar | statistics |
| 11.4 Some ways to reduce mass | |
| 11.5 Ways to cope | |
| Module 12: Keep your heart healthy | |
| 12.1 Why heart health matters | All about omega 3,6 |
| 12.2 How to keep your heart healthy | Healthy fats vs unhealthy fats |
| 12.3 How to be heart smart about fats | |
| 12.4 What do I need to know about fats? | |
| 12.5 Ways to cope | |
| Module 13: Take charge of your thoughts | |
| 13.1 Common challenges and struggles | Food adjustment |
| 13.2 Realize your thoughts | Junk food |
| 13.3 How to understand your mind? | Aggressive Monday |
| 13.4 Getting past plateau | Food availability |
| 13.5 Ways to cope | |
| Module 14: Make about sugar | |
| 14.1 History of sugar | Statistics |
| 14.2 Sugar and health | History |
| 14.3 Sugar substitutes | Sugar amounts in different beverages |
| 14.4 History of sugar substitutes | Sugar alcohol |
| 14.5 Ways to cope | Sugar substitutes |
| | Artificial sweetener |

TABLE 4-continued

| Example Modules | Example Content |
|---|---|
| Module 15: Maintaining healthy habits | |
| 15.1 Should I be on a diet? | Meeting the goal |
| 15.2 Sleep and health | Emphasizing the importance of setting |
| 15.3 The key to behavioral change | goals |
| 15.4 Focus on the right things | Friends, family, coworker support |
| 15.5 Ways to cope | |
| Module 16: Stay Motivated | |
| 16.1 Keep on going | Meeting the goal |
| 16.2 Finding support | |
| 16.3 Keep the great things going | Emphasizing the importance of setting |
| 16.4 Take control | goals |
| 16.5 Ways to cope | Friends, family, coworker support |

In the example of Table 3, a first module can include an introduction module having one or more submodules associated with, for example, a user's particular disease (for example, diabetes), health parameters, health scores, or the health coaching system, application, or interface itself, or other introductory submodules. In another example, a second module can include a food education module having one or more submodules associated with, for example, understanding nutritional values, how to plan meals, how meals interact with blood sugar, ways to cope with food related lifestyle changes, or other food related submodules. In another example, a third module can include a physical education related module having one or more submodules associated with, for example, why one should exercise, how blood sugar and exercise are correlated, how to get active, how activity can help with disease, ways to cope with exercise related lifestyle changes, or other exercise related submodules. In another example, a fourth module can include a food tracking module having one or more submodules associated with food tracking education, such as why to track food, how to measure food, how to read food labels, how and why to pay attention to your food intake, ways to cope with food tracking, or other food tracking related submodule. In another example, a fifth module can include an activity tracking module having one or more submodules, such as how to schedule your work out, increasing your activity, boosting your energy, strength training, ways to cope with exercise changes, or other activity related submodule. In another example, a sixth module can include a more detailed food tracking education module having one or more submodules, such as further education about carbohydrates, water intake, off tracking effects, blood sugar affects, ways to cope, or other food tracking submodule. In another example, a seventh module can include a more detailed activity education module having one or more submodules, such as calorie and weight gain education, other calories related education, ways to cope, or other calorie related submodule. In another example, an eighth module can include a module associated with education on how to improve one or more health related scores, such as a glucose score, having one or more submodules associated with educating a user about factors affecting a user's health risk or score, how to change the score or health risk, ways to cope, or other score related submodule. In another example, a ninth module can include education on how to shop healthy having one or more submodules, such as education on shopping lists, how to pick the best product, healthy shopping on a budget, ways to cope, or other shopping related submodule. In another example, a tenths module can include a healthy cooking education module having one or more submodules, such as how to cook healthy, how to sharpen your cooking skills, following one or more recipes, ways to cope, or other cooking related submodule. In another example, an eleventh module can include a stress management module having one or more submodules, such as a the cause of stress, how stress is correlated with disease, how stress can directly or indirectly impact blood sugar, some ways to reduce stress, ways to cope, or other stress related submodule. In another example, a twelfth module can include a module related to education on heart health, the module having one or more submodules, such as why heart health matters, how to keep a healthy heart, ways to cope, or other heart related submodule. In another example, a thirteenth module can include a module associated with mental health having one or more submodules, such as common challenges and struggles, realizing your thoughts, how to understand your mind, pushing past a plateau, ways to cope, or other thought or mental health related submodules. In another example, a fourteenth can include a module associated with more detailed information about sugar, the module having one or more submodules, such as a history of sugar, sugar and health, ways to cope, or other sugar related submodules. In another example, a fifteenth module can include a module associated with maintaining healthy habits, the module having or more submodules, such as sleep and health, the key to behavioral change, ways to cope, or other maintenance submodules. In another example, a sixteenth module can include a module associated with staying motivated, the module having one or more submodules, such as food and strength training, ways to cope, or other motivation related submodules.

I. 3RD PARTY INTEGRATION

The system 100 may integrate with a third party or third party application through the output engine 324. For example, the output engine 324 can include any number of processes for outputting data to a third party, third party device, or database. For example, the output engine 324 can output data collected, accessed, analyzed, or generated by the system 100, such as health risk or score, recommendations, physiological parameter predictions, user data logs, or other data associated with the user. The output engine 324 may include one or more processes the health coaching system 100 may share data with third parties who have an interest in the health of the user, such as an insurance carrier, an employer, a clinical care provider, or on a social media platform. The data may be shared for a fee, by user request, or as part of an incentive program for the user.

The health coaching system 100 may be part of an incentive program for the user. The incentive program may be provided through a party that has an interest in lowering the user's health risks, such as the user's employer or insurer. For example, an insurance provider may offer lowered rates to a user when they utilize the health coaching system. The incentive program may include monitoring devices to help monitor the user's progress within the system. For example, the user could be provided with a scale equipped with sensors to monitor the user's physiological changes as they proceed through the program, such as heart rate, waist circumference, and BMI, may be provided to a user.

In some configurations, the third party may be a health care provider. For example, the controller 300 may facilitate sharing data with clinicians to aid the user in improving their health. For example, the user's progress may be monitored by the health coaching system 100. This progress may be shared with the user's doctor. The doctor may use the progress information to modify the user's treatment regimen for ongoing health issues. For example, the doctor may lower a user's dose of blood sugar medication if the user's progress shows a reduced average blood glucose level.

In some configurations, data may be shared with other users as part of a user encouragement system. For example, if a user hasn't met any designated milestones for a set period, the system may share this information with a designated support user or coach who may reach out to the user for encouragement or to monitor the user in person. For example, as part of feedback, the system may also utilize social support groups and human health coaches. The controller 300 may connect a number of users to serve as a support group. The users may be connected randomly, by user request, or have some commonality. The commonality may be a shared health goal or goals, a common employer, a nearby geographic location, or shared personal interests. The system 100 may utilize the support group to provide encouragement to users as needed or through in person or virtual meetings. For example, if a user has not recorded their food in three weeks, the system can notify another member of the support group to check in with the user and encourage them to continue logging their food. Similarly, if a user is failing to meet their recommended milestones, the system could notify the human health coach to check in with the user and encourage them to continue with the recommended regimen.

In some examples, third party data 514 may be collected or stored in cloud based storage associated with the health coaching system 100. A controller 300 may be configured to authenticate the collected third party data 514 or other data using the third party data 514. For example, a controller 300 may be configured to corroborate a user input with third party data 514, such as electronic medical record data. For example, a user input may indicate that they have type 1 diabetes. The controller 300 may validate this information by accessing electronic medical record data (EMR) data to detect if type 1 diabetes has been diagnosed for the user. If the controller 300 determines that an input is incorrect or invalid, the controller 300 may notify the user, limit access to one or more aspects of the application or health coaching system 100, attempt to re-validate, or perform another action, such as described herein. If the controller 300 determines that an input is valid, the controller 300 may or may not notify the user, facilitate access to aspects of the application or health coaching system 100 (for example, appropriate educational modules), prompt a user for further inputs, or perform another action, such as described herein.

J. EXAMPLE HEALTH COACHING INTERFACE

Figure 14:
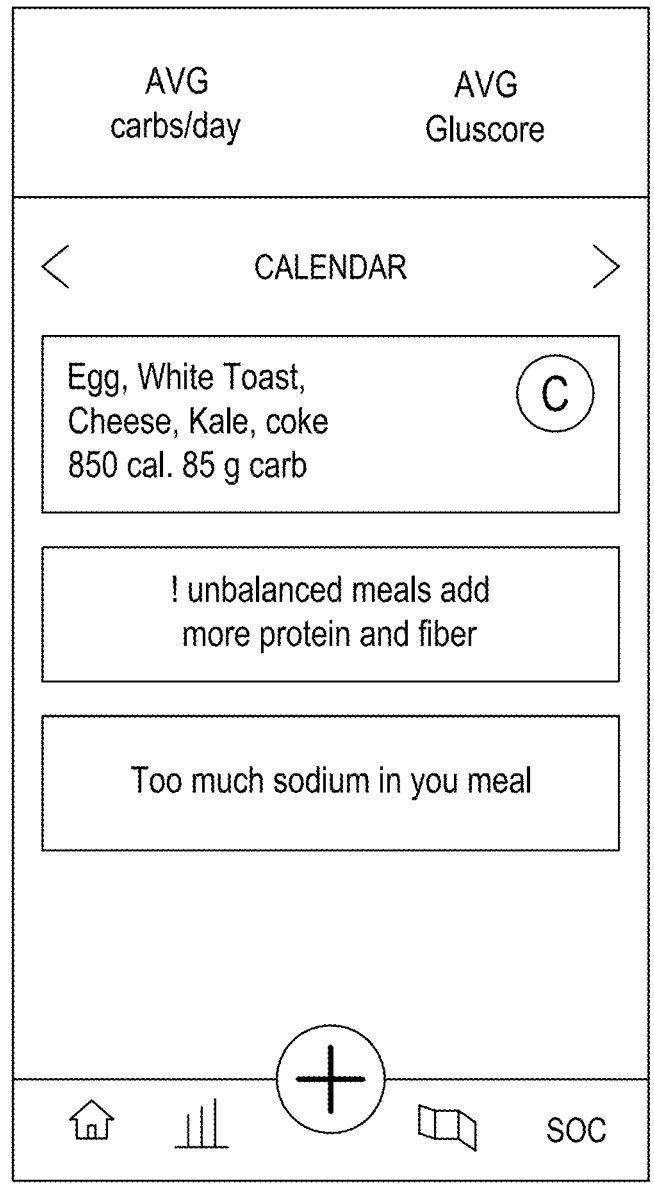

In some examples, a coaching system may utilize a story mode to help a user of the coaching system identify and discover their responses to certain foods, activities, or other lifestyle factors that may affect their health. Advantageously, the story mode may allow a user to more easily understand the factors affecting their health. FIGS. 14-16 illustrate example aspects of a health coaching interface that may facilitate easier use and understanding of the health coaching system and its recommendations.

In some configurations, a coaching system may utilize scheduling, planning, or preparation functionalities to help reduce barriers associated with a user's health coaching experience. FIGS. 14-16 illustrate aspects of a graphical user interface that utilize barrier reducing functionalities to aid in a health coaching experience. The graphical user interface may be accessible through any number of user, patient, caregiver, or other access points or portals, such as an application on a mobile device, computer, wearable device, patient monitor, the like or combination thereof. In some examples, the graphical user interface may be accessible through a web browser. In some examples, the graphical user interface may be accessible through application software.

A graphical user interface (or health coaching interface) may include a plurality of display screens that may enable a user to interact with content associated with the health coaching system. In some examples, the graphical user interface can include a home screen. The home interface may be displayed to a user of the graphical user interface upon initial opening of the application, web browser or other access portal for the health coaching system. FIGS. 14-16 illustrates examples of a home interface 1300 of a health coaching interface. For example, a home interface can include one or more parameter display sections, one or more interaction sections, one or more menu sections, one or more monetization sections, or other interface functionalities.

One or more parameter display sections can include an area 1314 of the interface configured to display one or more physiological parameters, logging values, health scores, health grades, or other values or parameters associated with a user's physical or mental health, parameters associated with a user's use of the application, the like, or some combination thereof. The parameters may be associated with a certain number of past days, most recent logging events, or some combination thereof. For example, as illustrated in FIGS. 15-16, the one or more physiological parameters can include an average weight over the last 7 days, average glucose score, average carbohydrates per day, other health parameters, the like or some combination thereof. In another example, the one or more physiological parameters can include an instant or most recent weight, GlusScore, blood glucose value, other health parameters, the like or some combination thereof.

One or more interaction sections can include an area of the interface configured to display notifications 1304, a calendar, interactive values, logging events, messages, or other coaching interaction components. The one or more interaction sections can be configured to be at a central portion of the screen. In some examples, more than one message or component may appear in the one or more interaction sections. In some examples, the one or more interaction sections can include a scrollable history of previous messages or components.

One or more menu sections can include an area 1310, 1312 of the interface configured to display or accept input associated with access to different functionalities of the health coaching system or graphical user interface. For example, the one or more menusections 1312 can include one or more interactive buttons or components configured to facilitate access to a different aspect of the health coaching system. The one or more interactive components can include a home button, an analytics button, a map button, a social button, a logging button, a chat button 1308, other button or interactive component, the like or some combination thereof.

One or more monetization sections can include an area of the interface configured to display ads 1306 or messages associated with paid content.

While certain types of sections are described with reference to the graphical user interface and/or home screen, the graphical user interface and/or home interface can include more or fewer sections and more or fewer interactive components.

1. Example Logging

Figure 17:
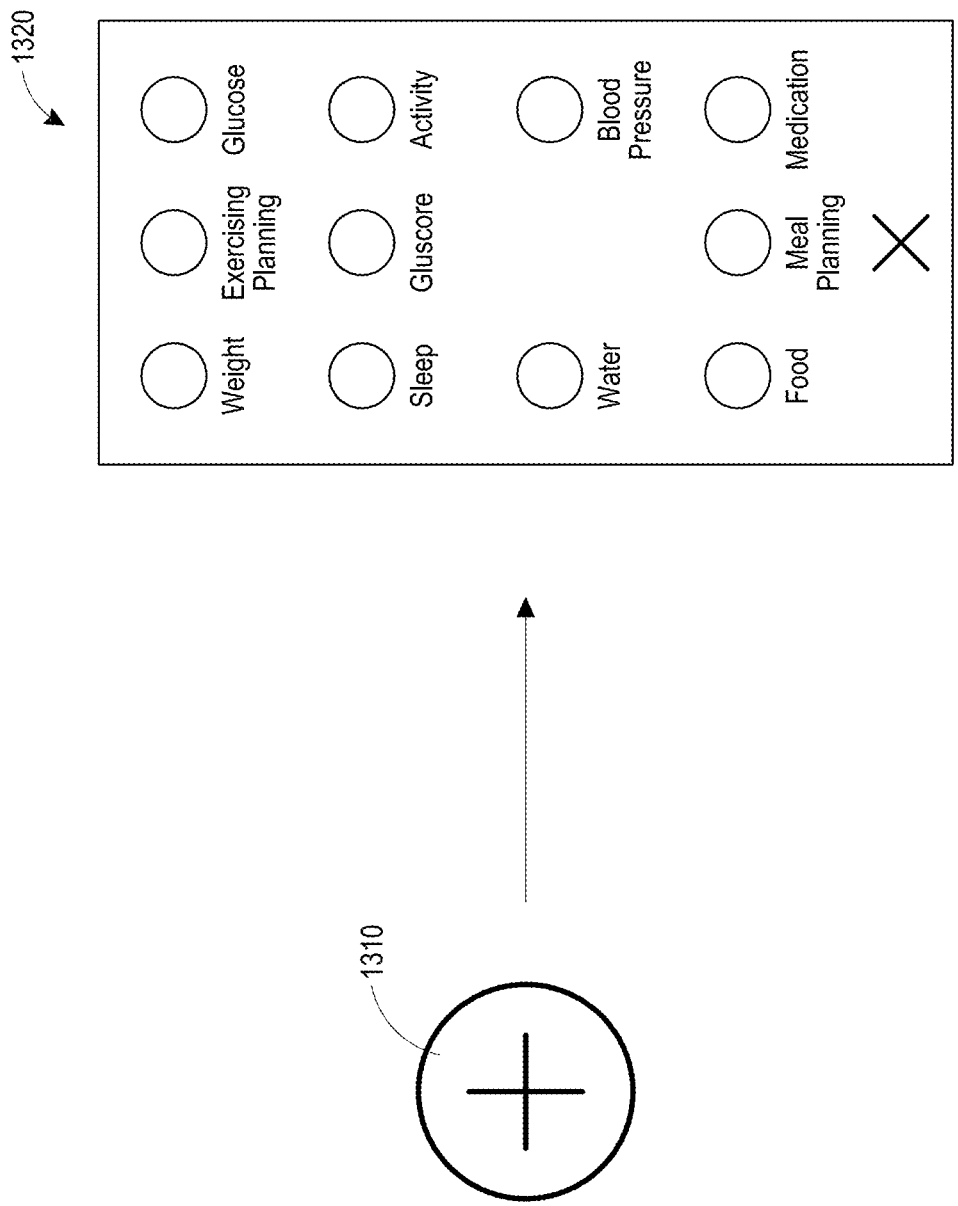
FIG. 17 illustrates an example logging interface that may be brought up by an example logging button on a home interface or other interface associated with a graphical user interface.

FIG. 17 illustrates an example logging interface 1320 that may be brought up by an example logging button 1310 on a home interface or other interface associated with a graphical user interface. The logging interface can include one or more logging options for a user to select that are associated with parameters tracked by the health coaching system. For example, a logging interface can include a weight option, a exercise planning option, a glucose option, a sleep option, an activity option, a food option, a meal planning option, a medication option, other tracking or planning option, the like or some combination thereof. The different logging options may facilitate a user's access to a parameter tracking or logging screen.

Figure 18A:
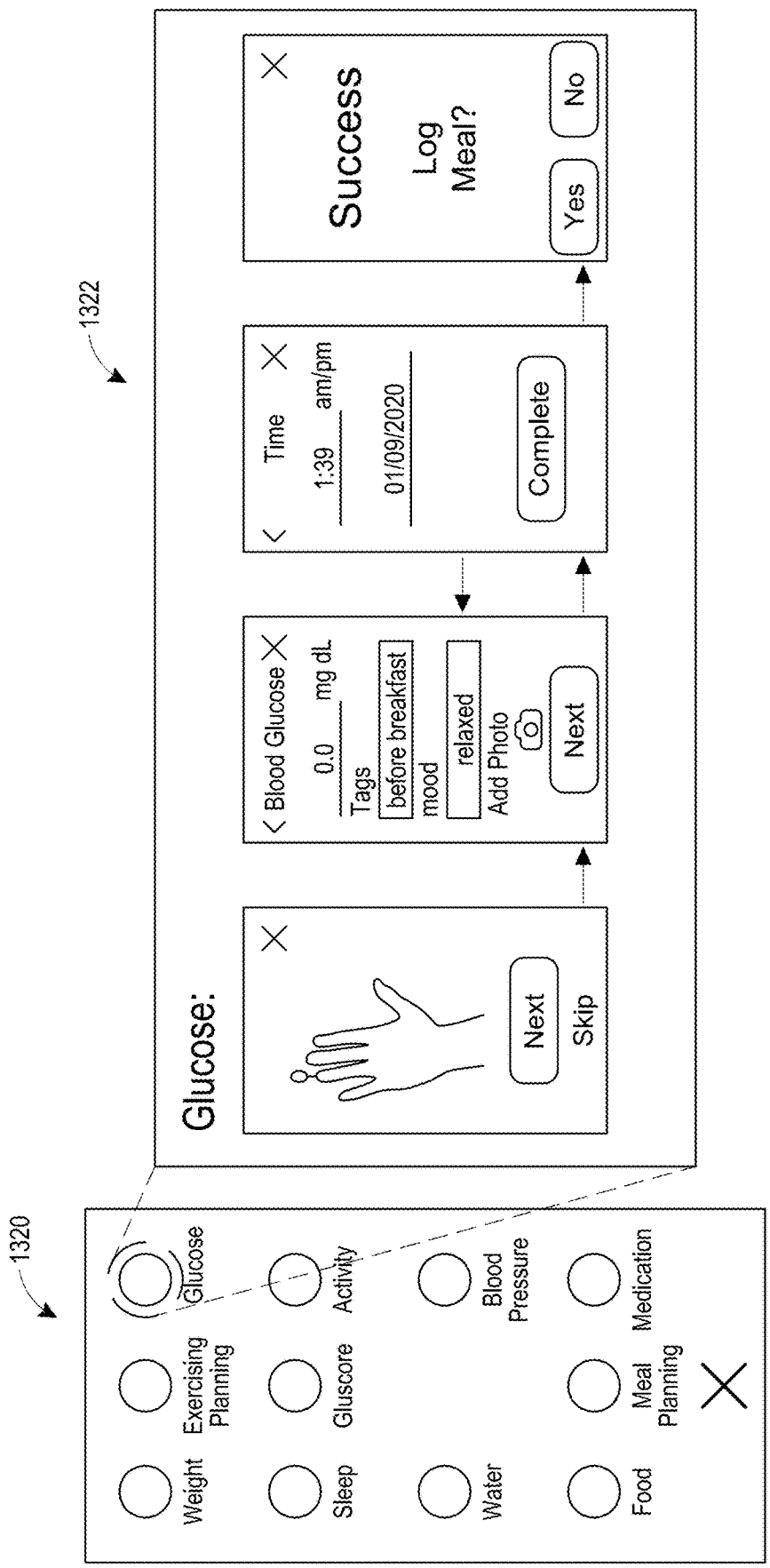
FIGS. 18A-I illustrate example tracking aspects of various parameters.

FIG. 18A illustrates an example glucose tracking aspect 1322 of a health coaching system that may be accessed by a glucose tracking option selection on a logging interface or other aspect of a graphical user interface. For example, a glucose tracking aspect 1322 may include one or more screens to facilitate logging of a blood glucose value. In some examples, a screen can include an instructive or introductory screen associated with measuring glucose through, for example, a blood prick. In another example, a screen can include inputs for blood glucose values, tags for timing of a blood glucose value (for example, before breakfast, after lunch, fasting, the like or a combination thereof), a mood of the user, and/or a photograph input. In another example, an aspect 1322 may include a date and time input. In some examples, an aspect 1322 can include a success or completion message or screen. In some examples, a tracking aspect may facilitate access to educational materials associated with blood glucose.

Figure 18B:
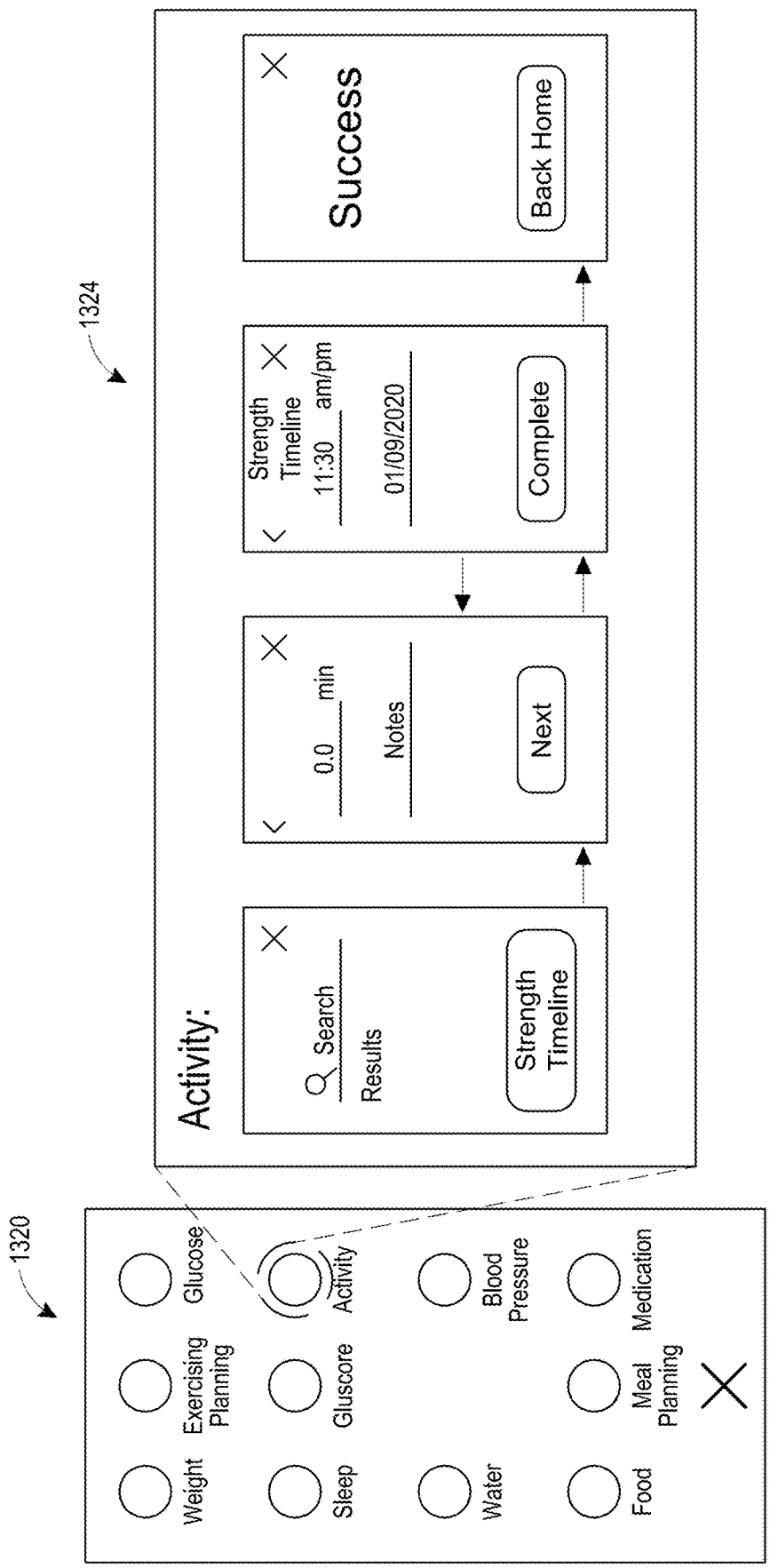

FIG. 18B illustrates an example activity tracking aspect 1324 of a health coaching system that may be accessed by an activity tracking option selection on a logging interface or other aspect of a graphical user interface. For example, a tracking aspect 1324 may include a search screen to facilitate searching and adding of different activity types, such as a strength training regimen. In another example, an aspect 1324 can include inputs for start, end times and/or duration of an activity. In another example, an aspect 1324 may include a success or completion message or screen. In some examples, a tracking aspect may facilitate access to educational materials associated with activity tracking or activities.

Figure 18C:
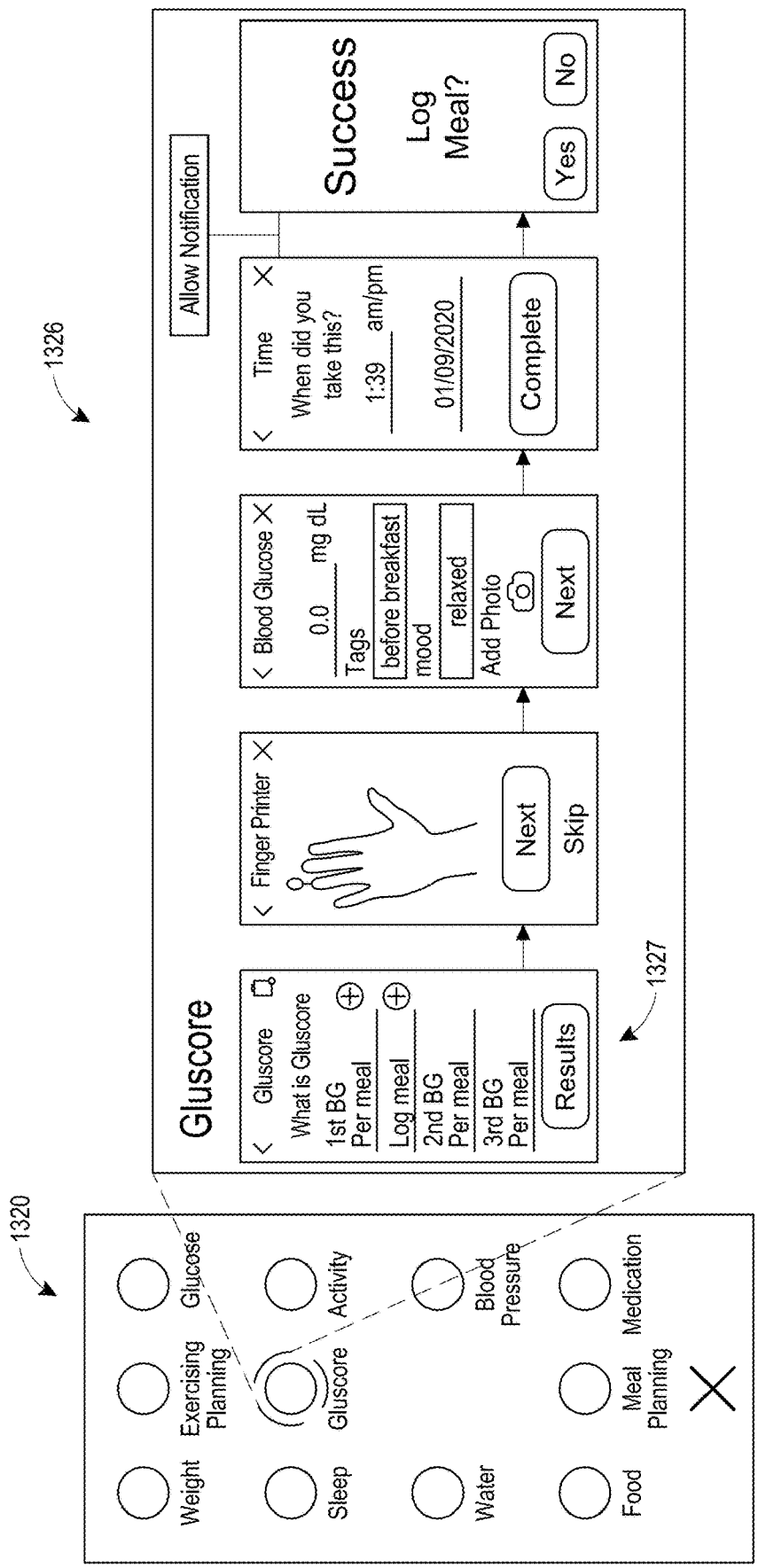

FIG. 18C illustrates an example glucose score or health risk score tracking aspect 1326 of a health coaching system that may be accessed by a glucose score or health risk score option selection on a logging interface or other aspect of a graphical user interface. For example, a tracking aspect 1326 may include GluScore logging related screens, such as one or more screens to facilitate recording of blood glucose data associated with different food intakes of a user. FIG. 18C-1 illustrates an example results aspect 1329 of a health coaching system that may be associated with a glucose score or health risk score. The results section may be accessed from an interactive portion of a glucose score or health risk score tracking screen. In some examples, the results option can include information associated with the glucose score or health risk score, such as a history of different foods and/or glucose score values. In some examples, the results option can include information associated with food related GluScores, such as grades for different types of foods. In some examples, the results option can include graphical data to display how a user's GluScores compare to other user scores eating similar or the same food. In some examples, the results option may include recommendations for foods to eat or avoid based on GluScores. In some examples, a tracking aspect may facilitate access to educational materials associated with GluScore.

Figure 18D:
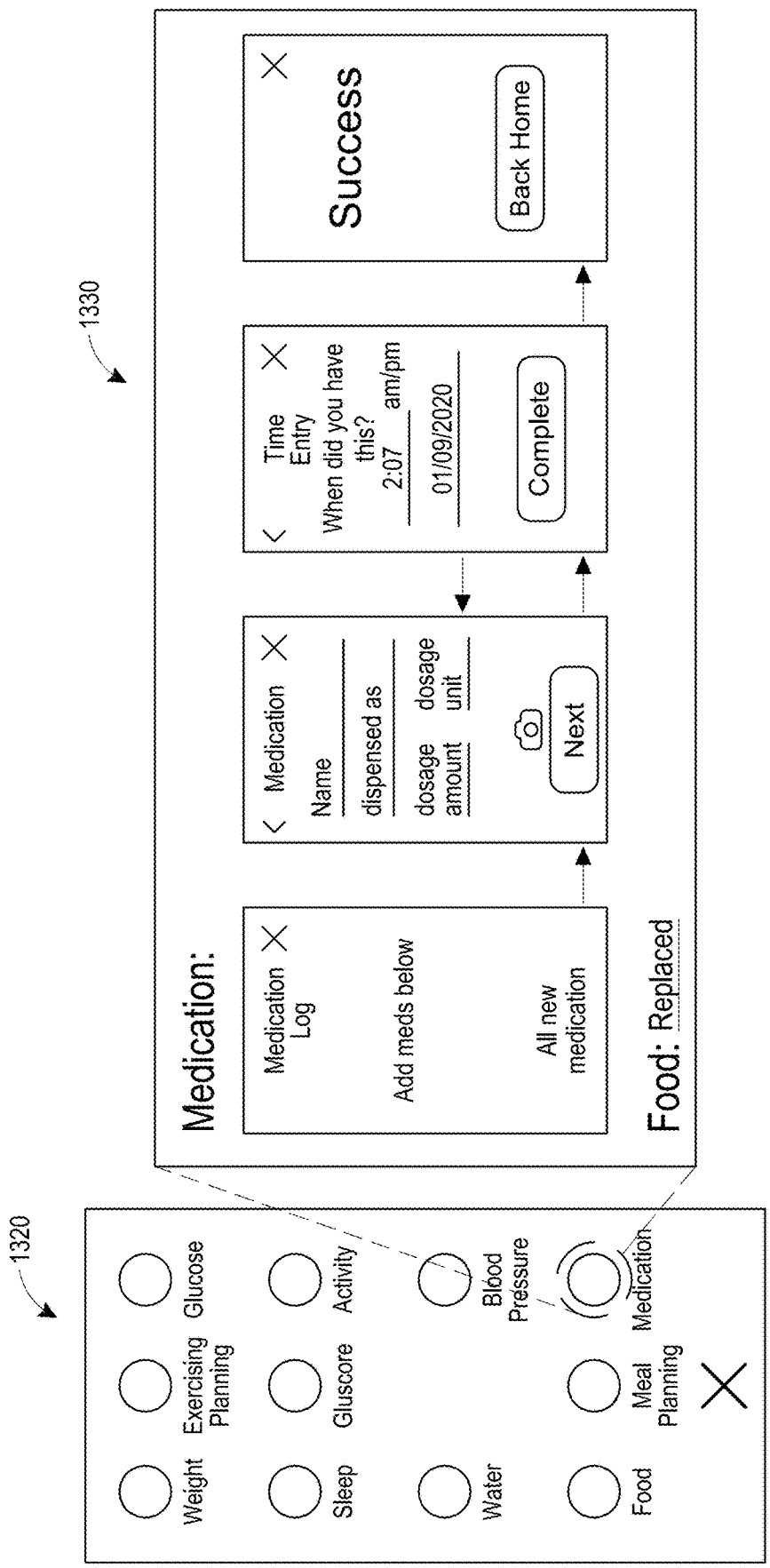

FIG. 18D illustrates an example medication tracking aspect 1330 of a health coaching system that may be accessed by a medication selection option on a logging interface or other aspect of a graphical user interface. A tracking aspect 1330 can include one or more screens for recording values in a medication log. In some examples, the tracking aspect 1330 can include inputs for adding data associated with a medication and when a user has taken the medication, such as a name, dispensation amount, and time of dispensation. In some examples, an aspect 1330 may include a success notification or screen. In some examples, a tracking aspect may facilitate access to educational materials associated with medication.

Figure 18E:
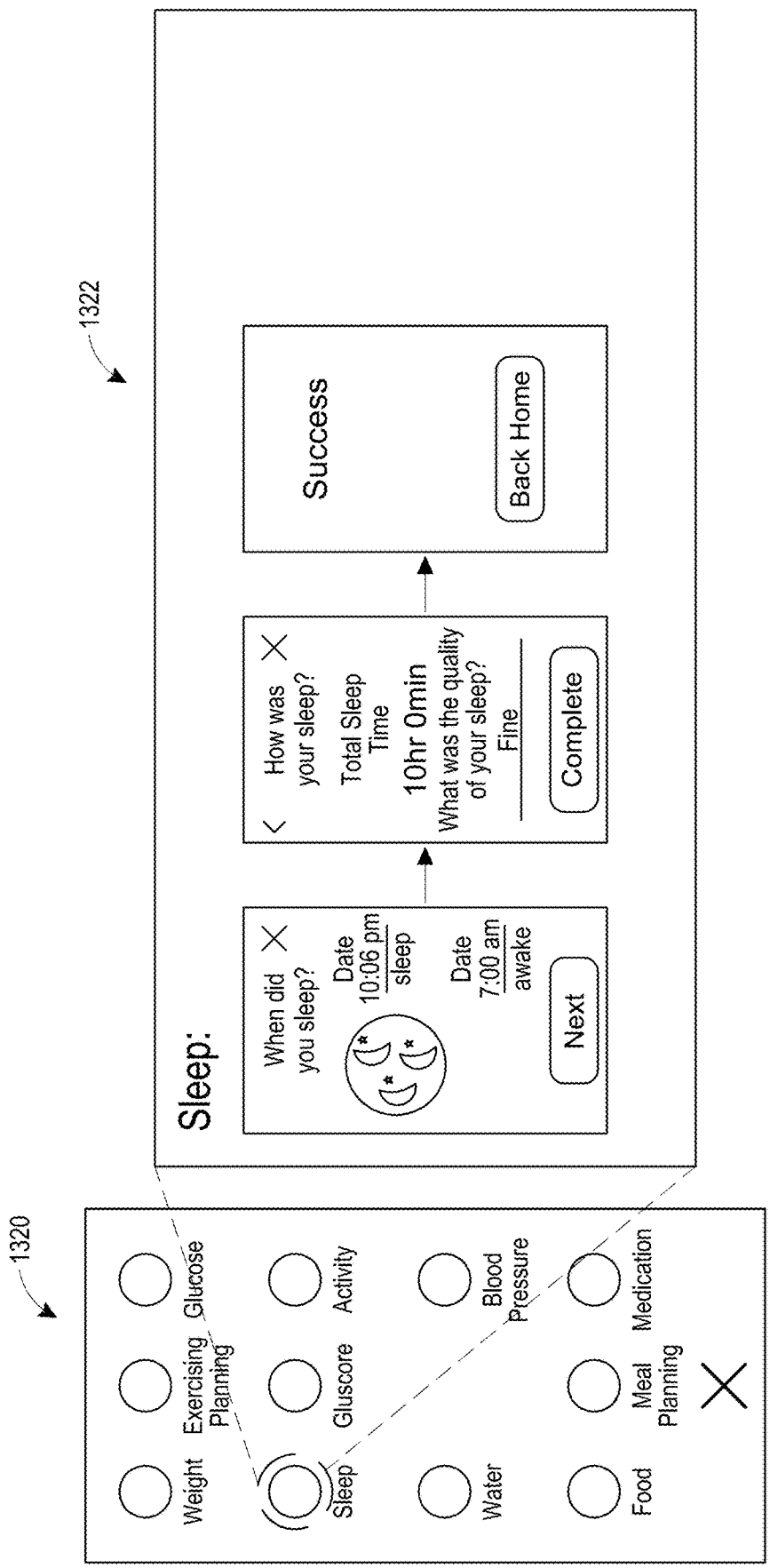

FIG. 18E illustrates an example sleep tracking aspect 1332 of a health coaching system that may be accessed by a sleep selection option on a logging interface or other aspect of a graphical user interface. A sleep tracking aspect 1332 may include one or more screens for accepting inputs for sleeping times, waking times, sleep duration, and sleep quality. In some examples, an aspect 1332 may include a success notification or screen. In some examples, a tracking aspect may facilitate access to educational materials associated with sleep.

Figure 18F:
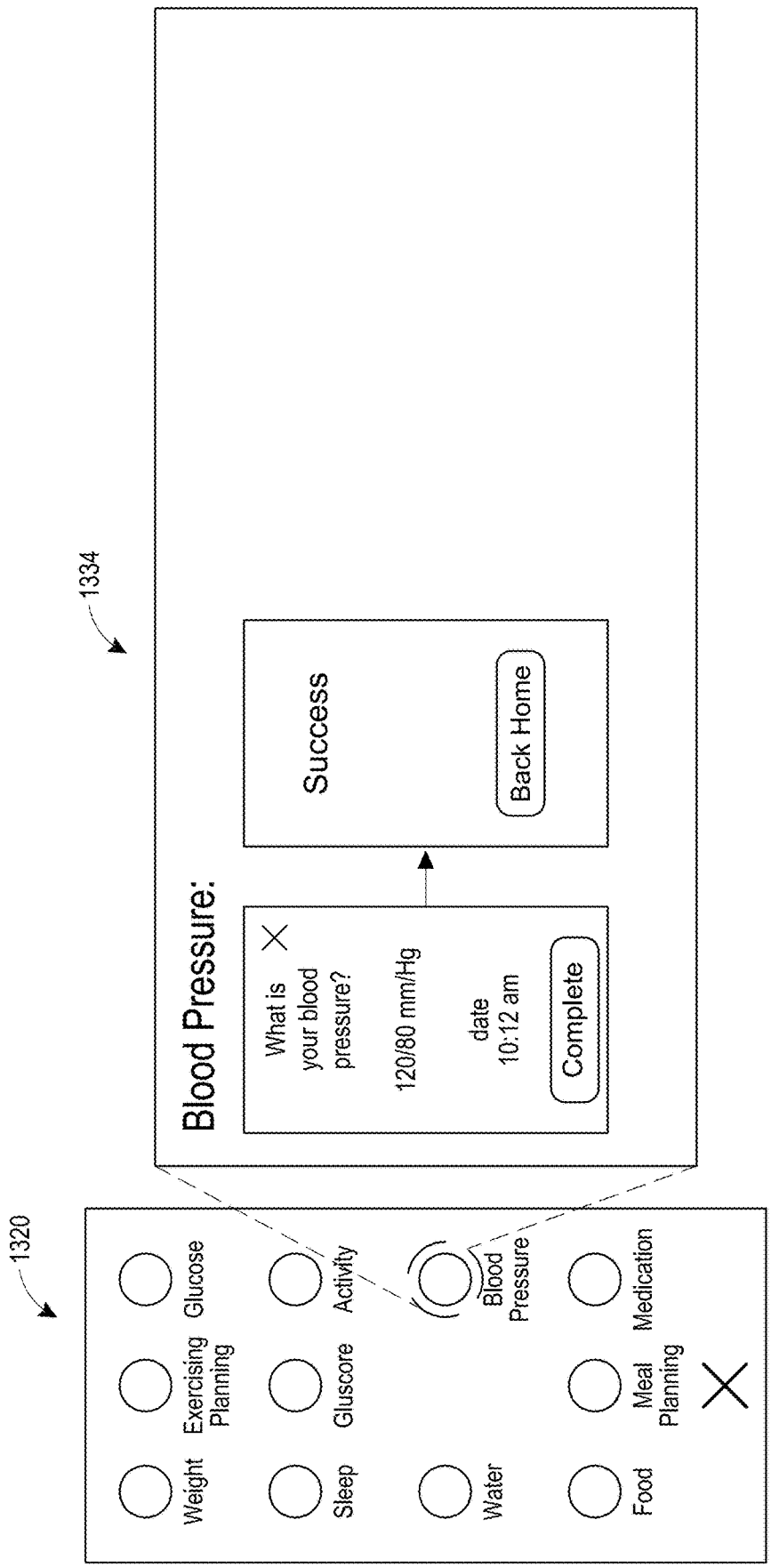

FIG. 18F illustrates an example blood pressure tracking aspect 1334 of a health coaching system that may be accessed by a blood pressure selection option on a logging interface or other aspect of a graphical user interface. A blood pressure tracking aspect 1334 may include one or more screens for tracking blood pressure. In some examples, an aspect 1334 may include inputs for tracking blood pressure, including a blood pressure value input, time of measurement, the like or a combination thereof. In some examples, an aspect 1334 can include a success notification or screen. In some examples, a tracking aspect may facilitate access to educational materials associated with blood pressure.

Figure 18G:
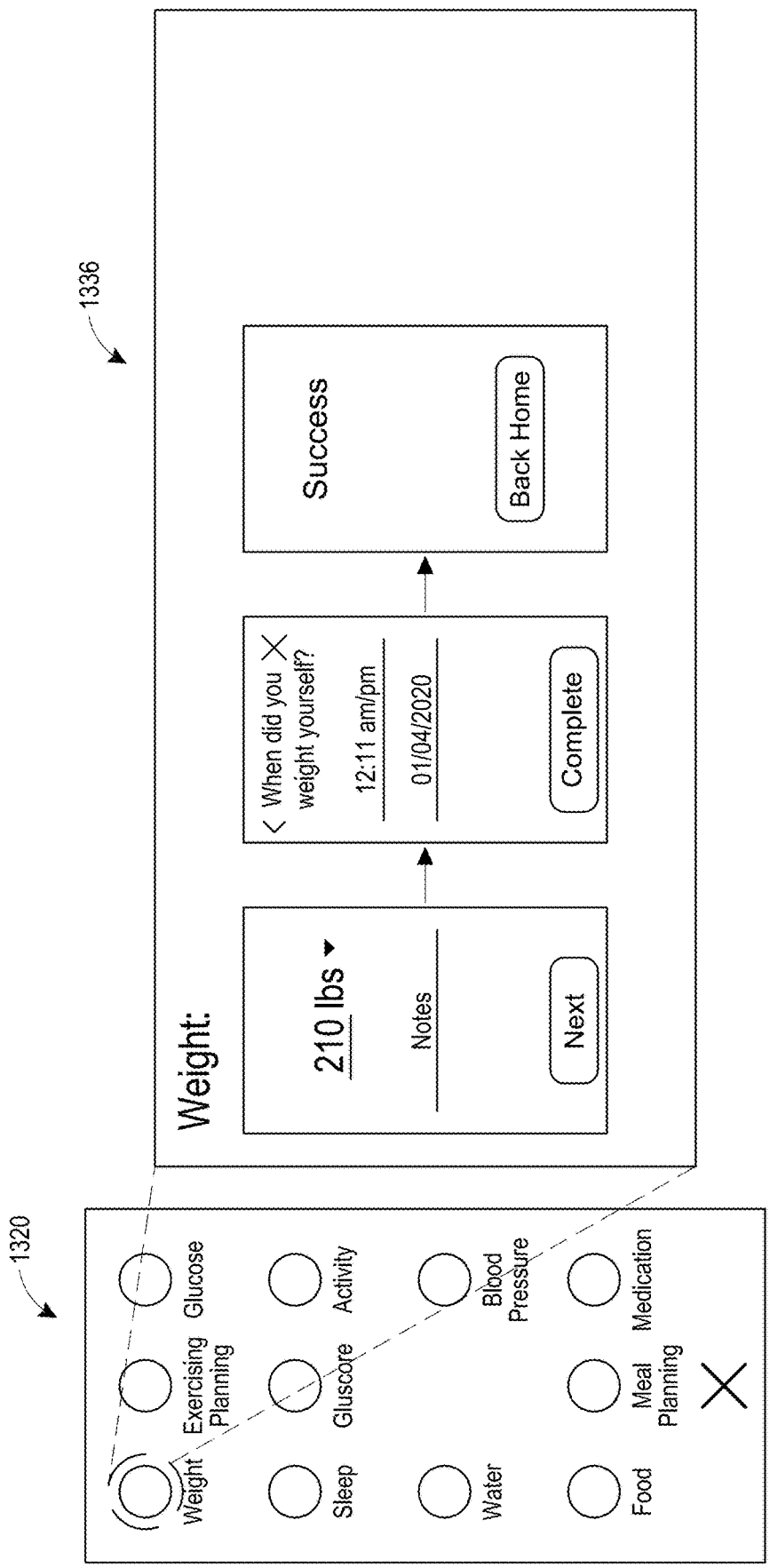

FIG. 18G illustrates an example weight tracking aspect 1336 of a health coaching system that may be accessed by a weight selection option on a logging interface or other aspect of a graphical user interface. A weight tracking aspect 1336 may include one or more screens for tracking weight. In some examples, an aspect 1336 may include inputs for weight, notes associated with a weight value, time and date of a weight in, the like or a combination thereof. In some examples, an aspect 1336 can include a success notification or screen. In some examples, a tracking aspect may facilitate access to educational materials associated with weight.

Figure 18H:
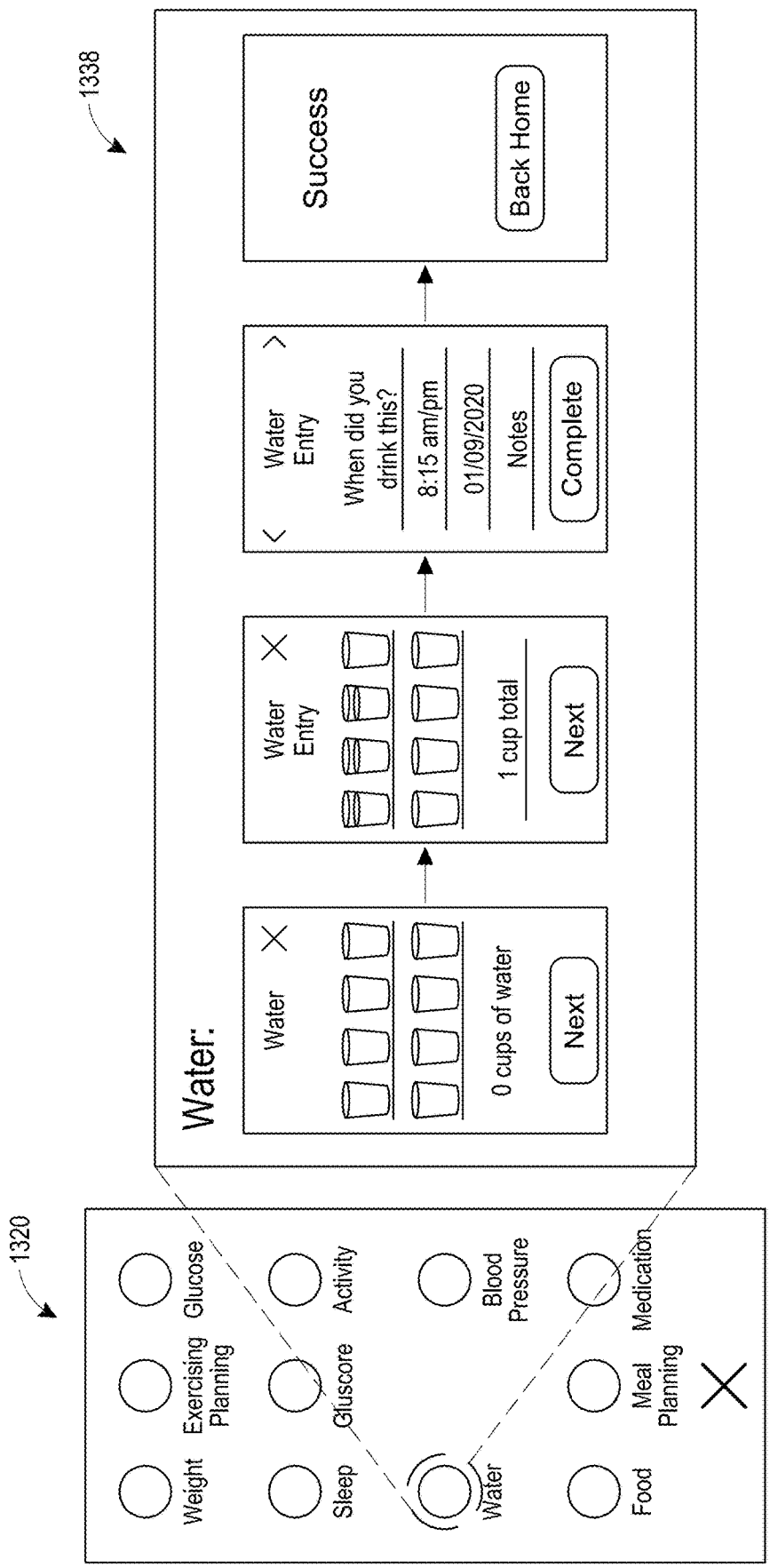

FIG. 18H illustrates an example water tracking aspect 1338 of a health coaching system that may be accessed by a water selection option on a logging interface or other aspect of a graphical user interface. A water tracking aspect 1338 may include one or more screens for tracking water or fluid intake. In some examples, an aspect 1338 may include inputs for a water goal, a water intake, a date and time for water intake, the like or a combination thereof. In some examples, an aspect 1338 can include a success notification or screen. In some examples, a tracking aspect may facilitate access to educational materials associated with water or fluid intake.

Figure 18I:
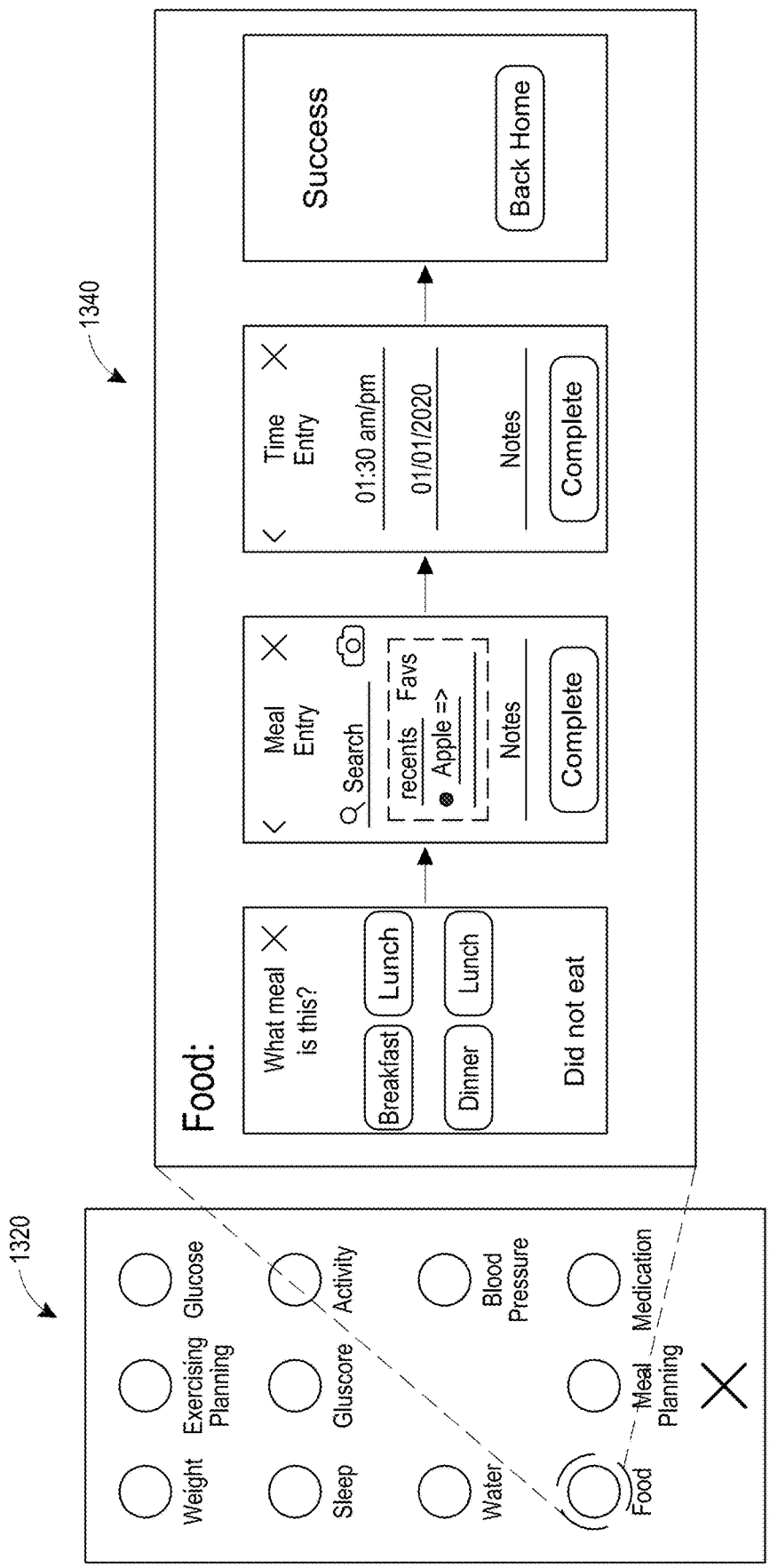

FIG. 18I illustrates an example food tracking aspect 1340 of a health coaching system that may be accessed by a food selection option on a logging interface or other aspect of a graphical user interface. However, other types of food tracking or other aspects of a graphical user interface associated with food tracking may also be possible. A food tracking aspect 1340 may include one or more screens for tracking food intake. In some examples, an aspect 1340 may include inputs or selections for a meal time, a lack of a meal time (such as an input of not having eaten), a search function for finding foods, inputs for adding recent or favorite foods, notes, inputs for a date or time entry of a meal or food intake, the like or a combination thereof. In some examples, an aspect 1340 can include a success notification or screen. In some examples, a tracking aspect may facilitate access to educational materials associated with food or food logging, such as healthy plate information.

a. Example Meal Logging

Figure 19A:
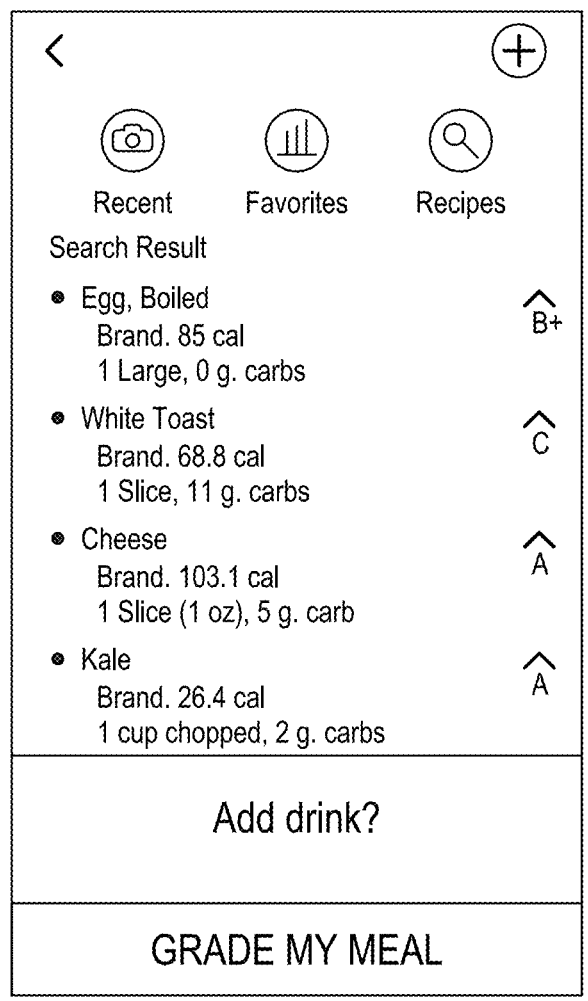

FIG. 19A illustrates an example meal logging (or food tracking) interface that may be associated with a health coaching system and/or graphical user interface. The meal logging interface can include one or more portions configured to display information associated with a person's meal choices or receive meal choice input. For example, a meal logging interface can include one or more search functions, such as a recently logged option, favorites option, and database or web search option. In another example, a meal logging interface can include one or more logged food sections. The one or more logged food sections can include information about logged food, such as a type of food, a brand of food, a calorie content of food, a quantity of food, macronutrient information about the food, and a food score associated with the food. The one or more logged food sections can include a section associated with drinks. For example, one or more logged sections can include a prompt for adding drinks with a meal being logged or display an already logged drink or drinks. The meal logging interface can include an interactive portion configured to allow access to a meal grade. For example, the interactive portion can include a button for to grade the currently logged meal.

Figure 19B:
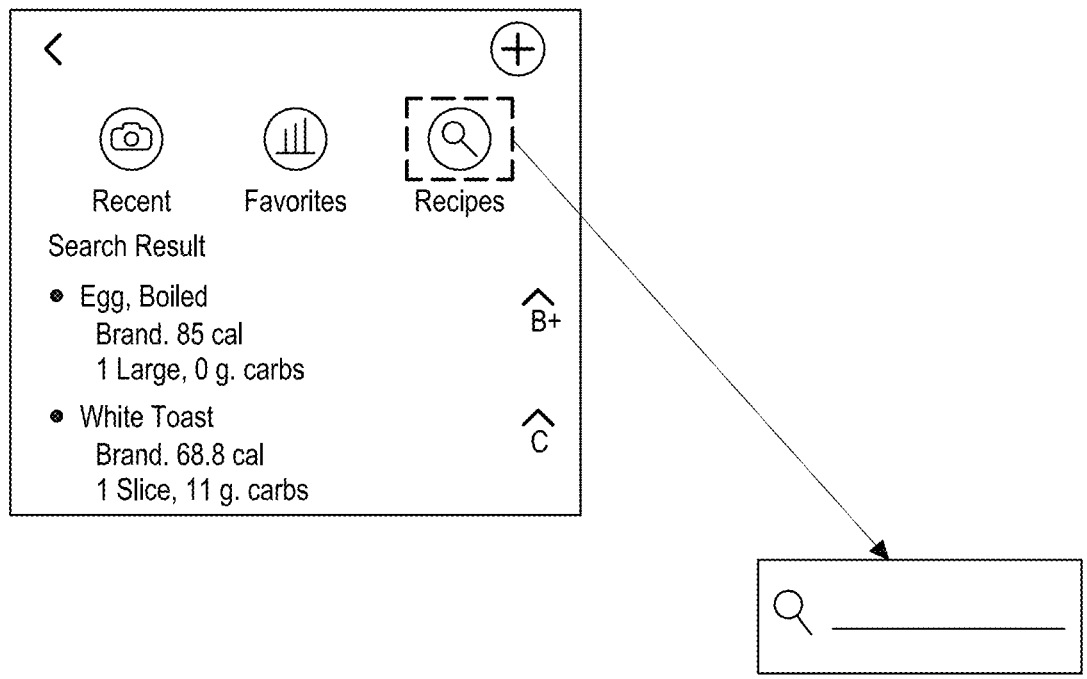

As illustrated in FIG. 19B, a food search button can allow a user to search a food database or the web.

Figure 19C:
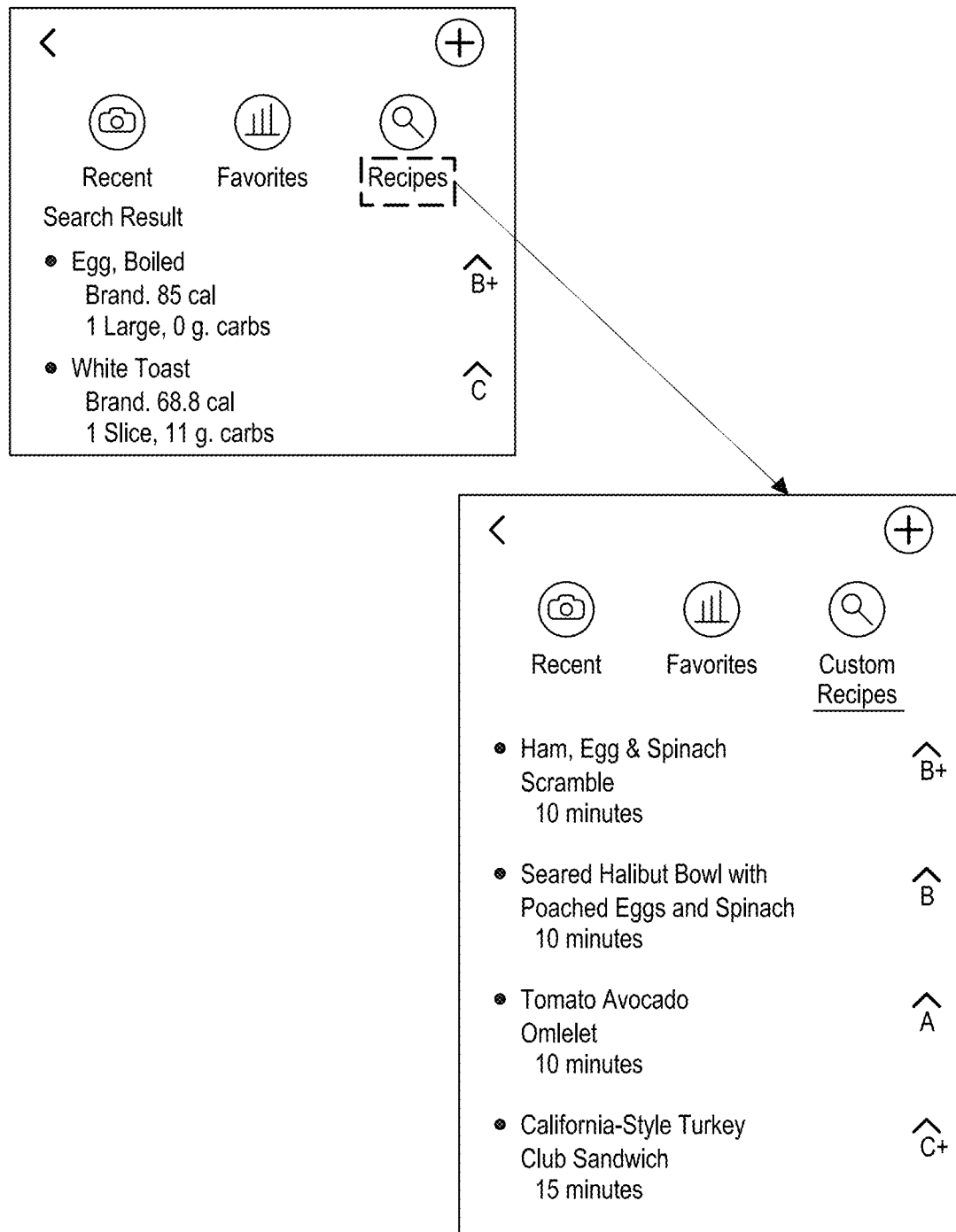

As illustrated in FIG. 19C, a meal logging interface can include a recipe search aspect. The recipe search function can include one or more previously saved recipes that the user may log, For example, the recipes can be recipes saved by the user, another user, from a web search, preloaded into the health coaching interface or from another source. A user may select the recipe to log the recipe as a meal. In another example, a user may upload a recipe or save a current meal as a recipe.

Figure 19D:
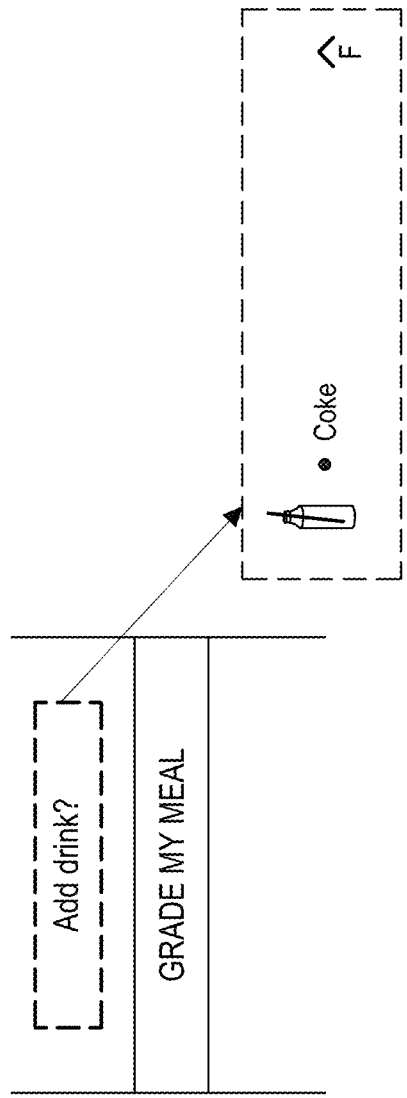

As illustrated in FIG. 19D, a meal logging interface can include an add drink option. The add drink option may include suggested drinks, such as water and provide suggestions for swaps for logged drinks. For example, a user may log a soda. The health coaching interface may grade the soda low on a health scale and suggest a different option. Additionally or alternatively, the health coaching interface may calculate a score for the meal as a whole given the chosen option and suggest an alternative in light of the whole meal.

Figure 19E:
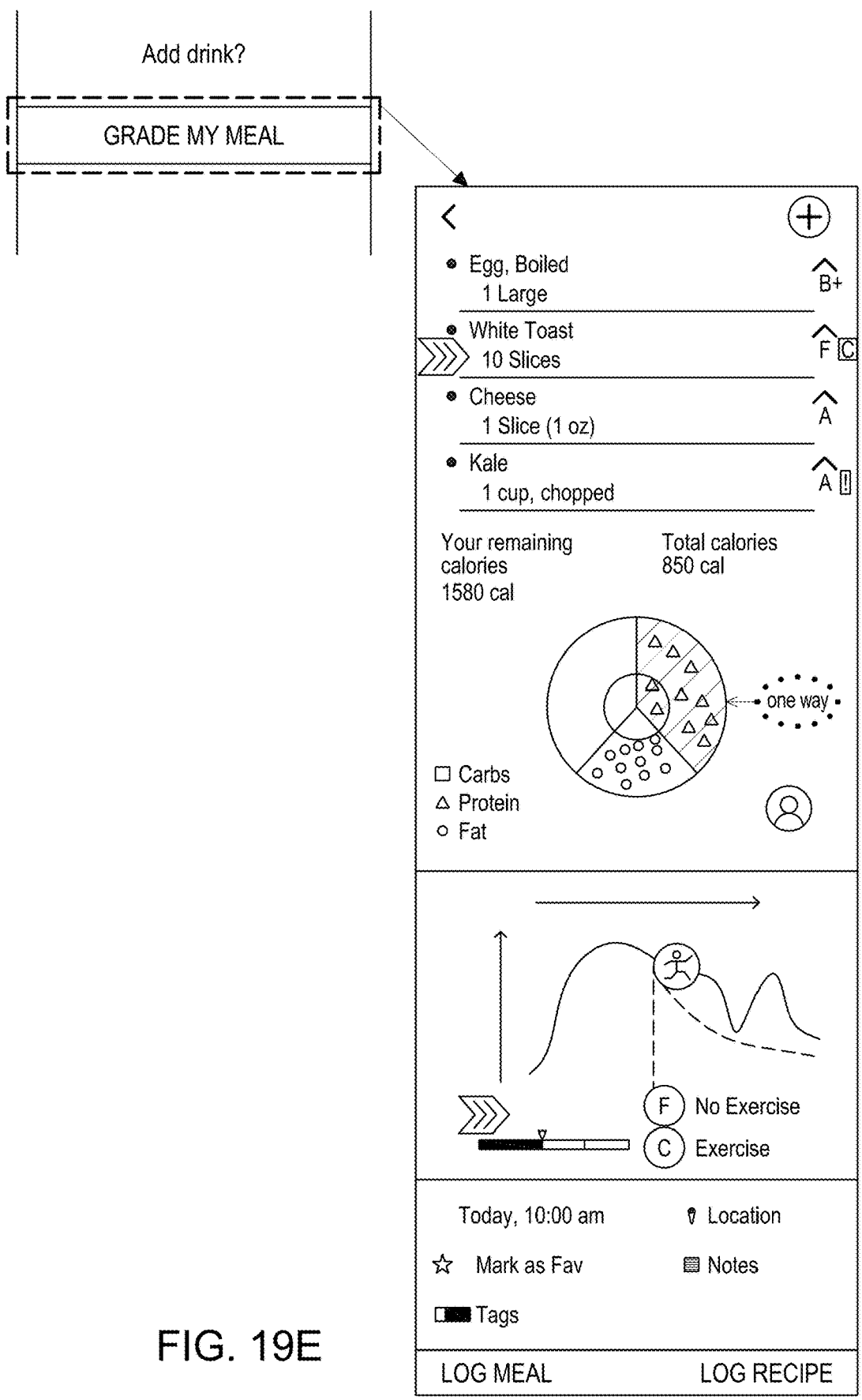

As illustrated in FIG. 19E, a meal logging interface can include a grade meal option. The grade meal option can include a button or other interactable element of the meal logging interface that may facilitate a user's access to one or more meal metrics.

Figure 19F:
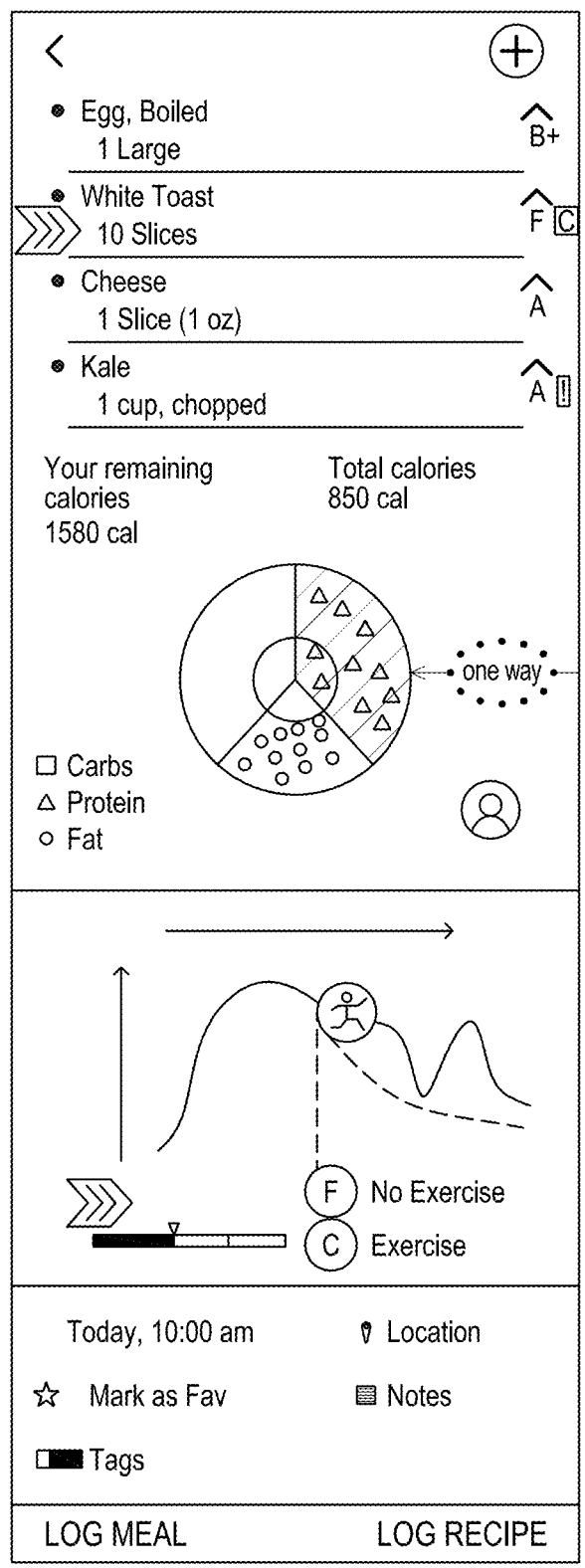
Figures 1A, 19F:
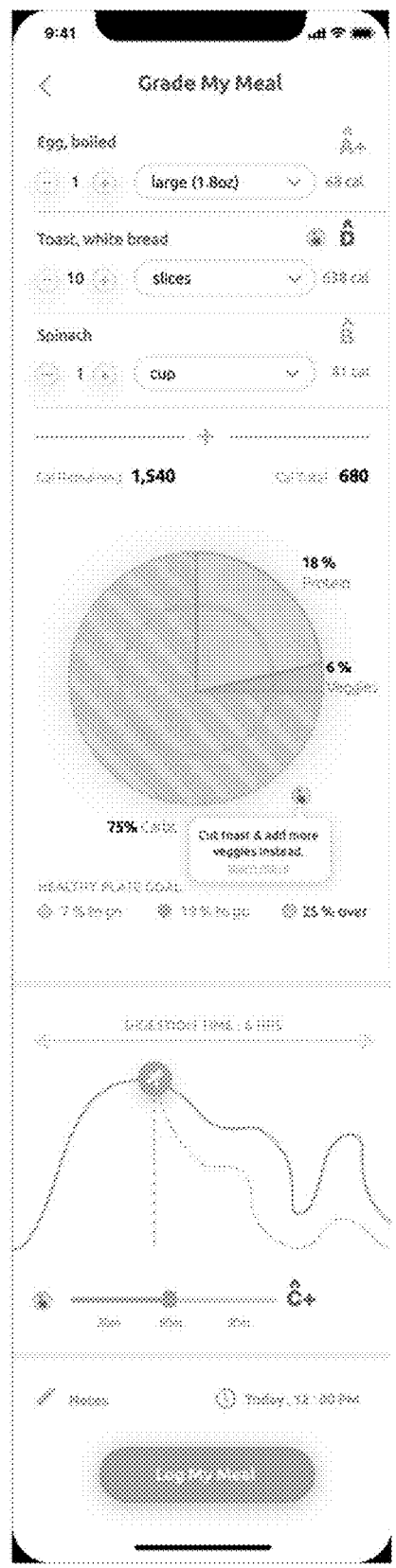
Figures 1, 19F:
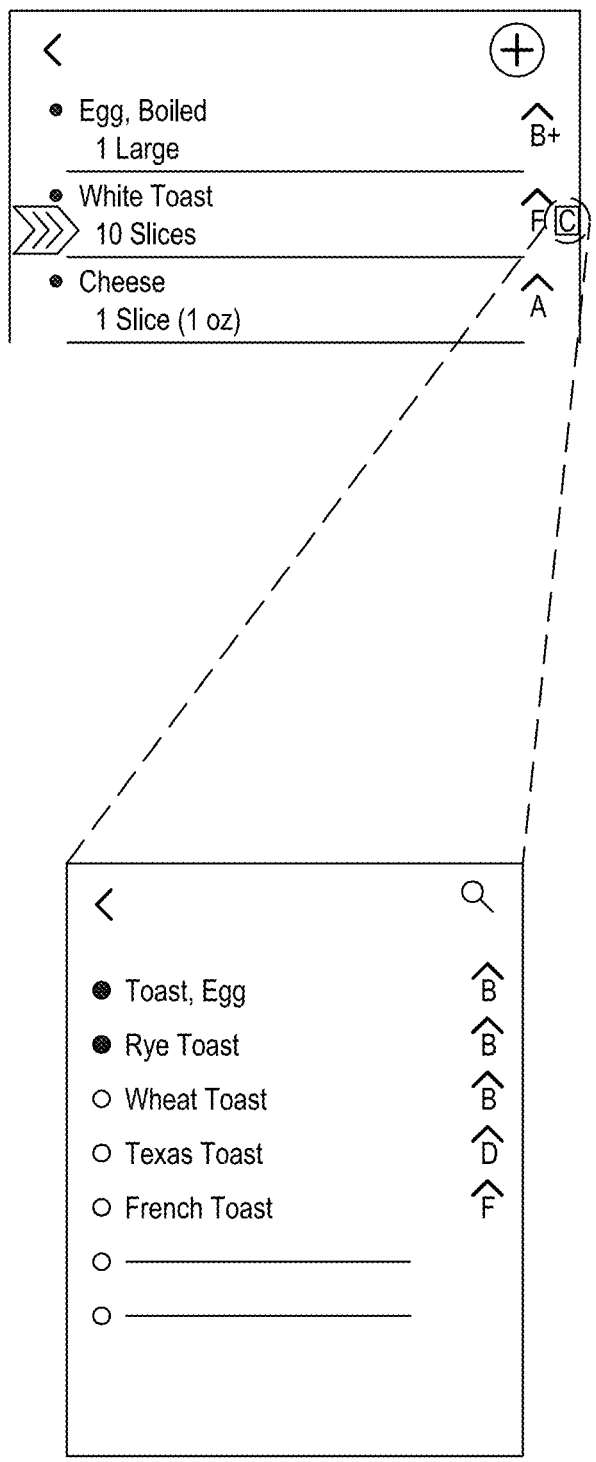
Figures 2, 19F:
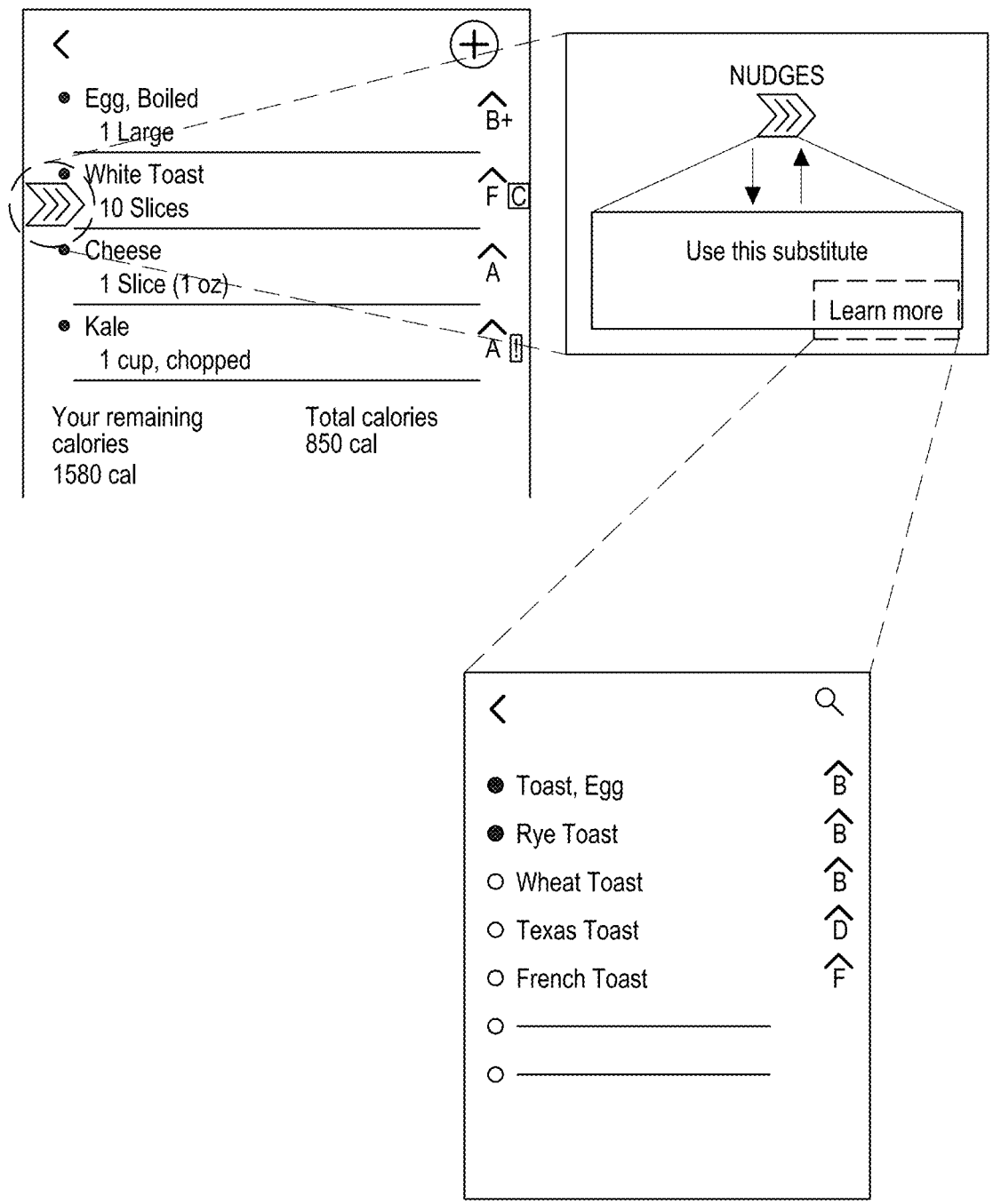
Figures 3, 19F:
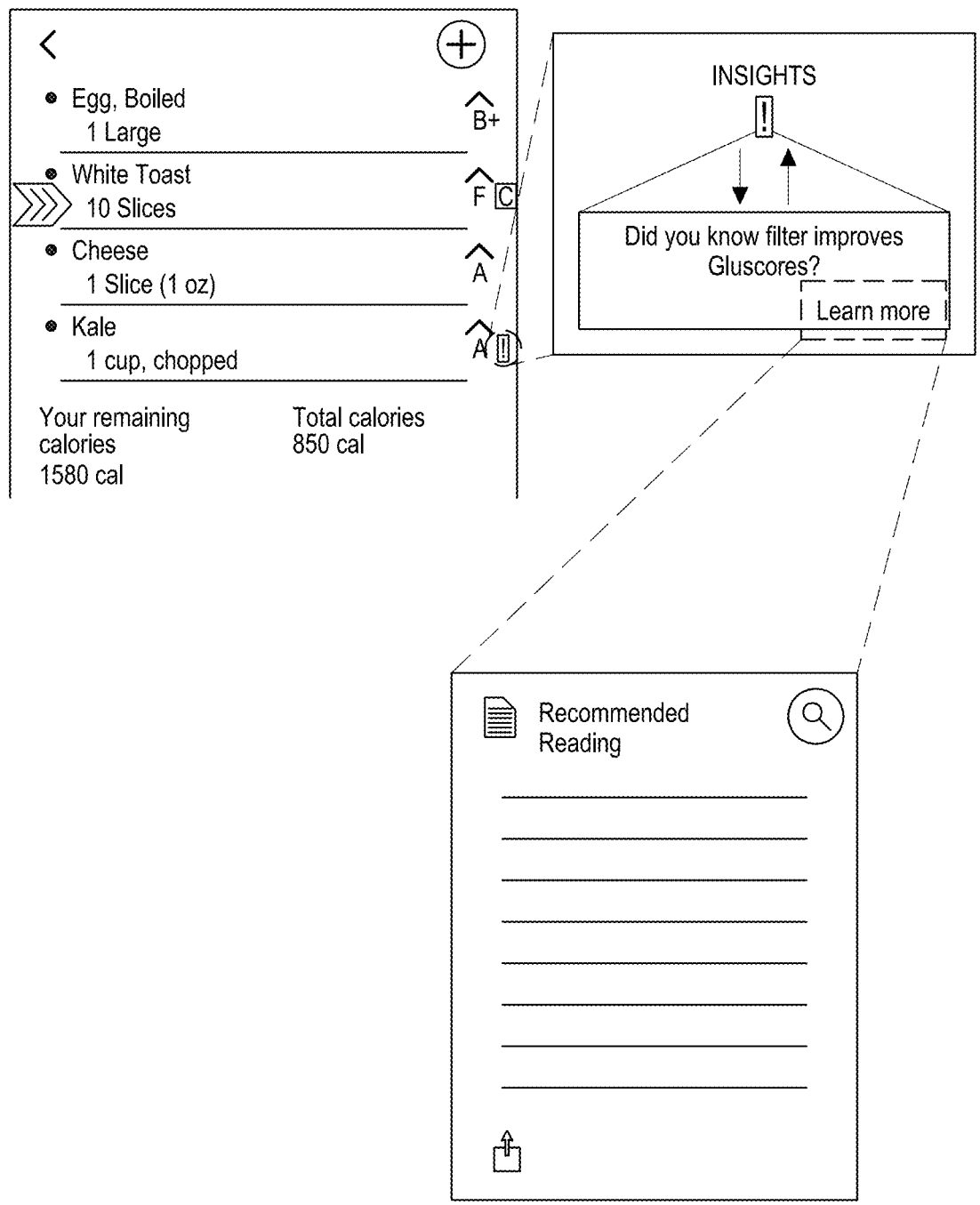
Figures 4, 19F:
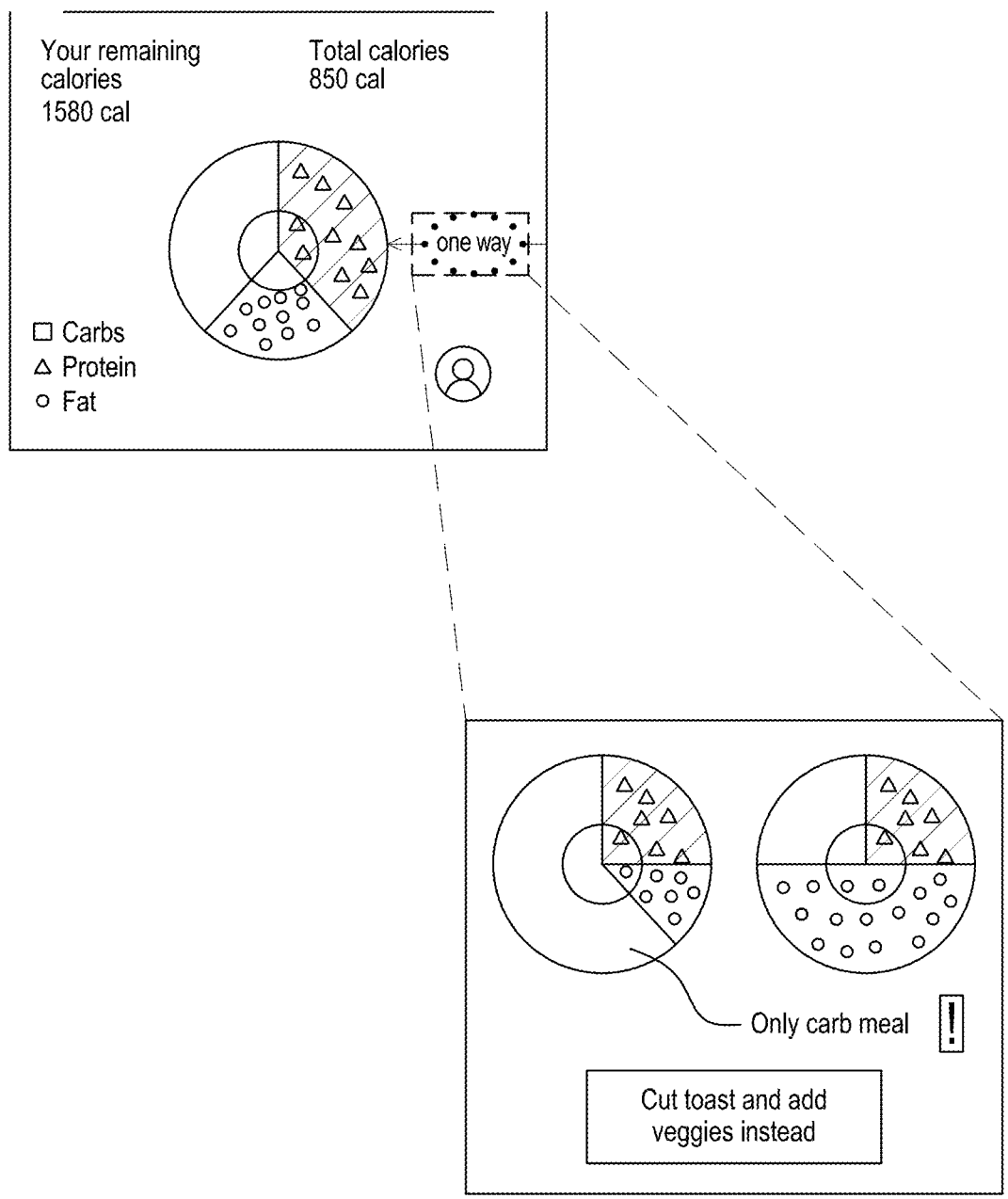
Figures 5, 19F:
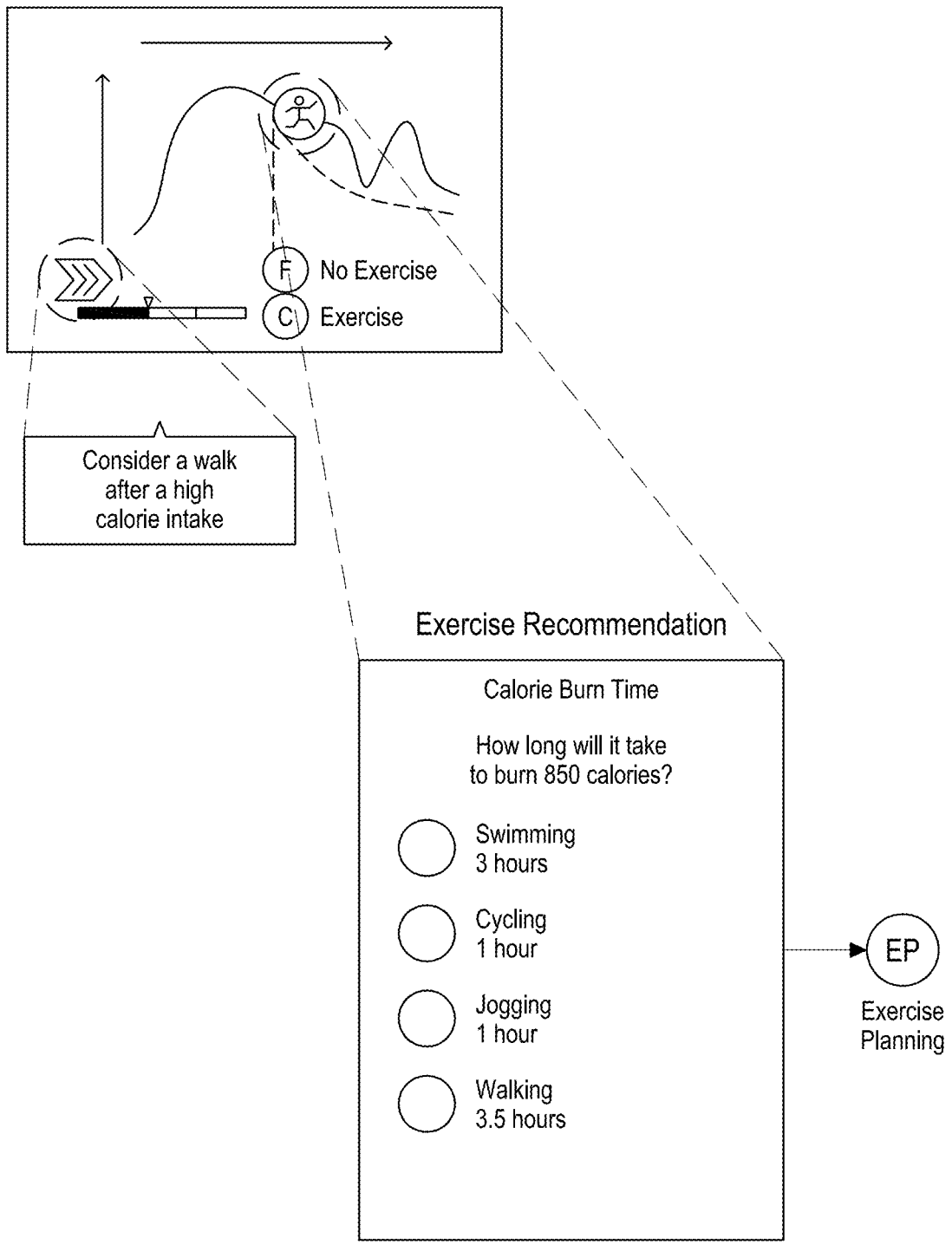

FIGS. 19F and 19F-1A illustrate example metrics display interfaces that may be accessed via the one or more interactable elements. In some examples, the metrics display interface can include some combination of scores for individual foods, metrics about the macronutrient and/or calorie content of a meal being logged, predictive parameters or metrics associated with an anticipated blood glucose, health risk score (such as a glucose score), suggestions related to how to improve a meal for the user's particular or general health, access to a coach or chat AI, other metrics or health coaching functionalities, or the like. In some examples, a user may be forced to go through the metrics display interface associated with a meal being logged prior to logging a meal or a recipe. Advantageously, this may force a user to confront the effects of their food choices.

FIG. 19F-1 illustrates an example food substitute interface that may be part of a meal logging interface. The food substitute interface may show one or more options that are identified by the health coaching system as reasonable substitutions for the food in the process of being logged. For example, if a user records 10 slices of white bread in a recipe, the health coaching system may identify that food as having a low health score. Additionally or alternatively, the health coaching system may suggest one or more foods similar to white bread, such as whole wheat bread, that may have an equivalent or higher quality health score. Access to the food substitute interface may be facilitated by an interactive button, area, or other portion of the meal logging interface. For example, a meal logging interface may indicate that the health coaching system 100 has a substitution recommendation next to a food with a low grade or score. In some examples, the interactive button, area, or other portion of the meal logging interface may include a recommendation graphic or notification.

FIG. 19F-2 illustrates an example food logging related nudge. The nudge may be triggered by a low health score of a food in the process of being logged. The health coaching system may display an interactable graphic associated with the nudge. In the illustrated example, the nudge includes a suggestion to substitute a food with a healthier option. In the illustrated example, the nudge may allow a user to access the food substitute interface discussed above with reference to FIG. 19F-1. A nudge notification may include a graphic, push notification, interactive button, area, or other portion of the meal logging interface. In some examples, interaction with a nudge notification may facilitate display of information associated with the nudge notification, such as information about the use of a substitution. In some examples, the displayed information may include one or more options to expand on the presented information, such as a link to information to "learn more" about the nudge, recommendation, or other interaction.

FIG. 19F-3 illustrates an example educational interface or aspect that may be part of a meal logging interface. The educational interface can include a nudge or insight associated with an identified aspect of the meal logging process. For example, a health coaching system may identify that a user is logging kale. The health coaching system may further identify that kale has a good or high health score. The health coaching system may display an interactable graphic associated with the insight. The interactable graphic may facilitate access to education content related to how kale has fiber or how fiber is good for a user's health or health risk score. An insight notification may include a graphic, push notification, interactive button, area, or other portion of the meal logging interface. In some examples, interaction with am insight notification may facilitate display of information associated with the insight notification, such as information about a GluScore or other aspect of tracking. In some examples, the displayed information may include one or more options to expand on the presented information, such as a link to information to "learn more" about the insight, recommendation, or other interaction, such as recommended reading relating to the insight.

FIG. 19F-4 illustrates an example aspect of a meal logging interface that may include meal metrics. For example, the meal logging interface can include information associated with a total calorie content of a meal, a remaining calorie content for a day, how a user's current meal fits in with the balance of what they have previously logged, recommend how a user's meal should break down in terms of macronutrients, show a current breakdown of macronutrients, provide nudges, insights, or other suggestions related to how to improve a meal's overall macronutrient balance, provide other meal related metrics, the like, or a combination thereof.

FIG. 19F-5 illustrates an example aspect of a meal logging interface that may include blood glucose metrics or other health risk related metrics. For example, a meal logging interface can include one or more graphics illustrating an estimated blood glucose response associated with the meal. The estimated blood glucose response can be based on a glucose insulin meal model (GIMM). In some examples, a meal logging interface can include an estimate of how an exercise or exercise recommendation can affect the predicted glucose response. For example, a health coaching system can include a grade for a meal with an exercise or without an exercise. In some examples, a health coaching system may provide an exercise recommendation based on an estimated calorie burn time needed to improve a meal grade. An exercise recommendation may include a graphic, push notification, interactive button, area, or other portion of the meal logging interface, such as a graphic associated with an exercise in context of predicted glucose values. In some examples, interaction with an a recommendation notification may facilitate display of information associated with the exercise recommendation, such as information about a burn or activity time for different types of exercise in relation to a certain number of calories. In some examples, the displayed information may include one or more options to expand on the presented information, such as a link to information to "learn more" about the recommendation or other interaction. In some examples, the interaction may facilitate access to an exercise planning aspect of an interface.

2. Example Analytics

Figure 20A:
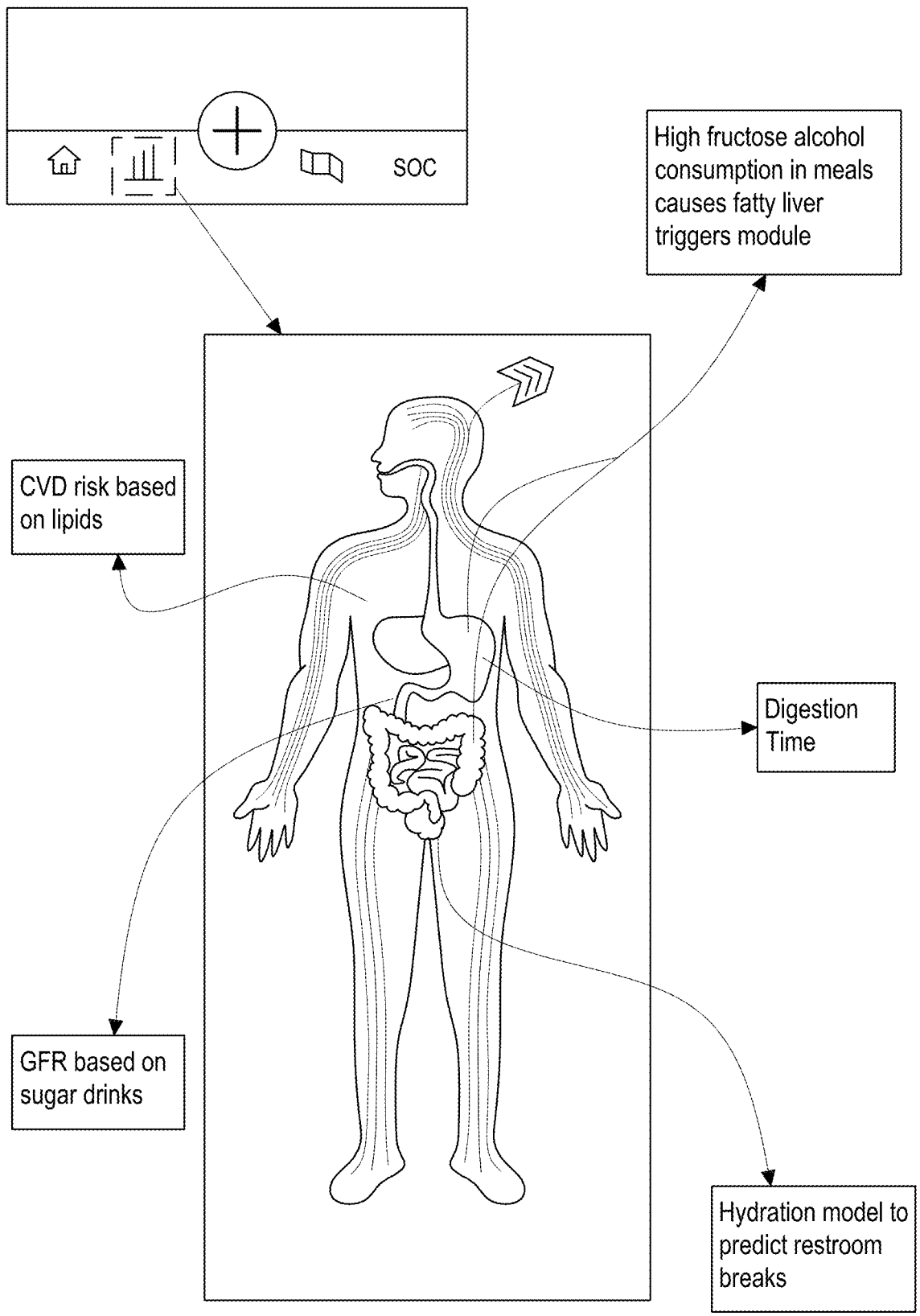
FIGS. 20A-J illustrate example aspects of an analytics interface.
Figure 20B:
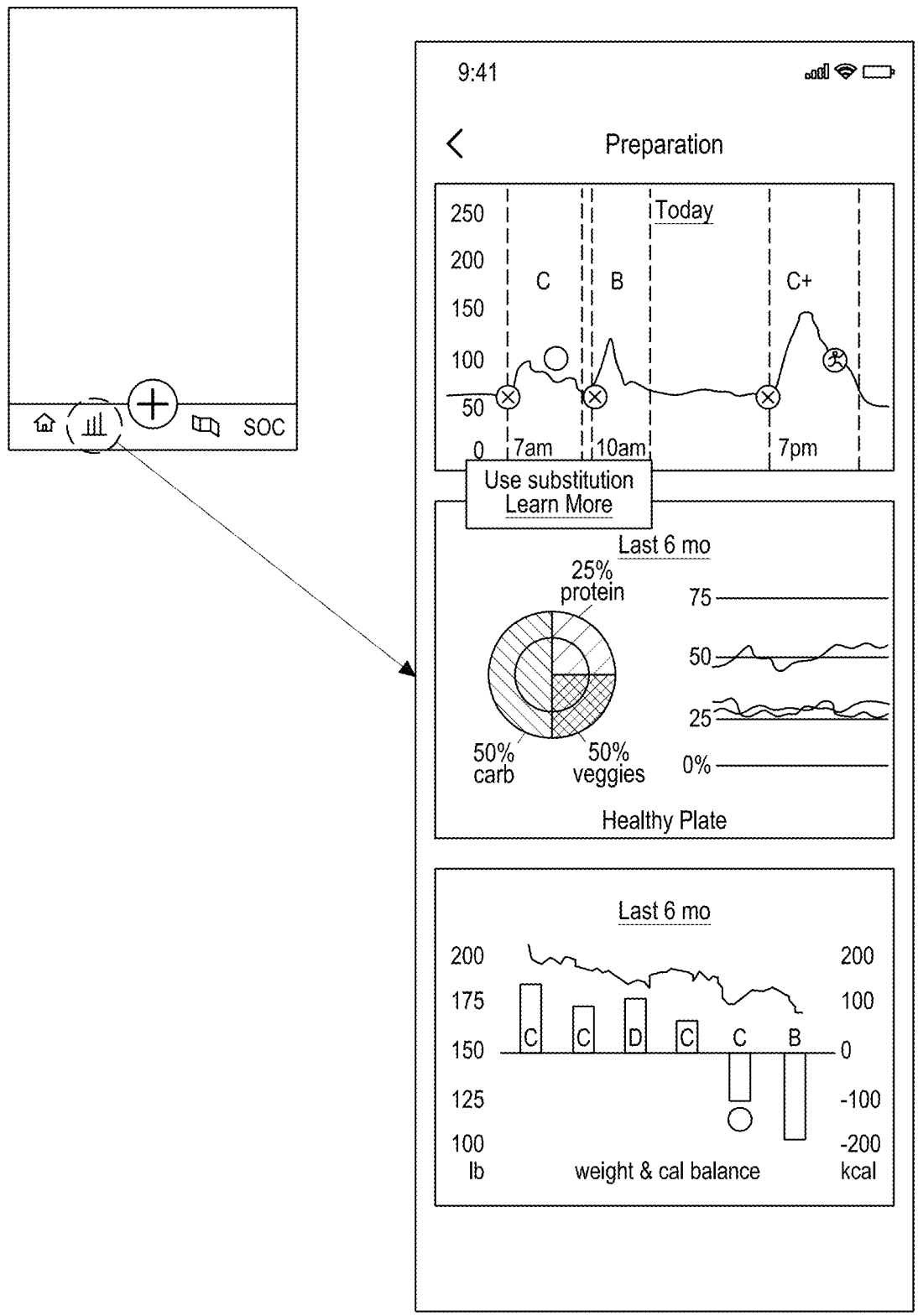
Figure 20C:
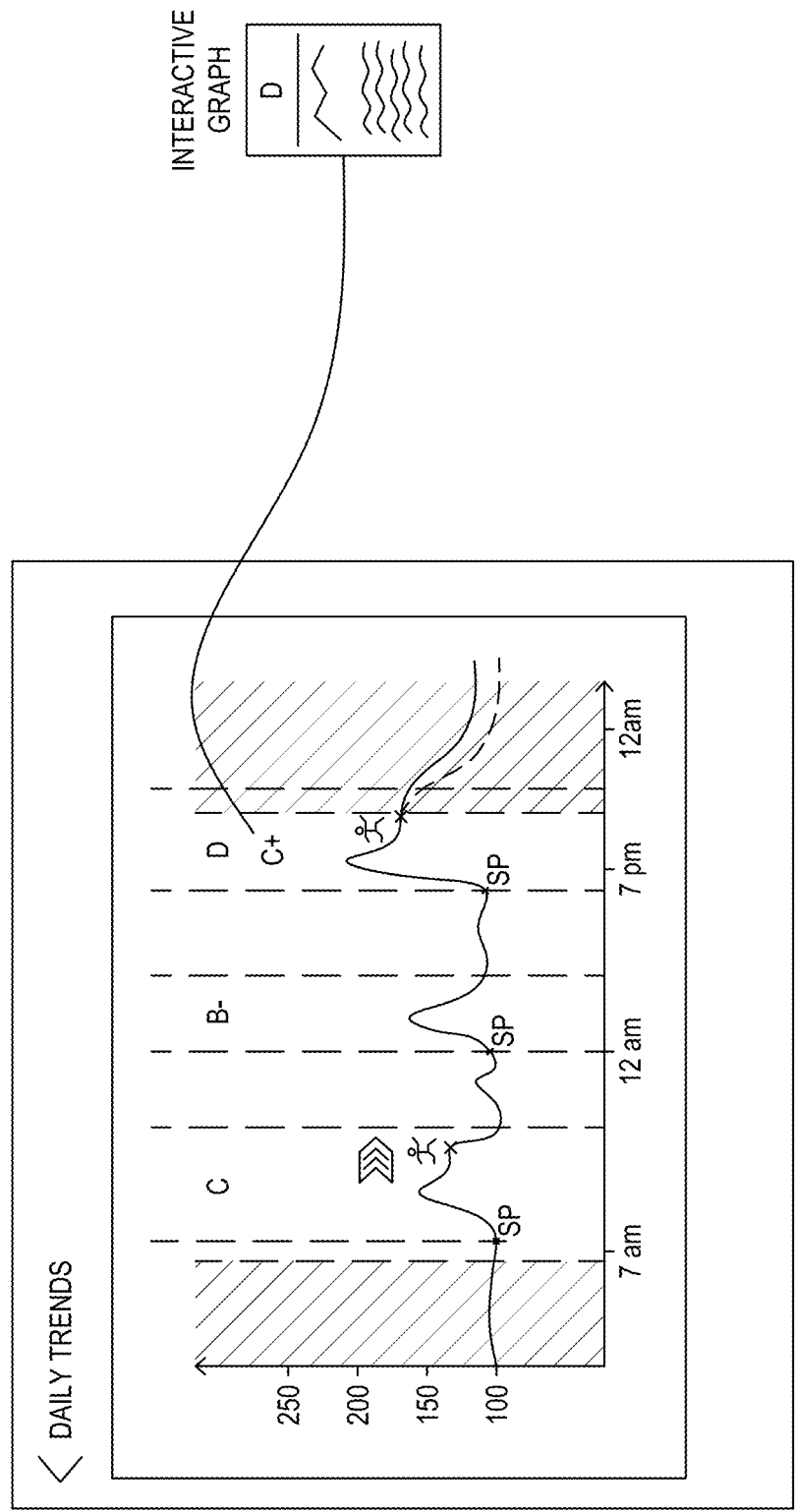
Figure 20D:
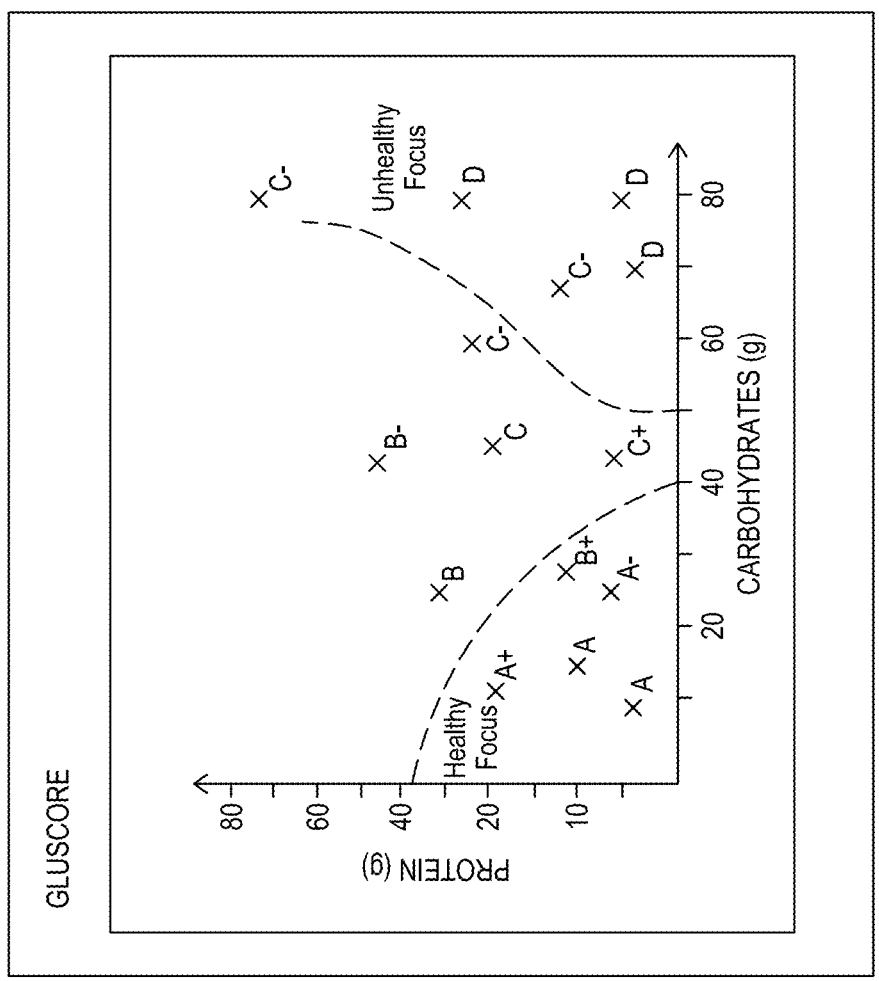
Figure 20E:
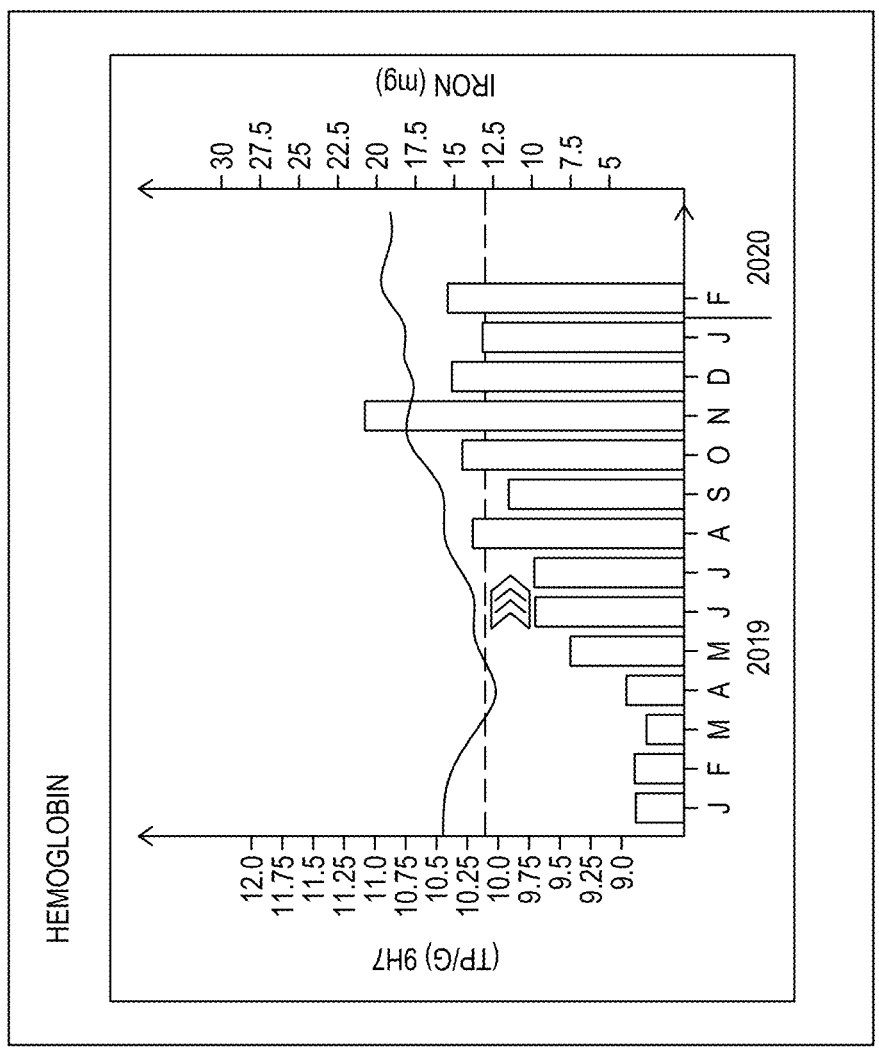
Figure 20F:
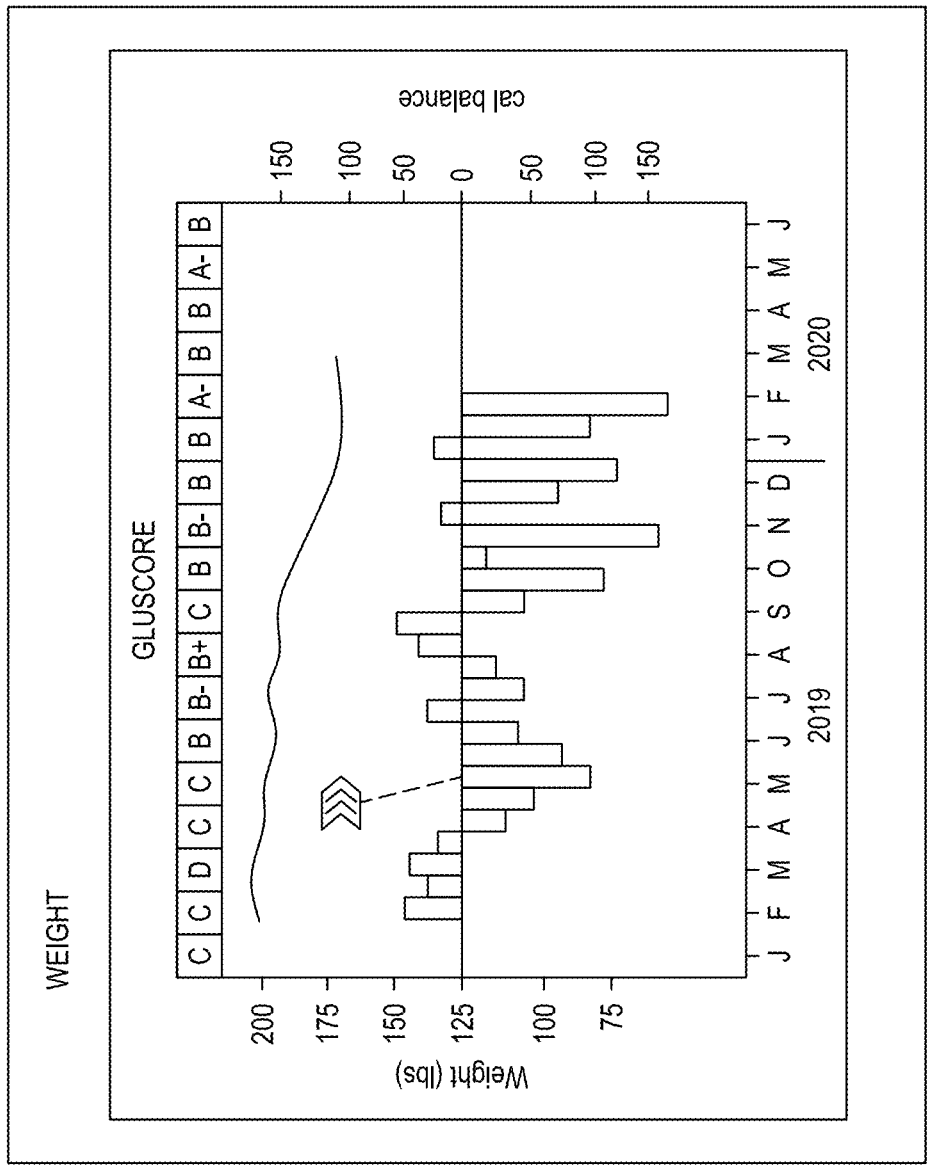
Figure 20G:
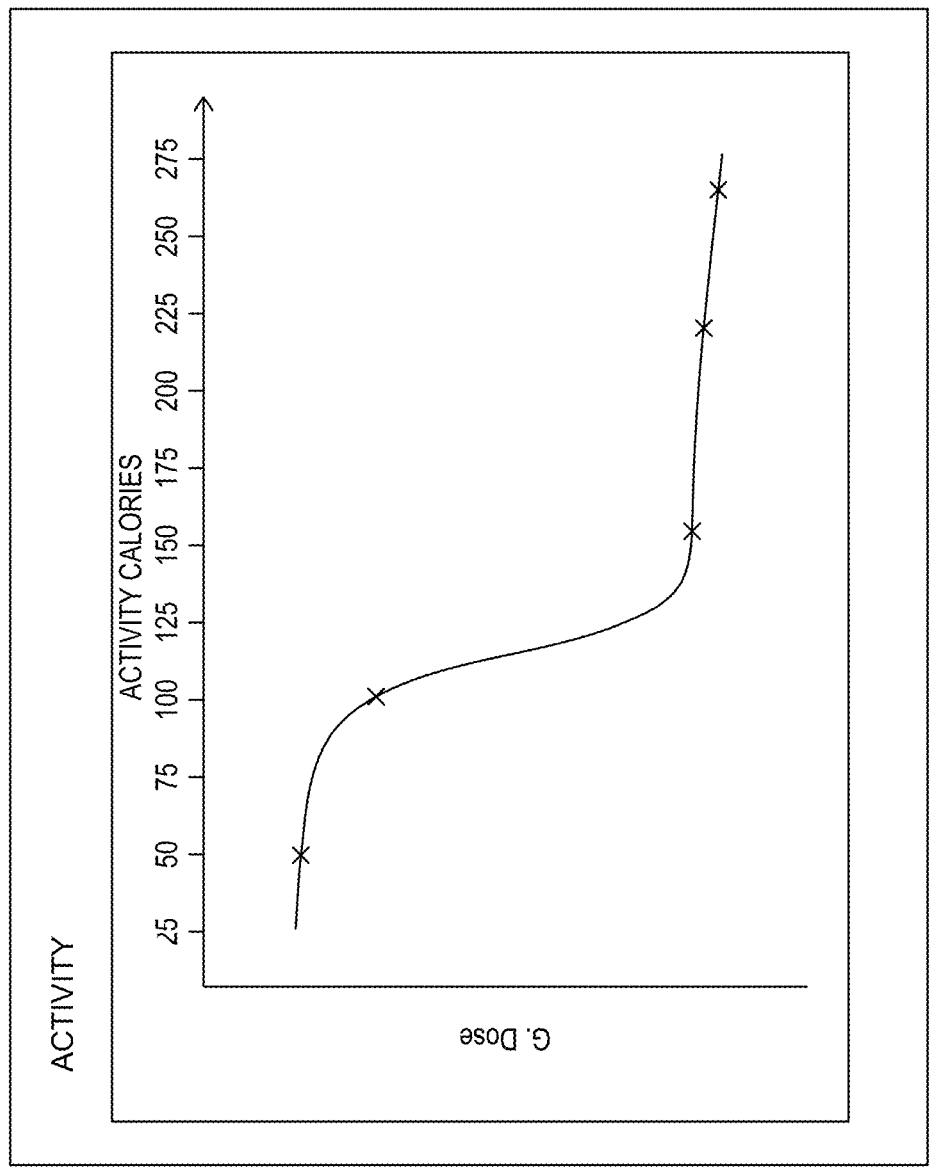
Figure 20H:
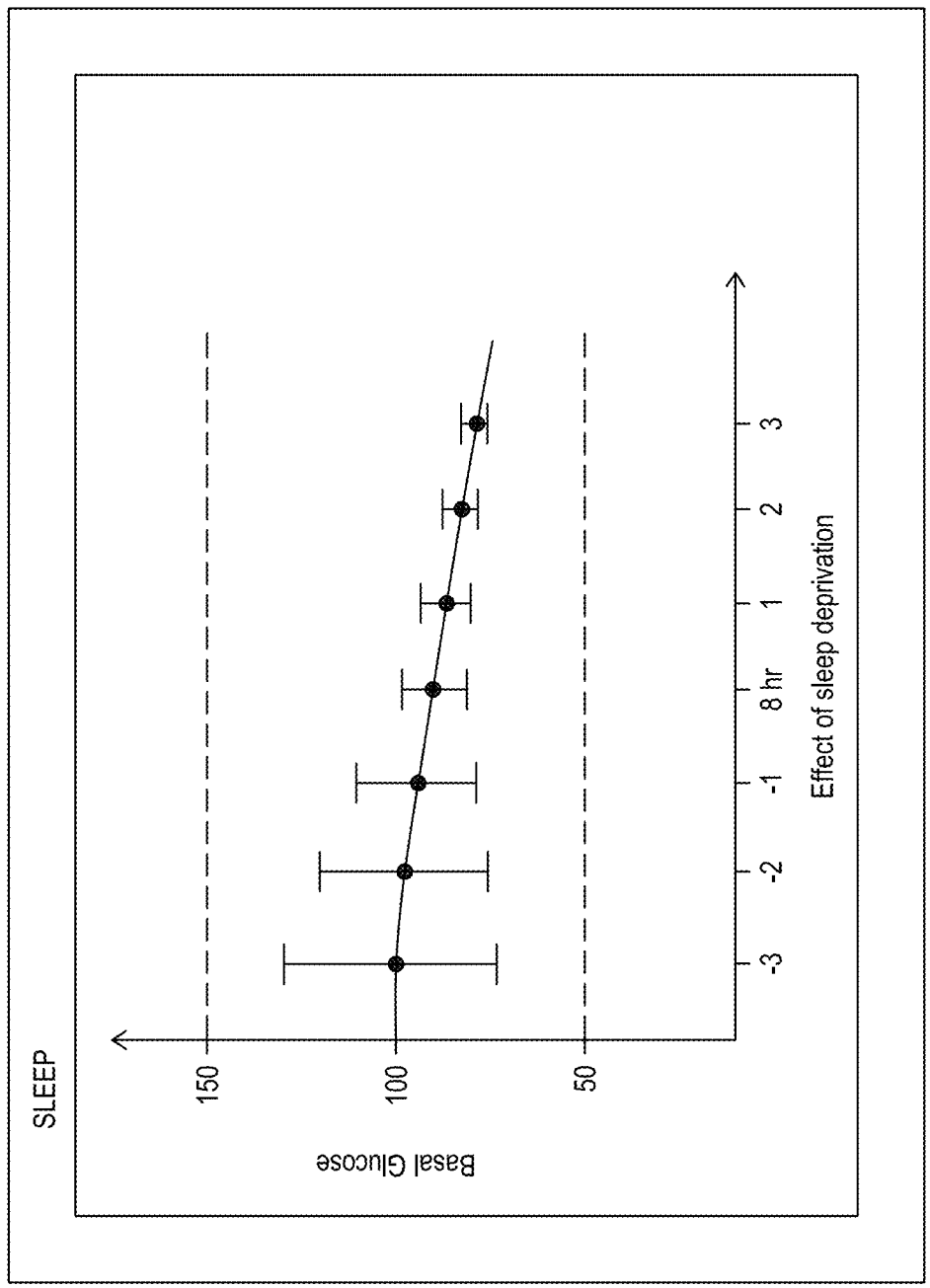
Figure 20I:
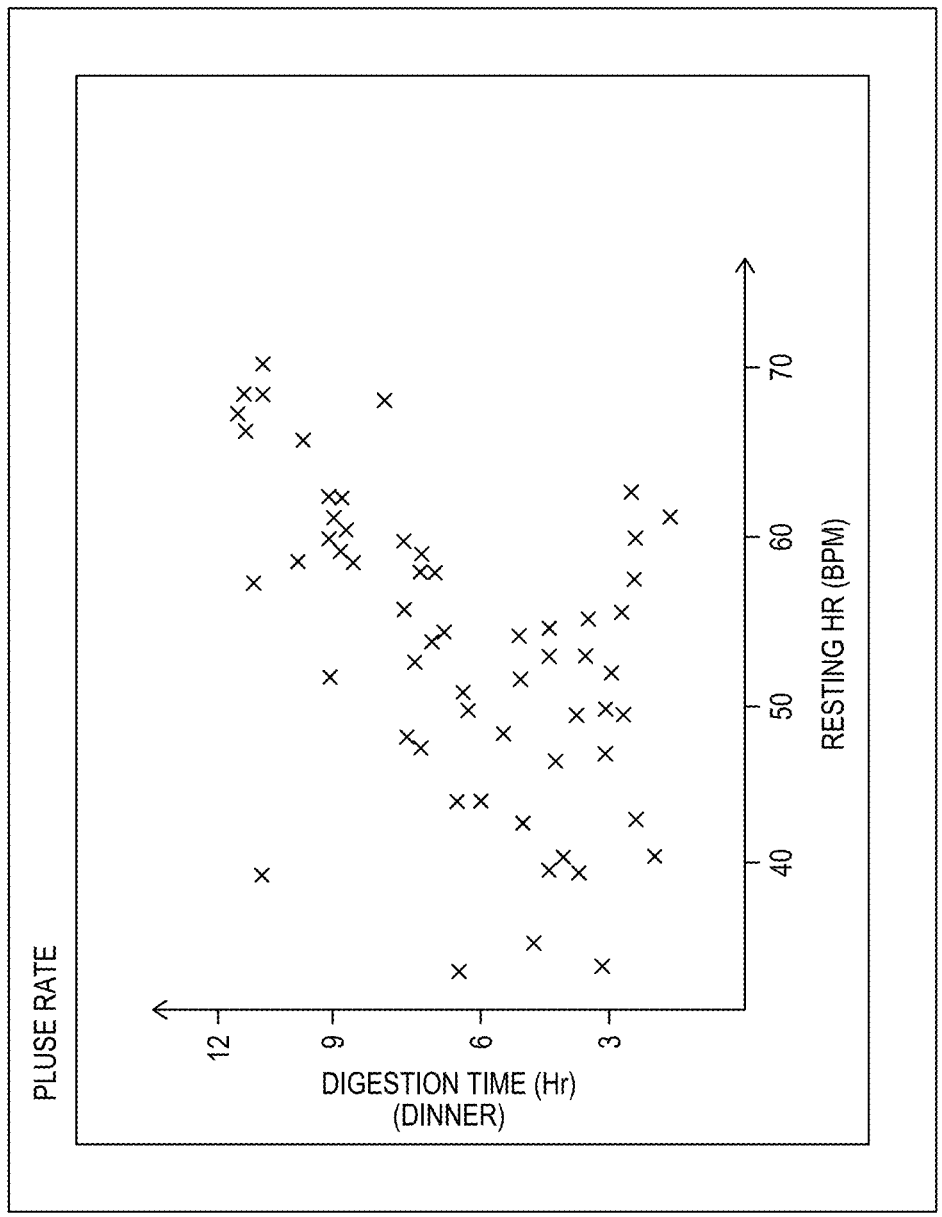
Figure 20J:
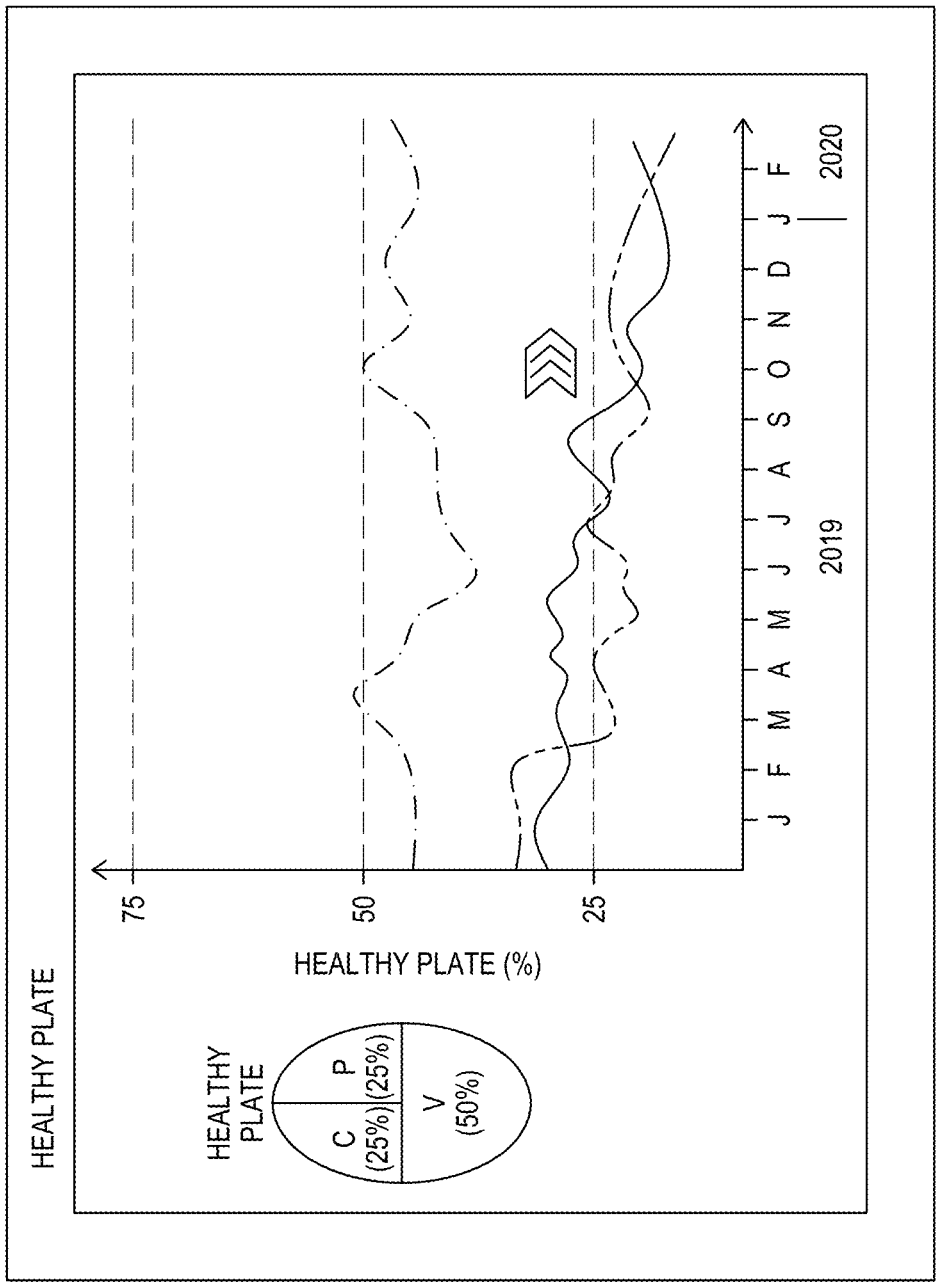

FIGS. 20A-B illustrates example analytics interface that may be accessed through an analytrics button or aspect of a graphical user interface. The analytics interface can include one or more graphics associated with different health parameters or information associated with the health coaching interface. For example, an analytics interface can include a graphic illustrating a human body and different interactive processes in a human body that may be affected by a user's logged values or determined parameters associated with the user, an analytics interface can include a graphics associated with daily trends of blood glucose, health score, hemoglobin, weight, activity, sleep, pulse rate, healthy plate or meal macronutrient parameters, other logging or health parameters, the like or some combination thereof. FIGS. 20C-J illustrate various example analytics graphics that may be part of a graphical user interface in, for example, such an analytics interface. For example, FIG. 20C illustrates a daily trend. The daily trend and other graphs may facilitate access to other interactive elements, such as recommendations, insights, or nudges. FIG. 20D illustrates an example GluScore graph as a function of protein and carbohydrate intake. FIG. 20E illustrates an example Hemoglobin graph of hemoglobin and hemoglobin associated values over time. FIG. 20F illustrates an example weight graph that may include information associated with a GluScore and carb balance as a function of time. FIG. 20G illustrates an example activity graph that may include the number of activity calories expended as a function of time for one or more recorded activities. FIG. 20H illustrates an example sleep graph that may include information associated with blood glucose and the sleep quality or quantity. FIG. 20I illustrates an example pulse rate graph that may include information associated with pulse rate, such as a resting pulse rate and digestion time. FIG. 20J illustrates an example healthy plate graph that may include information associated with a healthy plate include a percentage of protein, carbohydrates, vegetables or other contents of a healthy plate as a function of time. Other graphs to illustrate other aspects of a health coaching system 100 are also contemplated.

3. Example Personalized Journey

Figure 21:
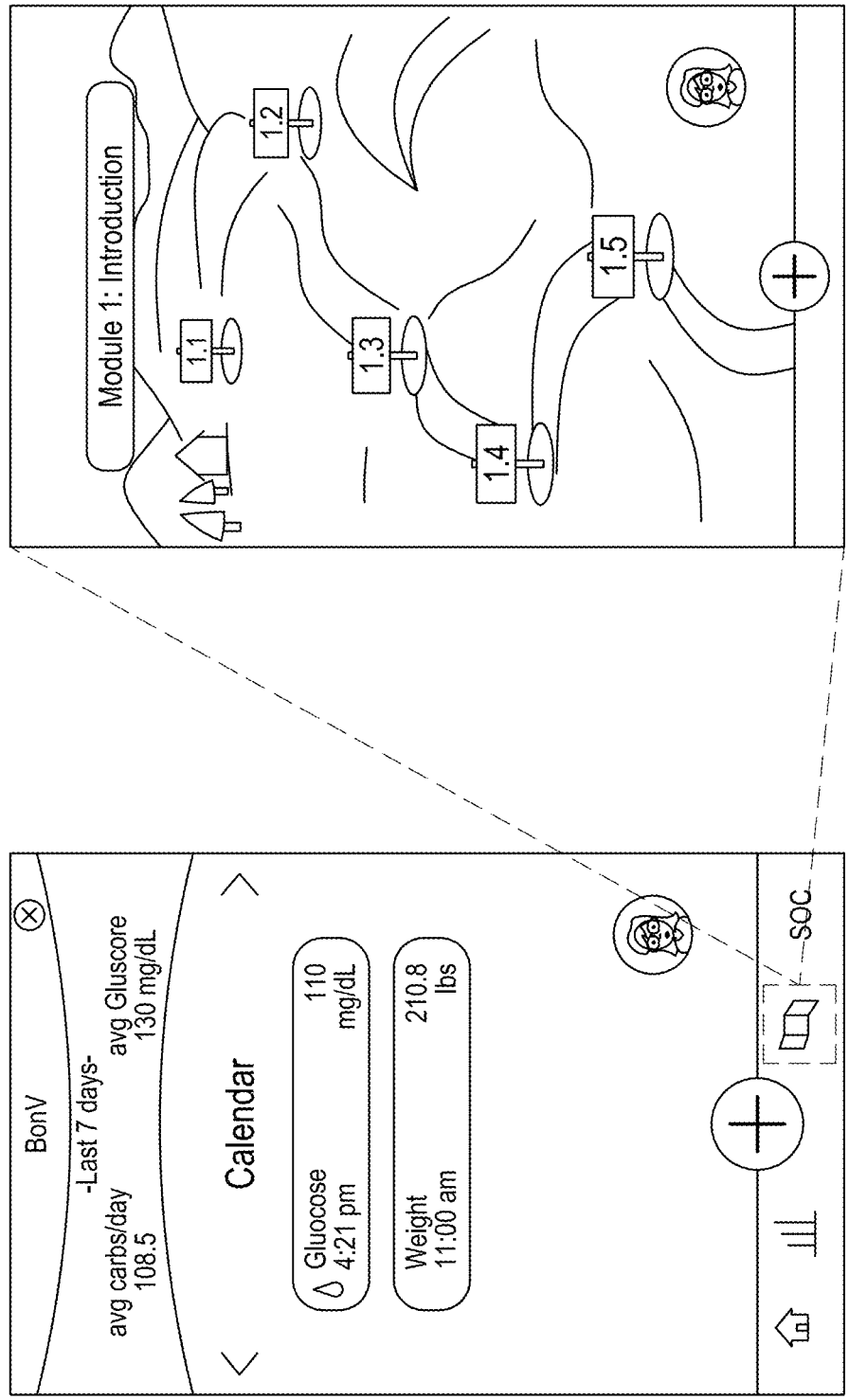
FIG. 21 illustrates example educational aspects of a personalized health coaching journey.

In some configurations, a coaching system may allow a user to further personalize their coaching experience by building their own story or journey. FIG. 21 shows an example graphical user interface of a health coaching system related to a personalized story mode. In some examples, a user may access different educational aspects of an educational module, such as those described above, by interacting with a story interface, such as illustrated in FIG. 21. As illustrated in FIG. 21, educational aspects can include audio lessons, articles, and games that may be accessed by interacting with different graphics displayed on a story interface. The graphics may be displayed on a road or story that may be part of a personalized journey.

a. Ingredient Choice

Figure 22A:
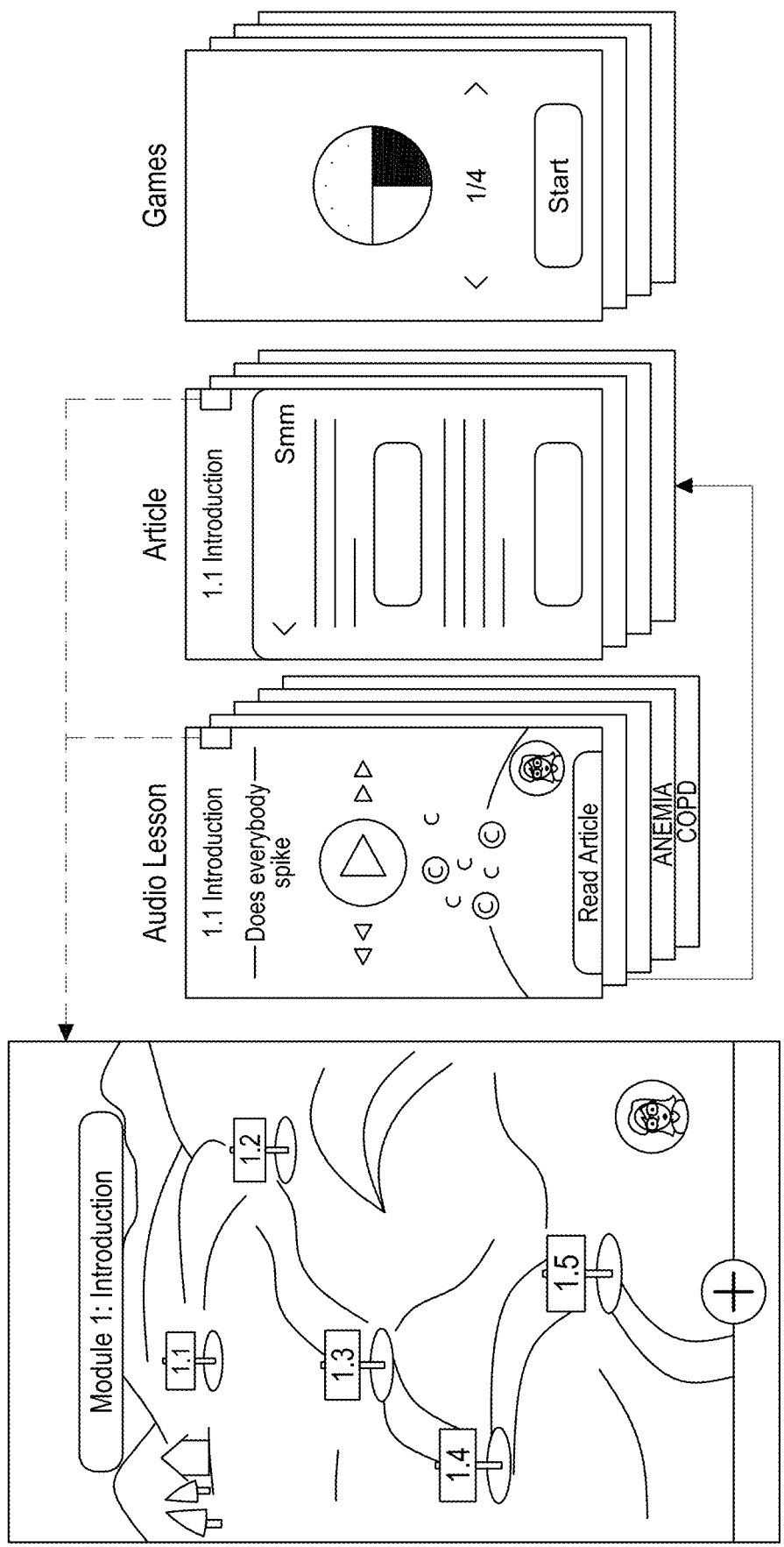

FIG. 22A shows an example graphical user interface of a health coaching system related to meal or ingredient choice. For example, FIG. 22A illustrates a meal journey interface 1101. A meal journey interface 1101 can allow a user to build aspects of a meal one ingredient at a time in order to improve a user's food intake according to one or more recommendations determined by the health coaching system.

The meal journey interface 1101 can include a window 1102 to display one or more food journeys based on a selection 1104. A food journey can include a set of graphics and/or text associated with a particular food or food type. In the example illustrated in FIG. 22B, a food journey includes graphics and text associated with grain based foods, such as quinoa, white rice, egg noodles, white pasta, and brown pasta. However, a meal journey interface 1101 may include multiple food journeys, including but not limited to a grain journey, a fruits journey, a vegetables and protein journey, a dairy and dairy substitution journey, or a build a meal journey.

Advantageously, the food journey may include content to aid a user in making food choices. For example, a food journey may help a user select a food type, such as a grain based food with a grain journey or a fruit in a fruit journey. In each journey, a user may be presented with a selection of ingredients. For example, in the grains journey illustrated in FIG. 22B, a user may be presented with different types of grain-based foods, such as quinoa, white rice, egg noodles, white pasta, or brown pasta. Each food type in the journey may be assigned a score. The score may be based on one or more factors associated with the food or the user. For example, a user may have type II diabetes.

Figure 22C:
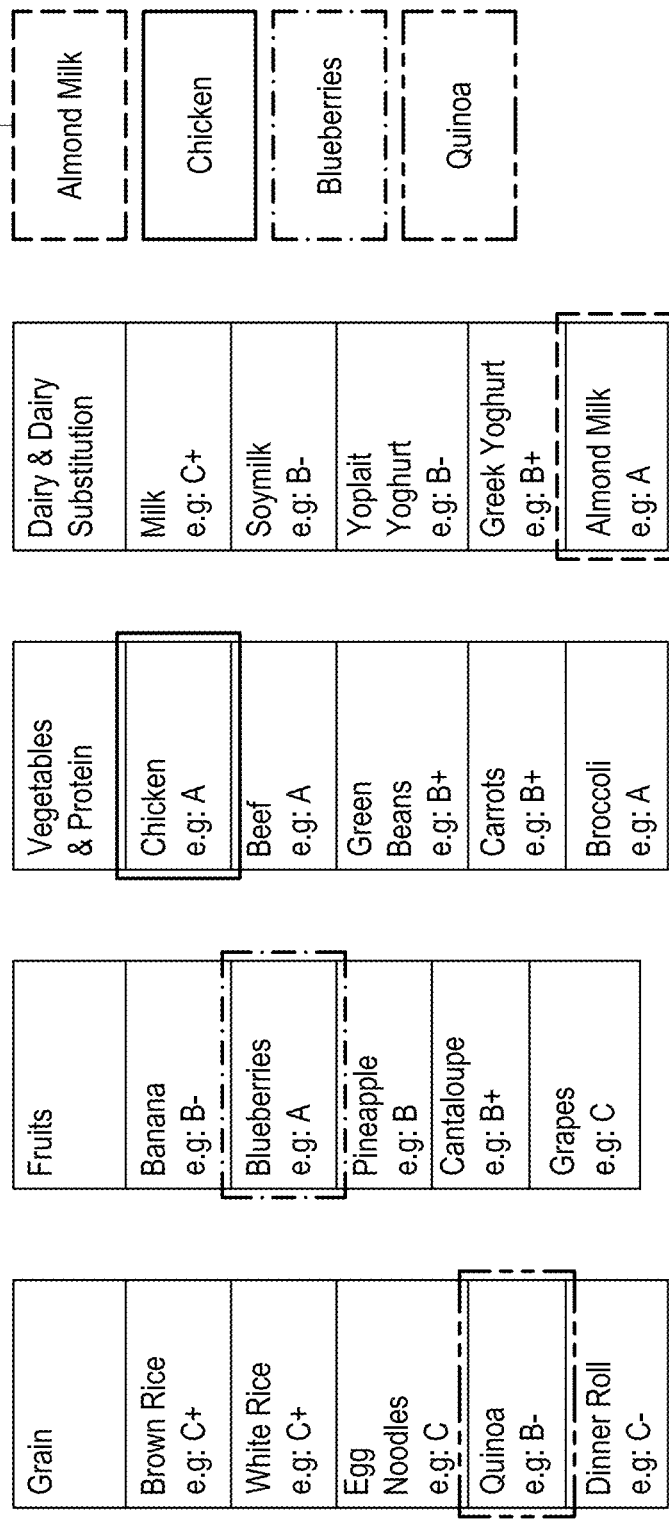

FIG. 22C shows example content associated with meal choice that may allow a user to build a personalized meal. For example, a health coaching system may help guide a user to select a healthier choice for different types of meal ingredients. In one example, a system may guide a user to select a grain having the healthiest grade, a fruit having the healthiest grade, a vegetable or protein having the healthiest grade, and a dairy or dairy substitution having the healthiest grade. Thus, an overall grade of a meal may be improved.

b. Comparing Food Items

Figure 23A:
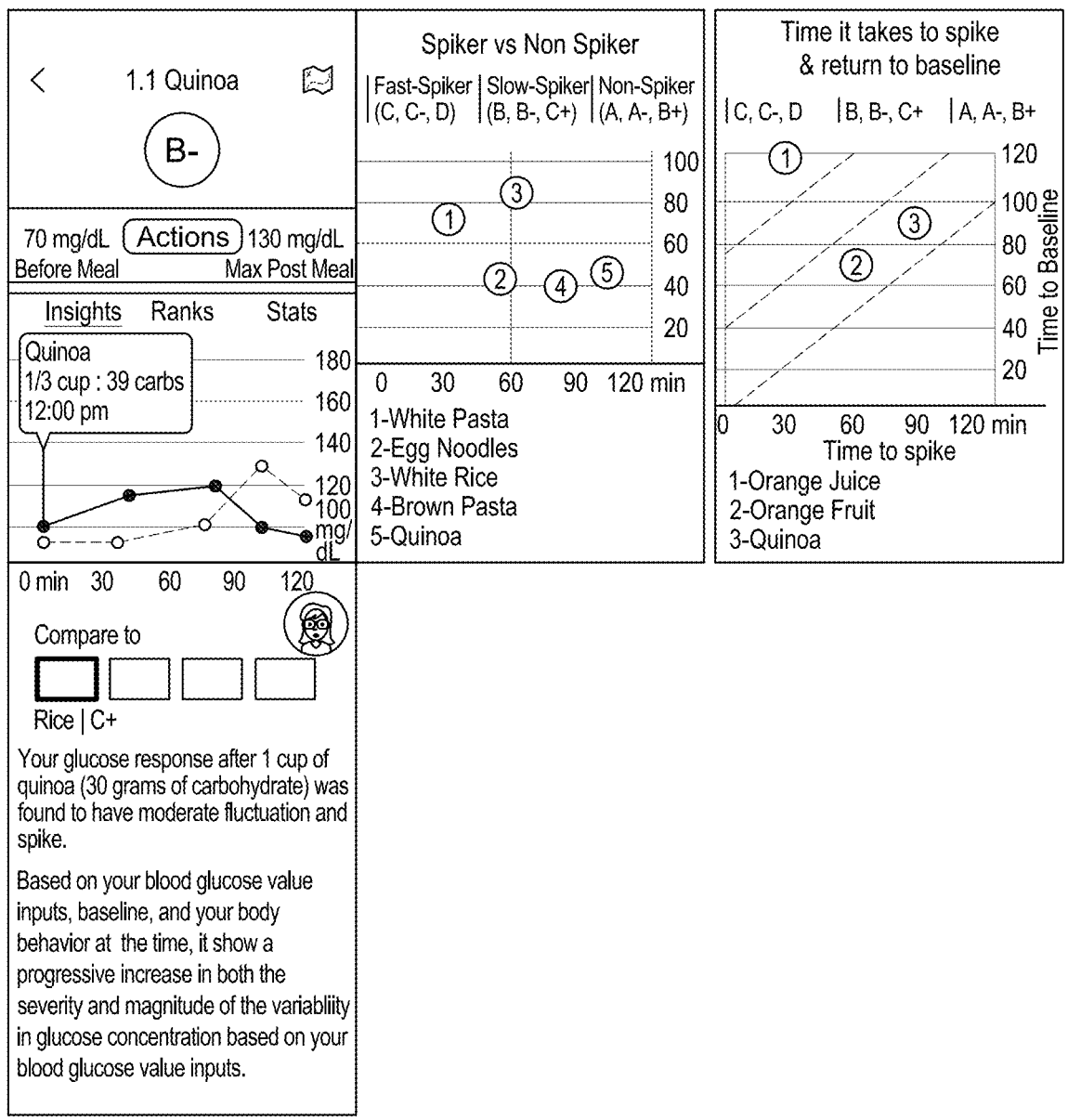

FIGS. 23A-23E shows aspects of an example graphical user interface of a health coaching system related to comparing food items based on user recommendations. In some examples, as illustrated in FIG. 23A, a health coaching system may provide educational content or insights related to ingredients. The educational content can include information associated with glucose response, information associated with alternative ingredients, how different related ingredients or ingredient substitutions may affect glucose, other information associated with the selected food or ingredient, the like or a combination thereof. Educational content associated with a particular food type that may be included in a meal logging or meal building content of a health coaching system.

In some examples, such as illustrated in FIG. 23A, a graphical user interface can include a graphical representation of a predicted glucose response as a result of ingestion of a selected food or beverage. In some examples, a graphical user interface can include an interactive comparison of a plurality of foods or beverages having a similarity with the selected food. A similarity can include a similar glycemic load, a same food group (for example, grain, vegetable, protein, or milk product), a similar food use (such as a thickener in a recipe, a sweetener, a fiber rich food, or a source of vitamin D), the like or a combination thereof. In some examples, the interactive comparison can include a graphical comparison of estimated glucose response as a result of ingestion of the compared foods or beverages. In some examples, the interactive comparison can include a scatter plot or similar graphical comparison of grades associated different types of food or beverage intake. In some examples, grades can include GluScores, such as described herein. In some examples, a GluScore may be associated with a speed of an insulin spike. The interactive comparison may include a graphical comparison of estimated time and intensity of peaks of blood glucose spikes as a result of ingesting different foods or beverages. In some examples, the interactive comparison may include a graphical representation of estimated time for a blood glucose value to return to baseline as a result of ingesting different foods or beverages. In some examples, a graphical user interface can include educational content associated with the compared foods, such as a reasoning for different scores given to different foods or the like.

Figure 23B:
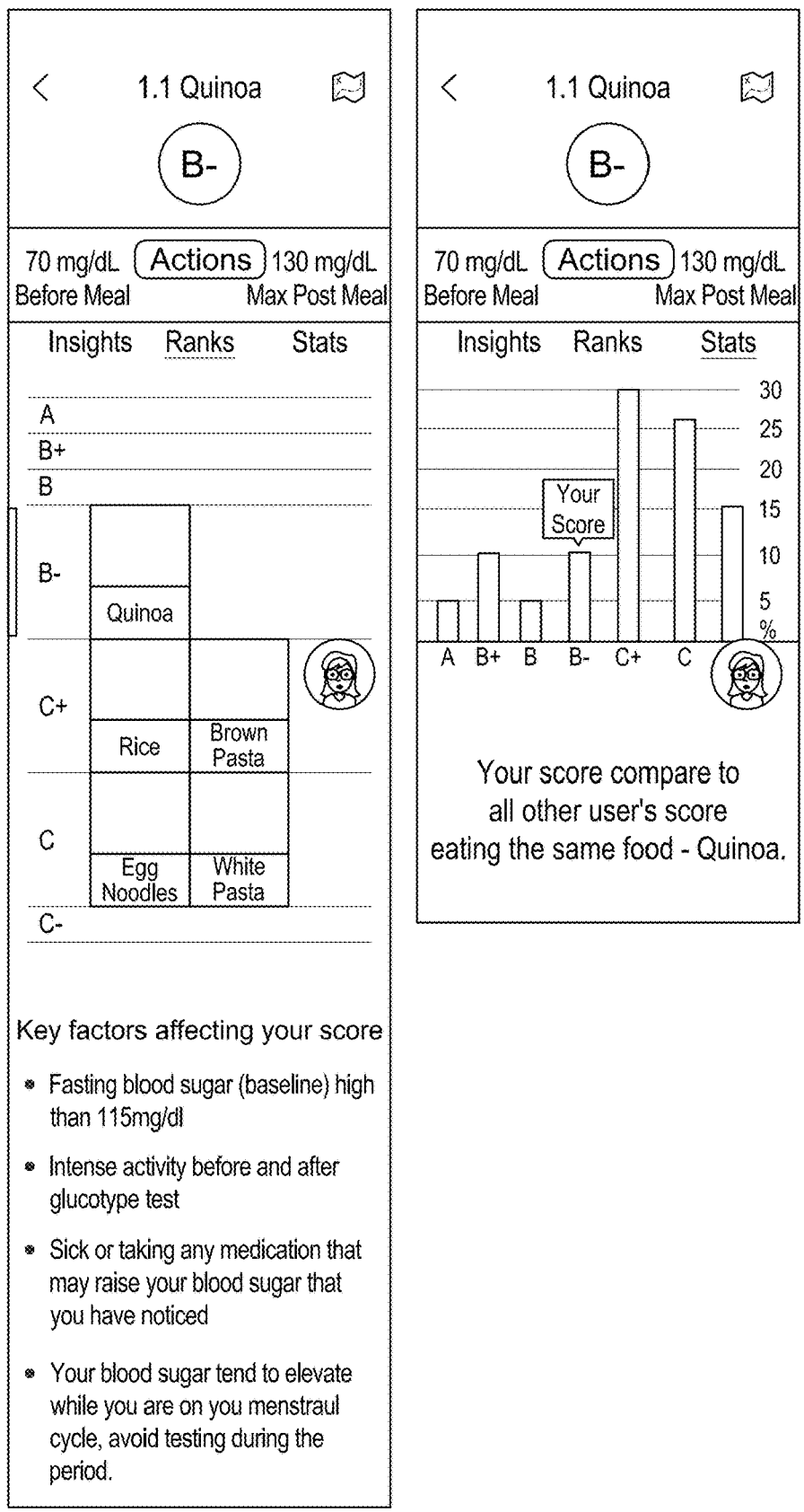

In some examples, as illustrated in FIG. 23B, a health coaching system can display a ranking associated with the ingredient in relation to other substitute ingredients and/or can display statistics associated with how a particular food may affect the user. The ranking may be based on health grades or scores of the ingredients or other parameters. In some examples, a graphical user interface may display a rank of the selected ingredient or food or beverage in comparison to other similar foods. In some examples, the rank may be displayed in the form of a graph or table. In some examples, a graphical user interface may display educational content associated with the selected ingredient or food or beverage, such as an explanation of factors that may affect a grade or score of the selected ingredient or food or beverage. For example, factors may include that a fasting blood sugar (or baseline) is higher than a threshold value (for example, 115 mg/dl), that there was an intense activity before setting a GluScore test that affected a glucose classification of a user (or GluScore), that a user was sick or taking medication that raised blood sugar, that blood sugar is elevated due to hormonal changes (such as a menstrual cycle), or other factors that may affect a GluScore, baseline, or other blood sugar related value. In some examples, the statistics can include how a particular food may affect the current user in contrast to other users or a user's particular health risk factors. In some examples, a graphical user interface may display a comparison of a user's score associated with an ingredient, food or beverage with other user scores associated with the same ingredient, food or beverage. The comparison may include a graph or table, such as a bar graph indicating percentage of users who have possible scores.

In some examples as illustrated in FIGS. 23C and 23D, a health coaching system can include suggested actions related to an ingredient. For example, suggested actions can include recommended substitutions, recommended foods to avoid, suggested pairings of food, suggested recipes for a selected food, or other information associated with a food.

Figure 23E:
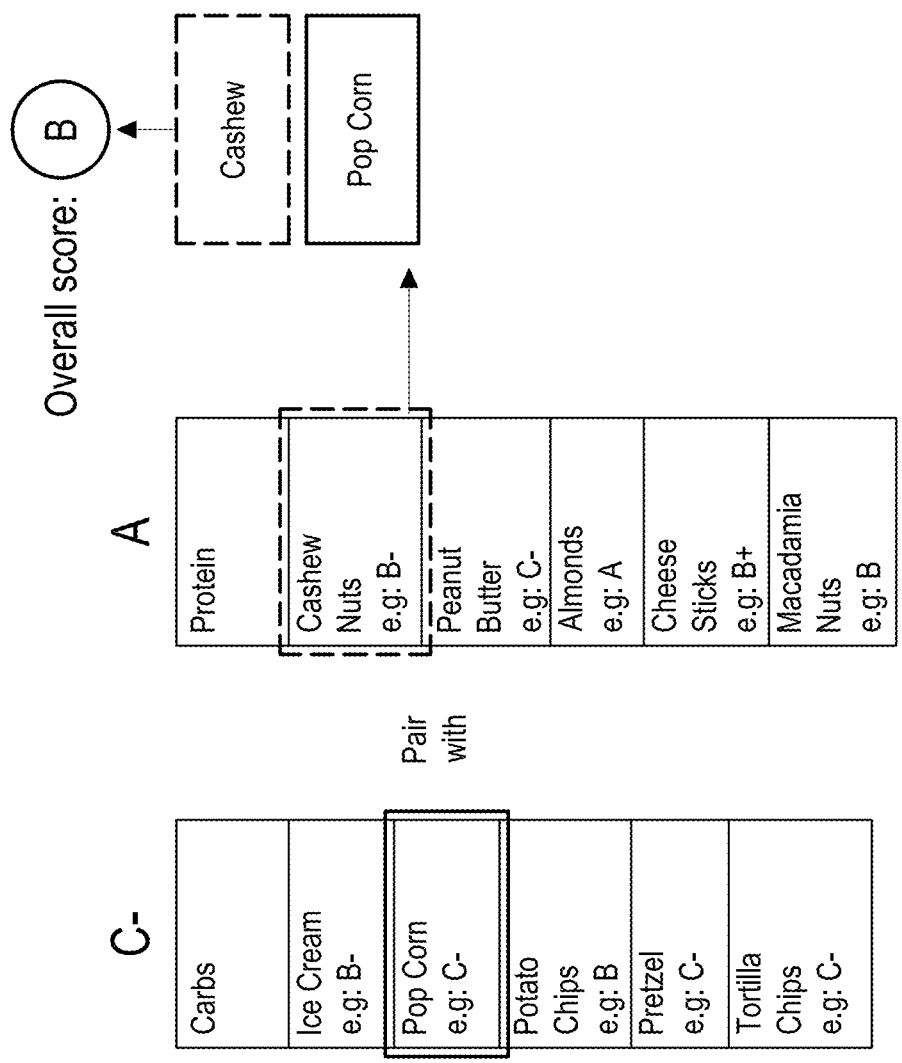

In some examples, as illustrated in FIG. 23E, a health coaching system may suggest pairings of foods. For example, if a user selects a food with a low health grade, a health coaching system may suggest a food, beverage, or ingredient with a good or better health grade to improve the health of an overall meal. In some examples, the health coaching system may determine an overall score or grade based on a weighted average of score or grades of the ingredients, foods, or beverages, within the meal. Other methods of combining scores or grades are also possible. For example, a score or grade for a plurality of ingredients may be generated based on a classification by a machine learning technique.

c. Example Meal Planning

Figure 24:
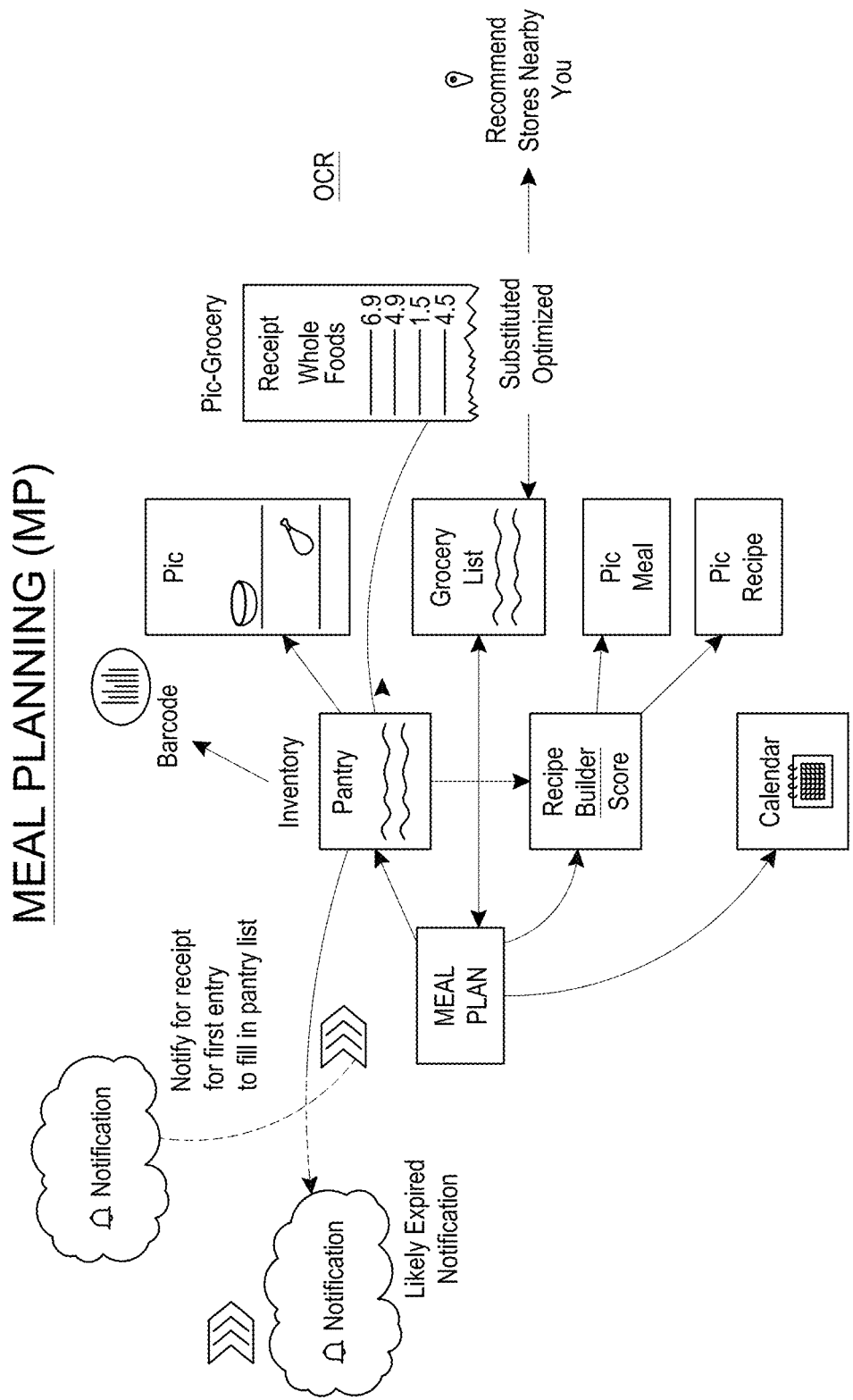
FIGS. 24 and 24B illustrate an example interaction of different aspects of meal planning that may be part of a health coaching system.

FIG. 24 shows an example interaction of different aspects of meal planning that may be a part of a health coaching system. Aspects of meal planning can include tools or functionalities such as a calendar, recipe log, food logging tools, pantry inventory, shopping assistance, other food related planning tools or functionalities, the like, or some combination thereof. In some examples, a health coaching system can facilitate meal planning by processing contents of a pantry. For example, pantry contents may be input by a user manually or through one or more pictures of a pantry. In some examples, pantry contents may be input using a barcode or object recognition algorithm. In some examples, pantry contents may be determined based on a picture of a grocery receipt using, for example, optical character recognition (OCR). In some examples, a health coaching system may identify likely expired items and notify a user accordingly. In some examples, a health coaching system can facilitate meal planning by processing a user input including a planned meal. The planned meal may include ingredients, food, or beverages. In some examples, the health coaching system may provide a recommendation or facilitate a recipe building process and notify a user of the recommended meal or recommended recipe. In some examples, the user may be prompted to log the meal or recipe for analysis by the health coaching system. In some examples, the health coaching system may prompt a user to record or plan a meal using a calendar tool. In some examples, a health coaching system may generate, add to, edit, or access a grocery list. In some examples, a health coaching system may recommend substitutions, additions, or deletions from the grocery list to optimize or improve a grocery list for a user's health condition, such as a GluScore or type 1 or type 2 diabetes. In some examples, a health coaching system may prompt a user to provide a receipt for processing if the system determines (by, for example, monitoring of a user's location or a user input) that a user has visited a grocery store or restaurant or other location in which a user may acquire food. In some examples, a health coaching system may recommend stores or products based on an analysis of a user's grocery list or meal plan.

Figure 24B:
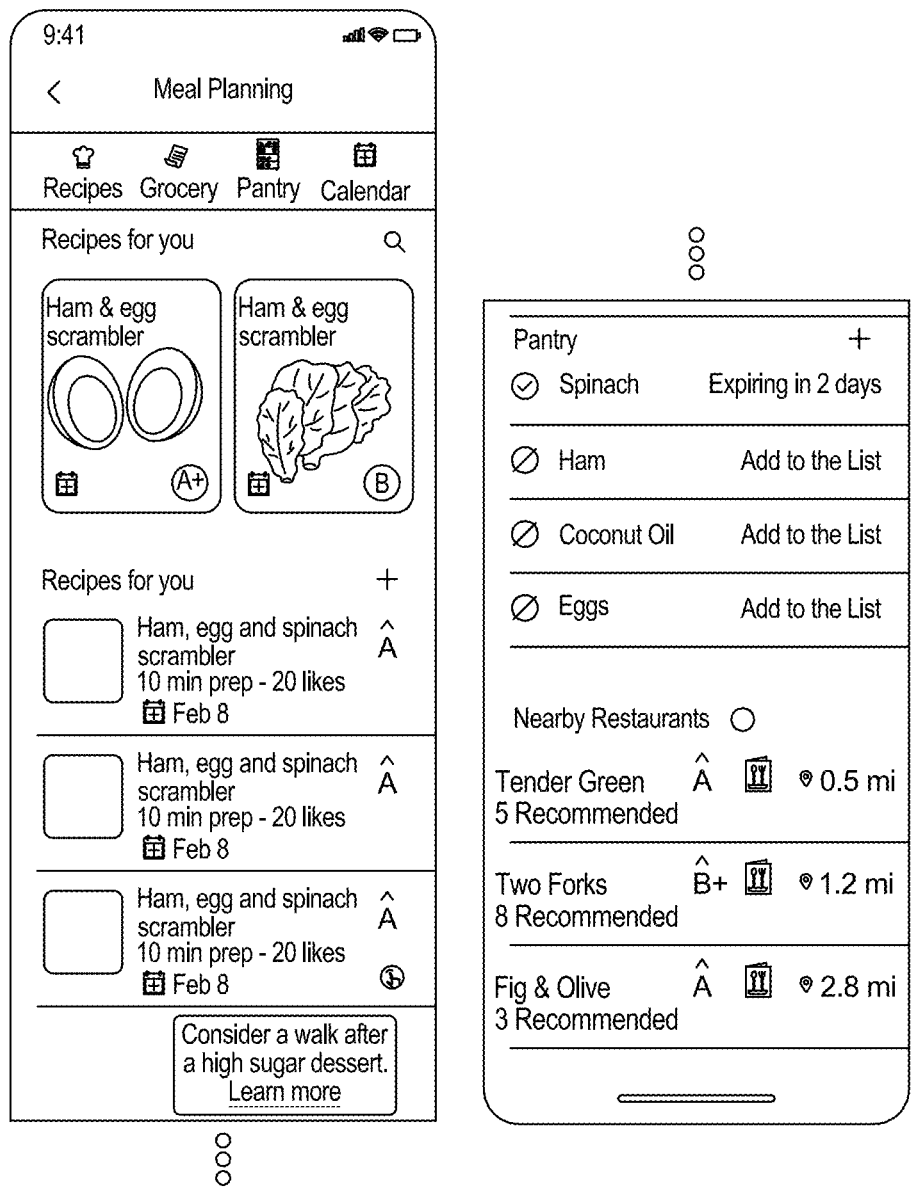

FIG. 24B illustrates an example meal planning interface that may be part of a health coaching system. The meal planning interface may aid a user in planning their meals or food intake. In some examples, the meal planning interface can include adaptive meal planning suggestions responsive to user logged values or detected lifestyle. In some examples, the meal planning interface can include health scores (such as a glucose score) associated with recipes and recipe suggestions. In some examples, a meal planning interface can include aspects that facilitate social interaction, such as competitions and challenges, household pantry and grocery lists that may be shared, potluck planning, recipe sharing, the like or a combination thereof.

Figure 25A:
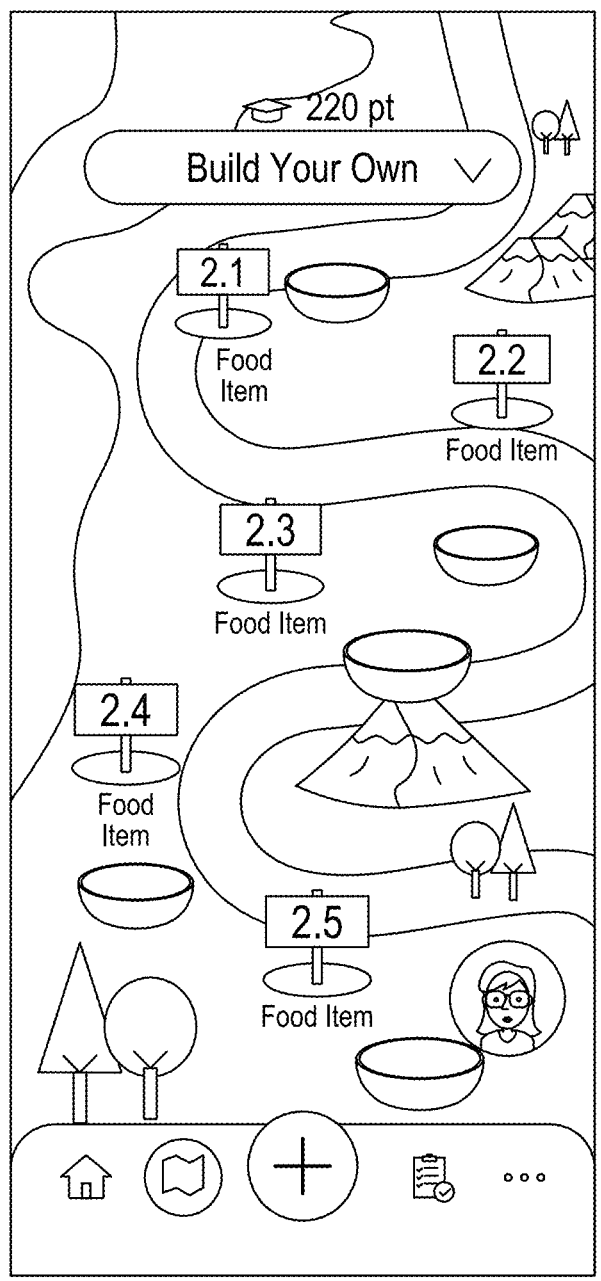

FIG. 25A illustrates an example educational meal building tool that may be associated with a meal planning aspect of a health coaching application. A meal building tool can include a meal story. For example, a meal story can include one or more inputs or tools for selecting different foods or food items in building a meal. The meal building tool can include educational components associated with a food or different types of food, such as described above. Additionally or alternatively, the meal building tool can include food pairing information, user specific health information, other meal related information, suggestions, or insights, the like or some combination thereof.

FIG. 25B illustrates an example calendar tool that may be associated with a meal planning aspect of a health coaching application. For example, a calendar tool can include scheduling of an anticipated meal. The calendar tool can allow a user to set a reminder or an alert for eating a meal. In another example, a calendar tool may allow a user to set reminders based on a meal of when to measure a blood glucose value. In some examples, the calendar tool may have one or more interactable portions that may facilitate access to other meal planning tools.

FIG. 25C illustrates an example meal preparation tool that may be associated with a meal planning aspect of a health coaching application. For example, a meal preparation tool can include information on how to prepare a particular ingredient or recipe, portion sizing for one or more ingredients, macronutrient and/or calorie content of one or more ingredients or recipe, cooking information, the like or some combination thereof. In some examples, the preparation tool may have one or more interactable portions that may facilitate access to other meal planning tools. For example, an interactable portion may include a button to add an ingredient or ingredients to a grocery list.

Figure 25D:
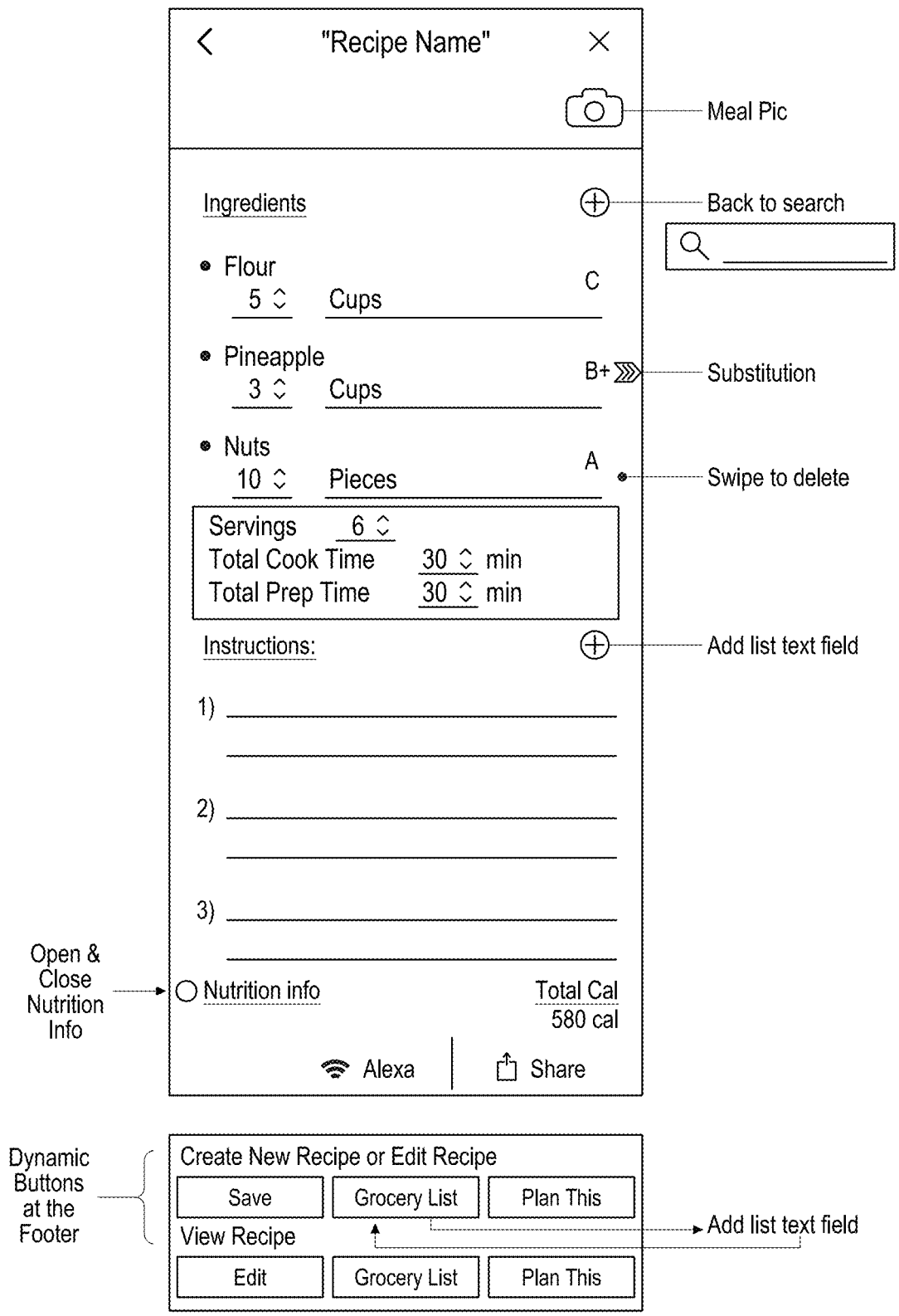

FIG. 25D illustrates an example recipe tool aspect of a graphical user interface that may be associated with a meal planning aspect of a health coaching application. A recipe tool can, for example, include a search function for ingredients, a log for ingredients, information associated with ingredients in a recipe, insights or nudges associated with different ingredients in a recipe, instructions on how to generate the recipe, information as to the macronutrients and/or calorie content of a total recipe, information as to a grade or health score of a recipe, options to save, upload, download, edit, or otherwise interact with a recipe, other recipe tools, the like, or a combination thereof. In some examples, a recipe tool can include components to allow a user to take a picture of the meal. The picture may be used to analyze the contents of the meal and/or be stored as a record of the meal. In some examples, a recipe tool aspect of a graphical user interface can include an interactable portion configured to facilitate addition or searching of ingredients for the recipe. The interactable portion can include a graphic, such as a plus sign or search symbol. The recipe tool can include aspects that facilitate modifying, accessing, or compiling information about the recipe, such as number of servings, cook time, preparation time, instructions, nutritional information, the like or a combination thereof. In some examples, a recipe tool aspect of a graphical user interface can include buttons or other interactive components the facilitate saving, editing, or viewing a recipe, planning to log, eat, or cook the recipe, or adding items within the recipe to a grocery list. In some examples, a recipe tool aspect of a graphical user interface may allow a user to access other recipes, a grocery list, or other aspects of a coaching system related to meal planning or otherwise. In some examples, a recipe tool aspect may include social media connectivity or otherwise facilitate sharing of the recipe. In some examples, a recipe tool aspect may facilitate sending a recipe to a smart device (such as a smart speaker, smart display, tablet computer, mobile device, or the like), printer, or other device or user.

Figures 25E, 25F:
Figures 1, 25E:
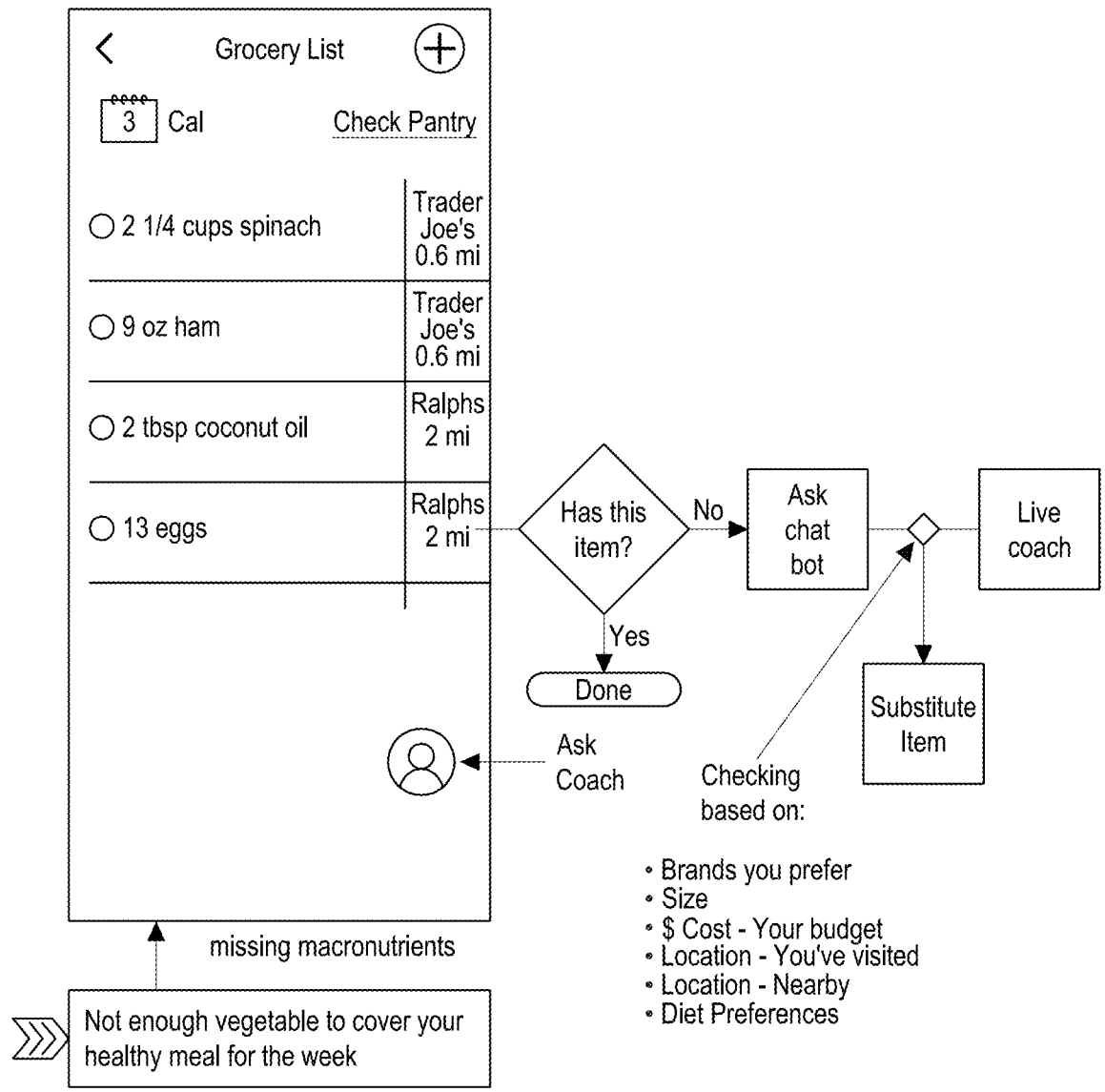
Figures 1, 25F:
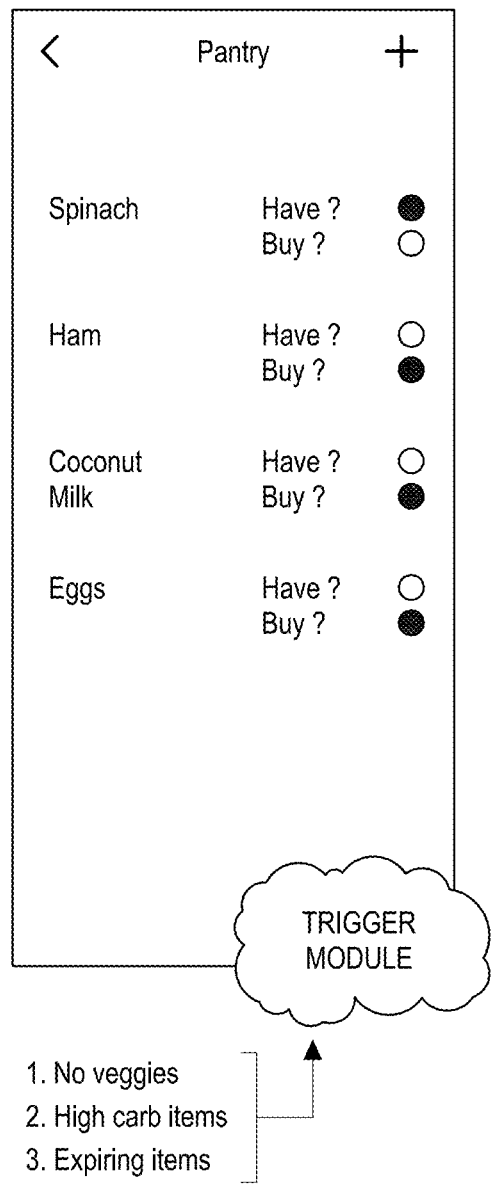
Figures 2, 25F:
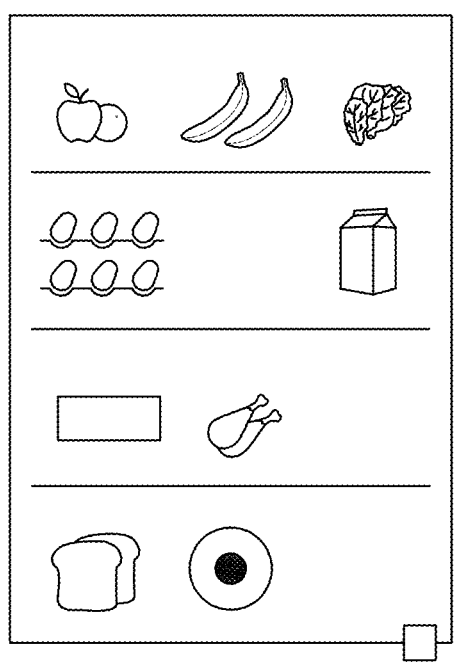

FIGS. 25E, 25E-1, 25F, 25F-1 and 25F-2 illustrates an example grocery list and pantry list that may be associated with a meal planning aspect of a health coaching application. A grocery list, such as illustrated in FIG. 25E, can include, for example, a list of items marked by a user or health coaching system to obtain or purchase. In some examples, the list may be grouped by goods or food type, such as grains, spices, condiments, protein, or the like. In some examples, a list can include brand names for different goods or foods on the list. In some examples, the list can include where to purchase the item, such as a suggested or identified store that typically sells the item or has the item in stock. In some examples, the list may include input to purchase the item from the identified or suggested store. In some examples a health coaching system may check or allow a user to check if an item or items on the grocery list are already in the user's pantry, such as illustrated in FIG. 25F. In some examples, such as illustrated in FIG. 25E-1, a health coaching system may provide recommendations associated with a grocery list. The recommendations can include a notification associated with a lack of balance (for example, missing vegetables), a substitution for healthier items, or other grocery related recommendations. In some examples, a grocery list may indicate a brand, store, or item based on one or more factors, including, but not limited to, brands the user has previously bought or indicated a preference for, an indicated amount or size of an item (such as 12 oz of broccoli or 4 oz of rice), a cost of an item (which may be in relation to an indicated budget), a location of the user, stores the user has frequented or previously visited, diet preferences, or other factors.

FIGS. 25F and 25F-1 illustrates an example pantry list or a subset of a pantry list that may be associated with a meal planning aspect of a health coaching application. A pantry list can include, for example, a list of ingredients that either the user or health coaching system has identified that the user needs to generate a recipe, has in their current pantry or inventory of ingredients, has previously purchased, or would like to purchase. As illustrated in FIG. 25F, a health coaching system may check a pantry list for items based on a grocery list or a selected recipe. In some examples, the health coaching system may update a grocery list based on the pantry contents. As illustrated in FIG. 25F-1, a health coaching system may check a pantry list for triggers to provide insights, nudges, or other recommendations. The triggers may include a lack of vegetables in the pantry, a presence of high carbohydrate items, a presence of expiring items, the like or a combination thereof.

In some examples, as illustrated in FIG. 25F-2, a system may utilize an image of a user's refrigerator or pantry to determine the presence or absence of one or more food or other items in a user's pantry or kitchen. In some examples, the list may be grouped by goods or food type, such as grains, spices, condiments, protein, or the like. In some examples, a list can include brand names for different goods or foods on the list. In some examples, a user may identify if an item is in their pantry or should be purchased. If a user or health coaching system identifies that an item should be purchased, the user or health coaching system may more that item to the user's grocery or shopping list.

Figure 25G:
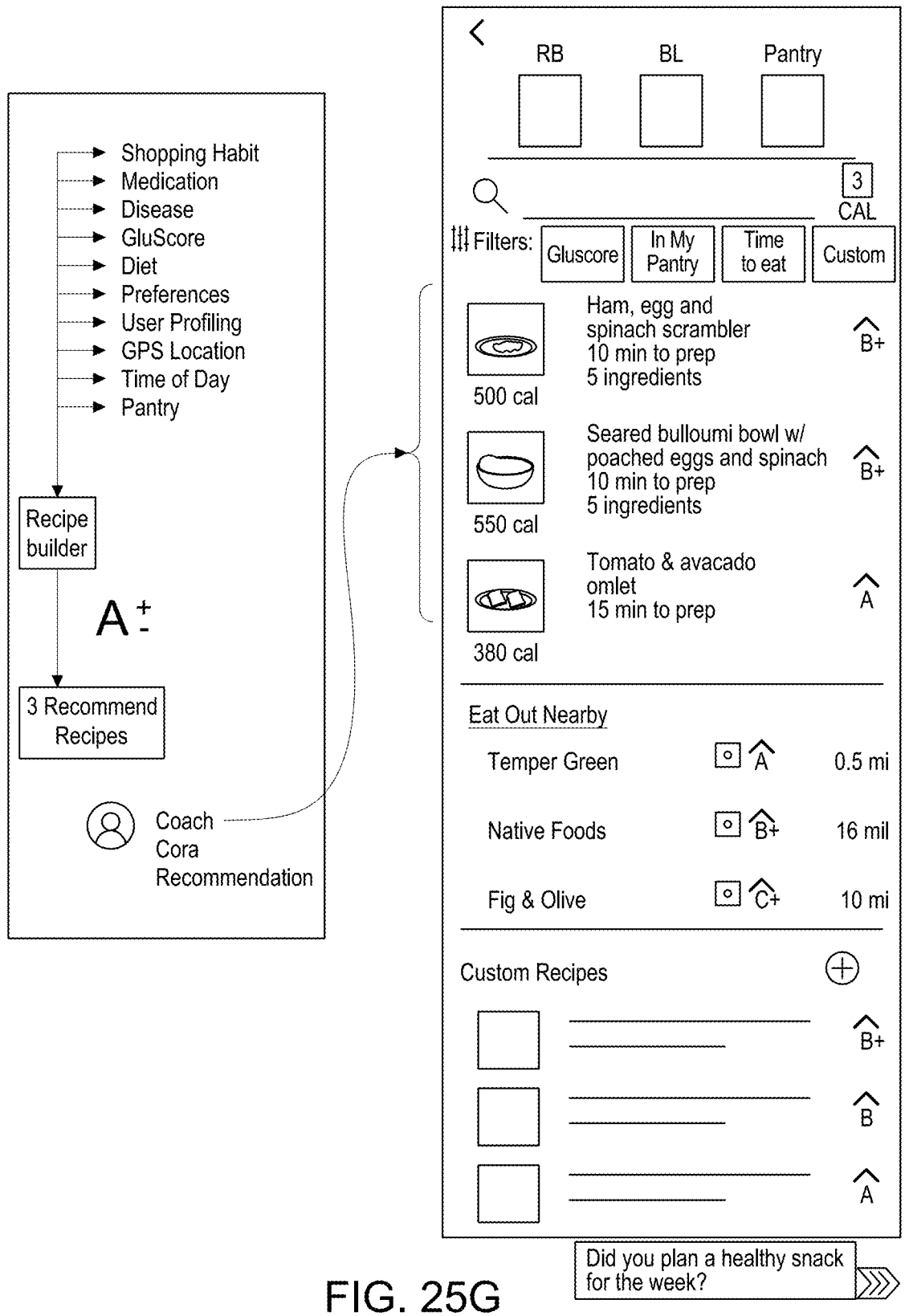

FIG. 25G illustrates another example aspect of a meal planning aspect of a health coaching system. The meal planning aspect may include a recipe builder, a pantry list, a grocery list tool, a restaurant tool or other aspects. A restaurant tool, for example, can include a search function, one or more suggestions for menu options from a selected restaurant, one or more options for nearby healthier restaurants or restaurant menu options, one or more stored options for customized orders or recipes, other restaurant information, the like, or a combination thereof. In some examples, a system may utilize a GPS location to determine some of the information associated with the restaurant tool. In some examples, the restaurant tool may be incorporated into another meal planning or food logging aspect of a health coaching application. In some examples, a meal planning aspect may recommend one or more recipes for a user to prepare or eat based on a variety of input, including, but not limited to, shopping habits, medication, disease, GluScore, diet, food preferences, user profiling, GPS location, time of day, and pantry contents. The inputs may be processed by a controller using a recipe building algorithm and the controller may output recommended recipes and information about those recipes, including but not limited to calorie content, GluScore, time to prepare, number of ingredients, the like or a combination thereof.

4. Example Rewards Notifications

Figure 26A:
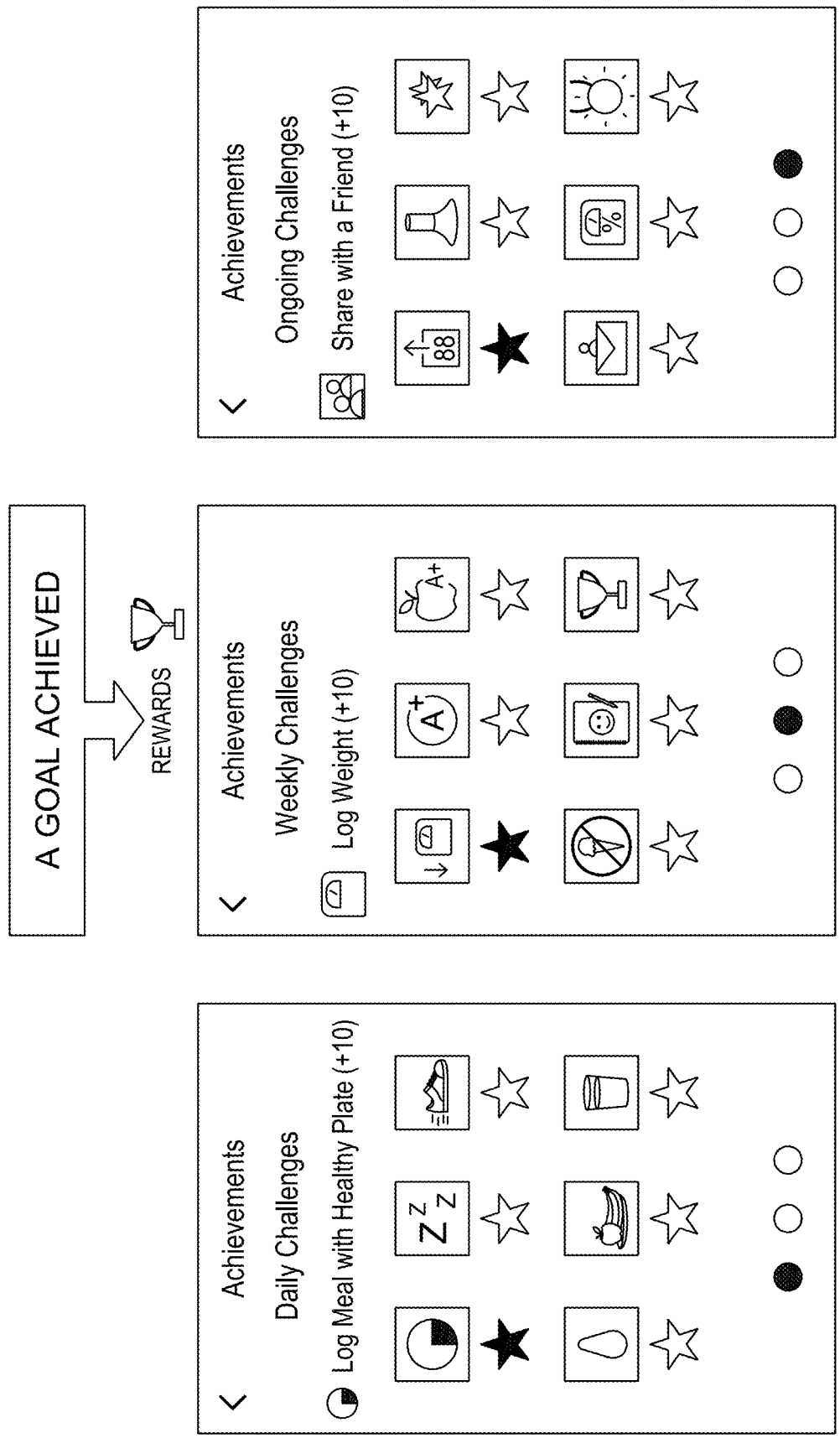
Figure 26B:
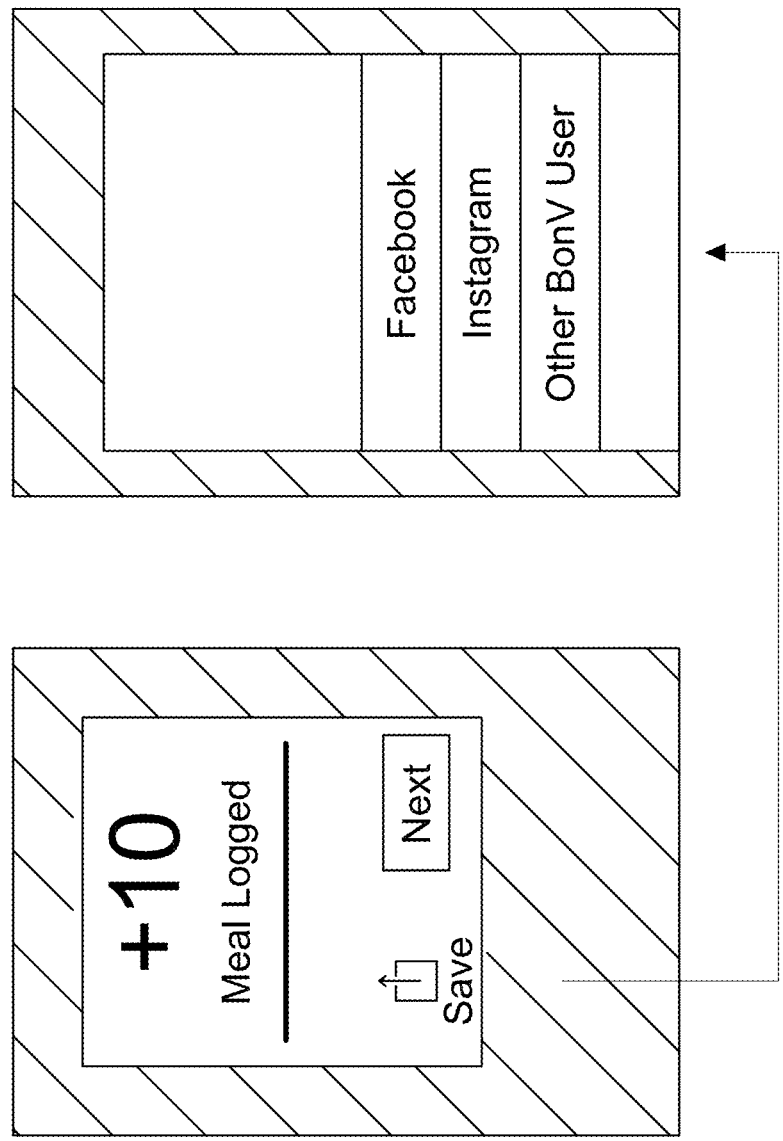

FIGS. 26A-C illustrate example aspects of a reward system that may be part of a health coaching system. In some examples, the reward system can include one or more achievement notifications, badges, or other positive reinforcement for a user's positive behavior in utilizing a health coaching system.

As illustrated in FIG. 26A, a health coaching system may reward a user with an achievement badge in response to a trigger, such as an achieved goal. The achievement badges or other rewards may be accessible at an achievements interface that may be part of a graphical user interface. In some examples, the achievements interface can include one or more screens or sections that may display a category of achievement. For example, a first section may display achievements associated with daily goals or challenges, a second section may display achievements associated with weekly goals or challenges, a third section may display achievements associated with ongoing goals or challenges. The achievements may be displayed as graphical badges or another type of identification of achievement, such as a graph, animation, or other display.

Goals or challenges may be associated with different aspects of the health coaching system, such as having a good meal grade for all 3 meals in a day, lowering the user's weight, meeting educational goals, the like or a combination thereof. In some examples, daily challenges can include meeting healthy plate goals, logging or doing a certain amount or quality of activity (such as 10 minutes of light exercise a day), glucose being within range, logging one or more parameters a certain number of times per day, the like or a combination thereof. In some examples, weekly challenges can include logging one or more parameters a certain number of times per week, bringing a parameter closer to a healthier value (such as lowering an overweight user's weight), eating healthier, getting a certain number of positive health risk scores (such as good glucose scores), being responsive to health coaching nudges, the like or a combination thereof. In some examples, ongoing challenges can include syncing a health coaching system with a third party device, logging lab results, sharing achievements with friends, inviting friends to join the health coaching system, reaching a certain percentage of weight lost, maintaining a certain level or quality of activity for a certain amount of time, running a marathon, getting good health risk scores for a certain amount of time, the like or a combination thereof.

FIG. 26B illustrates an example notification for reaching an example goal or fulfilling a challenge that may be part of a graphical user interface. For example, when a user gains an achievement or attains a goal a health coaching system may notify the user of the achievement. A notification can include a pop up window or other graphical indication that a goal or challenge has been achieved. The notification can include a description of the achievement, such as 10 meals logged, information associated with the achievement, one or more sharing options associated with the achievement, the like or a combination thereof. In some examples, the sharing option can include one or more interactive portions of the interface configured to facilitate access to publishing or otherwise sharing the achievement on social media, via email, via text, or by other means of sharing information with persons other than the user.

FIG. 26C illustrates an example progress insight aspect of a reward system that may be part of a health coaching system. In some examples, a progress insight aspect of a reward system can include one or more goal summary or progress interfaces. A goal summary (or progress) interface can include a user's progress towards one or more goals, such as a daily goal, a weekly goal, an ongoing goal. Or other goal. In some examples, the progress can include graphs, bars, text, or other indication of user progress towards one or more goals. In some examples, a notification, such as a push notification may be configured to bring a user to a reward system aspect of a graphical user interface. The notification may occur as a result of a trigger, such as a user reaching a goal, having not reached a goal within a threshold time frame, a user logging activities related to a goal progress or a lack of goal progress, the like or a combination thereof.

5. Example Social Interactions

A chat interface in the health coaching system can include a medium for the users to get more information about diabetes and general heath via a Q&A based BOT and can allow live coaches to interact with users as needed.

A health coaching system may have a chat interface to ask questions relating to diabetes management and general health and fitness. In some examples, the chat may be handled by a BOT, such as a Q&A BOT. In some examples, the chat may include a diagflow framework at a backend and/or trained agents. The BOT and/or the trained agents may be capable of answering questions relating to diabetes, exercise, diet, or other health or coaching system related questions.

a. Example Coach Side Interface

In some examples, a chat framework may be built to have a confidence value for each response from the BOT. In some examples, low confidence response(s) from the BOT may be routed to a live coach for additional review. FIG. 27A illustrates an aspect of an example chat interface that may be utilized by a live coach or trained agent. In some examples, the chat interface may be used for the live coach to review responses from the BOT. Via the chat interface, the health coaching system can enable a live coach to reach out to users and interact with them with expert advise and suggestions. The coach may use the coach dashboard to collect additional information about user's demographics and activity on the app.

FIG. 27A shows a screenshot of the dashboard's pipeline page, which is a prioritized queue of action items for the Coach. Users not interacting with the app by logging their meal or activities can be captured as events in the pipeline, enabling the coach to intervene with encouraging messages or questions.

Figure 27B:

FIG. 27B shows an example user profile interface of the coach dashboard, where a coach can gather more information about specific user. Through the profile interface, a coach may be able to view recent meals, physical activities, glucose score measurements, weight, or other information logged by or associated with the user. Advantageously, based on this information, a coach may be able to provide personalized recommendations to users.

In some examples, coach responses to specific triggers (events in the pipeline) may be recorded in the database and can be used to automate systems to respond to future user queries or triggers.

b. Example User Side Interface

Figure 27C:
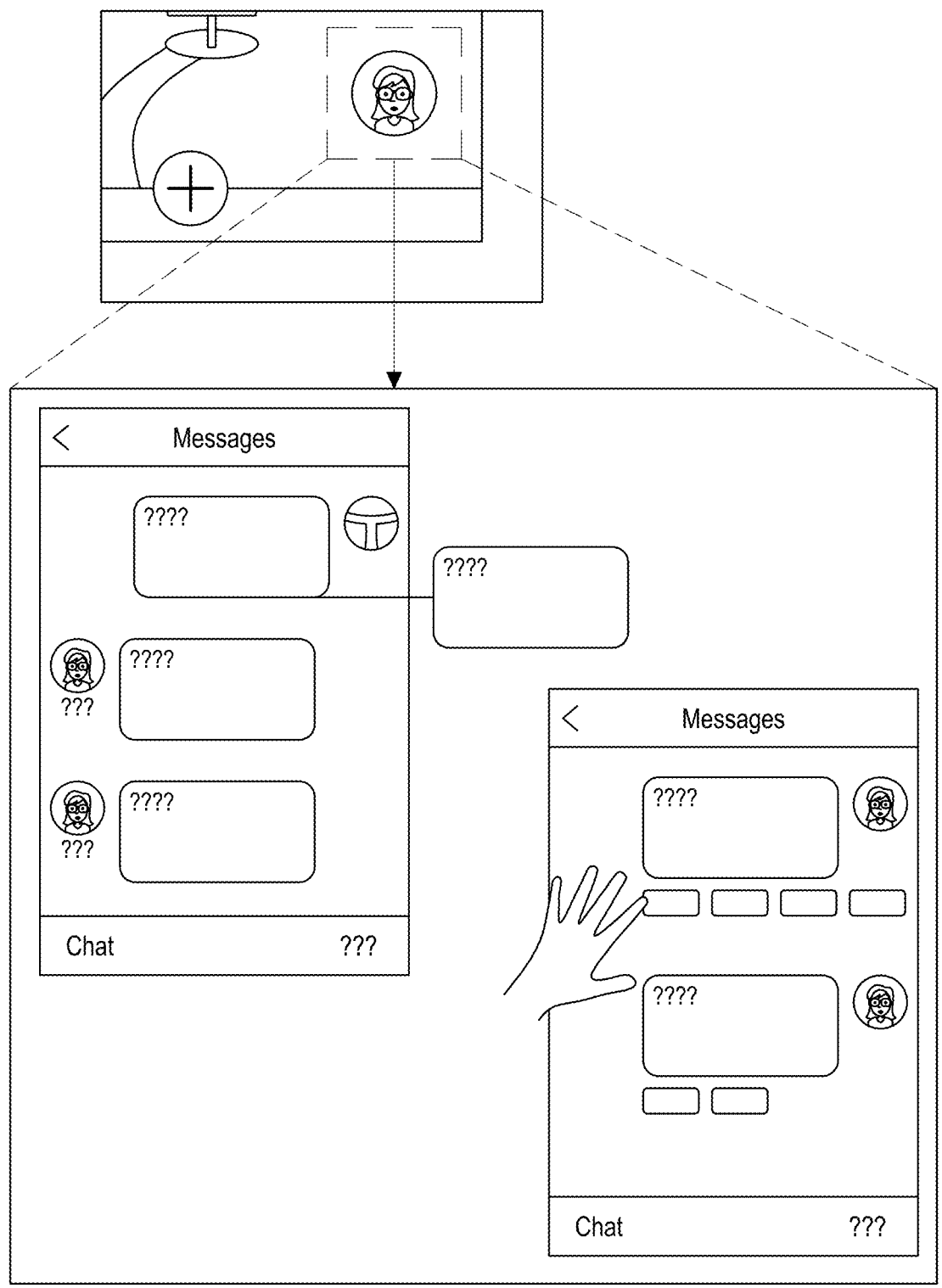

FIG. 27C illustrates an example user side interface that may be associated with a chat functionality of a health coaching system. In some examples, a user may be able to access a chat interface through the selection of a link, graphic, or by other command within a graphical user interface. In the illustrated example, a chat interface may be accessed by selection of a chat icon on a home interface or screen. A chat interface can include one or more sections for displaying a current and/or previous messages between the user, a live coach (or trained agent), a user's caregiver, other users, the chat BOT or AI, or other sources of messages. The chat interface can include one or more sections that allow a user to post content to the chat or send content to another user, live coach, caregiver, chat BOT or AI, or other receiver of content. The content can include text messages, graphics, animations, health parameters, or other information. In some examples, a chat interface can include suggested questions or responses based on recent user interactions with the health coach system. For example, a user may have entered the chat from a part of the graphical user interface associated with glucose scores, the health coaching system may populate a window or other part of the interface with suggested questions relating to glucose score. In some examples, in addition to or in the alternative to the user side chat interface, a similar chat interface and suggested responses or questions may be used for a coach side interface.

6. Example Organizational Functionalities

Figure 28A:
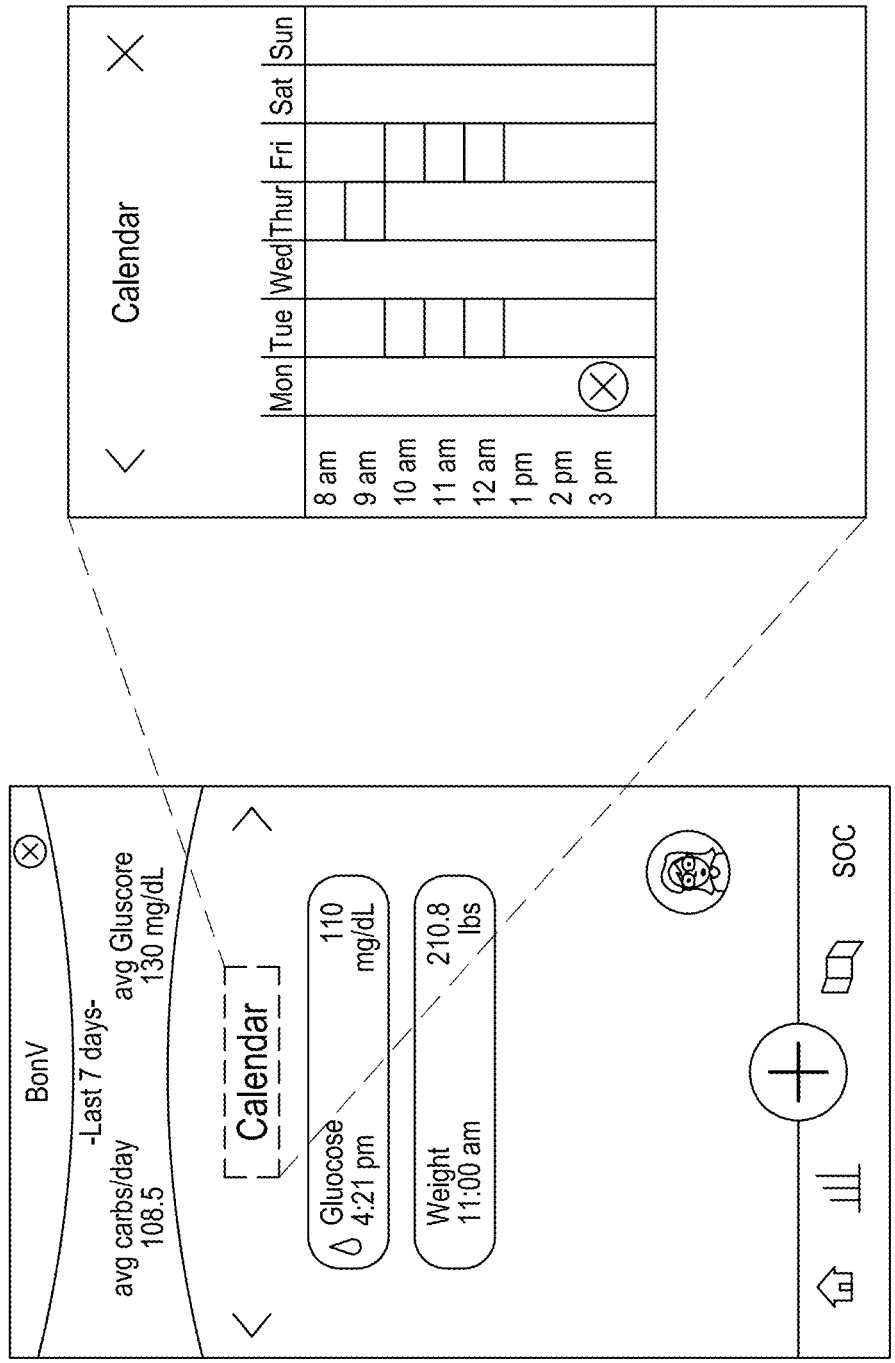
FIGS. 28A-C illustrate example aspects of a calendar tool that may be part of a health coaching system.
Figure 28B:
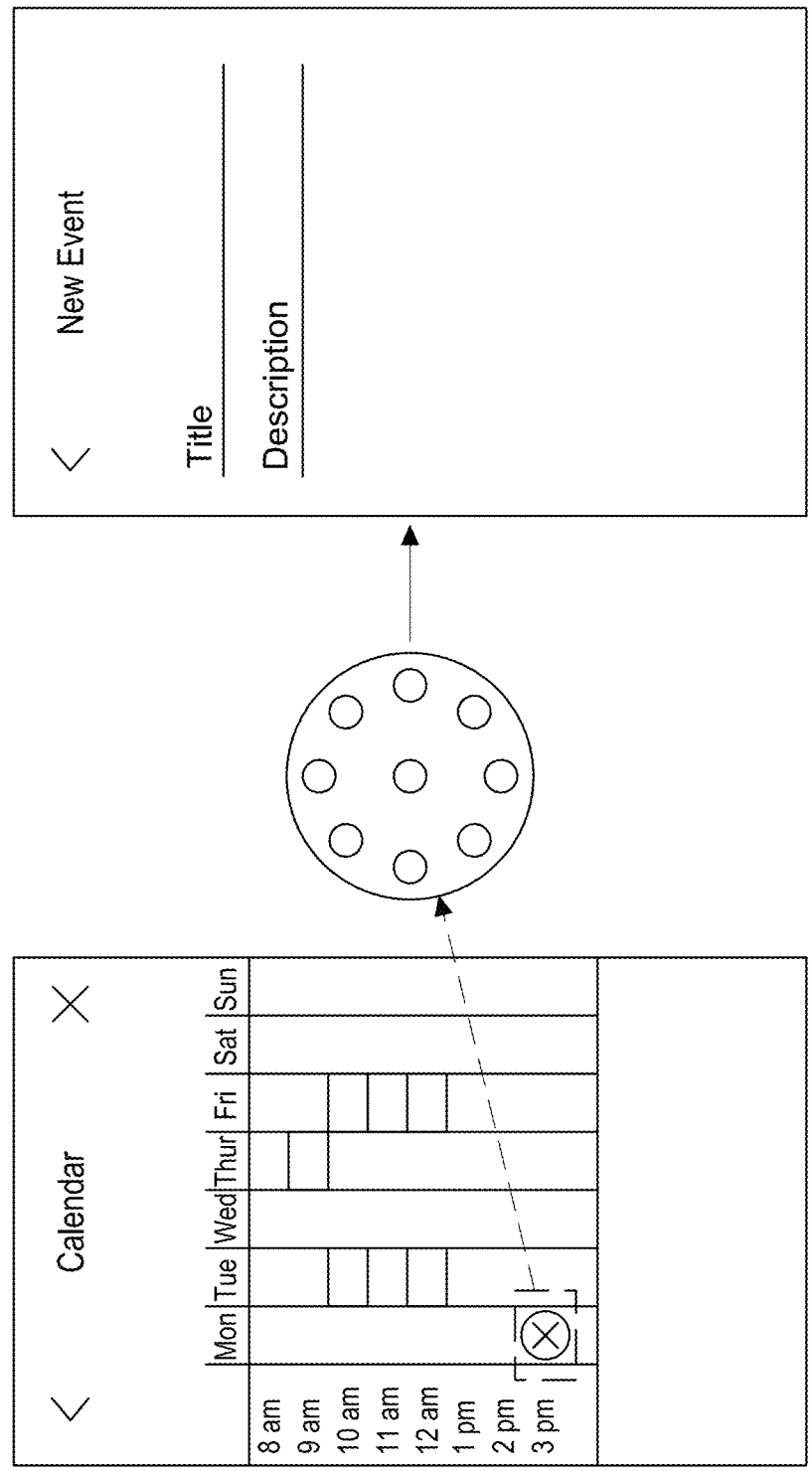
Figure 28C:
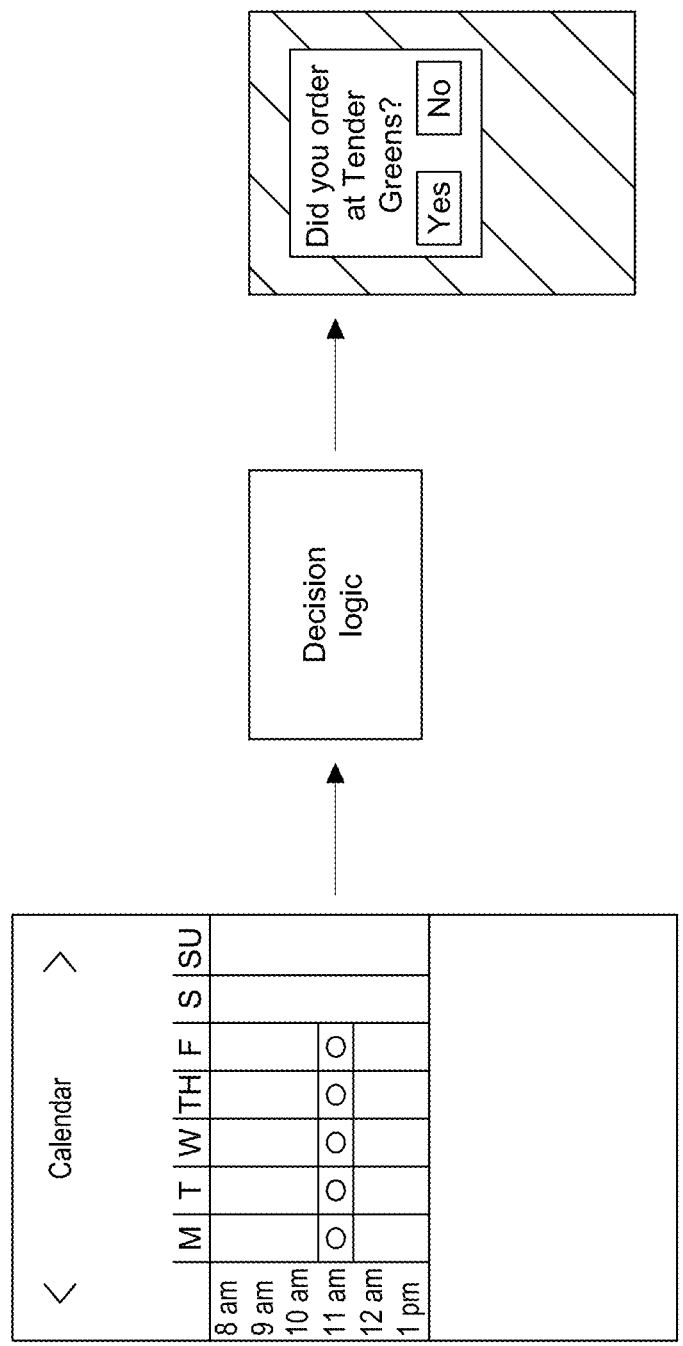

In some examples, a health coaching system can include one or more planning tools or functionalities. For example, a health coaching system can include a calendar tool as part of a graphical user interface. FIGS. 28A-C illustrate various aspects of an example calendar tool that may be part of a graphical user interface.

As illustrated in FIG. 28A, a calendar tool may be accessed by one or more interactable components in a graphical user interface, such as a link or graphic on a home screen or interface. In some examples, the calendar tool can include planned or logged meal times, parameter logging times, parameter measurement times (such as planned glucose measurements), planned interaction with educational content, personal calendar content (such as work or personal appointments or meetings), other events, planned content, appointments, or meetings, the like, or a combination thereof.

FIG. 28B illustrates an example event tool that may be part of a calendar tool. An event tool can, for example, include a graphic or other mode of input that is configured to facilitate a user to add an event or other content to their calendar. The graphic or other mode of input can include an overlay or other aspect of a graphical user interface can include a fan or wheel menu to allow a user to add an event related to one or more aspects of a health coaching system, such as a meal plan or exercise plan, or other calendar related items, such as a travel plan, holiday, or doctor appointment. In some examples, a health coaching system may analyze a calendar input to provide insights, nudges, or other recommendations based on the analysis. An event can include content such as a title, description, location, time, length, category, or other information.

FIG. 28C illustrates an example pattern recognition functionality that may be part of a health coaching system. The pattern recognition functionality can include, for example, a system configured to learn one or more patterns in a user's calendar. The patterns can include, for example, a recognized time at which a user typically logs or eat a meal. In some examples, the patterns may trigger one or more nudges or prompts by the health coaching system to perform an action. For example, if a system recognizes a pattern of a user logging a meal at 12 pm on Monday through Thursday and a user fails to log a meal at noon on Friday, the health coaching system may nudge or remind a user to log their meal. In some examples, if a health coaching system recognizes a pattern in logging or other activity, the health coaching system may prompt a user about automatic logging.

In some examples, the pattern recognition may be utilized as part of a recommendation engine of a health coaching system. For example, a system may recognize a pattern that if a user does not log exercise in the morning, they overeat or log too many calories. The system may recommend to a user to perform exercise in the morning in order to maintain a goal related to eating within calorie limits. Other recommendations based on pattern recognition may also be possible.

7. Example Settings Functionalities

In some examples, a graphical user interface can include one or more settings functionalities. FIGS. 29A-E illustrate example aspects of a graphical user interface that may be associated with settings functionalities.

Figure 29A:
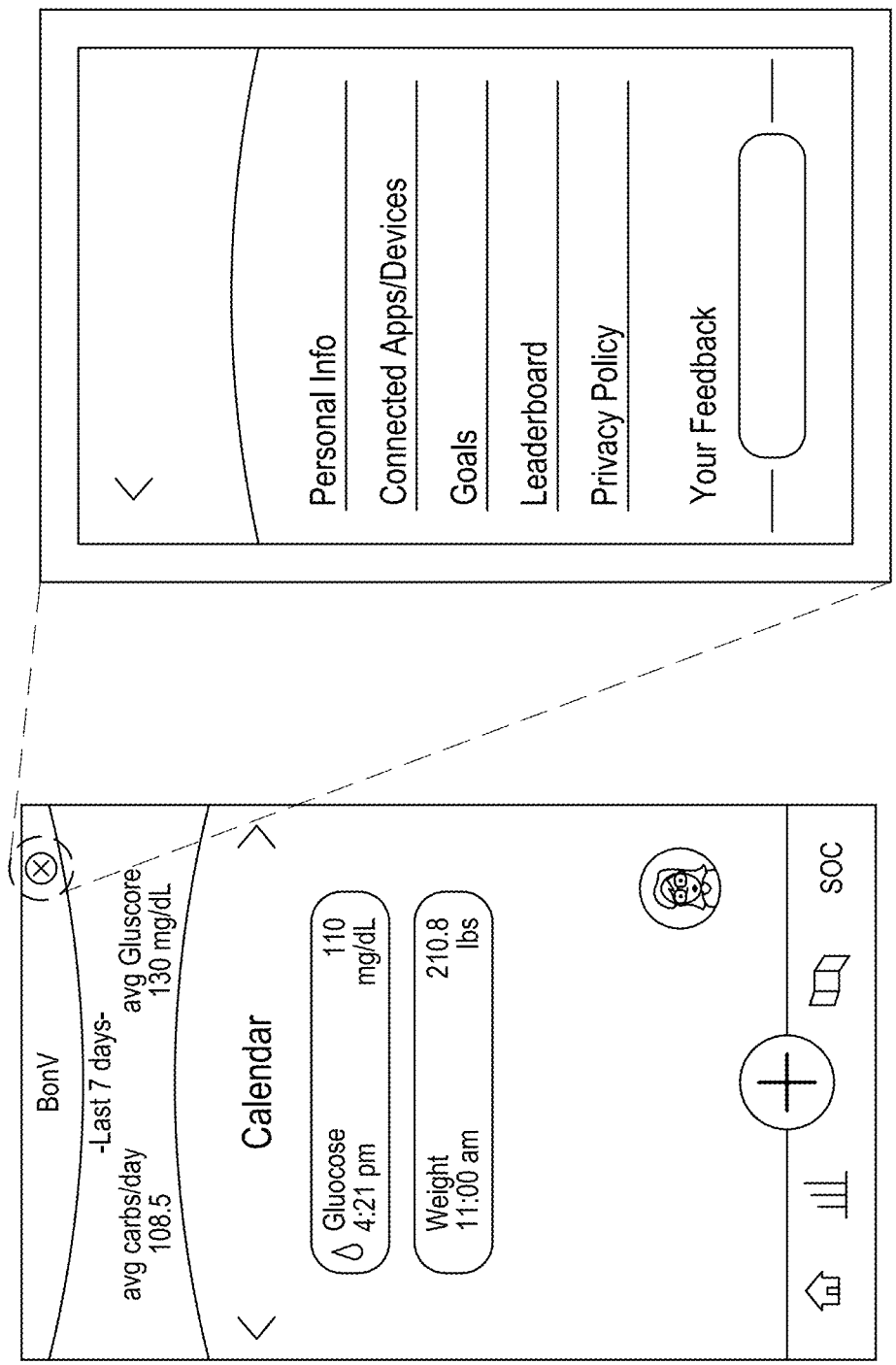
FIGS. 29A-E illustrate example aspects of settings or configuration tools that may be part of a health coaching system or graphical user interface.

As illustrated in FIG. 29A, a settings interface or menu having one or more settings and/or system information may be accessed through an input in the graphical user interface. An input can include, for example, a graphic or link on a home screen or interface. The settings and/or system information can include personal information settings, connected applications and devices settings, goals settings, information related to a privacy policy, information related to the graphical user interface, information relating to the health coaching system, an input for providing feedback about the health coaching system, the like or a combination thereof. In some examples, the settings interface or menu may be accessed by an interactive portion of an interface, such as a graphic on an interface screen.

Figure 29B:
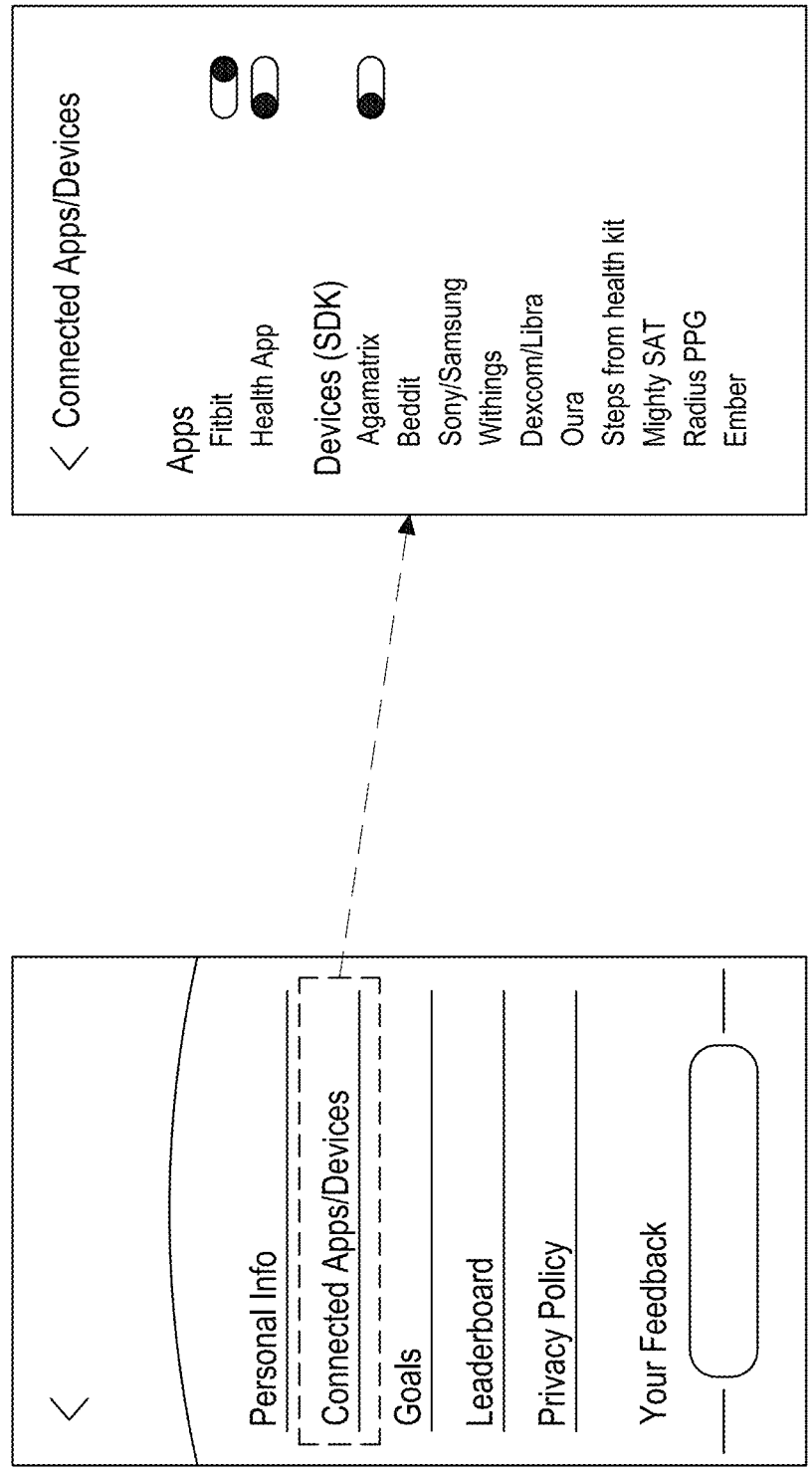

FIG. 29B illustrates an example connected applications and devices settings interface that may be accessed through a settings menu or interface. The connected applications and devices settings interface may include a list of applications or devices that share data with the health coaching system or are capable of sharing data with the health coaching system. In some examples, the interface can include a sharing or connectivity status of an application or device. Additionally or alternatively, the interface can include one or more sharing configurations for one or more of the connected applications or devices. For example, a sharing configuration can include whether sharing is one direction or bi-directional.

Figure 29C:
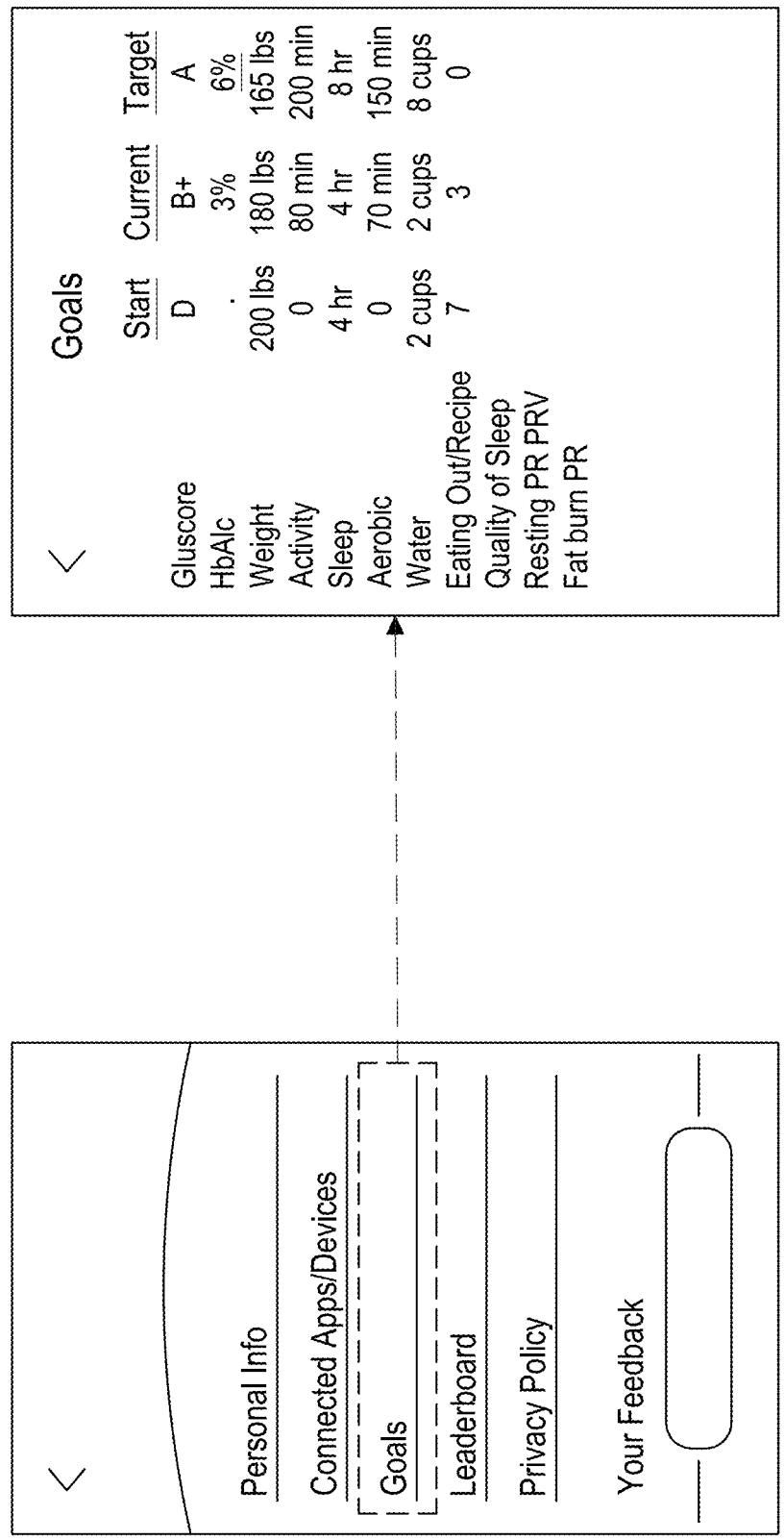

FIG. 29C illustrates an example goal settings interface that may be accessed through a settings menu or interface. The goal settings interface can include one or more goals and one or more inputs associated with those goals through which a user may personalize a health coaching experience. For example, a user may be able to select how quickly they want to lose weight, how much exercise they want to set as a current goal, how much water they would like to aim to drink, the like or a combination thereof. In some examples, progress towards one or more goals may be displayed. For example, a grade, score, or other metric associated with a goal may be displayed in relation to a start metric value, a current metric value, and a target metric value. For example, a weight goal can include a start weight of 200 lbs, a current weight of 180 lbs, and a goal weight of 165 lbs.

Figure 29D:
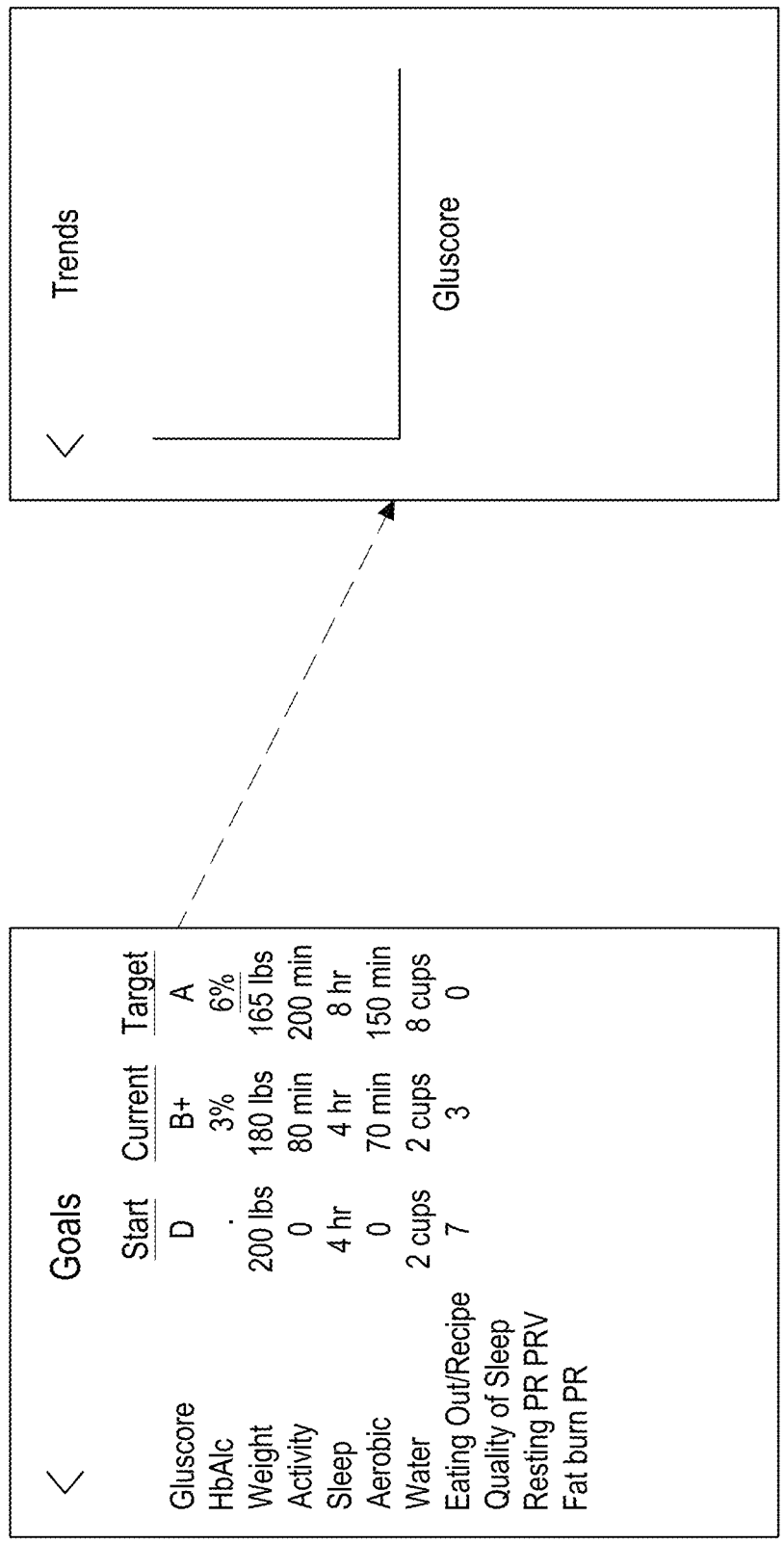

FIG. 29D illustrates an example aspect of a goal settings interface that can include how a user is performing in light of the current goal or how a user may expect to perform in light of a current goal. In the illustrated example, a goal settings interface may include a selection associated with trends in a particular goal. That selection may facilitate access to a graphical representation of the trends associated with that particular goal.

Figure 29E:
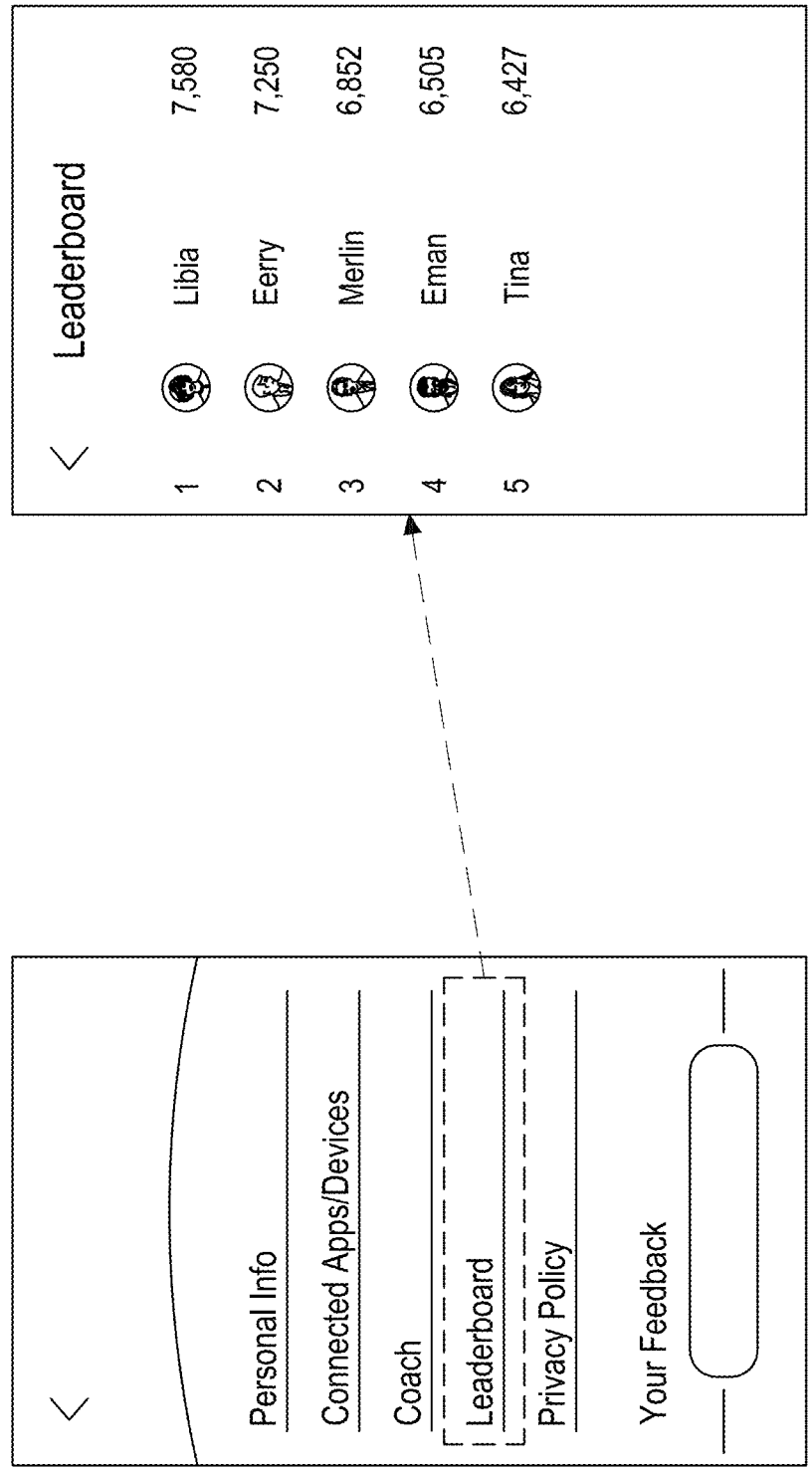

FIG. 29E illustrates an example achievements interface that may be accessed through a settings or menu interface. The achievements interface can include a leader board or other information associated with user achievements. The leaderboard can include data associated with where a user lies in relation to a group of users, such as a total number of users of a health coaching system 100 or a subset of the total number of users, such as a group of support users, friends, or coworkers of a user. The leaderboard can include points or other metric for measuring progress within the health coaching system 100. The points may be related to goal progress, interaction with the health coaching system 100, the like or a combination thereof.

K. EXAMPLE HARDWARE FOR OBTAINING USER DATA

As discussed above, user data may be obtained through a physiological sensor associated with the user. For example, the physiological sensor may include a body scale, glucose monitor, heart rate sensor, the like or some combination thereof. In some configurations, a body scale may be capable of detecting and transmitting one or more physiological parameters associated with the user to one or more hardware processors associated with the system 100 over a network. The body scale may be able to detect heart rate, heart rate variability, weight, or body fat percentage.

A body scale may be able to detect heart rate through a load sensing system. For example, the body scale may include a load sensor that can detect small variations in applied force as a result of a person's heart beating while standing on the scale. Rhythmic variations can be analyzed, recorded, or transmitted as the heart rate of the person.

The body scale may be able to detect a user's waist circumference through one or more imaging systems associated with the body scale. For example, waist circumference may be tracked using a device equipped with a camera or set of cameras or through manual input. For example, the device equipped with a camera or set of cameras may be a scale with a camera embedded in the base of the scale. The camera may capture images looking up towards a person standing on the scale. The images may show a profile of the person's waist from a ground-up perspective. That profile may be analyzed to determine the person's waist circumference.

The body scale may be able to detect a user's height through one or more imaging systems that may or may not be associated with the body scale or through manual input. For example, the height may calculated by a mobile device equipped with a camera. The device may capture images of the person standing next to a scale to determine height. Alternatively, the device may capture images of the person's shadow to determine the person's height based on the phone's position and the shadow distance and angle. In another example, the system may determine height using a device equipped with an acoustic sensor. For example, the device may be a body scale with embedded acoustic sensors. The scale may transmit sound waves through a person standing on the scale. Those sand waves may travel through the person's body and reflect off the top of the person's skull, traveling back down towards the person's feet, towards the scale. Acoustic sensors in the scale may determine the person's height based on the amount of time it took for the sound waves to reflect back to the person's feet.

Figure 30:
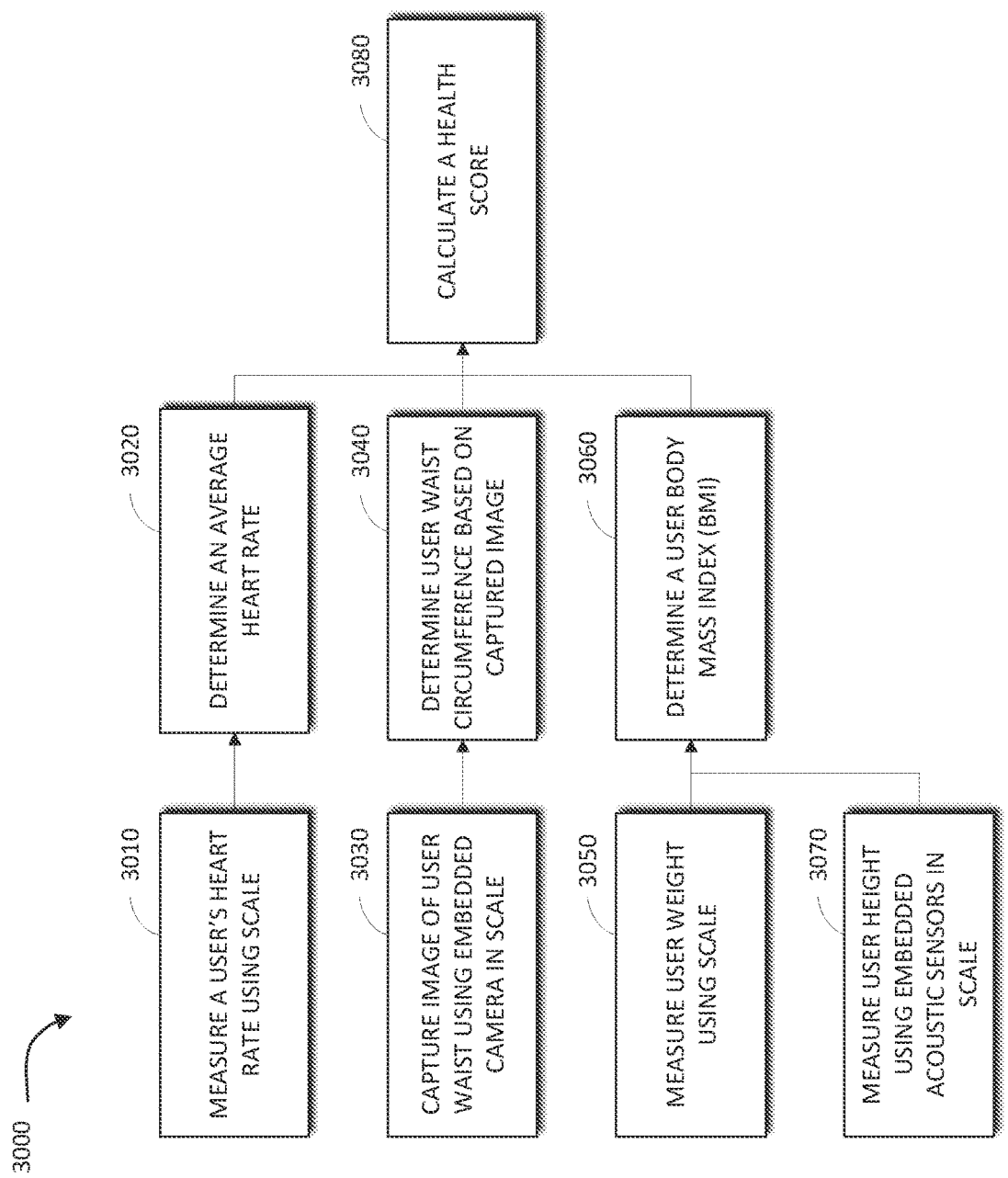
FIG. 30 illustrates an example coaching process using a body scale equipped with load sensors, acoustic sensors, and at least one camera.

FIG. 30 illustrates an example coaching process 3000 using a body scale equipped with physiological sensors, including but not limited to load sensors, acoustic sensors, and at least one camera. At a heart rate measuring step 3010, the body scale may detect the heart rate of the user through small variations in applied force as a result of the user's heart beating as they stand on the scale. The heart rate may be stored in a heart rate log. The user's average heart rate may be determined at an average heart rate determination step 3020 in which the system analyzes the heart rate log to find an average heart rate over a set period of time. At an image capture step 3030, images looking up towards a person standing on the scale may be captured by a camera within the body scale. The images may show a profile of the person's waist from a ground-up perspective. That profile may be analyzed to determine the person's waist circumference in a waist circumference determination step 3040. At a weight measurement step 3050, a user's weight may be measured using the load sensors on the scale. At a height measurement step 3070, the user's height may be measured using acoustic sensors within the scale. For example, the scale may transmit sound waves through a person standing on the scale, which may travel through the person's body and reflect off the top of the person's skull. Acoustic sensors in the scale may determine the person's height based on the amount of time it took for the sound waves to reflect back to the person's feet. In a Body Mass Index (BMI) determination step 3060, the user's height and weight may be analyzed to determine a user's BMI.

With continued reference to FIG. 30, the user's average heart rate, waist circumference, and BMI may be analyzed in a health score determination step 3080. The health score determination may involve various risk identification processes. For example, the health score determination step 3080 may include determining if the user's BMI contains an identified risk factor, such as if it falls within an overweight, or obese classification. In another example, the system 100 may also determine a health risk associated with an increased waist circumference. In another example, the system 100 may also determine the health risk associated with an increasing or decreasing average heart rate. In another example, the system 100 may analyze the user's weight gain or loss in conjunction with average heart rate to determine an increased health risk associated with a weight gain or static weight and an increasing average heart rate or a decreased health risk associated with a weight loss and a decreasing average heart rate. Once risks have been identified, the system 100 may calculate a health score in the form of a scaled score or percent.

L. ADDITIONAL EXAMPLES

Disclosed herein are additional examples of a health coaching system and methods. Any of the following examples may be combined.

Example 1

A personalized health coaching system comprising:
at least one sensor configured to detect blood glucose values of a user;
an input to receive the blood glucose values from the at least one sensor;
one or more hardware processors configured to:
analyze a plurality of historical glucose values to determine a GluScore of the user, wherein the GluScore comprises a variation of glucose values over a period of time;
determine a recommendation threshold based at least in part on the GluScore;
receive a glucose value from the at least one sensor;
determine that the current glucose value passes the recommendation threshold; and
generate a user recommendation based on the current glucose value.

Example 2

The system of Example 1, wherein the user recommendation comprises a food intake change.

Example 3

The system of any one of Examples 1 or 2, wherein the user recommendation comprises a glucose measurement schedule comprising times of day to measure glucose.

Example 4

The system of any one of Examples 1-3, wherein the user recommendation comprises interaction with educational materials.

Example 5

The system of any one of Examples 1-4, wherein the period of time comprises 2 hours.

Example 6

The system of any one of Examples 1-5, wherein the recommendation threshold comprises a glucose value over a threshold percentage of an average glucose value over the period of time.

Example 7

The system of any one of Examples 1-6, wherein the threshold percentage comprises a value greater than fifty percent of the maximum glucose value of the historical glucose values.

Example 8

The system of any one of Examples 1-7, wherein to analyze a plurality of historical glucose values, the one or more hardware processors is configured to classify the historical glucose values as being at least one of: low variability, moderate variability, and severe variability.

Example 9

The system of Example 8 wherein low variability comprises a variability in historical glucose values of less than twenty percent over two hours.

Example 10

The system of any one of Examples 8 or 9 wherein moderate variability comprises a variability in historical glucose values of between twenty and forty percent over two hours.

Example 11

The system of any one of Examples 8-10 wherein severe variability comprises a variability in historical glucose values of greater than forty percent over two hours.

Example 12

The system of any one of Examples 1-11, wherein the one or more hardware processors are configured to:
communicate the user recommendation to the user;
receive user data comprising at least one of a second glucose value; and
determine a user compliance with the recommendation based at least in part on the second glucose value.

Example 13

The system of any one of Examples 1-12, wherein the one or more hardware processors are configured to:
  determine a user encouragement based at least in part on the user compliance; and
  transmit the user encouragement.

Example 14

The system of any one of Examples 1-13, wherein the one or more hardware processors are configured to:
  determine a user reward based at least in part on the user compliance; and
  transmit the user reward.

Example 15

The system of any one of Examples 1-14, wherein the one or more hardware processors are configured to transmit the user compliance to a third party.

Example 16

The system of Example 15, wherein the third party comprises a support user.

Example 17

The system of any one of Examples 15 or 16, wherein the third party comprises an insurance provider.

Example 18

A system for providing personalized health coaching recommendations to a user, the system comprising:
  a non-transitory memory configured to store executable instructions;
  one or more hardware processors in communication with the non-transitory memory configured to:
    receive a first set of data associated with a user, the first set of data comprising data received from at least one of a tracking device, a third party, or a user input;
    analyze the first set of data to determine a first health score of the user;
    generate a lifestyle recommendation based on the first health score of the user;
    transmit the lifestyle recommendation to the user;
    receive a second set of data associated with the user, the second set of data comprising data received from at least one of a tracking device, a third party, or a user input;
    analyze the second set of data to determine a user compliance with the lifestyle recommendation; and
    transmit feedback to the user based on the user compliance.

Example 19

The system of Example 18, wherein the feedback comprises an encouragement or a reward.

Example 20

The system of Example 19, wherein the encouragement comprises an encouraging message.

Example 21

The system of any one of Examples 18 or 19, wherein the reward comprises access to a monetary discount on a retail item.

Example 22

The system of any one of Examples 18-21, wherein the one or more hardware processors are configured to transmit the user compliance to a third party.

Example 23

The system of Example 22, wherein the third party comprises a support user.

Example 24

The system of any one of Examples 12 or 23, wherein the third party comprises an insurance provider.

Example 25

The system of any one of Examples 18-24, wherein the lifestyle recommendation is based on a user goal.

Example 26

The system of any one of Examples 18-25, wherein the lifestyle recommendation is based on a clinician input.

Example 27

A system for providing health education materials to a user, the system comprising:
  a non-transitory memory configured to store executable instructions;
  one or more hardware processors in communication with the non-transitory memory configured to:
    receive a first set of data associated with a user, the first set of data comprising data received from at least one of a tracking device, a third party, or a user input;
    analyze the first set of data to determine a first health score of the user;
    determine educational content relevant to the user based on the first health score; and
    facilitate user access to at least a portion of the educational content according to a release schedule.

Example 28

The system of Example 27 wherein the one or more hardware processors are configured to:
  receive a user interaction comprising a question associated with the health of the user;
  determine a response to the user interaction;
  transmit the response to the user interaction to the user.

Example 29

The system of any one of Examples 27 or 28, wherein the response comprises educational content.

Example 30

The system of any one of Examples 27-29, wherein the educational content comprises interactive educational modules associated with the first health score.

Example 31

The system of any one of Examples 27-30, wherein the educational content comprises videos or articles associated with the first health score.

Example 32

The system of any one of Examples 27-31, wherein the release schedule comprises once a week.

Example 33

The system of any one of Examples 27-31, wherein the one or more hardware processors are configured to:
  receive a second set of data associated with the user, the second set of data comprising data received from at least one of a tracking device, a third party, or a user input;
  determine an amount of user interaction with the educational content;
  determine a feedback based on the amount of user interaction; and
  transmit the feedback to the user.

Example 34

The system of Example 33, wherein the feedback comprises an encouragement or a reward.

Example 35

The system of any one of Examples 23-34, wherein the one or more hardware processors are configured to transmit the amount of user interaction to a third party.

Example 36

The system of Example 35, wherein the third party comprises a support user.

Example 37

The system of any one of Examples 35 or 36, wherein the third party comprises an insurance provider.

Example 38

A system for providing health education materials to a user, the system comprising:
  a non-transitory memory configured to store executable instructions;
  one or more hardware processors in communication with the non-transitory memory configured to:
  receive a first set of data associated with a user, the first set of data comprising data received from at least one of a tracking device, a third party, or a user input;
  analyze the first set of data to determine a presence of one or more risk factors for a first health condition;
  analyze the first set of data to determine a presence of one or more mitigating factors for the first health condition; and
  determine a scaled score associated with the first health condition of the user based on the presence of the one or more risk factors and the presence of the one or more mitigating factors.

Example 39

The system of Example 38, wherein the first health condition comprises an athletic fitness level, an injury, or a disease.

Example 40

The system of any one of Examples 38 or 39, wherein the scaled score comprises a value between 1 and 10.

Example 41

The system of any one of Examples 38 or 39, wherein the scaled score comprises a percentage value between 0 and 100 percent.

Example 42

The system of any one of Examples 38-41, wherein the first health condition is associated with a user health goal.

Example 43

The system of any one of Examples 38-42, wherein the one or more hardware processors are configured to:
  generate a lifestyle recommendation based on the scaled score; and
  transmit the lifestyle recommendation to the user.

Example 44

The system of any one of Examples 38-43, wherein the one or more hardware processors are configured to:
  receive a second set of data associated with the user, the second set of data comprising data received from at least one of a tracking device, a third party, or a user input;
  analyze the second set of data to determine a user compliance with the lifestyle recommendation; and
  transmit feedback to the user based on the user compliance.

Example 45

The system of Example 44, wherein the feedback comprises an encouragement or a reward.

Example 46

The system of Example 45, wherein the encouragement comprises an encouraging message.

Example 47

The system of any one of Examples 45 or 46, wherein the reward comprises access to a monetary discount on a retail item.

Example 48

The system of any one of Examples 44-47, wherein the one or more hardware processors are configured to transmit the user compliance to a third party.

Example 49

The system of Example 48, wherein the third party comprises a support user.

Example 50

The system of any one of Examples 47 or 48, wherein the third party comprises an insurance provider.

Example 51

The system of any one of Examples 38-50, wherein the lifestyle recommendation is based on a user goal.

Example 52

The system of any one of Examples 38-51, wherein the lifestyle recommendation is based on a clinician input.

Example 53

A method of classifying a glucose response, the method comprising:
  determining a plurality of blood glucose values comprising blood glucose values measured from at least one sensor during a time window;
  assigning a first classification to a user's glucose response based on the plurality of blood glucose measurements using a classifier trained using machine learning;
  applying a bias correction to the plurality of blood glucose measurements to generate corrected blood glucose measurements;
  assigning a second classification to the user's glucose response based on the corrected blood glucose measurements; and
  determining a metric value for the user's glucose response based on the first classification and the second classification.

Example 54

The method of Example 53, wherein the first classification is associated with lifestyle factors.

Example 55

The method of Example 53, wherein the first classification is sensitive to an absolute value of blood glucose measurements during the time window.

Example 56

The method of Example 53, wherein the second classification is associated with meal sensitivity.

Example 57

The method of Example 53, wherein the second classification is associated with glucose variations during the time window.

Example 58

The method of Example 53, wherein the metric value is a grade on an alphanumeric grading scale.

Example 59

The method of Example 53 comprising associating a first meal intake with the metric value.

Example 60

The method of Example 59 comprising:
  receiving a user input of an intention to ingest the first meal intake; and
  recommend a substitute meal intake if the determined metric value falls below a threshold.

Example 61

The method of Example 60, wherein the intention to ingest is after the time window.

Example 62

The method of Example 59 comprising:
  receiving a user input of an intention to ingest a second meal intake;
  determine a relationship between the first meal intake and the second meal intake; and
  recommend a substitute meal intake based on the relationship if the determined metric value falls below a threshold.

Example 63

The method of Example 62, wherein the relationship comprises a similarity in relation to macronutrient composition.

Example 64

The method of Example 62, wherein the relationship comprises a similarity in glycemic load.

Example 65

The method of Example 53 wherein the time window is 2 hours.

Example 66

The method of Example 53 wherein the time window is 2.5 hours.

Example 67

The method of Example 53 wherein the plurality of blood glucose measurements comprises at least 3 values.

Example 68

The method of Example 53 wherein the plurality of blood glucose measurements comprises at least one measured value.

Example 69

The method of Example 68, wherein the plurality of blood glucose measurements comprises at least one estimated value based on a glucose estimation algorithm.

Example 70

The method of Example 53, wherein the at least one sensor comprises an invasive sensor.

Example 71

The method of Example 70, wherein the at least one sensor comprises a continuous glucose monitor.

Example 72

The method of Example 70, wherein the at least one sensor comprises a blood stick meter.

Example 73

The method of Example 53, wherein the at least one sensor comprises a non-invasive sensor.

Example 74

The method of Example 53, wherein the at least one sensor comprises a non-invasive sensor and an invasive sensor.

Example 75

A method of classifying a glucose response, the method comprising:
  receiving at least one value of a meal intake log;
  generating an estimated blood glucose response over a time window based on the at least one value;
  assigning a first classification to a user's glucose response based on the estimated blood glucose response using a classifier trained using machine learning;
  applying a bias correction to the estimated blood glucose response to generate a corrected blood glucose estimate;
  assigning a second classification to the user's glucose response based on the corrected blood glucose estimate; and
  determining a metric value for the user's glucose response based on the first classification and the second classification.

Example 76

The method of Example 75, wherein the first classification is associated with lifestyle factors.

Example 77

The method of Example 75, wherein the first classification is sensitive to an absolute value of blood glucose measurements during the time window.

Example 78

The method of Example 75, wherein the second classification is associated with meal sensitivity.

Example 79

The method of Example 75, wherein the second classification is associated with glucose variations during the time window.

Example 80

The method of Example 75, wherein the metric value is a grade on an alphanumeric grading scale.

Example 81

The method of Example 75 comprising associating a first meal intake with the metric value.

Example 82

The method of Example 75 comprising:
  receiving a user input of an intention to ingest the first meal intake; and
  recommend a substitute meal intake if the determined metric value falls below a threshold.

Example 83

The method of Example 82, wherein the intention to ingest is after the time window.

Example 84

The method of Example 81 comprising:
  receiving a user input of an intention to ingest a second meal intake;
  determine a relationship between the first meal intake and the second meal intake; and
  recommend a substitute meal intake based on the relationship if the determined metric value falls below a threshold.

Example 85

The method of Example 84, wherein the relationship comprises a similarity in relation to macronutrient composition.

Example 86

The method of Example 84, wherein the relationship comprises a similarity in glycemic load.

Example 87

A health coaching system comprising:
  a non-transitory computer storage medium configured to at least store computer-readable instructions; and
  one or more hardware processors in communication with the non-transitory computer storage medium, the one or more hardware processors configured to execute the computer-readable instructions to at least:
  receive a user input comprising at least one food or beverage;
  determine a grade associated with a glucose response of the user for the at least one food or beverage;
  generate in a window on a display, a graphical representation of the grade in the context of grades of other users who input the same food or beverage.

Example 88

The health coaching system of Example 87, wherein the graphical representation comprises a bar graph comprising a distribution of grades across users for the at least one food or beverage.

Example 89

The health coaching system of Example 87, wherein the at least one food or beverage comprises a plurality of foods ingested in a time window.

Example 90

The health coaching system of Example 87, wherein determining a grade comprises:
  generating an estimated blood glucose response over a time window based on the user input;
  assigning a first classification to a user's glucose response based on the estimated blood glucose response using a classifier trained using machine learning;
  applying a bias correction to the estimated blood glucose response to generate a corrected blood glucose estimate;
  assigning a second classification to the user's glucose response based on the corrected blood glucose estimate; and
  determining a metric value for the user's glucose response based on the first classification and the second classification.

Example 91

The health coaching system of Example 87, wherein determining a grade comprises:
  determining a plurality of blood glucose values comprising blood glucose values measured from at least one sensor during a time window;
  assigning a first classification to a user's glucose response based on the plurality of blood glucose measurements using a classifier trained using machine learning;
  applying a bias correction to the plurality of blood glucose measurements to generate corrected blood glucose measurements;
  assigning a second classification to the user's glucose response based on the corrected blood glucose measurements; and
  determining a metric value for the user's glucose response based on the first classification and the second classification.

Example 92

A health coaching system comprising:
  a non-transitory computer storage medium configured to at least store computer-readable instructions; and
  one or more hardware processors in communication with the non-transitory computer storage medium, the one or more hardware processors configured to execute the computer-readable instructions to at least:
  receive a user input comprising at least one food or beverage;
  determine a glucose response type of a user;
  determine a grade associated with a glucose response type of the user for the at least one food or beverage;
  generate in a window on a display, a recommendation based on the determined grade.

Example 93

The health coaching system of Example 92, wherein the recommendation comprises at least one similar food or beverage to avoid.

Example 94

The health coaching system of Example 93, wherein the at least one similar food or beverage is a food or beverage in the same food group.

Example 95

The health coaching system of Example 92, wherein the recommendation comprises at least one food or beverage to substitute.

Example 96

The health coaching system of Example 92, wherein the recommendation comprises at least one food or beverage to ingest in conjunction with the user input.

Example 97

The health coaching system of Example 92, wherein the recommendation comprises an activity recommendation.

Example 98

The health coaching system of Example 97, wherein the exercise recommendation comprises a length and type of activity.

Example 99

The health coaching system of Example 92, wherein the at least one food or beverage comprises a plurality of food or beverage and wherein the grade comprises an overall grade associated with the plurality of food or beverage.

Example 100

The health coaching system of Example 92, wherein determining a grade comprises:
  generating an estimated blood glucose response over a time window based on the user input;
  assigning a first classification to a user's glucose response based on the estimated blood glucose response using a classifier trained using machine learning;
  applying a bias correction to the estimated blood glucose response to generate a corrected blood glucose estimate;
  assigning a second classification to the user's glucose response based on the corrected blood glucose estimate; and
  determining a grade based on the first classification and the second classification.

Example 101

The health coaching system of Example 92, wherein determining a grade comprises:
- determining a plurality of blood glucose values comprising blood glucose values measured from at least one sensor during a time window;
- assigning a first classification to a user's glucose response based on the plurality of blood glucose measurements using a classifier trained using machine learning;
- applying a bias correction to the plurality of blood glucose measurements to generate corrected blood glucose measurements;
- assigning a second classification to the user's glucose response based on the corrected blood glucose measurements; and
- determining a grade based on the first classification and the second classification.

M. TERMINOLOGY

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting configurations of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A method of generating a recommendation based on a classification of a glucose response of a user, the method comprising:
   receiving an input comprising at least three blood glucose values of the user measured by at least one first sensor over a first period;
   assigning a first classification to the input using a first classifier trained using machine learning using historical glucose values of the user measured by the at least one first sensor and which classifies the input according to a variability of the at least three blood glucose values measured by the at least one first sensor, the first classification associated with a glucose sensitivity due to lifestyle of the user;
   generating a modified input by applying a bias correction to the input;
   assigning a second classification to the modified input using a second classifier, the second classification associated with glycemic load of a recent meal, a recent food, or a recent activity;
   determining a score for the user's glucose response during the first period based on the first classification and the second classification;
   determining that the score passes a recommendation threshold; and
   outputting to a display a user recommendation relating to the recent meal, the recent food, or the recent activity based on the score.

2. The method of claim 1, wherein generating the modified input is further based on lifestyle factors.

3. The method of claim 1, wherein generating the modified input is further based on an absolute value of blood glucose measurements during the first period.

4. The method of claim 1, wherein the second classification is associated with glucose variations during the first period.

5. The method of claim 1, wherein the score is a grade on an alphanumeric grading scale.

6. The method of claim 1, further comprising generating at least one glucose prediction based on the score.

7. The method of claim 1, wherein the classifier comprises a neural network having at least three layers.

8. The method of claim 1, wherein the first period is 2.5 hours.

9. The method of claim 1, wherein the at least three blood glucose values are sampled at a frequency of 5-7 minutes.

10. The method of claim 1, wherein the first and second sensors are the same.

11. The method of claim 1, further comprising outputting the score to a meal log of the display.

12. A health coaching system comprising:
   a non-transitory computer storage medium configured to at least store computer-readable instructions; and
   one or more hardware processors in communication with the non-transitory computer storage medium, the one or more hardware processors configured to execute the computer-readable instructions to at least:
   receive a user input comprising at least three blood glucose values of a user measured by at least one first sensor over a first period;
   assign a first classification to the user input using a first classifier trained using machine learning using historical glucose values of the user measured by the at least one first sensor and which classifies the user input according to a variability of the at least three blood glucose values measured by the at least one first sensor, the first classification associated with a glucose sensitivity due to lifestyle of the user;
   generate a modified input by applying a bias correction to the user input;
   assign a second classification to the modified input using a second classifier, the second classification associated with glycemic load of a recent meal, a recent food, or a recent activity;
   determine a score associated with a glucose response during the first period based on the first classification and the second classification;
   determine that the score passes a recommendation threshold;
   generate in a window on a display, a recommendation relating to the recent meal, the recent food, or the recent activity based on the determined score.

13. The health coaching system of claim 12, wherein the recommendation comprises at least one similar food or beverage to avoid.

14. The health coaching system of claim 12, wherein the recommendation comprises at least one food or beverage to substitute.

15. The health coaching system of claim 12, wherein the recommendation comprises at least one food or beverage to ingest in conjunction with the user input.

16. The health coaching system of claim 12, wherein the recommendation comprises an activity recommendation.

17. The health coaching system of claim 16, wherein the activity recommendation comprises a length and type of activity.

18. The health coaching system of claim 12, wherein the at least one recent food comprises a plurality of food or beverage and wherein the score comprises an overall score associated with the plurality of food or beverage.

19. The health coaching system of claim 12, wherein the first classifier is a neural network having at least three layers.

20. The health coaching system of claim 12, wherein the one or more hardware processors are further configured to output the score to a meal log of the display.

* * * * *